(12) United States Patent
Hettel et al.

(10) Patent No.: US 12,096,938 B2
(45) Date of Patent: *Sep. 24, 2024

(54) DEVICES AND METHODS FOR INCREASING BLOOD PERFUSION TO A DISTAL EXTREMITY

(71) Applicant: LimFlow GmbH, Dresden (DE)

(72) Inventors: Rowan Olund Hettel, Saint-Germain-en-Laye (FR); David Hugo Deaton, Crownsville, MD (US); Sophie Humbert, Arbusigny (FR)

(73) Assignee: LimFlow GmbH, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/189,847

(22) Filed: Mar. 24, 2023

(65) Prior Publication Data

US 2023/0225732 A1 Jul. 20, 2023

Related U.S. Application Data

(63) Continuation of application No. 17/731,588, filed on Apr. 28, 2022, now Pat. No. 11,612,397, which is a (Continued)

(51) Int. Cl.
*A61M 1/36* (2006.01)
*A61B 17/11* (2006.01)
(Continued)

(52) U.S. Cl.
CPC ........ *A61B 17/11* (2013.01); *A61B 17/12036* (2013.01); *A61B 17/12109* (2013.01);
(Continued)

(58) Field of Classification Search
CPC ........ A61B 17/12036; A61B 17/12109; A61B 17/22097; A61B 17/11; A61B 2017/00252; A61B 2017/1107; A61M 1/3613
See application file for complete search history.

(56) References Cited

U.S. PATENT DOCUMENTS 3,848,579 A 11/1974 Villa-Real
4,249,539 A 2/1981 Vilkomerson et al.
(Continued)

FOREIGN PATENT DOCUMENTS

AU 2012258395 3/2013
CN 102083376 6/1944
(Continued)

OTHER PUBLICATIONS

Schreve et al., "Venous Arterialisation for Salvage of Critically Ischaemic Limbs: A Systematic Review and Meta-Analysis". Eur J Vasc Endovasc Surg. Mar. 1, 2017;53(3): 387-402.
(Continued)

*Primary Examiner* — Laura A Bouchelle
(74) *Attorney, Agent, or Firm* — Perkins Coie LLP

(57) ABSTRACT

Devices and methods divert blood flow from a first vessel to a second vessel and maintain blood flow in the first vessel. The device includes a first segment and a second segment. The first segment is configured to anchor in the first vessel. The first segment includes a window to allow blood to flow into the first segment, through the window, and distal in the first vessel. The second segment is configured to anchor in the second vessel. The second segment is configured to allow blood to flow into the first segment, through the second segment, and into the second vessel.

27 Claims, 101 Drawing Sheets

Related U.S. Application Data continuation of application No. PCT/US2020/058263, filed on Oct. 30, 2020.

(60) Provisional application No. 63/072,423, filed on Aug. 31, 2020, provisional application No. 63/004,763, filed on Apr. 3, 2020, provisional application No. 62/929,366, filed on Nov. 1, 2019.

(51) Int. Cl.
    *A61B 17/12*     (2006.01)
    *A61F 2/07*     (2013.01)
    *A61M 25/10*     (2013.01)
    *A61B 90/00*     (2016.01)

(52) U.S. Cl.
    CPC .......... *A61B 17/12136* (2013.01); *A61F 2/07* (2013.01); *A61M 1/3613* (2014.02); *A61M 1/3653* (2013.01); *A61M 25/10* (2013.01); *A61B 2017/1107* (2013.01); *A61B 2017/1139* (2013.01); *A61B 2090/3966* (2016.02)

(56) References Cited

U.S. PATENT DOCUMENTS

| | | |
|---|---|---|
| 4,560,374 A | 12/1985 | Hammerslag |
| 4,586,919 A | 5/1986 | Taheri |
| 4,655,746 A | 4/1987 | Daniels et al. |
| 4,739,760 A | 4/1988 | Chin et al. |
| 4,757,821 A | 7/1988 | Snyder |
| 4,768,508 A | 9/1988 | Chin et al. |
| 4,952,215 A | 8/1990 | Ouriel et al. |
| 5,047,041 A | 9/1991 | Samuels |
| 5,092,872 A | 3/1992 | Segalowitz |
| 5,203,777 A | 4/1993 | Lee |
| 5,234,450 A | 8/1993 | Segalowitz |
| 5,284,478 A | 2/1994 | Nobles et al. |
| 5,304,189 A | 4/1994 | Goldberg et al. |
| 5,352,232 A | 10/1994 | Cohen |
| 5,397,339 A | 3/1995 | Desai |
| 5,443,497 A | 8/1995 | Venbrux |
| 5,591,226 A | 1/1997 | Trerotola et al. |
| 5,601,580 A | 2/1997 | Goldberg et al. |
| 5,639,278 A | 6/1997 | Dereume et al. |
| 5,655,548 A | 8/1997 | Nelson et al. |
| 5,676,670 A | 10/1997 | Kim |
| 5,720,776 A | 2/1998 | Chuter et al. |
| 5,759,174 A | 6/1998 | Fischell et al. |
| 5,782,904 A | 7/1998 | White et al. |
| 5,792,056 A | 8/1998 | Prince |
| 5,797,920 A | 8/1998 | Kim |
| 5,800,522 A | 9/1998 | Campbell et al. |
| 5,824,071 A | 10/1998 | Nelson et al. |
| 5,830,222 A | 11/1998 | Makower |
| 5,830,224 A | 11/1998 | Cohn et al. |
| 5,843,171 A | 12/1998 | Campbell et al. |
| 5,897,495 A | 4/1999 | Aida et al. |
| 5,916,264 A | 6/1999 | von Oepen et al. |
| 5,938,697 A | 8/1999 | Killion et al. |
| 5,951,599 A | 9/1999 | McCrory |
| 5,976,178 A | 11/1999 | Goldsteen et al. |
| 6,007,544 A | 12/1999 | Kim |
| 6,015,405 A | 1/2000 | Schwartz et al. |
| 6,036,702 A | 3/2000 | Bachinski et al. |
| 6,068,638 A | 5/2000 | Makower |
| 6,071,292 A | 6/2000 | Makower et al. |
| 6,081,738 A | 6/2000 | Hinohara et al. |
| 6,099,542 A | 8/2000 | Cohn et al. |
| 6,099,559 A | 8/2000 | Nolting |
| 6,102,884 A | 8/2000 | Squitieri |
| 6,106,548 A | 8/2000 | Roubin et al. |
| 6,117,165 A | 9/2000 | Becker |
| 6,126,649 A | 10/2000 | VanTassel et al. |
| 6,129,756 A | 10/2000 | Kugler et al. |
| 6,159,225 A | 12/2000 | Makower |
| 6,159,238 A | 12/2000 | Killion et al. |
| 6,164,281 A | 12/2000 | Zhao |
| 6,165,185 A | 12/2000 | Shennib et al. |
| 6,186,972 B1 | 2/2001 | Nelson et al. |
| 6,190,353 B1 | 2/2001 | Makower et al. |
| 6,190,379 B1 | 2/2001 | Heuser et al. |
| 6,193,745 B1 | 2/2001 | Fogarty et al. |
| 6,193,763 B1 | 2/2001 | Mackin |
| 6,206,912 B1 | 3/2001 | Goldsteen et al. |
| 6,217,527 B1 | 4/2001 | Selmon et al. |
| 6,221,049 B1 | 4/2001 | Selmon et al. |
| 6,231,546 B1 | 5/2001 | Milo et al. |
| 6,231,587 B1 | 5/2001 | Makower |
| 6,241,744 B1 | 6/2001 | Imran et al. |
| 6,251,116 B1 | 6/2001 | Shannib et al. |
| 6,254,610 B1 | 7/2001 | Darvish et al. |
| 6,280,388 B1 | 8/2001 | Koger et al. |
| 6,283,951 B1 | 9/2001 | Flaherty et al. |
| 6,283,983 B1 | 9/2001 | Makower et al. |
| 6,287,317 B1 | 9/2001 | Makower et al. |
| 6,287,336 B1 | 9/2001 | Globerman et al. |
| 6,298,261 B1 | 10/2001 | Rex |
| 6,302,875 B1 | 10/2001 | Makower et al. |
| 6,302,905 B1 | 10/2001 | Goldsteen et al. |
| 6,330,884 B1 | 12/2001 | Kim |
| 6,364,900 B1 | 4/2002 | Heuser |
| 6,375,615 B1 | 4/2002 | Flaherty et al. |
| 6,379,319 B1 | 4/2002 | Garibotto et al. |
| 6,432,127 B1 | 8/2002 | Kim et al. |
| 6,447,539 B1 | 9/2002 | Nelson et al. |
| 6,458,140 B2 | 10/2002 | Akin et al. |
| 6,464,665 B1 | 10/2002 | Heuser |
| 6,464,681 B1 | 10/2002 | Heuser |
| 6,464,709 B2 | 10/2002 | Shennib et al. |
| 6,475,170 B1 | 11/2002 | Doron et al. |
| 6,475,222 B1 | 11/2002 | Berg et al. |
| 6,475,226 B1 | 11/2002 | Belef et al. |
| 6,477,402 B1 | 11/2002 | Lynch et al. |
| 6,485,509 B2 | 11/2002 | Killion et al. |
| 6,491,707 B2 | 12/2002 | Makower |
| 6,508,824 B1 | 1/2003 | Flaherty et al. |
| 6,511,458 B2 | 1/2003 | Milo et al. |
| 6,511,491 B2 | 1/2003 | Grudem et al. |
| 6,517,558 B2 | 2/2003 | Gittings et al. |
| 6,536,949 B1 | 3/2003 | Heuser |
| 6,544,230 B1 | 4/2003 | Flaherty et al. |
| 6,554,842 B2 | 4/2003 | Heuser et al. |
| 6,561,998 B1 | 5/2003 | Roth et al. |
| 6,569,145 B1 | 5/2003 | Shmulewitz et al. |
| 6,569,193 B1 | 5/2003 | Cox et al. |
| 6,579,311 B1 | 6/2003 | Makower |
| 6,582,409 B1 | 6/2003 | Squitieri |
| 6,585,650 B1 | 7/2003 | Solem |
| 6,589,164 B1 | 7/2003 | Flaherty |
| 6,602,241 B2 | 8/2003 | Makower et al. |
| 6,610,087 B1 | 8/2003 | Zarbatany et al. |
| 6,613,081 B2 | 9/2003 | Kim et al. |
| 6,616,675 B1 | 9/2003 | Evard et al. |
| 6,638,293 B1 | 10/2003 | Makower et al. |
| 6,652,576 B1 | 11/2003 | Stalker |
| 6,655,386 B1 | 12/2003 | Makower et al. |
| 6,660,024 B1 | 12/2003 | Flaherty et al. |
| 6,669,709 B1 | 12/2003 | Cohn et al. |
| 6,669,723 B2 | 12/2003 | Killian et al. |
| 6,685,648 B2 | 2/2004 | Flaherty et al. |
| 6,685,671 B1 | 2/2004 | Oishi et al. |
| 6,685,716 B1 | 2/2004 | Flaherty et al. |
| 6,699,280 B2 | 3/2004 | Camrud et al. |
| 6,709,444 B1 | 3/2004 | Makower |
| 6,711,429 B1 | 3/2004 | Gilboa et al. |
| 6,719,781 B1 | 4/2004 | Kim |
| 6,726,677 B1 | 4/2004 | Flaherty et al. |
| 6,730,116 B1 | 5/2004 | Wolinsky et al. |
| 6,746,426 B1 | 6/2004 | Flaherty et al. |
| 6,746,464 B1 | 6/2004 | Makower |
| 6,824,549 B1 | 11/2004 | Chao |
| 6,858,037 B2 | 2/2005 | Penn et al. |
| 6,858,038 B2 | 2/2005 | Heuser |
| 6,863,684 B2 | 3/2005 | Kim et al. |

(56) References Cited

U.S. PATENT DOCUMENTS

| | | | |
|---|---|---|---|
| 6,881,199 B2 | 4/2005 | Wilk et al. |
| 6,926,690 B2 | 8/2005 | Renati |
| 6,929,009 B2 | 8/2005 | Makower et al. |
| 6,945,949 B2 | 9/2005 | Wilk |
| 7,018,401 B1 | 3/2006 | Hyodoh et al. |
| 7,022,131 B1 | 4/2006 | Derowe et al. |
| 7,025,773 B2 | 4/2006 | Gittings et al. |
| 7,056,325 B1 | 6/2006 | Makower et al. |
| 7,059,330 B1 | 6/2006 | Makower et al. |
| 7,083,588 B1 | 8/2006 | Shmulewitz et al. |
| 7,094,230 B2 | 8/2006 | Flaherty et al. |
| 7,134,438 B2 | 11/2006 | Makower et al. |
| 7,137,962 B2 | 11/2006 | Gittings et al. |
| 7,159,592 B1 | 1/2007 | Makower et al. |
| 7,166,088 B2 | 1/2007 | Heuser |
| 7,179,250 B2 | 2/2007 | Heuser |
| 7,179,270 B2 | 2/2007 | Makower |
| 7,195,637 B2 | 2/2007 | Mika |
| 7,191,015 B2 | 3/2007 | Lamson et al. |
| 7,214,241 B2 | 5/2007 | Zarbatany et al. |
| 7,294,115 B1 | 11/2007 | Wilk |
| 7,300,459 B2 | 11/2007 | Heuser |
| 7,303,571 B2 | 12/2007 | Makower et al. |
| 7,316,655 B2 | 1/2008 | Garibotto et al. |
| 7,351,247 B2 | 4/2008 | Kupiecki et al. |
| 7,357,794 B2 | 4/2008 | Makower et al. |
| 7,374,567 B2 | 5/2008 | Heuser |
| 7,387,636 B2 | 6/2008 | Cohn et al. |
| 7,402,141 B2 | 7/2008 | Heuser |
| 7,407,506 B2 | 8/2008 | Makower |
| 7,578,828 B2 | 8/2009 | Gittings et al. |
| 7,578,829 B2 | 8/2009 | Goldsteen et al. |
| 7,582,108 B2 | 9/2009 | Hierlemann et al. |
| 7,606,615 B2 | 10/2009 | Makower et al. |
| 7,618,374 B2 | 11/2009 | Barnes et al. |
| 7,621,902 B2 | 11/2009 | Nita et al. |
| 7,628,768 B2 | 12/2009 | Faul et al. |
| 7,632,303 B1 | 12/2009 | Stalker et al. |
| 7,637,870 B2 | 12/2009 | Flaherty et al. |
| 7,648,517 B2 | 1/2010 | Makower et al. |
| 7,655,033 B2 | 2/2010 | Fearnot et al. |
| 7,670,329 B2 | 3/2010 | Flaherty et al. |
| 7,704,222 B2 | 4/2010 | Wilk et al. |
| 7,717,930 B2 | 5/2010 | Paul, Jr. et al. |
| 7,722,658 B2 | 5/2010 | Richter et al. |
| 7,722,663 B1 | 5/2010 | Austin |
| 7,722,664 B2 | 5/2010 | Zarbatany et al. |
| 7,729,738 B2 | 6/2010 | Flaherty et al. |
| 7,736,327 B2 | 6/2010 | Wilk et al. |
| RE41,448 E | 7/2010 | Squitieri |
| 7,749,239 B2 | 7/2010 | De Winter |
| 7,771,409 B2 | 8/2010 | Chang et al. |
| 7,780,719 B2 | 8/2010 | Killion et al. |
| 7,806,829 B2 | 10/2010 | Hauck |
| 7,846,172 B2 | 12/2010 | Makower |
| 7,849,860 B2 | 12/2010 | Makower et al. |
| 7,850,705 B2 | 12/2010 | Bachinski et al. |
| 7,892,246 B2 | 2/2011 | Akin et al. |
| 7,892,247 B2 | 2/2011 | Conston et al. |
| 7,914,492 B2 | 3/2011 | Heuser |
| 7,955,343 B2 | 6/2011 | Makower et al. |
| 7,966,057 B2 | 6/2011 | Macaulay et al. |
| 7,967,769 B2 | 6/2011 | Faul et al. |
| 8,048,016 B2 | 11/2011 | Faul et al. |
| 8,062,321 B2 | 11/2011 | Heuser et al. |
| 8,062,346 B2 | 11/2011 | Quigley et al. |
| 8,066,674 B2 | 11/2011 | Heuser |
| 8,075,580 B2 | 12/2011 | Makower |
| 8,083,708 B2 | 12/2011 | Flaherty et al. |
| 8,090,430 B2 | 1/2012 | Makower et al. |
| 8,109,947 B2 | 2/2012 | Berg et al. |
| 8,142,387 B2 | 3/2012 | Heise et al. |
| 8,172,861 B2 | 5/2012 | Fuller et al. |
| 8,197,499 B2 | 6/2012 | Gurtner et al. |
| 8,216,259 B2 | 7/2012 | Gurtner et al. |
| 8,226,592 B2 | 7/2012 | Brenneman et al. |
| 8,231,646 B2 | 7/2012 | Kassab et al. |
| 8,235,916 B2 | 8/2012 | Whiting et al. |
| 8,251,943 B1 | 8/2012 | Spencer et al. |
| 8,282,591 B2 | 10/2012 | Khan et al. |
| 8,343,087 B2 | 1/2013 | Formichi |
| 8,343,089 B2 | 1/2013 | Chang |
| 8,361,101 B2 | 1/2013 | Kassab |
| 8,414,516 B2 | 4/2013 | Chang |
| 8,439,963 B2 | 5/2013 | Dickinson et al. |
| 8,506,516 B2 | 8/2013 | Kassab et al. |
| 8,540,668 B2 | 9/2013 | Griffin et al. |
| 8,545,418 B2 | 10/2013 | Heuser |
| 8,551,032 B2 | 10/2013 | Faul et al. |
| 8,574,185 B2 | 11/2013 | Faul et al. |
| RE44,639 E | 12/2013 | Squitieri |
| 8,636,791 B1 | 1/2014 | Raju et al. |
| 8,652,084 B2 | 2/2014 | Akingba |
| 8,727,988 B2 | 5/2014 | Flaherty et al. |
| 8,747,344 B2 | 6/2014 | Khan |
| 8,747,345 B2 | 6/2014 | Salloum |
| 8,753,366 B2 | 6/2014 | Makower et al. |
| 8,771,305 B2 | 7/2014 | Shriver |
| 8,784,474 B2 | 7/2014 | Sargent, Jr. |
| 8,808,358 B2 | 8/2014 | Khoury |
| 8,815,278 B2 | 8/2014 | Roorda |
| 8,858,490 B2 | 10/2014 | Chou et al. |
| 8,858,579 B2 | 10/2014 | Suyker et al. |
| 8,870,805 B2 | 10/2014 | Chang |
| 8,888,733 B2 | 11/2014 | Kassab |
| 8,894,681 B2 | 11/2014 | Kassab |
| 8,900,115 B2 | 12/2014 | Bolling et al. |
| 8,905,962 B2 | 12/2014 | Asano et al. |
| 8,915,934 B2 | 12/2014 | Nielsen et al. |
| 8,926,545 B2 | 1/2015 | Brenneman et al. |
| 8,945,039 B2 | 2/2015 | Kassab |
| 8,951,222 B2 | 2/2015 | Tarlian, Jr. et al. |
| 8,968,230 B2 | 3/2015 | Kassab |
| 8,979,786 B2 | 3/2015 | Kassab |
| 9,017,323 B2 | 4/2015 | Miller et al. |
| 9,039,702 B2 | 5/2015 | Miller et al. |
| 9,056,171 B2 | 6/2015 | Ward et al. |
| 9,108,018 B2 | 8/2015 | Dickinson et al. |
| 9,179,916 B2 | 11/2015 | Brenneman et al. |
| 9,192,491 B1 | 11/2015 | Raju et al. |
| 9,259,340 B2 | 2/2016 | Heuser et al. |
| 9,301,830 B2 | 4/2016 | Heuser et al. |
| 9,314,329 B2 * | 4/2016 | Dickinson .......... A61B 17/3478 |
| 9,314,556 B2 | 4/2016 | Tuseth |
| 9,326,792 B2 | 5/2016 | Dickinson et al. |
| 9,381,018 B2 | 7/2016 | Cully et al. |
| 9,486,276 B2 | 11/2016 | Rios et al. |
| 9,504,781 B2 | 11/2016 | Kassab et al. |
| 9,522,016 B2 | 12/2016 | Kellerman et al. |
| 9,532,803 B2 | 1/2017 | Dickenson et al. |
| 9,539,124 B1 | 1/2017 | Raju et al. |
| 9,545,263 B2 | 1/2017 | Lenihan et al. |
| 9,649,157 B1 | 5/2017 | Buelna |
| 9,706,998 B2 | 7/2017 | Dickinson et al. |
| 9,724,214 B2 | 8/2017 | Kassab |
| 9,757,542 B2 | 9/2017 | Lupton |
| 9,782,201 B2 | 10/2017 | Dickinson et al. |
| 9,872,693 B2 | 1/2018 | Furuya et al. |
| 9,931,164 B2 | 4/2018 | Kellerman et al. |
| 9,955,970 B2 | 5/2018 | Brenneman et al. |
| 9,955,972 B1 | 5/2018 | Buelna |
| 10,092,427 B2 | 10/2018 | Bonsignore et al. |
| 10,136,987 B2 | 11/2018 | Dickinson et al. |
| 10,159,822 B2 | 12/2018 | Lentz et al. |
| 10,182,902 B2 | 1/2019 | Heuser et al. |
| 10,231,771 B2 | 3/2019 | Kellerman et al. |
| 10,265,206 B2 | 4/2019 | Heuser et al. |
| 10,278,851 B2 | 5/2019 | Reis et al. |
| 10,285,800 B2 | 5/2019 | Dickinson et al. |
| 10,314,591 B2 | 6/2019 | Shields et al. |
| 10,363,354 B2 | 7/2019 | Kassab et al. |
| 10,390,933 B2 | 9/2019 | Dickinson et al. |
| 10,398,580 B2 | 9/2019 | Dickinson et al. |
| 10,405,967 B1 | 9/2019 | Dickinson et al. |

(56) References Cited

U.S. PATENT DOCUMENTS

| | | |
|---|---|---|
| 10,434,293 B2 | 10/2019 | Park et al. |
| 10,492,936 B2 | 12/2019 | Syed et al. |
| 10,517,637 B2 | 12/2019 | Dickinson et al. |
| 10,524,894 B1 | 1/2020 | Dickinson et al. |
| 10,543,308 B2 | 1/2020 | Lenihan et al. |
| 10,596,356 B2 | 3/2020 | Lenihan et al. |
| 10,603,040 B1 | 3/2020 | Berman et al. |
| 10,632,005 B2 | 4/2020 | Gianotti et al. |
| 10,632,293 B2 | 4/2020 | Paris et al. |
| 10,695,065 B1 | 6/2020 | Kellerman et al. |
| 10,695,534 B2 | 6/2020 | Pate |
| 10,736,729 B2 | 8/2020 | Kassab et al. |
| 10,751,461 B2 | 8/2020 | Hull et al. |
| 10,799,259 B2 | 10/2020 | Furuya et al. |
| 10,821,217 B2 | 11/2020 | Pate |
| 10,835,367 B2 | 11/2020 | Dickinson et al. |
| 10,869,717 B2 | 12/2020 | Rios et al. |
| 10,874,422 B2 | 12/2020 | Cohn et al. |
| 10,881,429 B2 | 1/2021 | Dickinson et al. |
| 10,925,710 B2 | 2/2021 | Hall et al. |
| 10,926,068 B2 | 2/2021 | Narayan et al. |
| 10,987,106 B2 | 4/2021 | Paris et al. |
| 11,007,075 B2 | 5/2021 | Bagaoisan et al. |
| 11,026,743 B2 | 6/2021 | Pate et al. |
| 11,051,880 B2 | 7/2021 | Miller et al. |
| 11,090,177 B2 | 8/2021 | Reis et al. |
| 11,116,943 B2 | 9/2021 | Deaton et al. |
| 11,129,965 B2 | 9/2021 | Humbert et al. |
| 11,241,304 B2 | 2/2022 | Dickinson et al. |
| 11,285,028 B2 | 3/2022 | Pate et al. |
| 11,311,700 B2 | 4/2022 | Deaton et al. |
| 11,446,170 B2 | 9/2022 | Dickinson et al. |
| 11,471,262 B2 | 10/2022 | Dickinson et al. |
| 11,478,614 B2 | 10/2022 | Deaton et al. |
| 11,612,397 B2 * | 3/2023 | Hettel ............... A61B 17/12136 604/96.01 |
| 11,826,504 B2 | 11/2023 | Lenihan et al. |
| 11,850,379 B2 | 12/2023 | Humbert et al. |
| 2001/0003161 A1 | 6/2001 | Vardi et al. |
| 2001/0041930 A1 | 11/2001 | Globerman et al. |
| 2001/0044652 A1 | 11/2001 | Moore |
| 2002/0048310 A1 | 4/2002 | Heuser |
| 2002/0052644 A1 | 5/2002 | Shaolian et al. |
| 2002/0068869 A1 | 6/2002 | Brisken et al. |
| 2002/0089262 A1 | 7/2002 | Topa et al. |
| 2002/0161383 A1 | 10/2002 | Akin et al. |
| 2002/0173784 A1 | 11/2002 | Sliwa, Jr. et al. |
| 2003/0092667 A1 | 5/2003 | Tachibana et al. |
| 2003/0100916 A1 | 5/2003 | Lee et al. |
| 2003/0109827 A1 | 6/2003 | Lavi et al. |
| 2003/0125799 A1 | 7/2003 | Limon |
| 2003/0139802 A1 | 7/2003 | Wulfman et al. |
| 2003/0153969 A1 | 8/2003 | Dehdashtian et al. |
| 2003/0236542 A1 | 12/2003 | Makower |
| 2004/0064081 A1 | 4/2004 | Stanish |
| 2004/0073282 A1 | 4/2004 | Stanish |
| 2004/0088042 A1 | 5/2004 | Kim et al. |
| 2004/0097990 A1 | 5/2004 | Zhao |
| 2004/0122508 A1 | 6/2004 | White et al. |
| 2004/0133225 A1 | 7/2004 | Makower |
| 2004/0148005 A1 | 7/2004 | Heuser |
| 2004/0158143 A1 | 8/2004 | Flaherty et al. |
| 2004/0199177 A1 | 10/2004 | Kim |
| 2004/0199243 A1 | 10/2004 | Yodfat |
| 2004/0215220 A1 | 10/2004 | Dolan et al. |
| 2004/0230289 A1 | 11/2004 | DiMatteo et al. |
| 2004/0249335 A1 | 12/2004 | Faul et al. |
| 2005/0004648 A1 | 1/2005 | Boekstegers |
| 2005/0021124 A1 | 1/2005 | Cunniffe et al. |
| 2005/0038501 A1 | 2/2005 | Moore, Jr. et al. |
| 2005/0080475 A1 | 4/2005 | Andreas et al. |
| 2005/0113798 A1 | 5/2005 | Slater et al. |
| 2005/0165469 A1 | 7/2005 | Hogendijk |
| 2005/0192606 A1 | 9/2005 | Paul, Jr. |
| 2005/0203549 A1 | 9/2005 | Realyvasquez |
| 2005/0209617 A1 | 9/2005 | Koven et al. |
| 2005/0234288 A1 | 10/2005 | Aboul-Hosn et al. |
| 2006/0111770 A1 | 5/2006 | Pavcnik et al. |
| 2006/0116625 A1 | 6/2006 | Renati et al. |
| 2006/0116700 A1 | 6/2006 | Crow |
| 2006/0116713 A1 | 6/2006 | Sepetka et al. |
| 2006/0122554 A1 | 6/2006 | Wilk |
| 2006/0173475 A1 | 8/2006 | LaFontaine et al. |
| 2006/0195172 A1 | 8/2006 | Luo et al. |
| 2006/0287709 A1 | 12/2006 | Rao |
| 2007/0051681 A1 | 3/2007 | Nardo et al. |
| 2007/0055344 A1 | 3/2007 | Gittings et al. |
| 2007/0106147 A1 | 5/2007 | Altmann et al. |
| 2007/0123811 A1 | 5/2007 | Squitieri |
| 2007/0179590 A1 | 8/2007 | Lu et al. |
| 2007/0185513 A1 | 8/2007 | Woolfson et al. |
| 2007/0185567 A1 | 8/2007 | Heuser et al. |
| 2007/0203515 A1 | 8/2007 | Heuser et al. |
| 2007/0203572 A1 | 8/2007 | Heuser et al. |
| 2007/0213808 A1 | 9/2007 | Roubin et al. |
| 2007/0250153 A1 | 10/2007 | Cully et al. |
| 2007/0265563 A1 | 11/2007 | Heuser |
| 2007/0270902 A1 | 11/2007 | Slazas et al. |
| 2007/0276468 A1 | 11/2007 | Holzer et al. |
| 2008/0009936 A1 | 1/2008 | Kim et al. |
| 2008/0154153 A1 | 6/2008 | Heuser |
| 2008/0161901 A1 | 7/2008 | Heuser et al. |
| 2008/0161904 A1 | 7/2008 | Heuser et al. |
| 2008/0177249 A1 | 7/2008 | Heuser et al. |
| 2008/0194939 A1 | 8/2008 | Dickinson et al. |
| 2008/0228209 A1 | 9/2008 | Demello et al. |
| 2008/0234813 A1 | 9/2008 | Heuser |
| 2008/0255595 A1 | 10/2008 | Buchbinder et al. |
| 2008/0255657 A1 | 10/2008 | Gregorich et al. |
| 2008/0306499 A1 | 12/2008 | Katoh et al. |
| 2009/0012429 A1 | 1/2009 | Heuser |
| 2009/0093791 A1 | 4/2009 | Heuser |
| 2009/0125096 A1 | 5/2009 | Chu et al. |
| 2009/0182360 A1 | 7/2009 | Makower |
| 2009/0192485 A1 | 7/2009 | Heuser |
| 2009/0292199 A1 | 11/2009 | Bielewicz et al. |
| 2009/0306755 A1 | 12/2009 | Dickinson et al. |
| 2009/0312617 A1 | 12/2009 | Creed et al. |
| 2010/0016709 A1 | 1/2010 | Gilboa et al. |
| 2010/0069820 A1 | 3/2010 | Zotz |
| 2010/0082058 A1 | 4/2010 | Kassab |
| 2010/0087732 A1 | 4/2010 | Eberle et al. |
| 2010/0094391 A1 | 4/2010 | Heraty et al. |
| 2010/0113919 A1 | 5/2010 | Maschke |
| 2010/0131000 A1 | 5/2010 | Demello et al. |
| 2010/0174357 A1 | 7/2010 | LeMaitre et al. |
| 2010/0198056 A1 | 8/2010 | Febro et al. |
| 2010/0241214 A1 | 9/2010 | Holzer et al. |
| 2010/0307541 A1 | 12/2010 | Jayaraman et al. |
| 2011/0009740 A1 | 1/2011 | Hauck |
| 2011/0046720 A1 | 2/2011 | Shalev et al. |
| 2011/0054589 A1 | 3/2011 | Bashiri et al. |
| 2011/0077680 A1 | 3/2011 | Heuser |
| 2011/0082490 A1 | 4/2011 | Connelly et al. |
| 2011/0152994 A1 | 6/2011 | Hendriksen et al. |
| 2011/0160751 A1 | 6/2011 | Granja Filho |
| 2011/0197900 A1 | 8/2011 | Heuser |
| 2011/0208109 A1 | 8/2011 | Kassab |
| 2011/0230955 A1 | 9/2011 | Orion et al. |
| 2011/0251482 A1 | 10/2011 | Kellerman et al. |
| 2011/0251671 A1 | 10/2011 | Heraty et al. |
| 2011/0264104 A1 | 10/2011 | Naoum |
| 2011/0319902 A1 | 12/2011 | Epstein |
| 2012/0010556 A1 | 1/2012 | Faul et al. |
| 2012/0046678 A1 | 2/2012 | Lemaitre et al. |
| 2012/0046730 A1 | 2/2012 | von Oepen et al. |
| 2012/0065652 A1 | 3/2012 | Cully et al. |
| 2012/0095500 A1 | 4/2012 | Heuser |
| 2012/0116354 A1 | 5/2012 | Heuser |
| 2012/0123512 A1 | 5/2012 | Asfora et al. |
| 2012/0150092 A1 | 6/2012 | McAllister et al. |
| 2012/0179238 A1 | 7/2012 | Sarac et al. |
| 2012/0203329 A1 | 8/2012 | Heuser |
| 2012/0239137 A1 | 9/2012 | Heuser et al. |

(56) References Cited

U.S. PATENT DOCUMENTS

| | | |
|---|---|---|
| 2012/0271396 A1 | 10/2012 | Zheng et al. |
| 2012/0271400 A1 | 10/2012 | Lyons et al. |
| 2012/0277774 A1 | 11/2012 | Guo |
| 2012/0296368 A1 | 11/2012 | Kassab et al. |
| 2012/0296406 A1 | 11/2012 | Minion |
| 2012/0310319 A1 | 12/2012 | Tieu et al. |
| 2013/0023813 A1 | 1/2013 | Roorda |
| 2013/0030342 A1 | 1/2013 | Scheremet et al. |
| 2013/0030461 A1 | 1/2013 | Marks et al. |
| 2013/0041305 A1 | 2/2013 | Tarlian, Jr. et al. |
| 2013/0041306 A1 | 2/2013 | Faul et al. |
| 2013/0053732 A1 | 2/2013 | Heuser |
| 2013/0060323 A1 | 3/2013 | McHugo |
| 2013/0079697 A1 | 3/2013 | Kaye |
| 2013/0103137 A1 | 4/2013 | Asano et al. |
| 2013/0116500 A1 | 5/2013 | Kohl et al. |
| 2013/0116715 A1 | 5/2013 | Weber |
| 2013/0138139 A1 | 5/2013 | Stanley |
| 2013/0144373 A1 | 6/2013 | Shahriari |
| 2013/0190676 A1 | 7/2013 | Dickinson et al. |
| 2013/0197621 A1 | 8/2013 | Ryan et al. |
| 2013/0204176 A1 | 8/2013 | Duffy et al. |
| 2013/0226067 A1 | 8/2013 | Ward et al. |
| 2013/0226285 A1 | 8/2013 | Strommer |
| 2013/0261531 A1 | 10/2013 | Gallagher et al. |
| 2013/0324901 A1 | 12/2013 | Pillai |
| 2013/0331762 A1 | 12/2013 | Kassab et al. |
| 2014/0039538 A1 | 2/2014 | Kassab et al. |
| 2014/0052170 A1 | 2/2014 | Heuser et al. |
| 2014/0088623 A1 | 3/2014 | Yevzlin et al. |
| 2014/0088681 A1 | 3/2014 | Iyer et al. |
| 2014/0088685 A1 | 3/2014 | Yevzlin et al. |
| 2014/0100508 A1 | 4/2014 | Khan |
| 2014/0100510 A1 | 4/2014 | Yevzlin et al. |
| 2014/0135897 A1 | 5/2014 | Cully et al. |
| 2014/0142677 A1 | 5/2014 | Heuser et al. |
| 2014/0142679 A1 | 5/2014 | Motaganahalli |
| 2014/0148751 A1 | 5/2014 | Kassab et al. |
| 2014/0194910 A1 | 7/2014 | Orion et al. |
| 2014/0207179 A1 | 7/2014 | Farhangnia et al. |
| 2014/0236274 A1 | 8/2014 | Dickinson et al. |
| 2014/0270067 A1 | 9/2014 | Clark |
| 2014/0276335 A1 | 9/2014 | Pate |
| 2014/0324155 A1 | 10/2014 | Paul |
| 2014/0330194 A1 | 11/2014 | Roorda |
| 2014/0336451 A1 | 11/2014 | Gellman et al. |
| 2014/0336746 A1 | 11/2014 | Woerne |
| 2014/0343582 A1 | 11/2014 | Asfora et al. |
| 2014/0350593 A1 | 11/2014 | Laroya et al. |
| 2014/0358064 A1 | 12/2014 | Dorn |
| 2014/0358221 A1 | 12/2014 | Ho et al. |
| 2014/0364882 A1 | 12/2014 | Tulleken et al. |
| 2014/0371653 A1 | 12/2014 | Criado et al. |
| 2015/0005872 A1 | 1/2015 | Theobald et al. |
| 2015/0011925 A1 | 1/2015 | Buckman, Jr. et al. |
| 2015/0025616 A1 | 1/2015 | Chang |
| 2015/0032095 A1 | 1/2015 | Heuser |
| 2015/0045728 A1 | 2/2015 | Heuser |
| 2015/0126920 A1 | 5/2015 | Dickinson et al. |
| 2015/0133845 A1 | 5/2015 | Dickinson et al. |
| 2015/0173782 A1 | 6/2015 | Garrison et al. |
| 2015/0174379 A1 | 6/2015 | Bagaosian et al. |
| 2015/0209526 A1 | 7/2015 | Matsubara et al. |
| 2015/0223817 A1 | 8/2015 | Paris et al. |
| 2015/0250500 A1 | 9/2015 | Dickinson et al. |
| 2015/0258308 A1 | 9/2015 | Pate |
| 2015/0297259 A1 | 10/2015 | Matsubara et al. |
| 2015/0313668 A1 | 11/2015 | Miller et al. |
| 2015/0366580 A1 | 12/2015 | Lenihan et al. |
| 2015/0374486 A1 | 12/2015 | Dickinson et al. |
| 2016/0058956 A1 | 3/2016 | Cohn et al. |
| 2016/0066933 A1 | 3/2016 | Root et al. |
| 2016/0096008 A1 | 4/2016 | Park et al. |
| 2016/0100855 A1 | 4/2016 | Lemaitre et al. |
| 2016/0128855 A1 | 5/2016 | Heuser et al. |
| 2016/0151066 A1 | 6/2016 | Paris et al. |
| 2016/0166754 A1 | 6/2016 | Kassab et al. |
| 2016/0175087 A1 | 6/2016 | Heuser et al. |
| 2016/0175569 A1 | 6/2016 | Heuser |
| 2016/0199626 A1 | 7/2016 | Paris et al. |
| 2016/0206317 A1 | 7/2016 | Dickinson et al. |
| 2016/0213462 A1 | 7/2016 | Szabolcs et al. |
| 2016/0242896 A1 | 8/2016 | Dickinson et al. |
| 2017/0071721 A1 | 3/2017 | Kassab et al. |
| 2017/0105834 A1 | 4/2017 | Dickinson et al. |
| 2017/0119464 A1 | 5/2017 | Rios et al. |
| 2017/0128704 A1 | 5/2017 | Lenihan et al. |
| 2017/0202603 A1* | 7/2017 | Cohn .................. A61F 2/2475 |
| 2017/0202616 A1 | 7/2017 | Pate et al. |
| 2017/0216032 A1 | 8/2017 | Van Bladel et al. |
| 2017/0239035 A1 | 8/2017 | Schreck et al. |
| 2017/0303927 A1 | 10/2017 | Dickinson et al. |
| 2017/0354416 A1 | 12/2017 | Dickenson et al. |
| 2017/0367734 A1 | 12/2017 | Dickinson et al. |
| 2018/0000512 A1 | 1/2018 | Dickinson et al. |
| 2018/0071120 A1 | 3/2018 | Sullivan |
| 2018/0098869 A1 | 4/2018 | Reis et al. |
| 2018/0116522 A1 | 5/2018 | Brenneman et al. |
| 2018/0185563 A1 | 7/2018 | Pillai |
| 2018/0243115 A1 | 8/2018 | Ehnes et al. |
| 2018/0271637 A1 | 9/2018 | Hall et al. |
| 2018/0271638 A1 | 9/2018 | Hall et al. |
| 2018/0333283 A1 | 11/2018 | Fleming |
| 2018/0344396 A1 | 12/2018 | Miller et al. |
| 2019/0083228 A1 | 3/2019 | Dickinson et al. |
| 2019/0083717 A1 | 3/2019 | Matsubara et al. |
| 2019/0126017 A1 | 5/2019 | Hall et al. |
| 2019/0133678 A1 | 5/2019 | Pate et al. |
| 2019/0134349 A1 | 5/2019 | Cohn et al. |
| 2019/0246631 A1 | 8/2019 | Tillman et al. |
| 2019/0254846 A1 | 8/2019 | Gianotti et al. |
| 2019/0262118 A1 | 8/2019 | Eigler et al. |
| 2019/0262124 A1 | 8/2019 | Dickinson et al. |
| 2019/0269888 A1 | 9/2019 | Chao et al. |
| 2019/0274855 A1 | 9/2019 | Pate et al. |
| 2019/0275293 A1 | 9/2019 | Lenihan et al. |
| 2019/0290828 A1 | 9/2019 | Deur |
| 2019/0298909 A1 | 10/2019 | Cully et al. |
| 2019/0321606 A1 | 10/2019 | Lenihan et al. |
| 2019/0358020 A1 | 11/2019 | Dickinson et al. |
| 2019/0366062 A1 | 12/2019 | Park et al. |
| 2019/0380826 A1 | 12/2019 | Dickinson et al. |
| 2020/0022829 A1 | 1/2020 | Reis et al. |
| 2020/0054469 A1 | 2/2020 | Dickinson et al. |
| 2020/0061338 A1 | 2/2020 | Pate |
| 2020/0086094 A1 | 3/2020 | Paris et al. |
| 2020/0121845 A1 | 4/2020 | Batiste |
| 2020/0161144 A1 | 5/2020 | Lenihan et al. |
| 2020/0171282 A1 | 6/2020 | Sullivan |
| 2020/0187879 A1 | 6/2020 | Purcell |
| 2020/0214827 A1 | 7/2020 | Dickinson et al. |
| 2020/0246531 A1 | 8/2020 | Lenihan et al. |
| 2020/0289149 A1 | 9/2020 | Cohn et al. |
| 2020/0305951 A1 | 10/2020 | Reu et al. |
| 2020/0353153 A1 | 11/2020 | Hull et al. |
| 2020/0368047 A1 | 11/2020 | Kum |
| 2021/0128228 A1 | 5/2021 | Rios et al. |
| 2021/0166950 A9 | 6/2021 | Lenihan et al. |
| 2021/0177420 A1 | 6/2021 | Paris et al. |
| 2021/0220616 A1 | 7/2021 | Deaton et al. |
| 2021/0220623 A1 | 7/2021 | Humbert et al. |
| 2021/0244434 A1 | 8/2021 | Popa et al. |
| 2021/0267675 A1 | 9/2021 | Pate et al. |
| 2021/0322189 A1 | 10/2021 | Schwartz et al. |
| 2021/0322728 A1 | 10/2021 | Deaton et al. |
| 2021/0338412 A1 | 11/2021 | MacTaggart et al. |
| 2021/0361317 A1 | 11/2021 | Dickinson et al. |
| 2021/0369343 A1 | 12/2021 | Miller et al. |
| 2021/0369344 A1 | 12/2021 | Miller et al. |
| 2022/0008693 A1 | 1/2022 | Humbert et al. |
| 2022/0125572 A1 | 4/2022 | Dickinson et al. |
| 2022/0152358 A1 | 5/2022 | Deaton et al. |
| 2022/0183867 A1 | 6/2022 | Reis et al. |
| 2022/0249094 A1 | 8/2022 | Hettel et al. |

(56) References Cited

U.S. PATENT DOCUMENTS

| | | | |
|---|---|---|---|
| 2022/0249757 A1 | 8/2022 | Hettel et al. | |
| 2023/0225732 A1 | 7/2023 | Hettel et al. | |
| 2023/0270538 A1 | 8/2023 | Dickinson et al. | |

FOREIGN PATENT DOCUMENTS

| | | |
|---|---|---|
| CN | 1204242 | 1/1999 |
| CN | 1204244 | 1/1999 |
| CN | 1303250 A | 7/2001 |
| CN | 1460029 | 12/2003 |
| CN | 2728440 Y | 9/2005 |
| CN | 1736349 | 2/2006 |
| CN | 2843384 Y | 12/2006 |
| CN | 2912562 | 6/2007 |
| CN | 201189310 | 2/2009 |
| CN | 101945608 A | 1/2011 |
| CN | 102307542 A | 1/2012 |
| CN | 103584928 | 2/2014 |
| EP | 0 467 516 A1 | 1/1992 |
| EP | 0 248 761 B1 | 4/1992 |
| EP | 1 307 163 | 5/2003 |
| EP | 0 910 298 B1 | 8/2003 |
| EP | 0 994 682 B1 | 12/2003 |
| EP | 0 888 094 B1 | 2/2004 |
| EP | 1 066 804 B1 | 7/2004 |
| EP | 1 229 863 B1 | 9/2004 |
| EP | 0 951 251 B1 | 3/2005 |
| EP | 0 973 577 B1 | 3/2005 |
| EP | 1 126 796 B1 | 6/2005 |
| EP | 1 059 894 B1 | 7/2005 |
| EP | 0 949 889 B1 | 9/2005 |
| EP | 1 067 869 B1 | 11/2005 |
| EP | 1 129 673 B1 | 11/2005 |
| EP | 1 295 575 B1 | 1/2006 |
| EP | 1 613 373 | 1/2006 |
| EP | 1 295 573 B1 | 2/2006 |
| EP | 1 051 129 B1 | 4/2006 |
| EP | 1 112 043 B1 | 4/2006 |
| EP | 0 909 198 B1 | 6/2006 |
| EP | 1 295 572 B1 | 7/2006 |
| EP | 0 888 093 B2 | 12/2006 |
| EP | 1 119 387 B1 | 2/2007 |
| EP | 0 964 636 B1 | 8/2007 |
| EP | 1 359 967 B1 | 8/2007 |
| EP | 1 187 559 B1 | 9/2007 |
| EP | 1 299 145 B1 | 9/2007 |
| EP | 1 377 335 B1 | 10/2007 |
| EP | 1 112 042 B1 | 11/2007 |
| EP | 1 477 133 B9 | 11/2007 |
| EP | 1 295 574 B1 | 4/2008 |
| EP | 1 117 458 | 2/2009 |
| EP | 1 286 628 B1 | 3/2009 |
| EP | 1 253 859 B1 | 4/2009 |
| EP | 1 600 110 B1 | 4/2009 |
| EP | 1 653 885 B1 | 4/2009 |
| EP | 0 955 933 B1 | 8/2009 |
| EP | 0 893 977 B2 | 10/2009 |
| EP | 1 827 307 B1 | 5/2010 |
| EP | 1 598 031 B1 | 6/2010 |
| EP | 1 790 314 B1 | 6/2010 |
| EP | 1 779 809 B1 | 8/2010 |
| EP | 1 341 482 B1 | 10/2010 |
| EP | 1 047 341 B1 | 12/2010 |
| EP | 1 820 436 B1 | 12/2010 |
| EP | 1 496 956 B1 | 4/2011 |
| EP | 1 815 803 B1 | 5/2011 |
| EP | 1 317 908 B1 | 7/2011 |
| EP | 1 527 751 B1 | 7/2011 |
| EP | 1 658 812 B1 | 10/2011 |
| EP | 1 447 052 B1 | 2/2012 |
| EP | 1 614 400 B1 | 4/2012 |
| EP | 2 582 306 A1 | 4/2013 |
| EP | 2 640 280 | 9/2013 |
| EP | 1 550 479 B1 | 9/2015 |
| EP | 2 613 822 B1 | 11/2017 |
| EP | 3 267 951 | 1/2018 |
| EP | 2 379 130 B1 | 2/2018 |
| EP | 2 841 027 B1 | 8/2018 |
| EP | 2 063 823 | 10/2018 |
| EP | 3 322 470 | 11/2018 |
| EP | 3 322 471 | 11/2018 |
| EP | 3 402 426 | 11/2018 |
| EP | 3 402 432 | 11/2018 |
| EP | 3 402 561 | 11/2018 |
| EP | 2 968 852 | 7/2019 |
| EP | 3 515 322 | 7/2019 |
| EP | 3 302 231 | 8/2019 |
| EP | 2 812 063 B1 | 3/2020 |
| EP | 3 099 372 | 11/2020 |
| EP | 3 064 171 B1 | 1/2021 |
| EP | 3 275 402 B1 | 8/2021 |
| GB | 2536362 | 3/2017 |
| JP | S62-298347 | 12/1987 |
| JP | H10-502567 | 3/1998 |
| JP | 2001-508318 | 6/2001 |
| JP | 2002-516704 | 6/2002 |
| JP | 2004-501675 | 1/2004 |
| JP | 2004-501720 | 1/2004 |
| JP | 2010-269161 | 12/2010 |
| JP | 2012-040394 | 3/2012 |
| JP | 2012-192209 | 10/2012 |
| JP | 2013-528112 | 7/2013 |
| WO | WO 1991/001689 | 2/1991 |
| WO | WO 1997/013463 | 4/1997 |
| WO | WO 1997/013471 | 4/1997 |
| WO | WO2000009041 | 2/2000 |
| WO | WO 2000/020064 | 4/2000 |
| WO | WO2000033770 | 6/2000 |
| WO | WO 2000/045886 | 8/2000 |
| WO | WO 2001/49187 | 7/2001 |
| WO | WO 2002/002163 | 1/2002 |
| WO | WO 2004/098684 | 11/2004 |
| WO | WO 2005/065579 | 7/2005 |
| WO | WO2006027599 | 3/2006 |
| WO | WO2007122396 | 11/2007 |
| WO | WO 2009/107142 | 9/2009 |
| WO | WO 2009/150099 | 12/2009 |
| WO | WO 2010/107950 | 9/2010 |
| WO | WO 2011/107249 | 9/2011 |
| WO | WO 2011/163322 | 12/2011 |
| WO | WO2012068273 | 5/2012 |
| WO | WO 2013/033215 | 3/2013 |
| WO | WO 2013/113704 | 8/2013 |
| WO | WO 2013/163227 | 10/2013 |
| WO | WO 2014/145021 | 9/2014 |
| WO | WO2014137830 | 9/2014 |
| WO | WO 2014/162067 | 10/2014 |
| WO | WO 2014/176458 | 10/2014 |
| WO | WO 2015/017714 | 2/2015 |
| WO | WO 2015/108984 | 7/2015 |
| WO | WO 2015/195668 | 12/2015 |
| WO | WO 2016/145202 | 9/2016 |
| WO | WO 2017/011402 | 1/2017 |
| WO | WO 2018/057095 | 3/2018 |
| WO | WO 2018/164766 | 9/2018 |
| WO | WO 2018/189593 | 10/2018 |
| WO | WO 2019/202339 | 10/2019 |
| WO | WO 2019/236900 | 12/2019 |
| WO | WO 2020/072717 | 4/2020 |
| WO | WO 2020/076833 | 4/2020 |
| WO | WO 2020/242491 | 12/2020 |
| WO | WO 2021/087294 | 5/2021 |
| WO | WO 2021/137851 | 7/2021 |
| WO | WO 2021/221607 | 11/2021 |

OTHER PUBLICATIONS

Alexandrescu et al., "Deep calf veins arterialization for inferior limb preservation in diabetic patients with extended ischaemic wounds, unfit for direct arterial reconstruction: preliminary results according to an angiosome model of perfusion", Cardiovasc. Revasc. Med., Jan.-Feb. 2011, vol. 12, pp. 10-19.

(56) References Cited

OTHER PUBLICATIONS

Busato et al., "The great saphenous vein in situ for the arterialization of the venous arch of the foot", J. Vasc. Bras., 2010, vol. 9, No. 3, pp. 119-123.

Djoric et al., "Distal Venous Arterialization and Reperfusion Injury: Focus on Oxidative Status", Eur. Surg. Res., 2012, vol. 48, pp. 200-207.

Djoric, "Early individual experience with distal venous arterialization as a lower limb salvage procedure", Am. Surg., Jun. 2011, vol. 77, No. 6, pp. 726-730 (Abstract Only).

Engelke et al., "Distal Venous Arterialization for Lower Limb Salvage: Angiographic Appearances and Interventional Procedures", Radiographics, Sep.-Oct. 2001, vol. 21, No. 5, pp. 1239-1248.

Gasparis et al., "Distal venous arterialization for limb salvage—a case report", Vasc. Endovascular Surg., Nov.-Dec. 2002, vol. 36, No. 6, pp. 469-472 (Abstract Only).

Gavrilenko et al., "Long-term results of venous blood flow arterialization of the leg and foot in patients with critical lower limb ischemia", Angiol. Sosud. Khir., 2007, vol. 13, No. 2, pp. 95-103 (Abstract Only).

Houlind et al., "Early results from an angiosome-directed open surgical technique for venous arterialization in patients with critical limb ischemia", Diabet. Foot Ankle, Dec. 2013, vol. 17, No. 4.

Jacob et al., "Vascular surgical society of great britain and ireland: distal venous arterialization for non-reconstructable arterial disease", Br. J. Surg., May 1999, vol. 86, No. 5, p. 694 (Abstract Only).

Kassab et al., "Coronary venous retroperfusion: an old concept, a new approach", J. Appl. Physiol., Feb. 2008, vol. 104, pp. 1266-1272.

Keshelava et al., "Foot venous system arterialization for salvage of non-reconstructable acute ischemic limb: a case report", J. Vasc. Nurs., Mar. 2009, vol. 27, No. 1, pp. 13-16 (Abstract Only).

Kopelman et al., "Prevention of limb loss in critical ischaemia by arterialization of the superficial venous system: an experimental study in dogs", Cardiovasc. Surg., Aug. 1998, vol. 6, No. 4, pp. 384-388 (Abstract Only).

Lengua et al., "Arterialization of the distal veins of the foot for limb salvage in arteritis—Techniques and results", Ann. Chir., Sep. 2001, vol. 126, No. 7, pp. 629-638 (Abstract Only).

Lu et al., "Meta-analysis of the Clinical Effectiveness of Venous Arterialization for Salvage of Critically Ischaemic Limbs", Eur. J. Vasc. Endovasc. Surg., May 2006, vol. 31, pp. 493-499.

Matarrese et al., "Revascularization of the ischemic hand with arterialization of the venous system", J. Hand. Surg. Am., Dec. 2011, vol. 36, No. 12, pp. 2047-2051 (Abstract Only).

Miasnik et al., "Scintigraphic evaluation of the efficacy of nonstandard methods of treating critical ischemia of the lower limbs", Khirurgiia (Mosk), 2002, vol. 6, pp. 48-51 (Abstract Only).

Mutirangura et al., "Pedal bypass with deep venous arterialization: the therapeutic option in critical limb ischemia and unreconstructable distal arteries", Vascular, Dec. 2011, vol. 19, No. 6, pp. 313-319.

Nguyen et al., "Treatment of hand ischemia with arterialization of the venous system of the hand: report of three cases", Ann. Chir. Plast. Esthet., Jun. 2011, vol. 56, No. 3, pp. 200-206 (Abstract Only).

Pederson, "Revascularization of the chronically ischemic hand", Hand Clin, Nov. 1999, vol. 15, No. 4, pp. 629-642 (Abstract Only).

Pokrovsky et al., "Arterialization of the hand venous system in patients with critical ischemia and thromboangiitis obliterans", Angiol. Sosud. Khir., 2007, vol. 13, No. 2, pp. 105-111 (Abstract Only).

Rowe et al., "Initial experience with dorsal venous arch arterialization for limb salvage", Ann. Vasc. Surg., Feb.-Mar. 2002, vol. 16, No. 2, pp. 187-192 (Abstract Only).

Sangiorgi et al., "The Cutaneous Microvascular Architecture of Human Diabetic Toe Studied by Corrosion Casting and Scanning Electron Microscopy Analysis", Anat. Rec., Oct. 2010, vol. 293, pp. 1639-1645.

Sasajima et al., "Combined distal venous arterialization and free flap for patients with extensive tissue loss", Ann. Vasc. Surg., Apr. 2010, vol. 24, No. 3, pp. 373-381 (Abstract Only).

Schreve et al., "Comparative study of venous arterialization and pedal bypass in a patient cohort with critical limb ischemia", Ann. Vasc. Surg., Jul. 2014; vol. 28, No. 5, pp. 1123-1127 (Abstract Only).

Sheil, "Treatment of critical ischaemia of the lower limb by venous arterialization : an interim report", Br. J. Surg., Mar. 1977, vol. 64, No. 3, pp. 197-199 (Abstract Only).

Tang et al., "The effects of stent porosity on the endovascular treatment of intracranial aneurysms located near a bifurcation", J. Biomedical Science and Engineering, 2013, vol. 6, pp. 812-822.

Augsburger et al., "Effect of Flow Diverter Porosity on Intraaneurysmal Blood Flow," Clinical Neuroradiology, 2009, No. 3, pp. 204-214.

\* cited by examiner

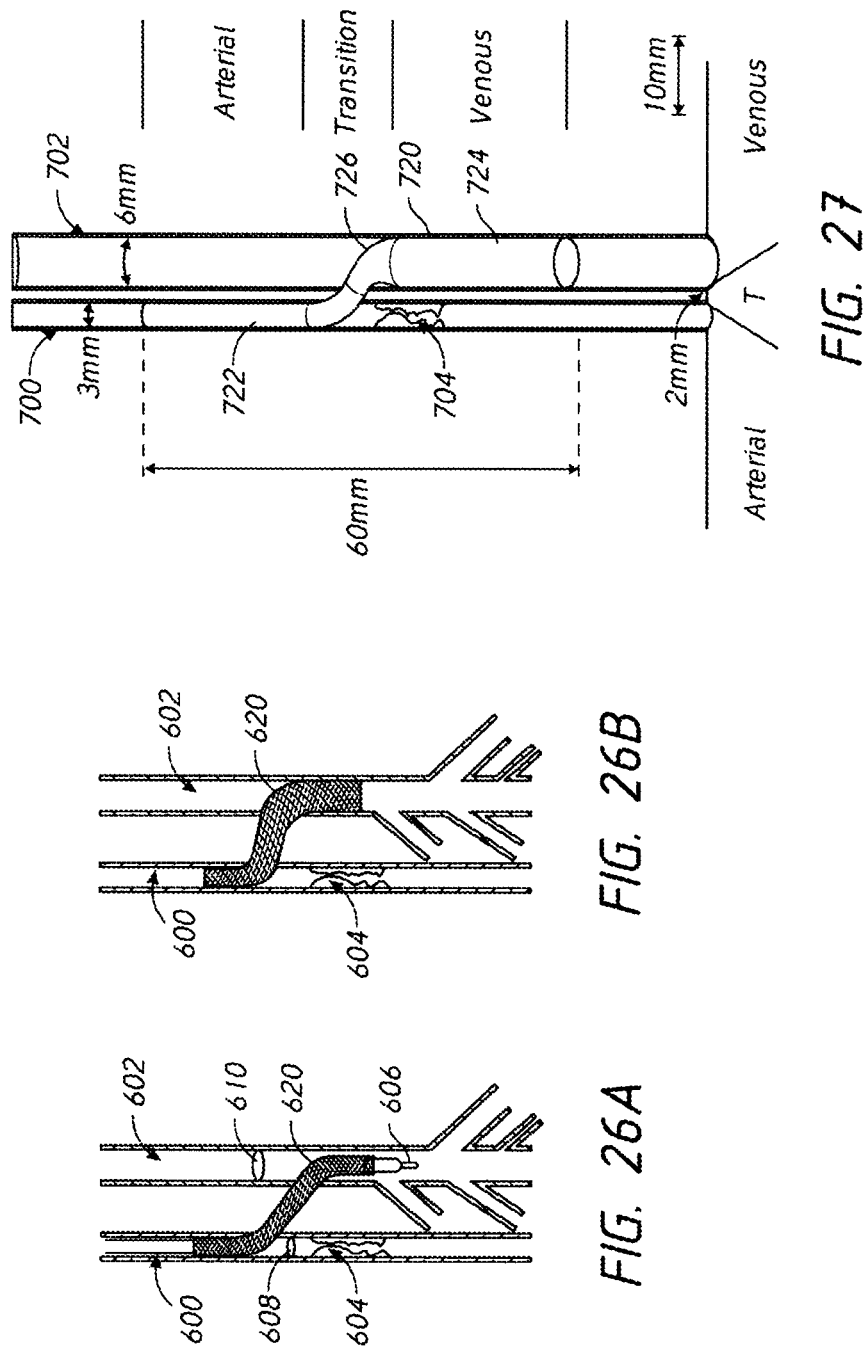

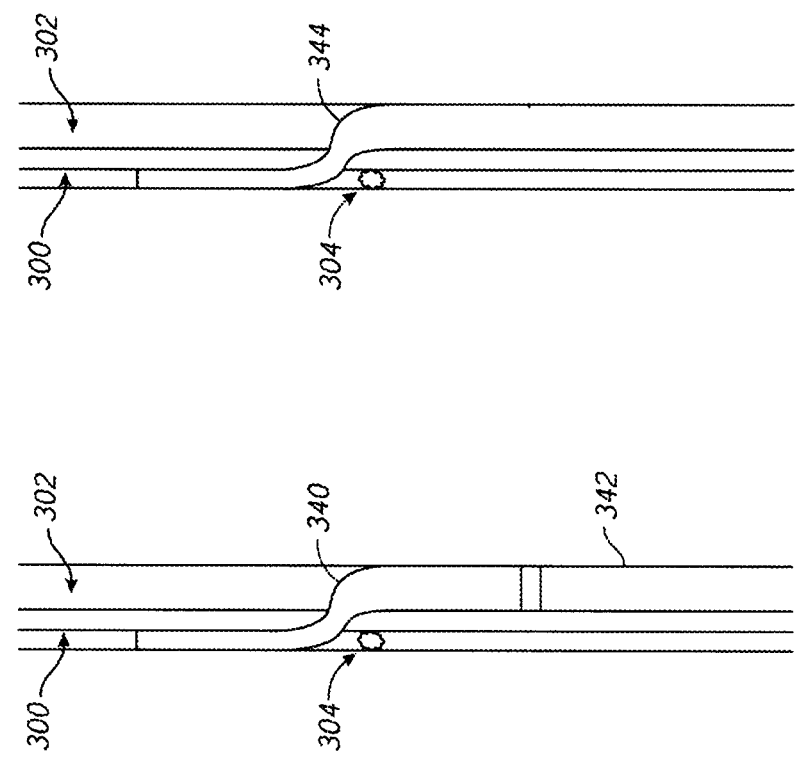

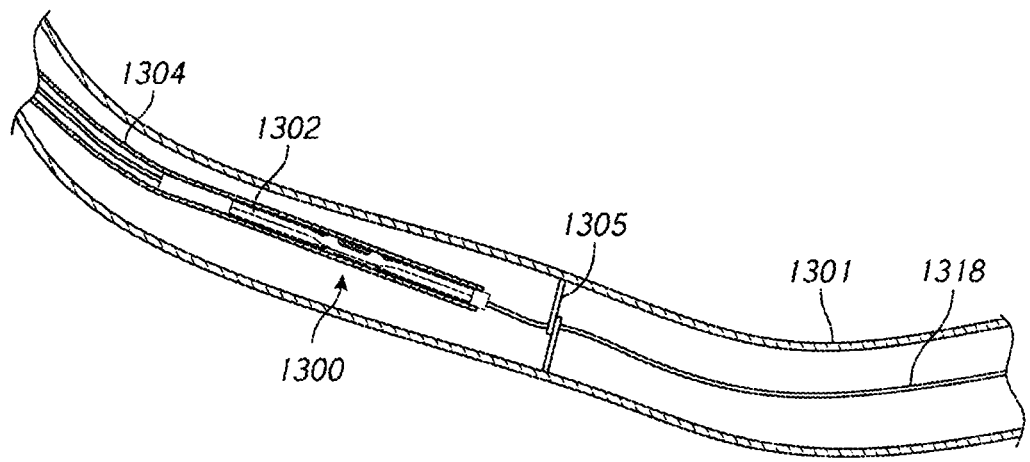
FIG. 37Ki
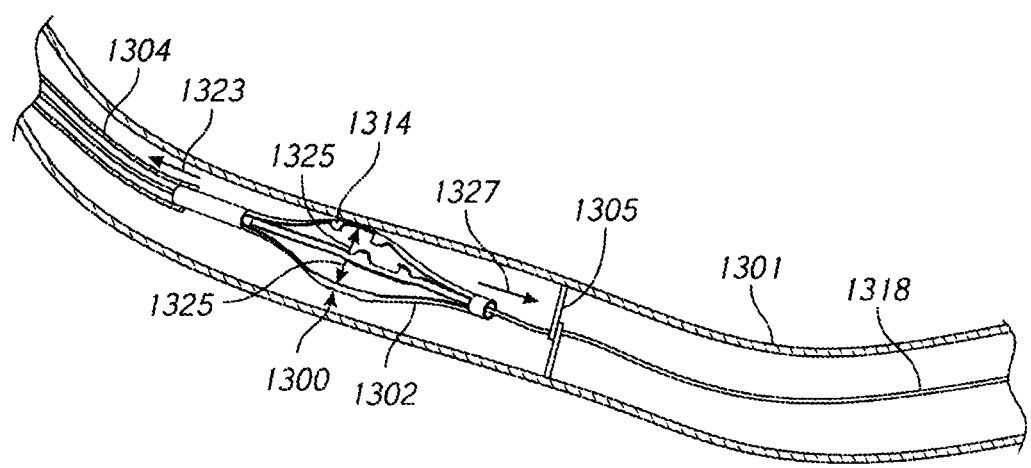
FIG. 37Kii

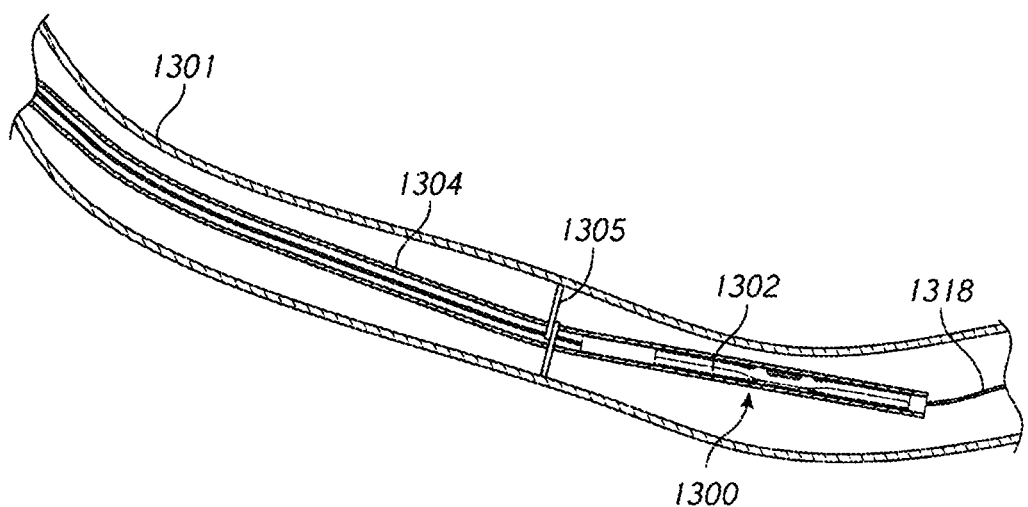
FIG. 37Li
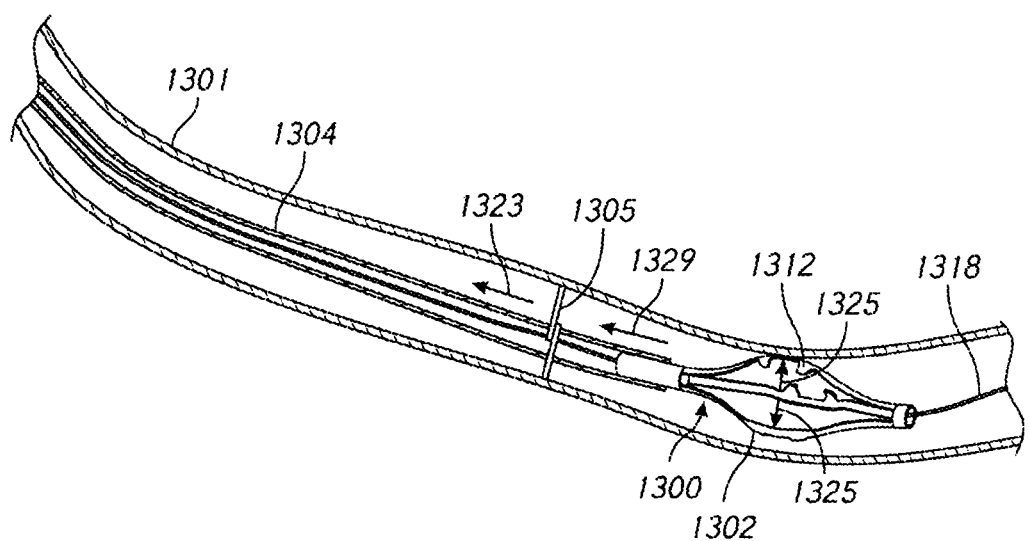
FIG. 37Lii

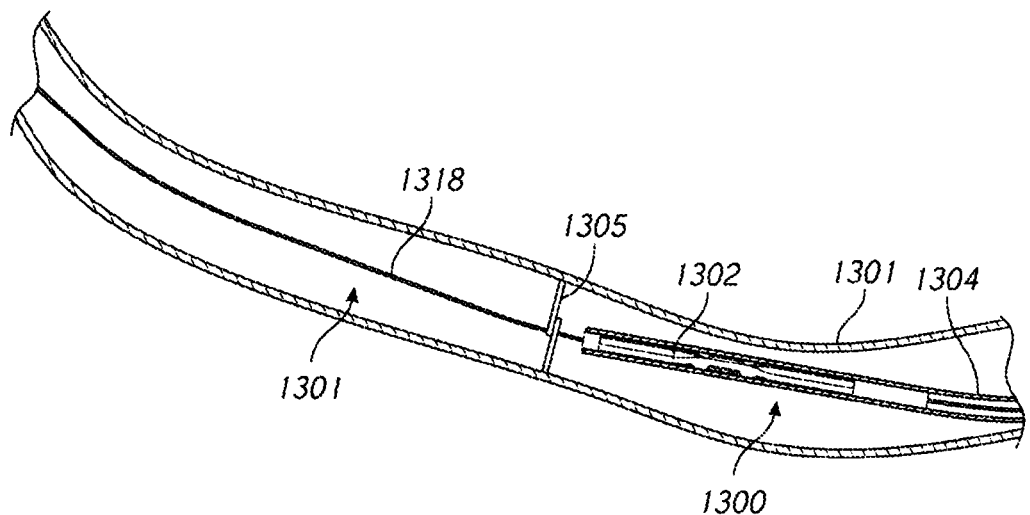
FIG. 37Mi
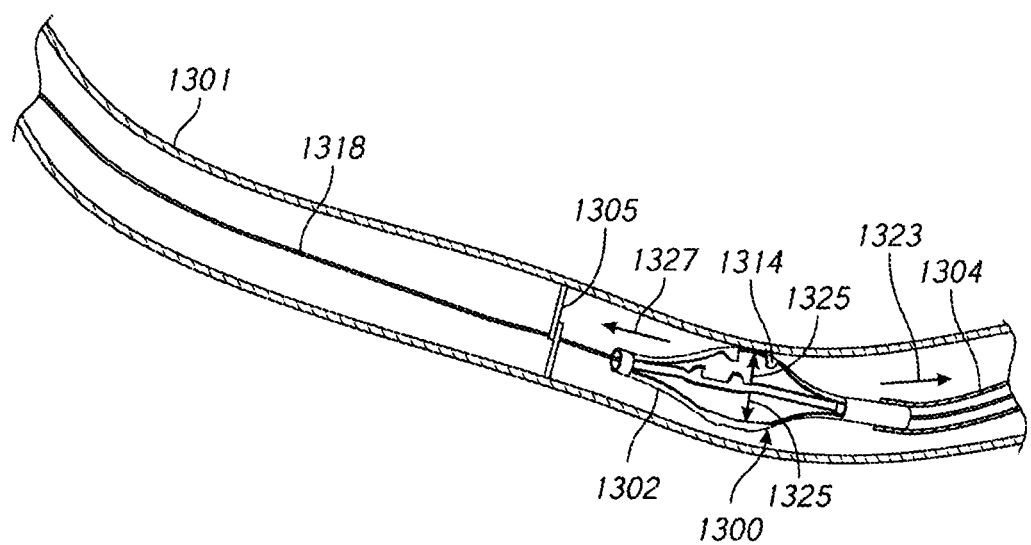
FIG. 37Mii

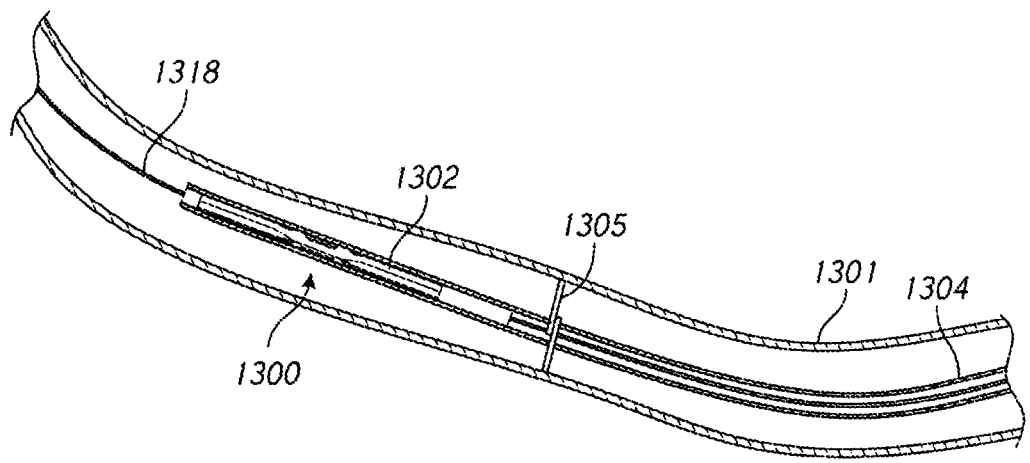
FIG. 37Ni
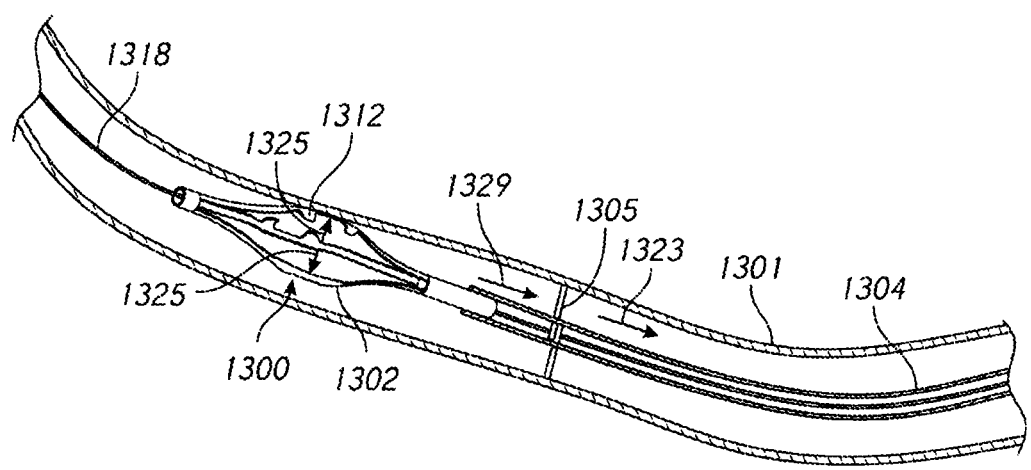
FIG. 37Nii

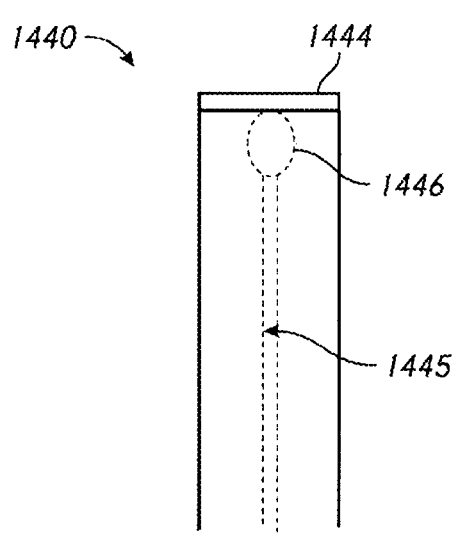
FIG. 38Ei
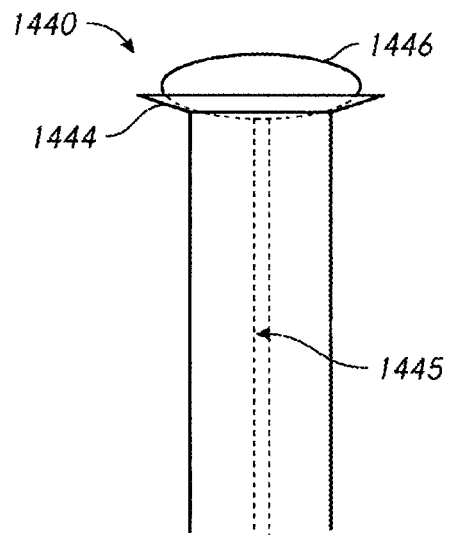
FIG. 38Eii
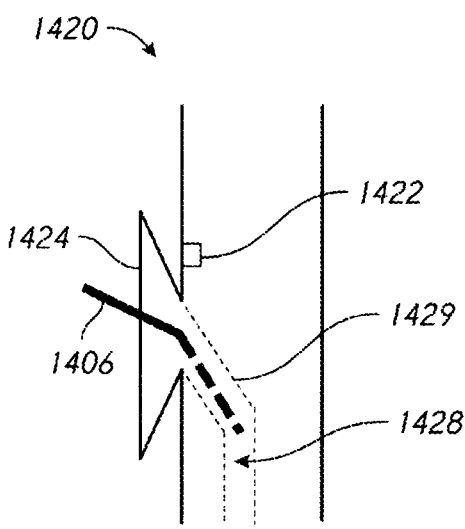
FIG. 38F
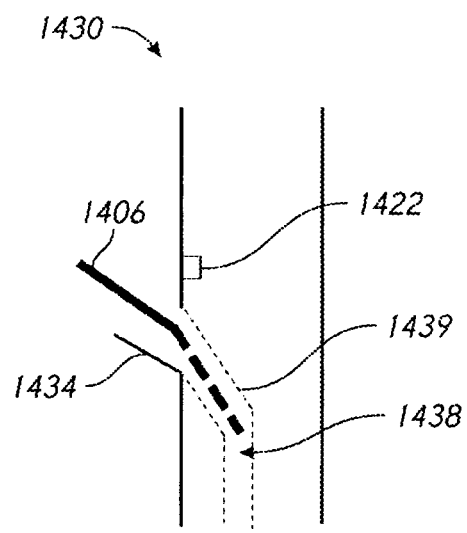
FIG. 38G

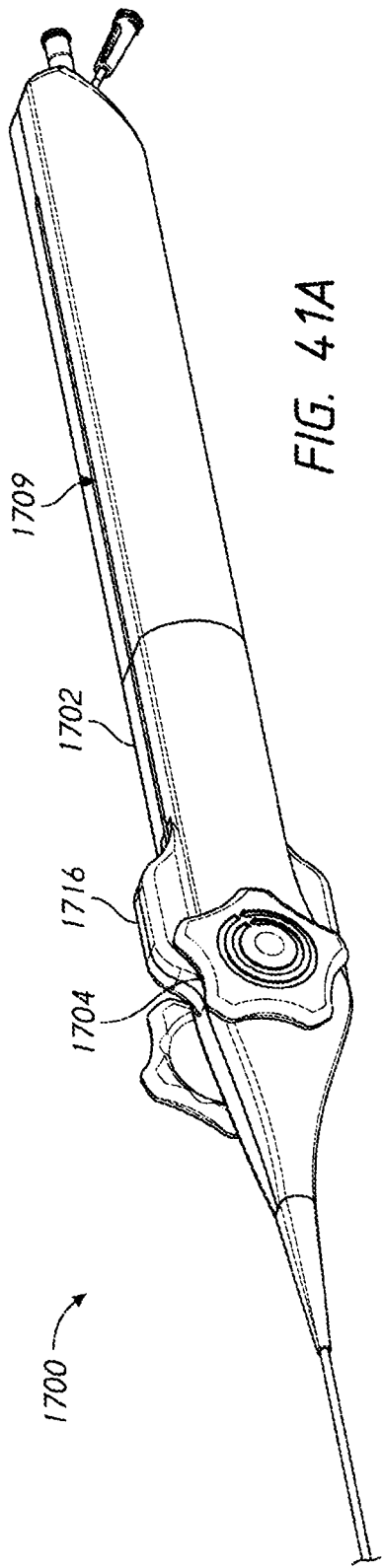
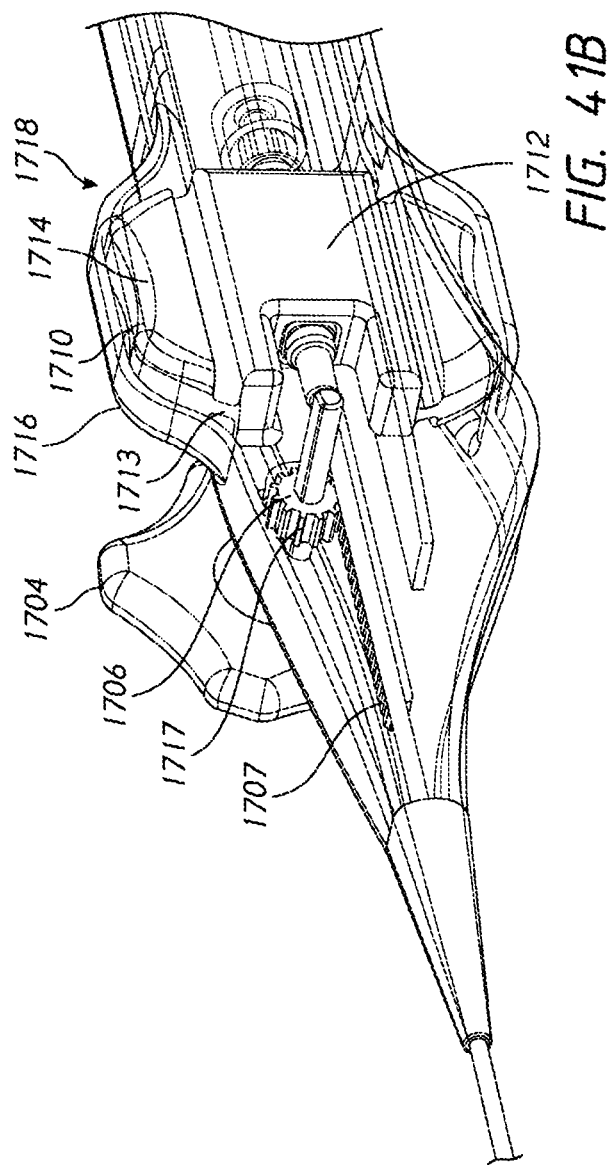
FIG. 41A
FIG. 41B

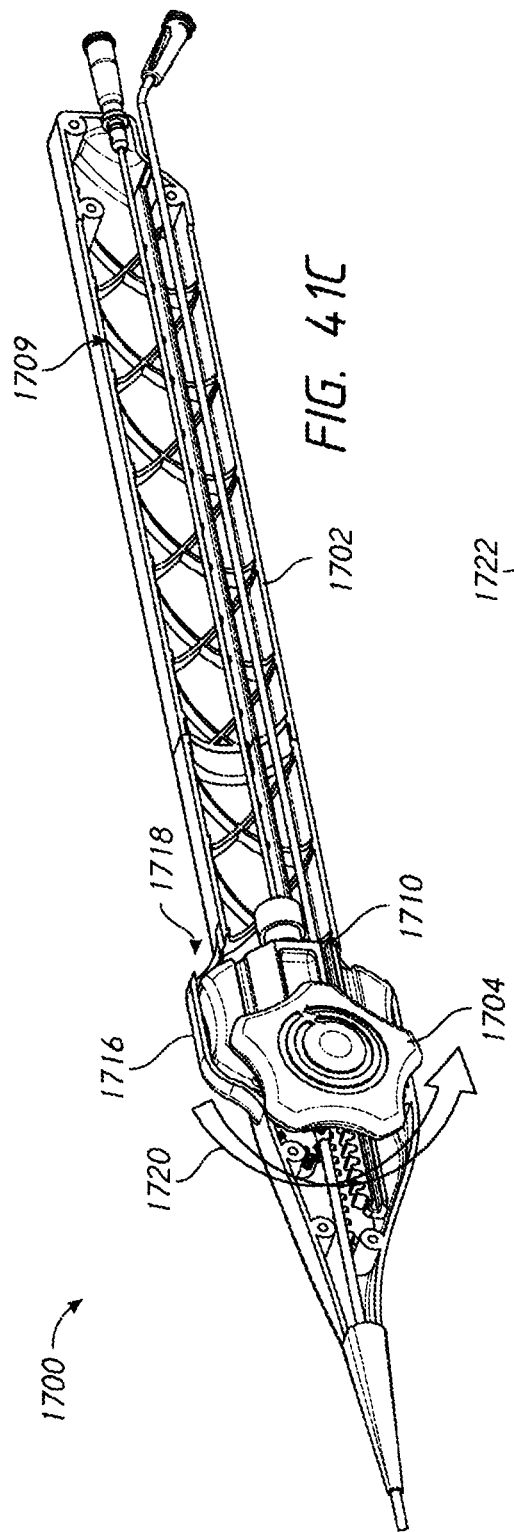
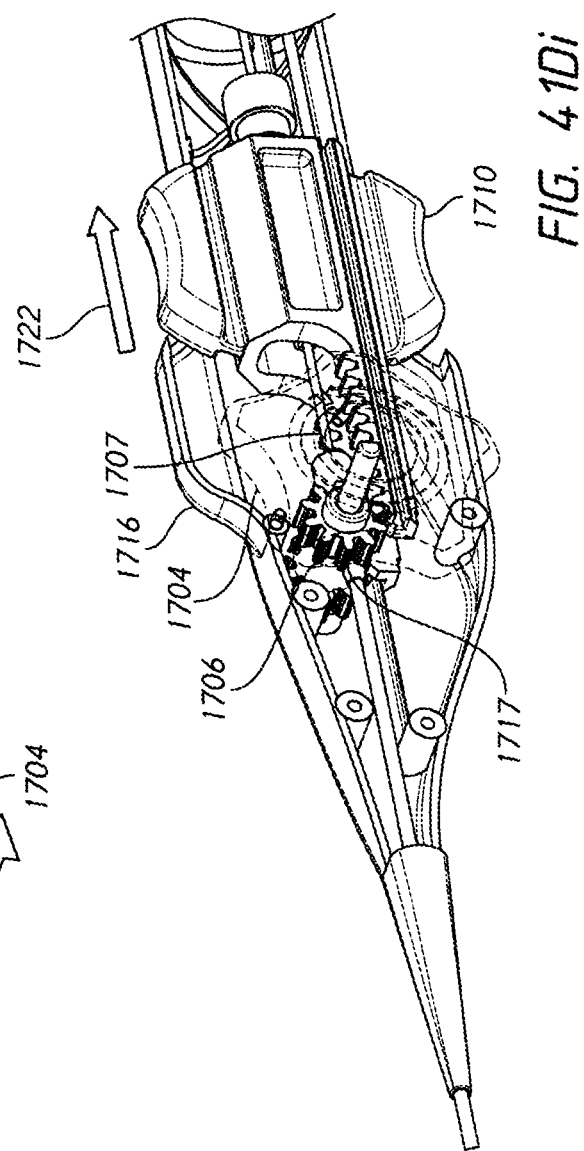

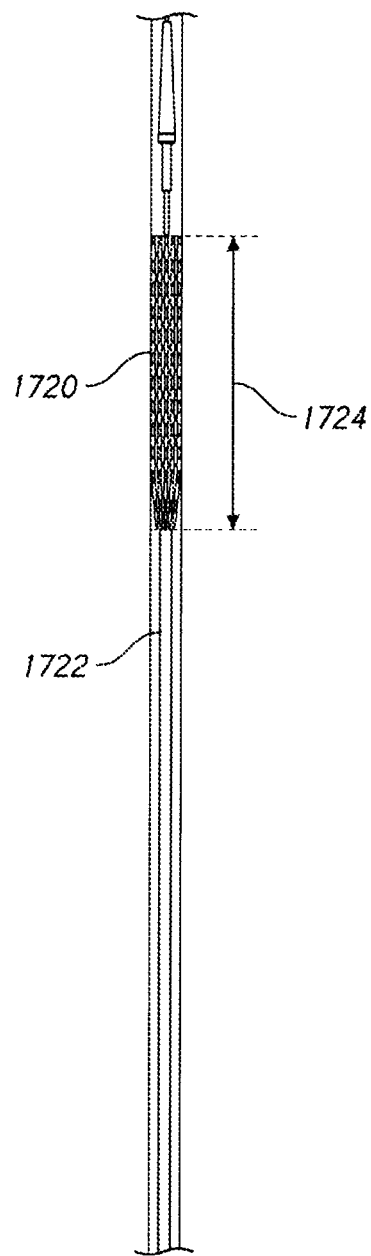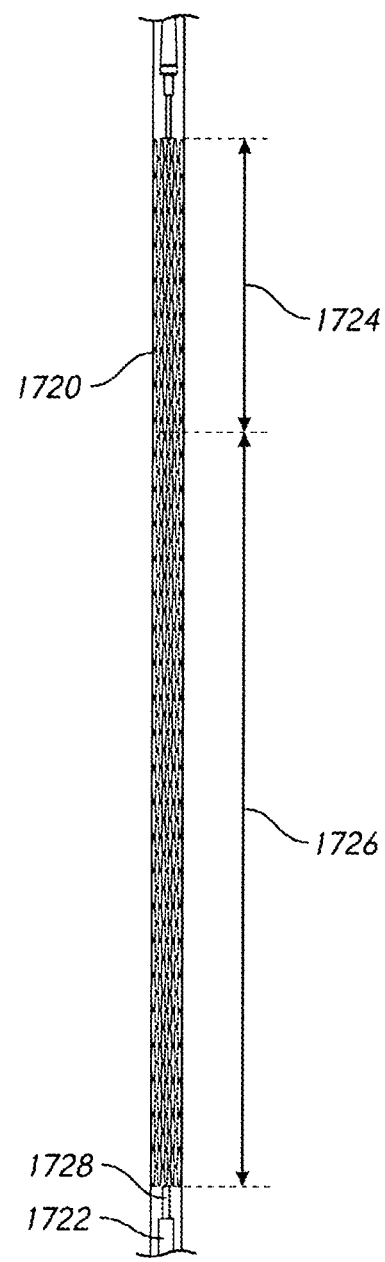
FIG. 41Dii    FIG. 41Eiii

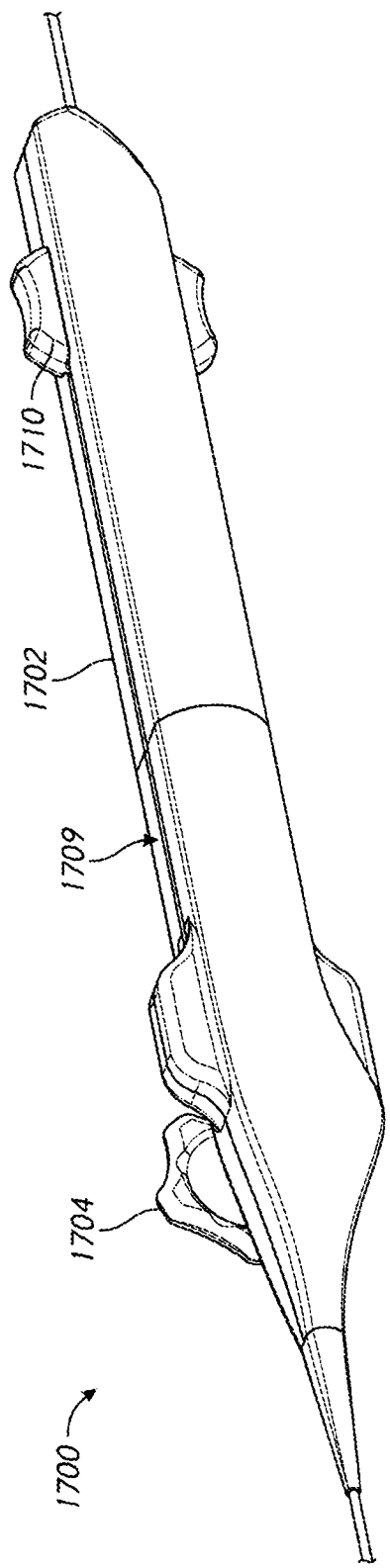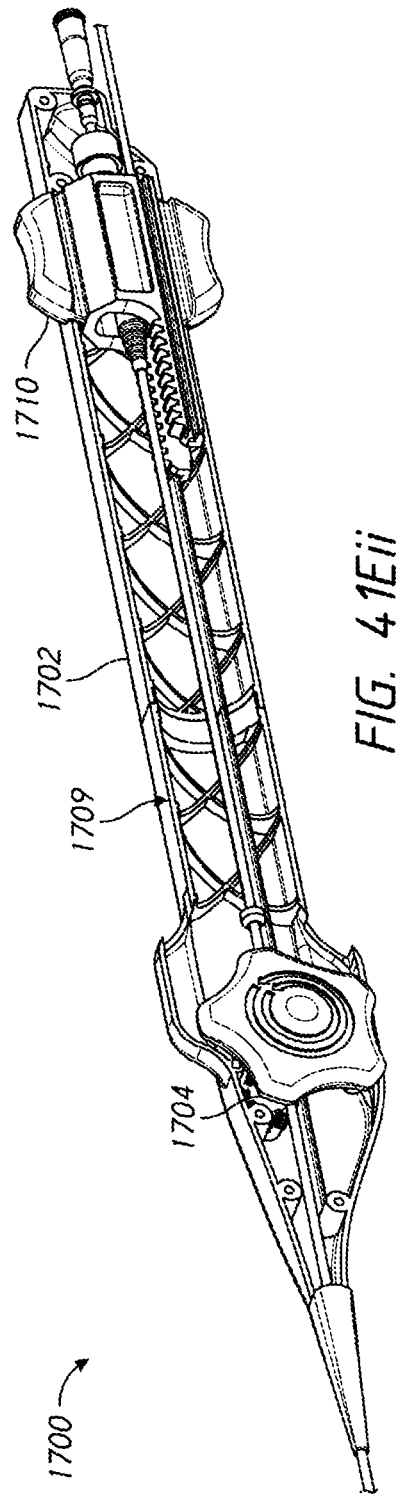

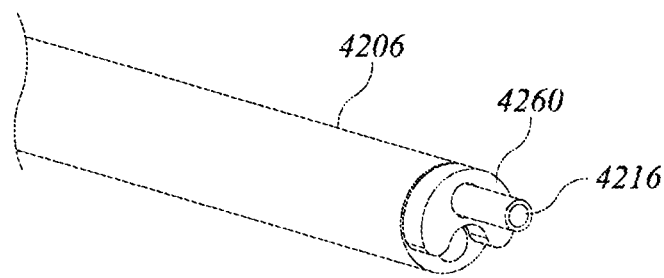
Fig. 42Cii
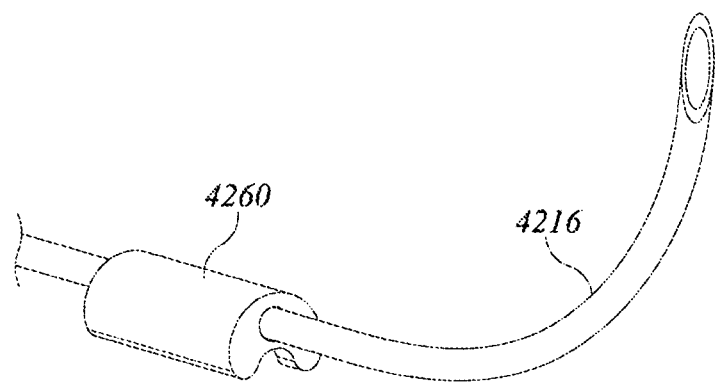
Fig. 42Ciii
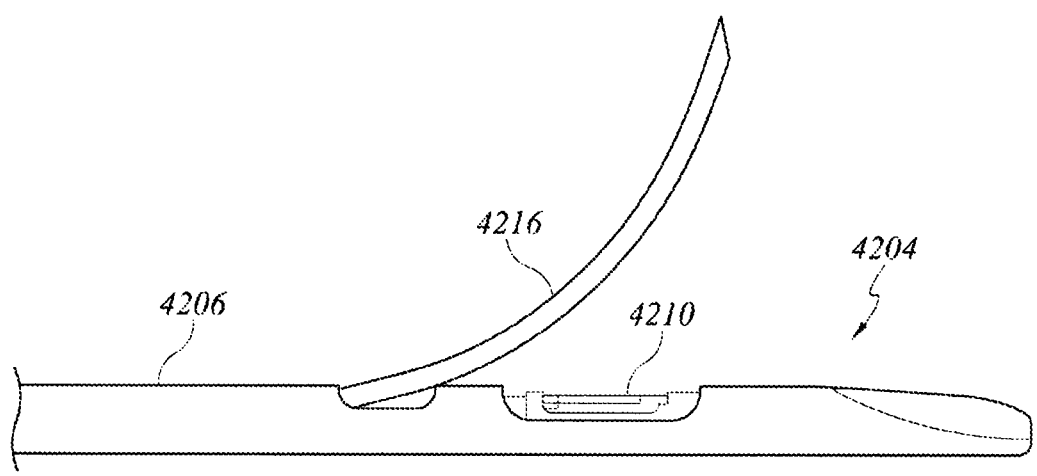
Fig. 42D

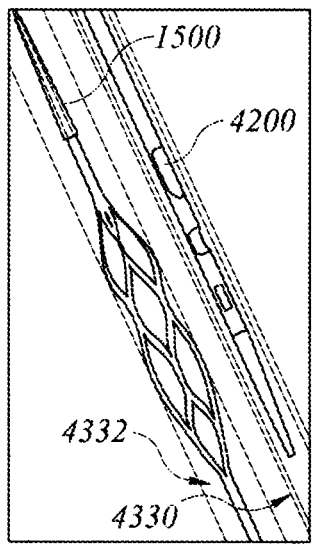
Fig. 43Oi
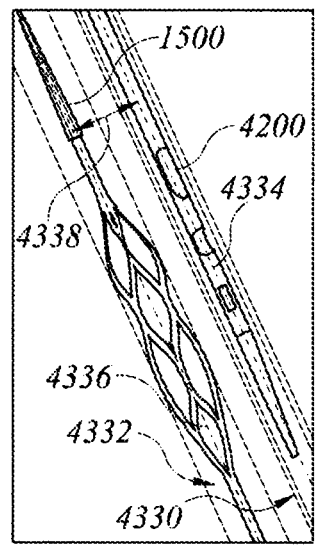
Fig. 43Oii
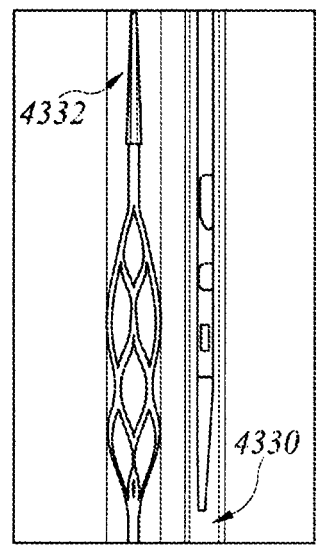
Fig. 43Oiii
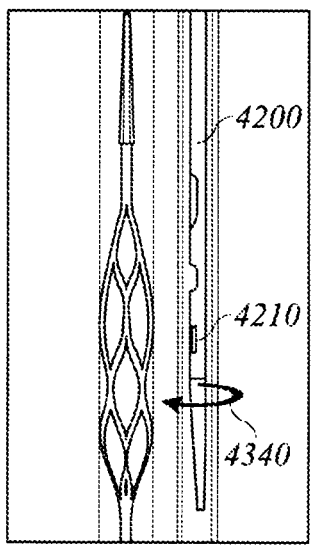
Fig. 43Oiv
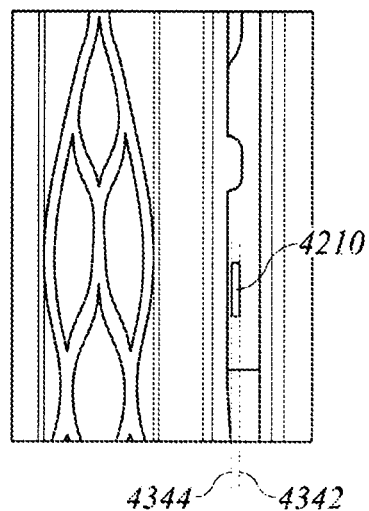
Fig. 43Ov
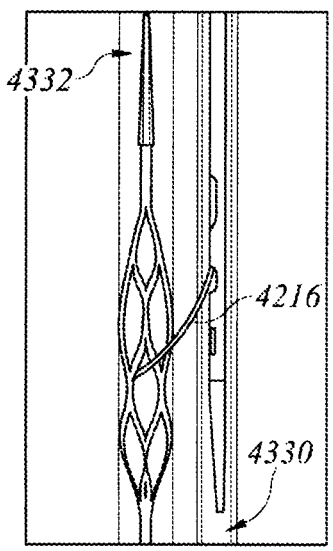
Fig. 43Ovi

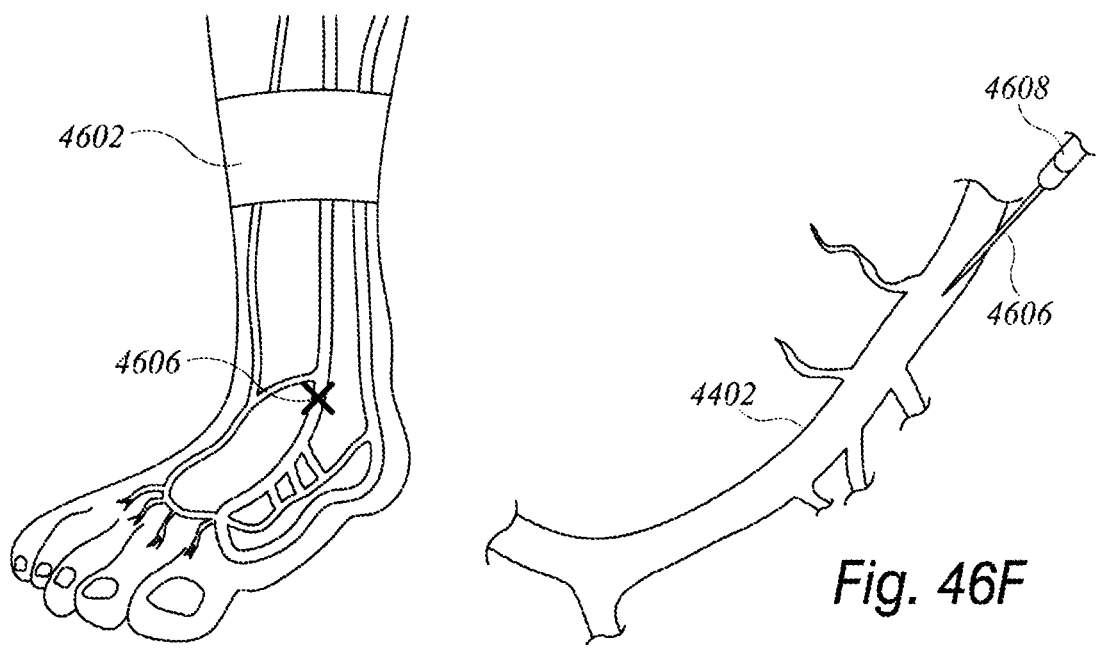
Fig. 46E
Fig. 46F
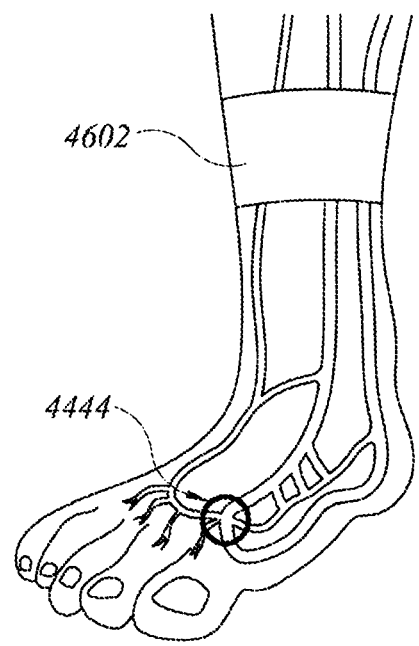
Fig. 46G

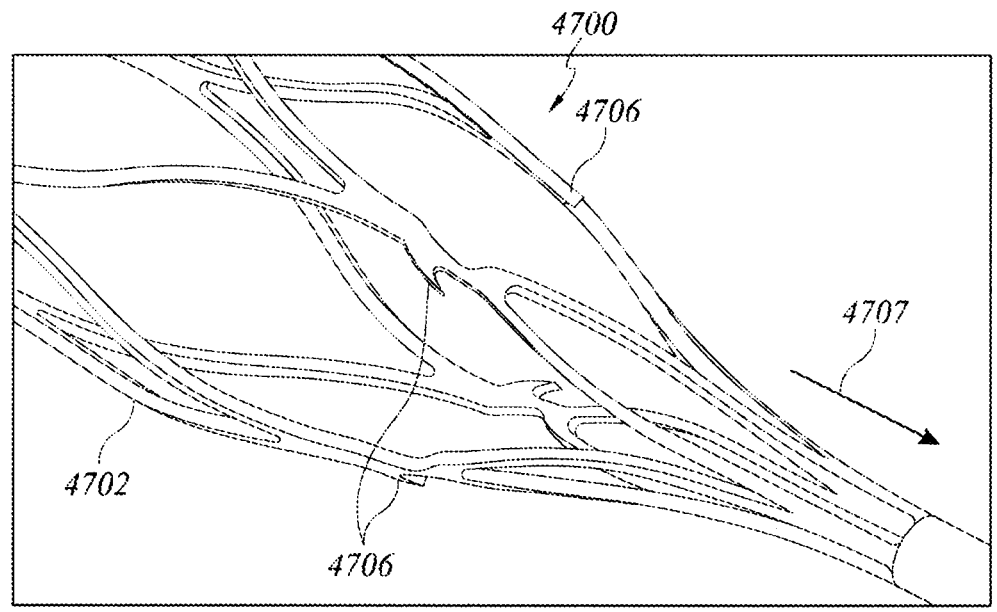
Fig. 47A
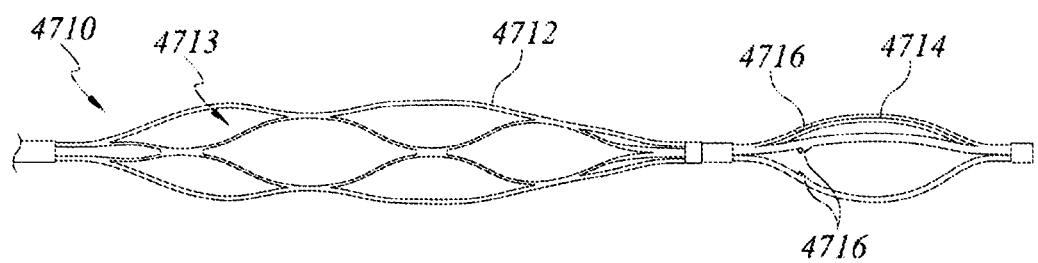
Fig. 47Bi
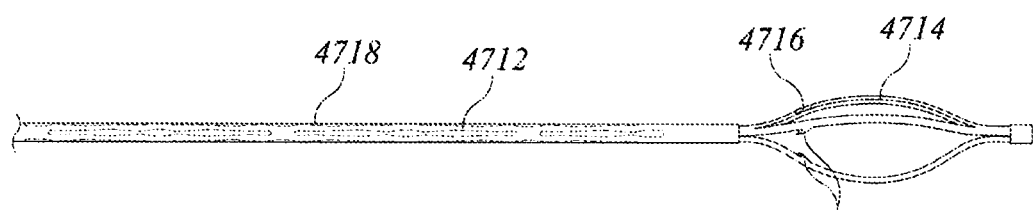
Fig. 47Bii

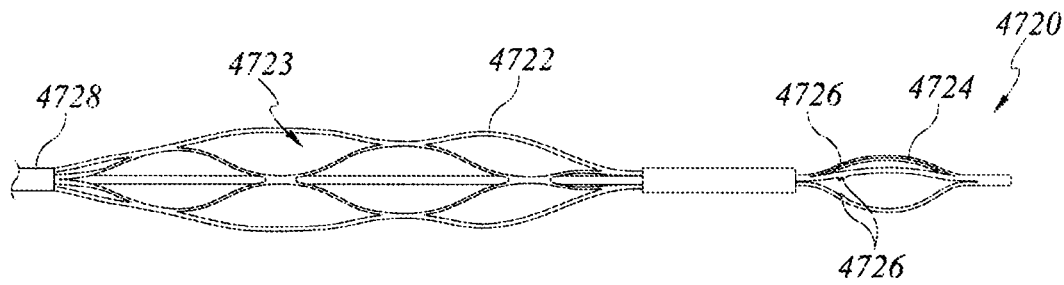
Fig. 47Ci
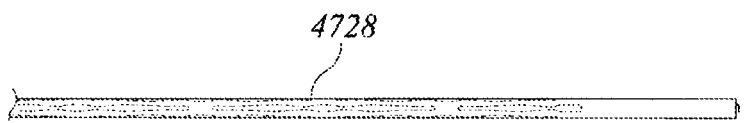
Fig. 47Cii
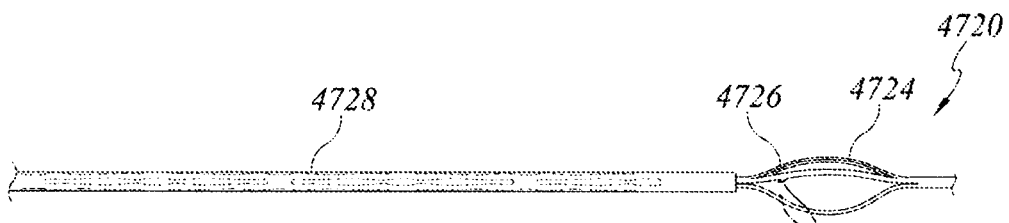
Fig. 47Ciii
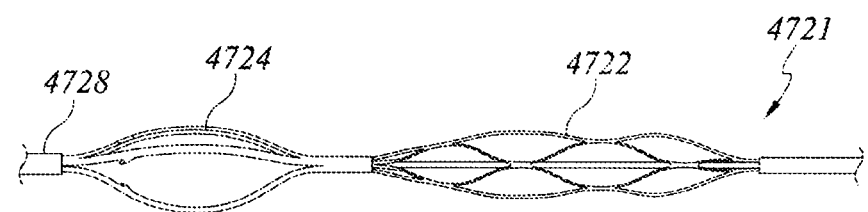
Fig. 47Civ

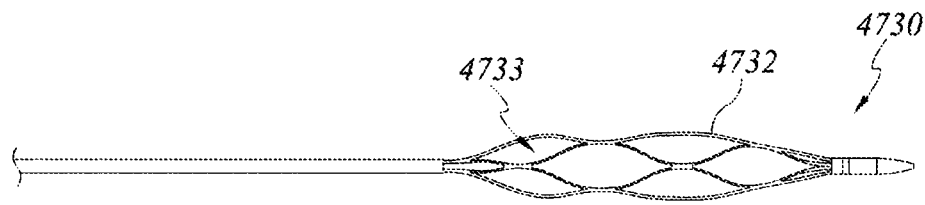
Fig. 47Di
Fig. 47Dii
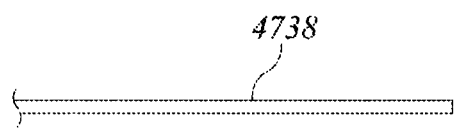
Fig. 47Diii
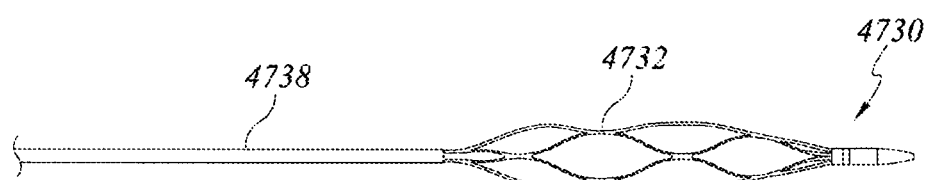
Fig. 47Div
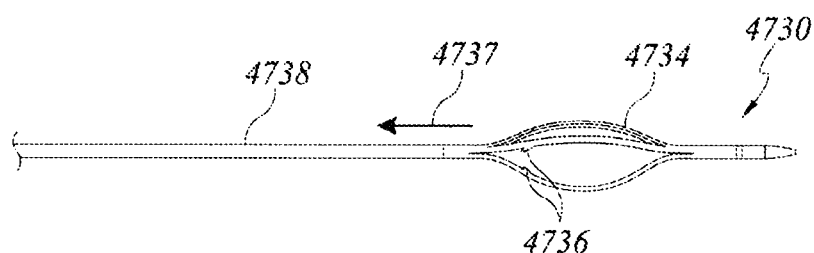
Fig. 47Dv

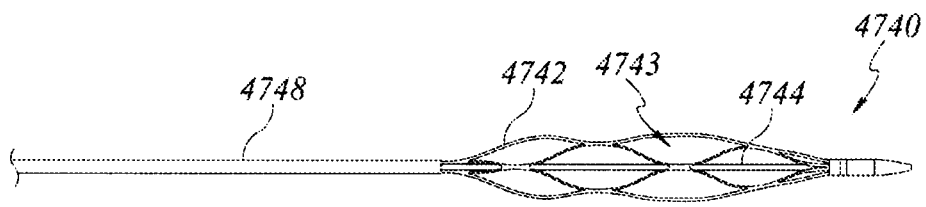
Fig. 47Ei
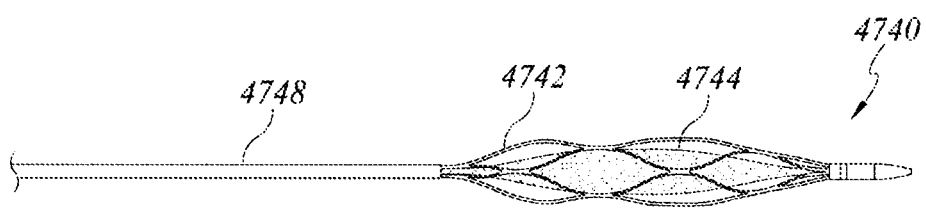
Fig. 47Eii
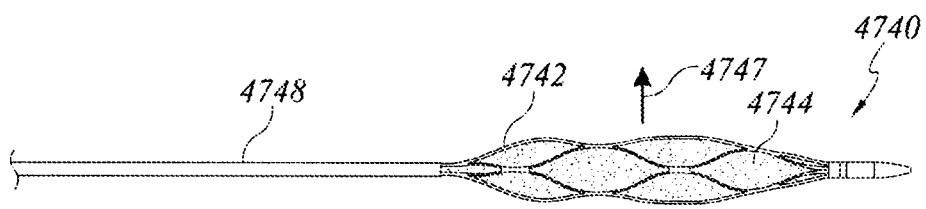
Fig. 47Eiii
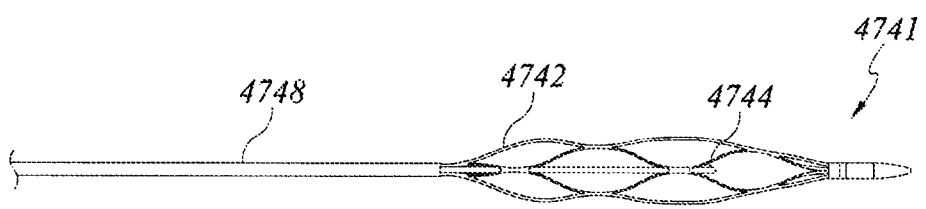
Fig. 47Eiv

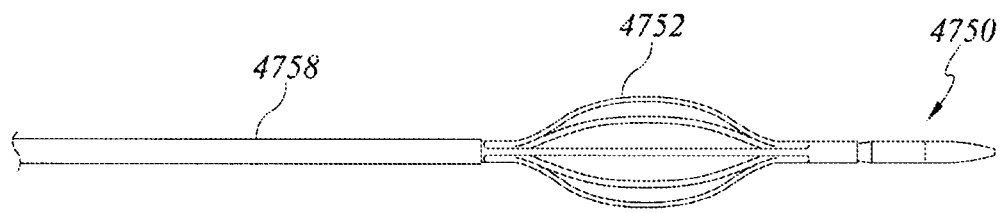
Fig. 47Fi
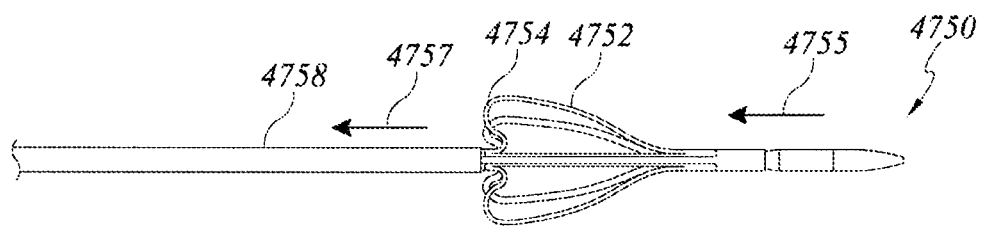
Fig. 47Fii
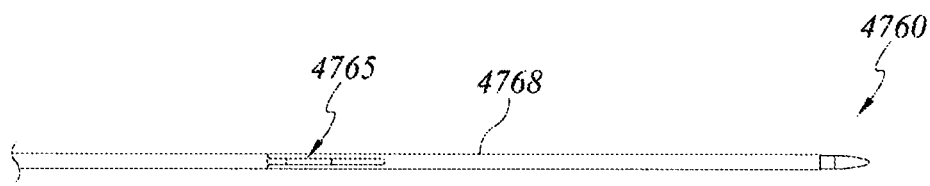
Fig. 47Gi
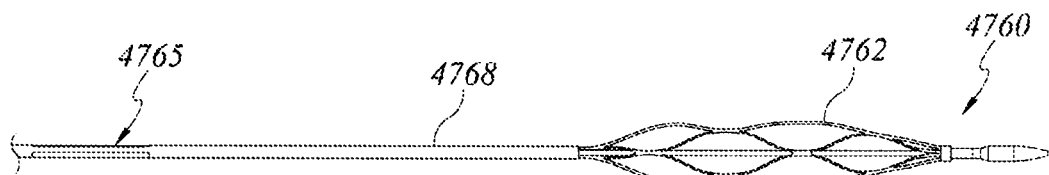
Fig. 47Gii
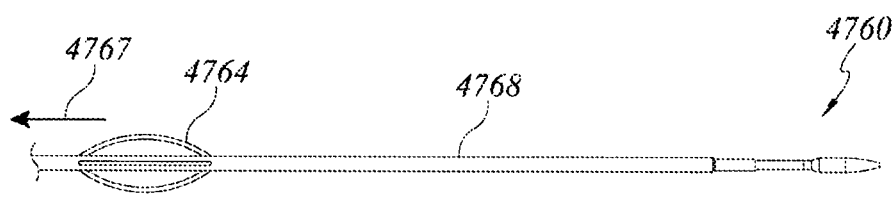
Fig. 47Giii

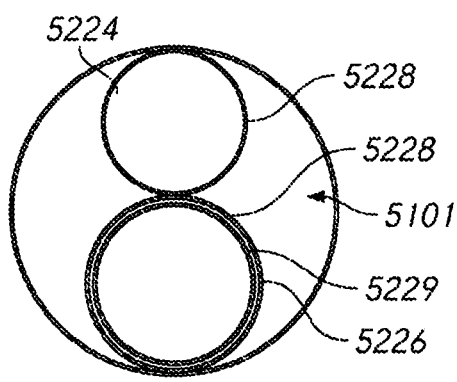
FIG. 52Bii
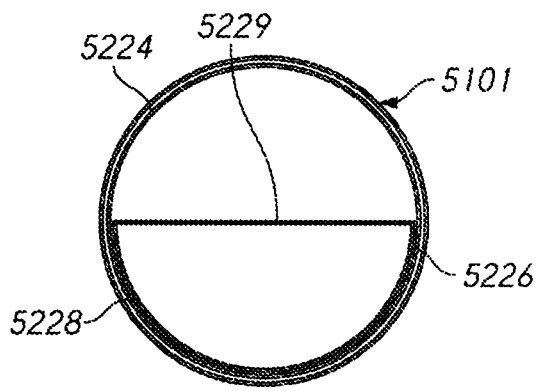
FIG. 52Biii
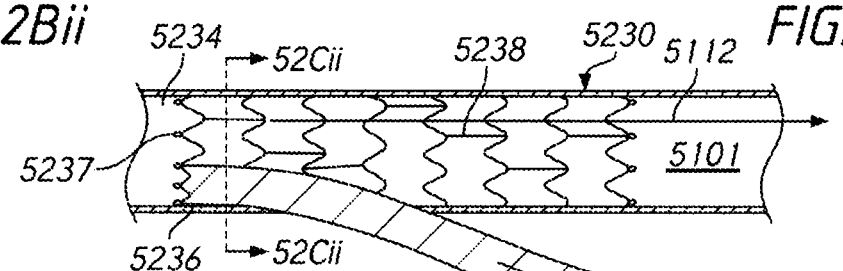
FIG. 52Ci
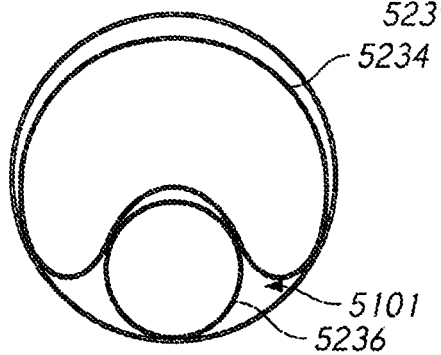
FIG. 52Cii
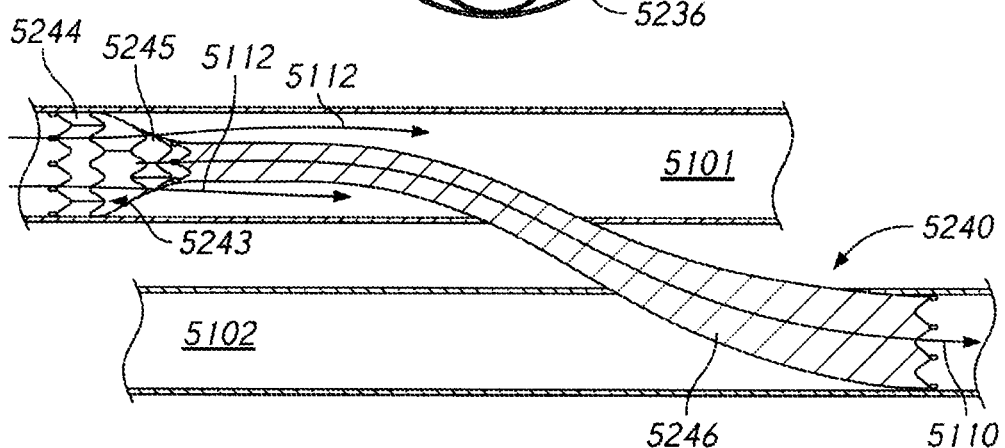
FIG. 52D

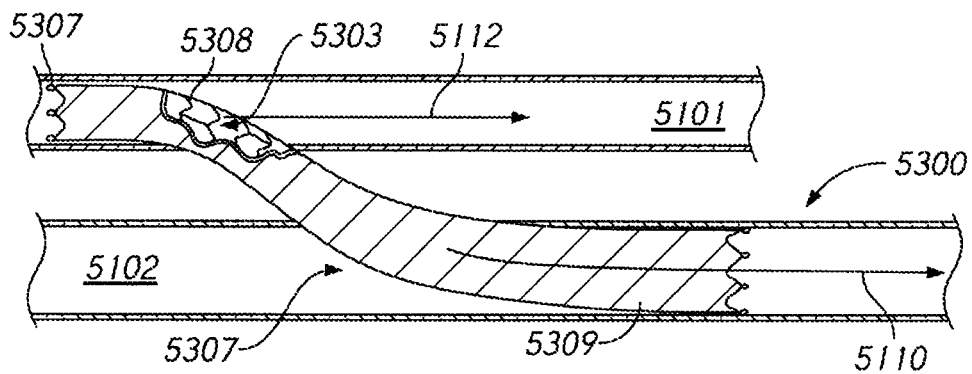
FIG. 53A
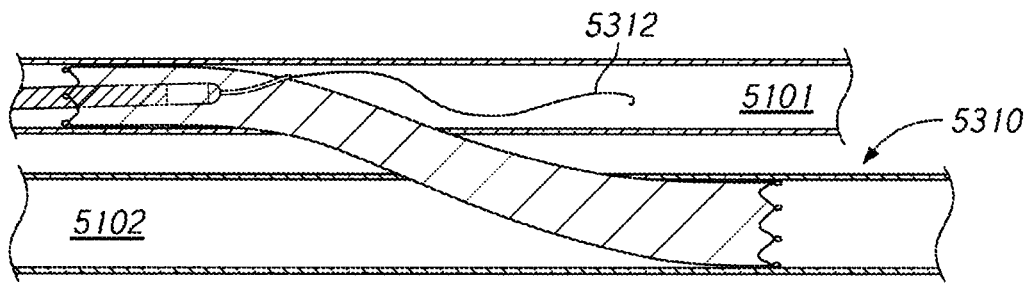
FIG. 53Bi
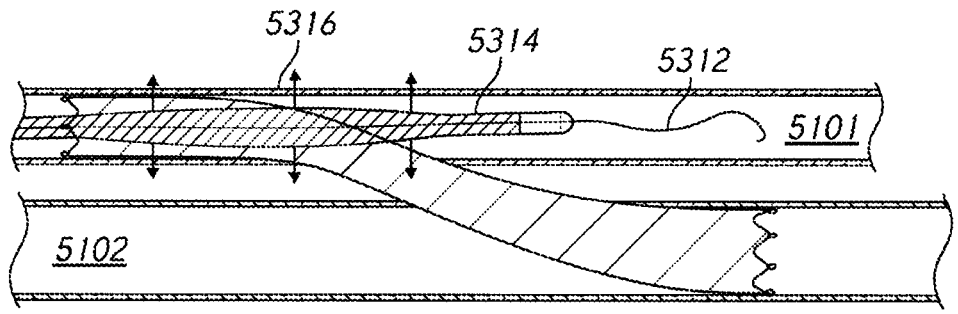
FIG. 53Bii
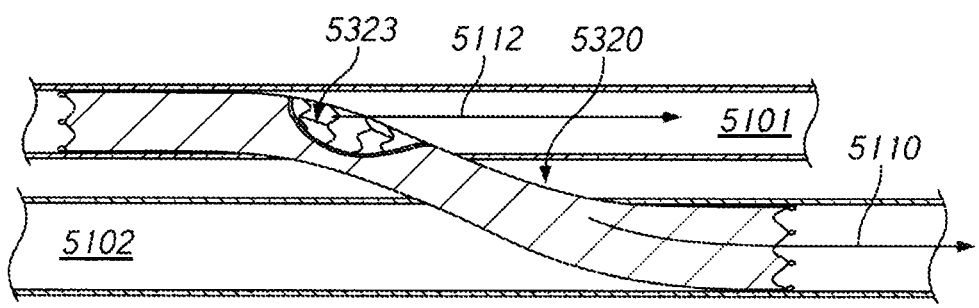
FIG. 53Biii

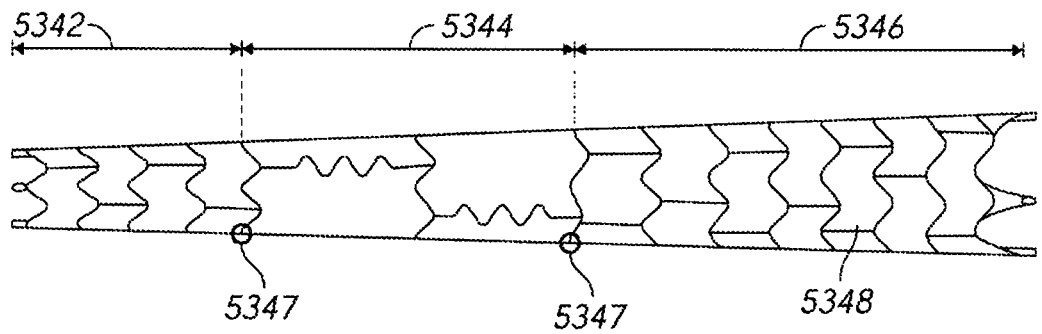
FIG. 53Ci
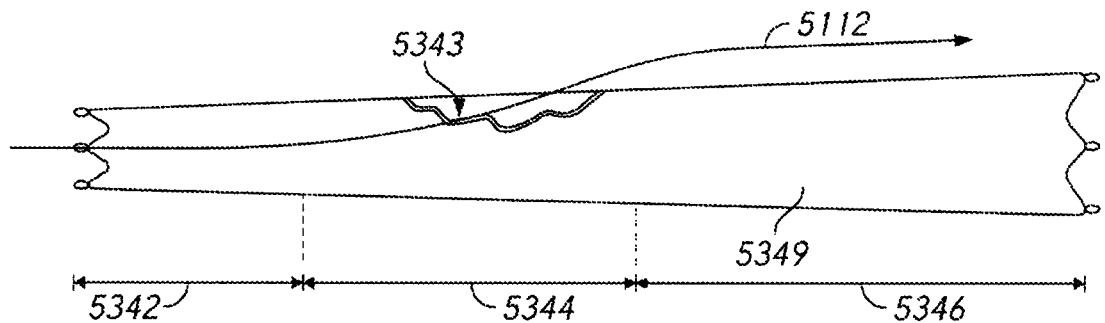
FIG. 53Cii
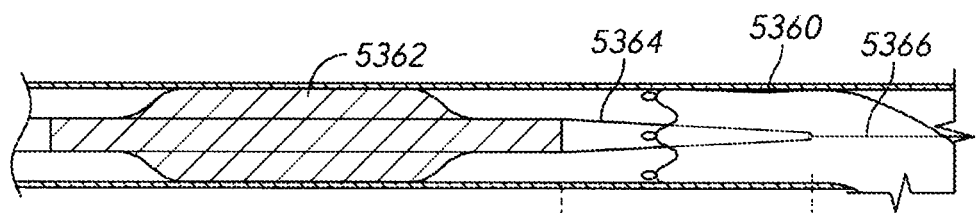
FIG. 53Di
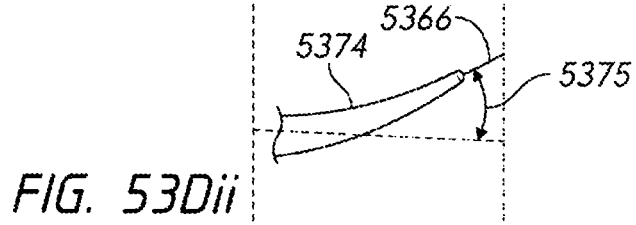
FIG. 53Dii
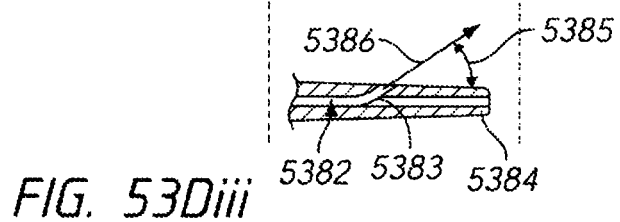
FIG. 53Diii

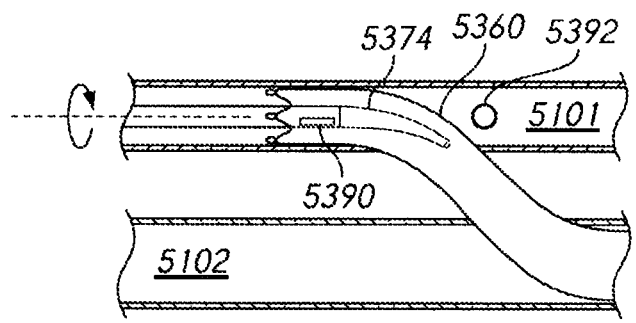
FIG. 53Ei
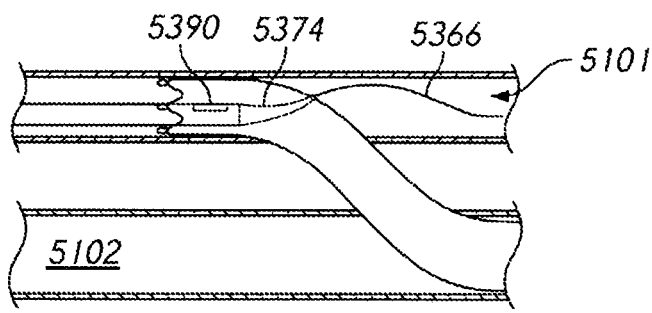
FIG. 53Eii
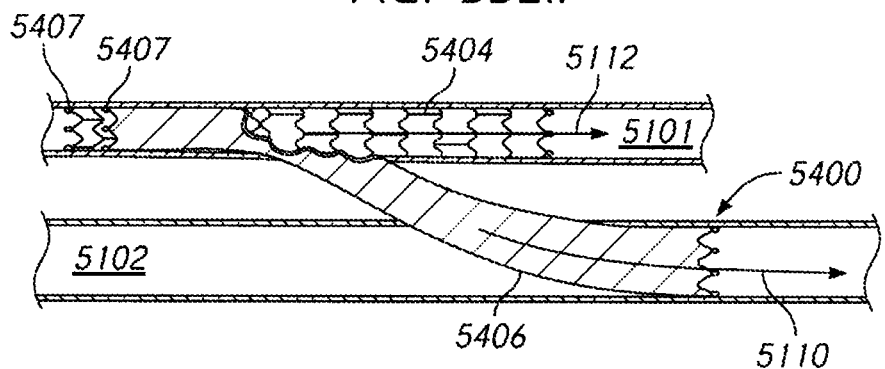
FIG. 54A
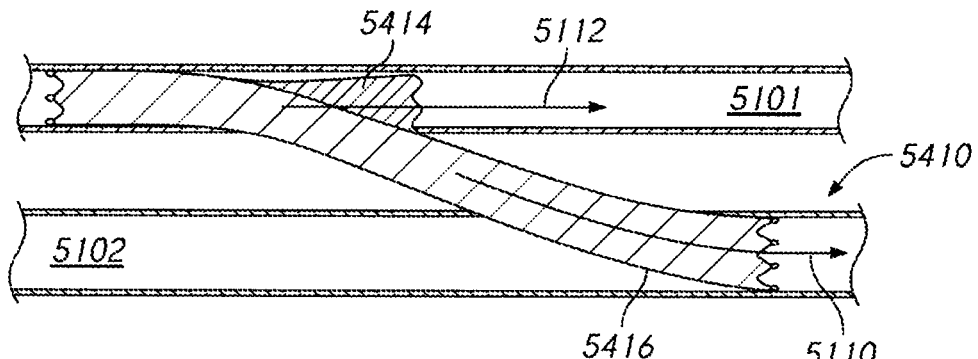
FIG. 54Bi

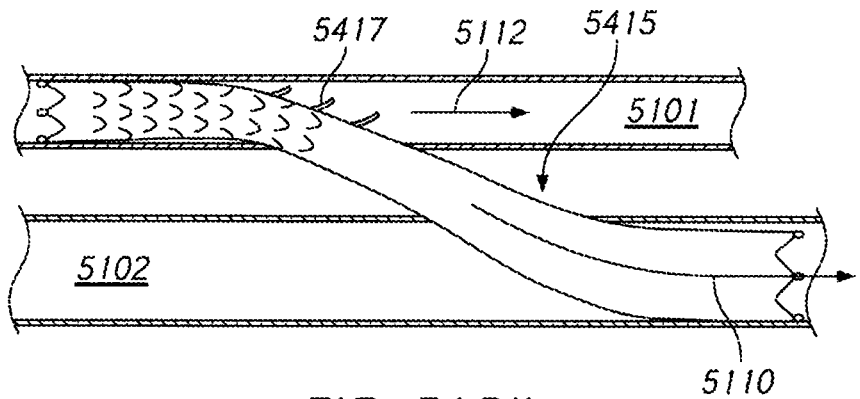
FIG. 54Bii
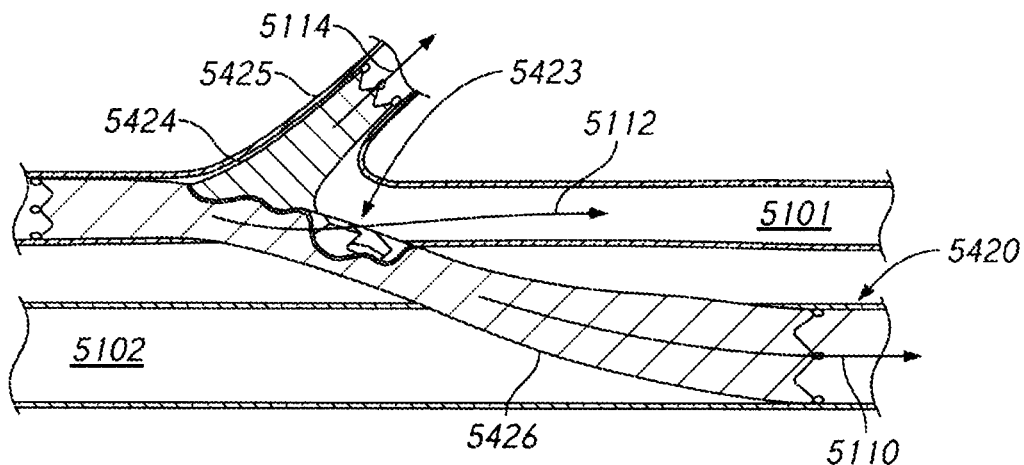
FIG. 54C
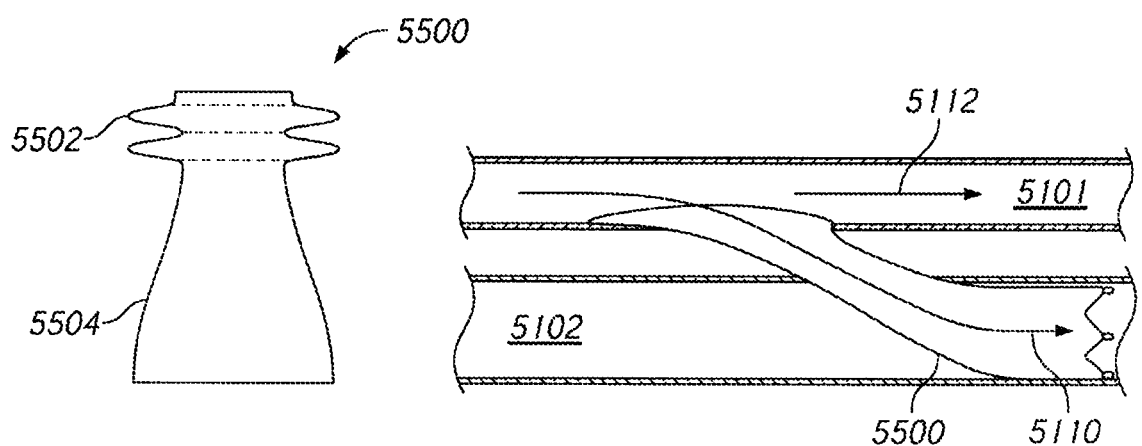
FIG. 55A
FIG. 55B

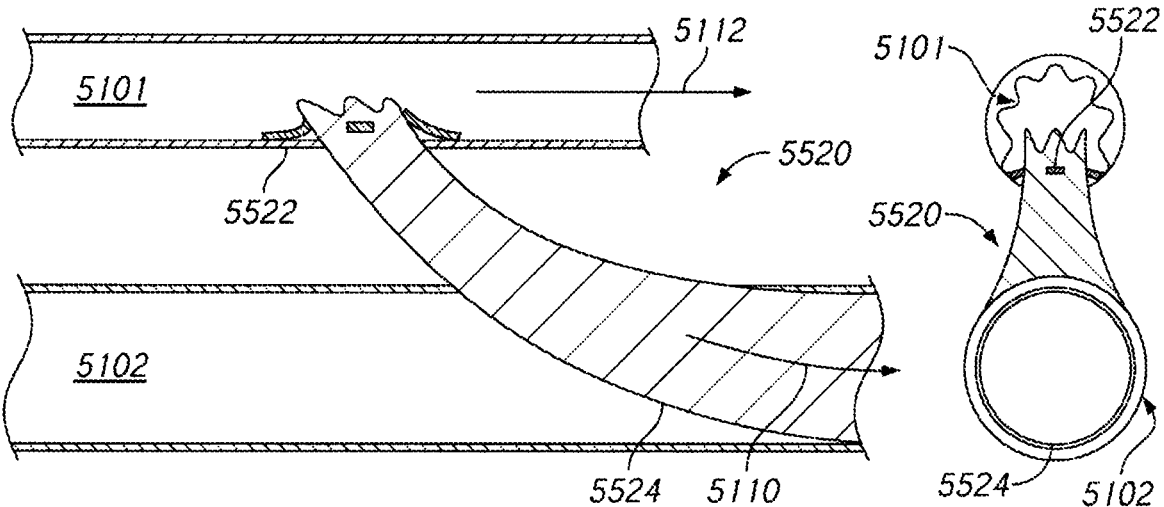
FIG. 55C
FIG. 55D
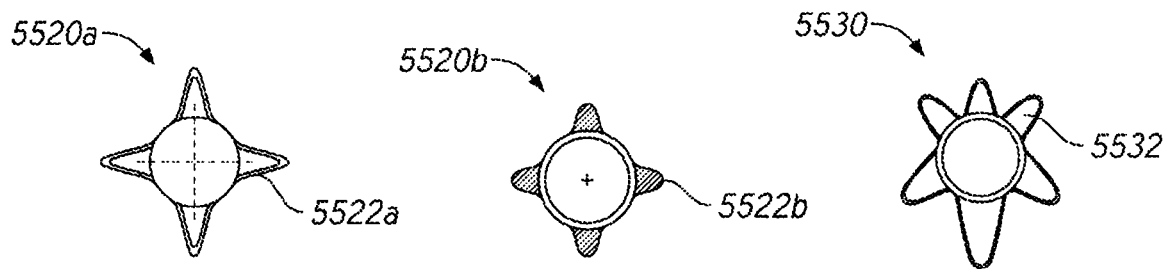
FIG. 55Ei
FIG. 55Eii
FIG. 55G
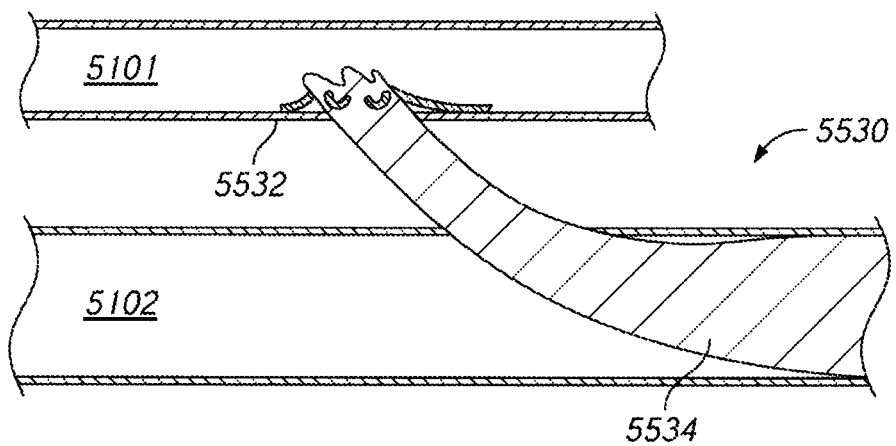
FIG. 55F

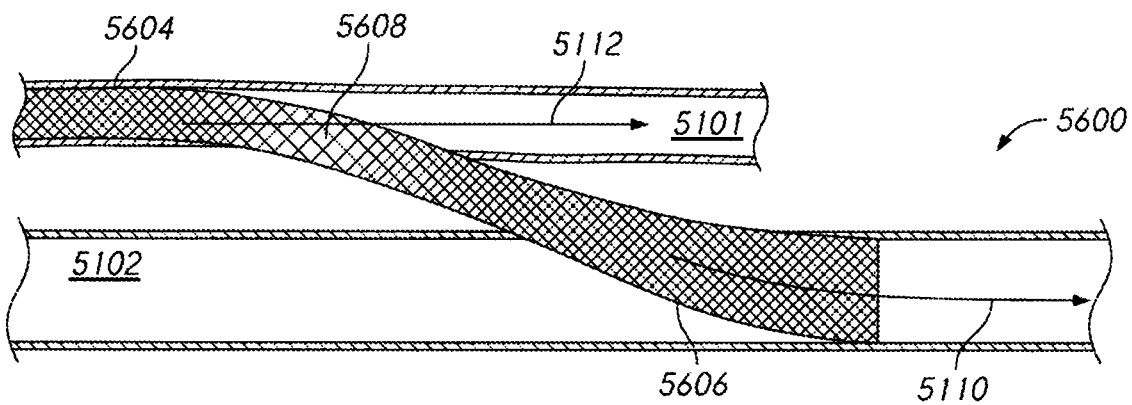
FIG. 56A
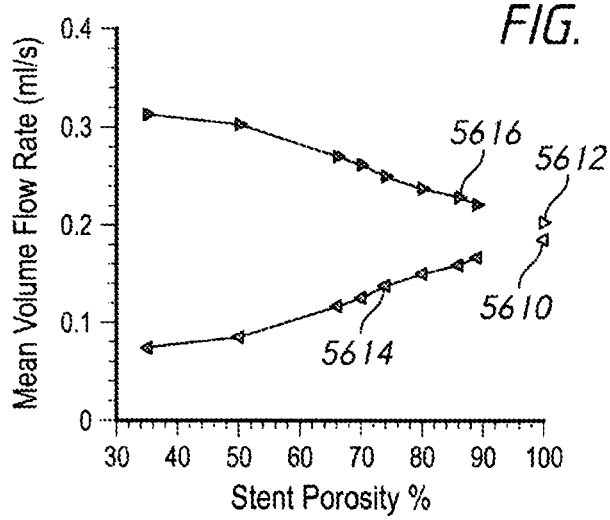
FIG. 56B
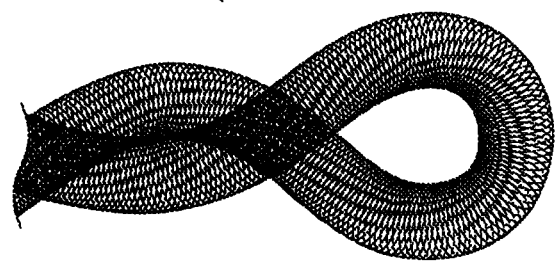
FIG. 57A
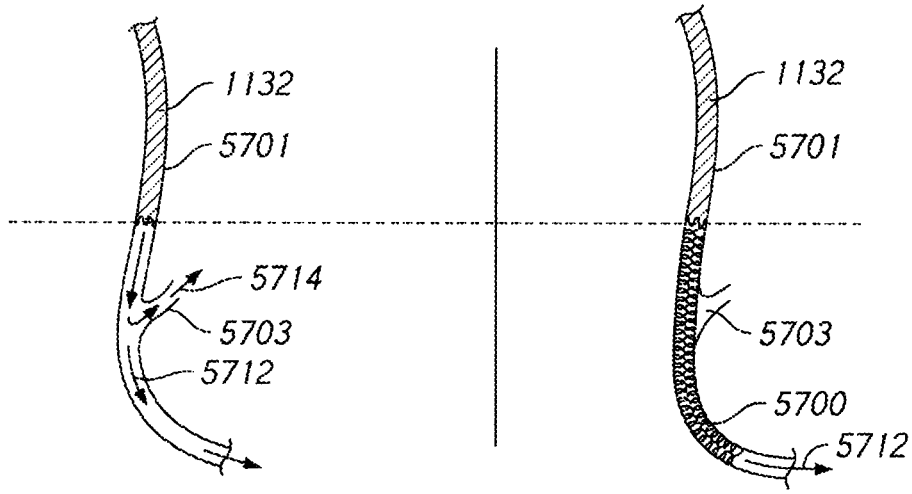
FIG. 57Bi      FIG. 57Bii

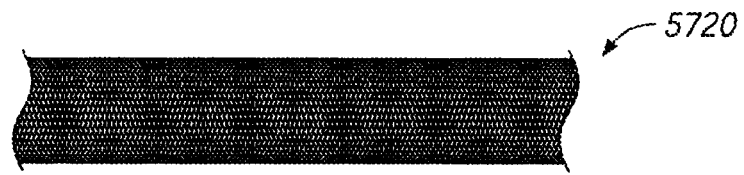
FIG. 57Ci
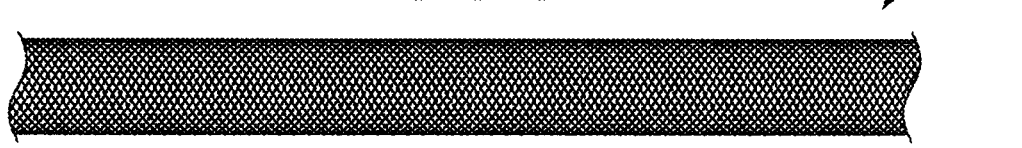
FIG. 57Cii
FIG. 57Ciii
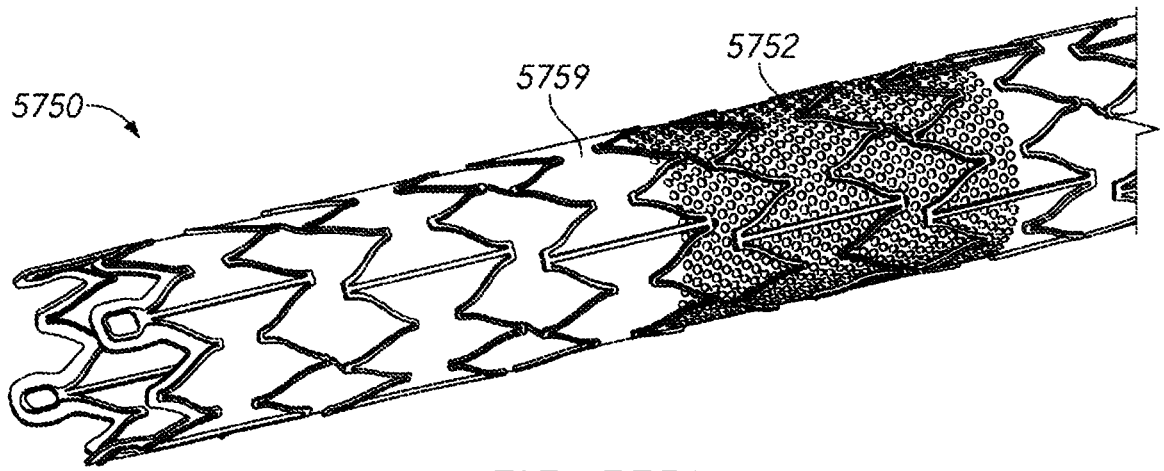
FIG. 57Di
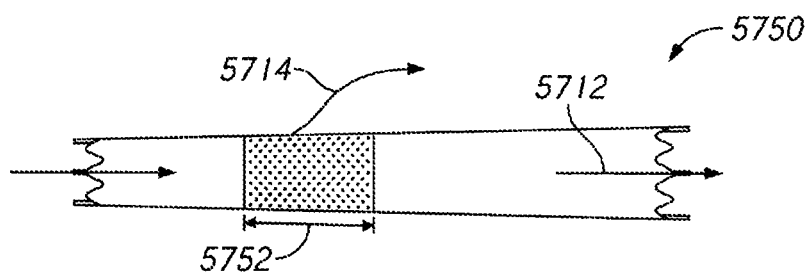
FIG. 57Dii

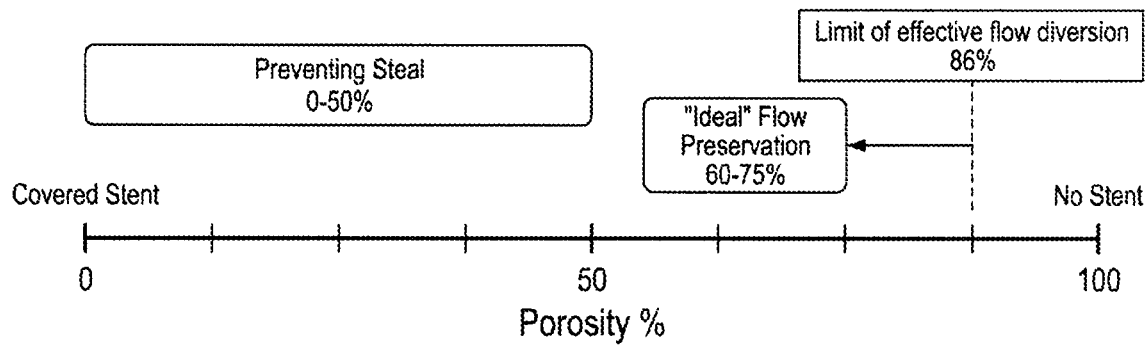
FIG. 57E
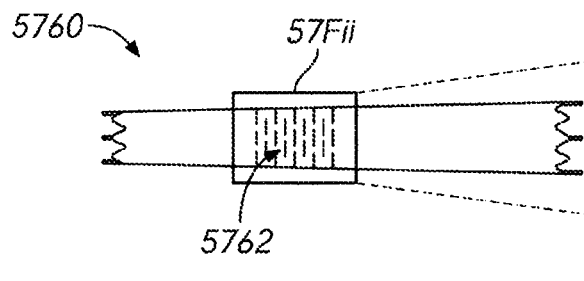
FIG. 57Fi
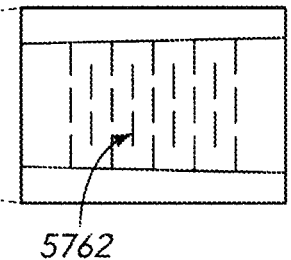
FIG. 57Fii
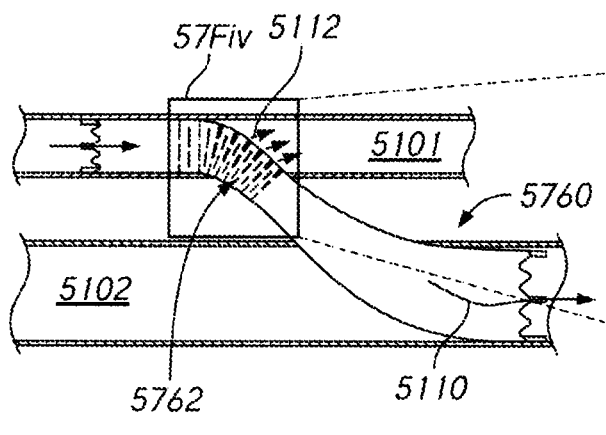
FIG. 57Fiii
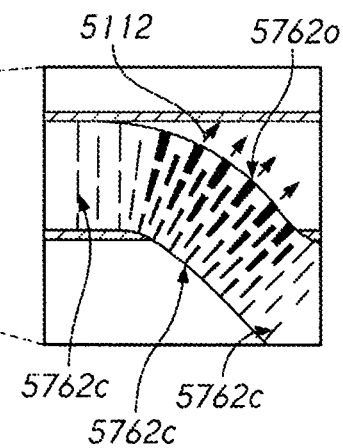
FIG. 57Fiv

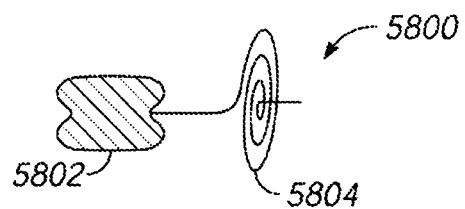
FIG. 58A
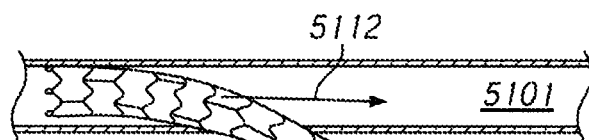
FIG. 58Bi
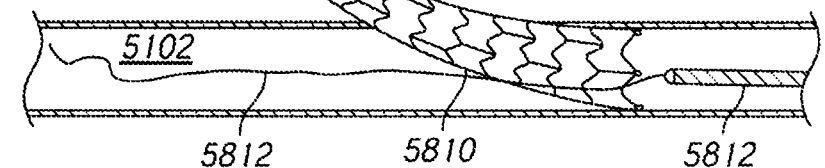
FIG. 58Bii
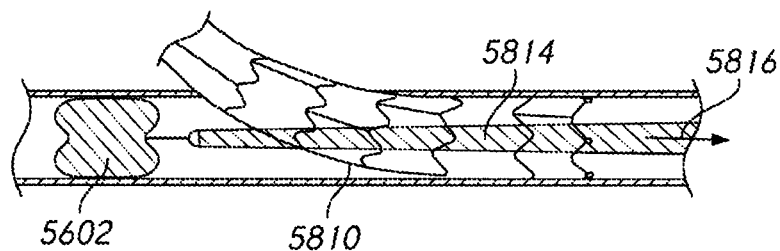
FIG. 58Biii
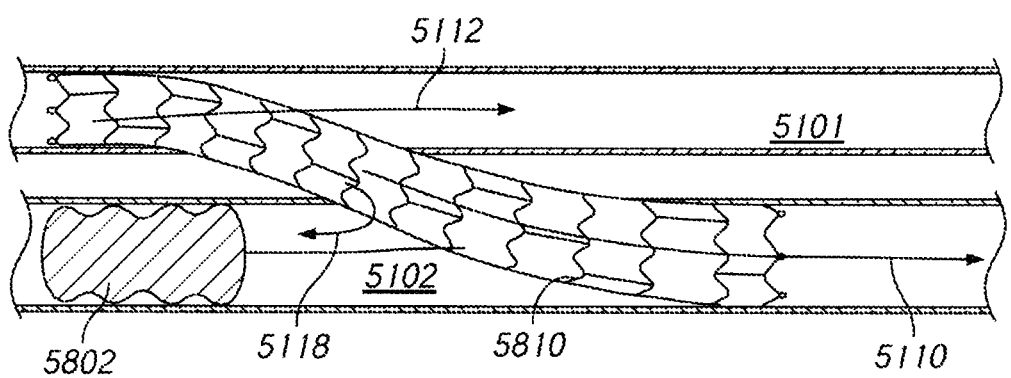
FIG. 58C

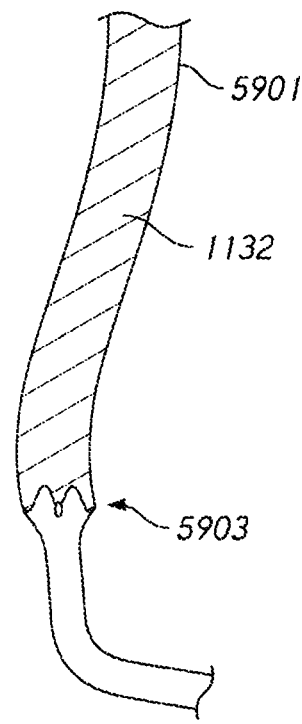
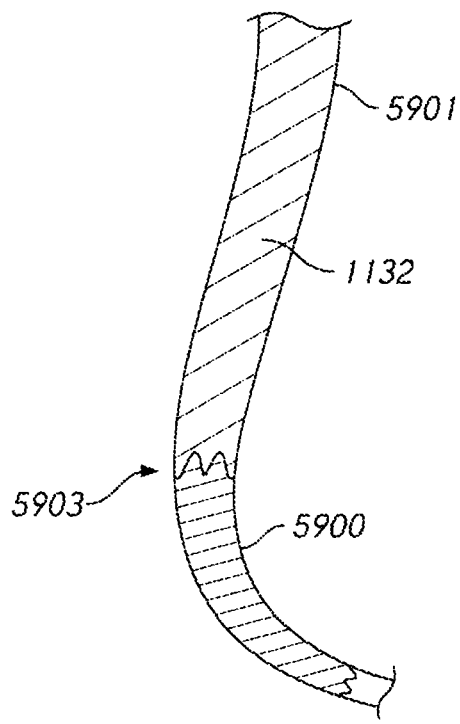
FIG. 59Ai
FIG. 59Aii
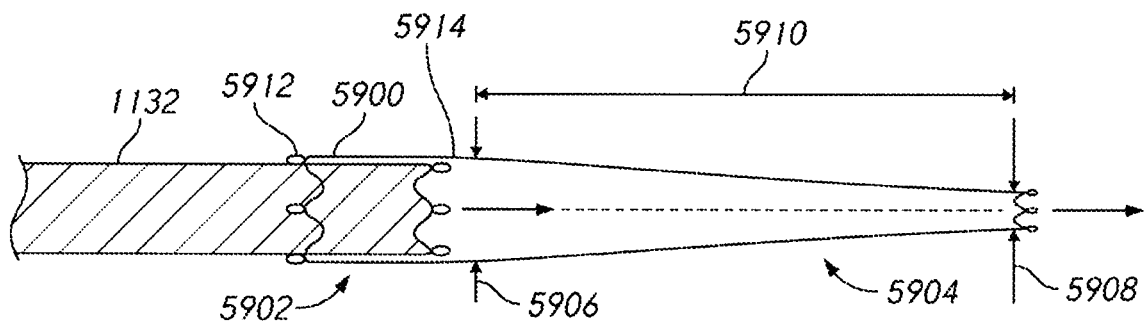
FIG. 59B

DEVICES AND METHODS FOR INCREASING BLOOD PERFUSION TO A DISTAL EXTREMITY

INCORPORATION BY REFERENCE

Any and all applications for which a foreign or domestic priority claim is identified in the Application Data Sheet as filed with the present application are hereby incorporated by reference under 37 CFR 1.57.

BACKGROUND

Field

The present application relates to methods and systems for use in percutaneous interventional surgery. In particular, the present application relates to methods and systems for providing or maintaining fluid flow through body passages such as heart cavities and blood vessels.

Description of the Related Art

Minimally invasive percutaneous surgery, or "key-hole" surgery, is a surgical technique in which surgical devices are inserted into a patient's body cavity through a small aperture cut in the skin. This form of surgery has become increasingly popular as it allows patients to endure less surgical discomfort while retaining the benefits of conventional surgery. Patients treated by such techniques are exposed to lower levels of discomfort, need for general anesthesia, trauma, and risk of infection, and their recovery times can be significantly reduced compared to conventional surgical procedures.

Key-hole surgery can be used, for example, for laparoscopic surgery and to treat cardiovascular diseases. In treating cardiovascular diseases, balloon angioplasty, in which a balloon catheter is inserted into an artery usually near the patient's groin and guided to the patient's heart where a balloon at a distal portion of the catheter is inflated to widen or dilate an occluded vessel to help restore blood flow to the cardiac tissue, may be used to treat a partially occluded coronary artery as an alternative to open heart surgery. A tubular supporting device (e.g., stent) may be deployed at the site of the blockage to prevent future occlusion (restenosis) or collapse of the blood vessel. The stent may, for example, be an expandable metal mesh tube carried on the balloon of the balloon catheter, or be self-expanding. The balloon-expandable stent expands when the balloon is inflated, so that the stent pushes against the wall of the blood vessel. The stent is arranged to retain its expanded shape when it reaches its expanded position, for example by plastic deformation or by means of a mechanical locking mechanism, so as to form a resilient scaffold or support in the blood vessel. The support structure (e.g., stent) supports and dilates the wall of the blood vessel to maintain a pathway for blood to flow through the vessel. Self-expanding stents are also available, which are held in a collapsed state by a suitably adapted catheter for transport through the artery and which adopt an expanded state when deployed at the site of the blockage. The catheter may, for example, include a retaining sleeve which retains the stent in a compressed or unexpanded state. Upon removal or withdrawal of the sleeve from the stent, the stent expands to support and dilate the wall of the blood vessel.

Balloon angioplasty is not always a suitable measure, for example in acute cases and in cases where a coronary artery is completely occluded. In these instances, the typical treatment is to employ coronary bypass. Coronary bypass surgery is an open-chest or open-heart procedure, and typically involves grafting a piece of healthy blood vessel onto the coronary artery so as to bypass the blockage and restore blood flow to the coronary tissue. The healthy blood vessel is usually a vein harvested from the patient's leg or arm during the course of the bypass operation. To perform the procedure, the patient's heart must be exposed by opening the chest, separating the breastbone, and cutting the pericardium surrounding the heart, resulting in significant surgical trauma.

Conventional coronary bypass surgery is not always an option. Certain patients are unsuitable as candidates for conventional coronary bypass surgery due low expectation of recovery or high risk from the significant trauma due to surgery, high risk of infection, absence of healthy vessels to use as bypass grafts, significant co-morbidities, and expected long and complicated recovery time associated with open-chest surgery. For example, factors such as diabetes, age, obesity, and smoking may exclude a proportion of candidate patients who are in genuine need of such treatment.

SUMMARY

The present application provides methods and systems for overcoming certain deficiencies and/or improving percutaneous methods and systems. For example, according to several embodiments, the methods and systems described herein can improve targeting and localization of therapy administration, which may advantageously provide treatment via percutaneous techniques to patients unsuitable for more invasive surgery. Certain embodiments described herein can provide fluid flow in passages such as coronary and/or peripheral blood vessels by creating a bypass using minimally invasive percutaneous surgical techniques.

In some examples, a launching catheter for targeting a second vessel from a first vessel comprises a catheter comprising a proximal portion and a distal portion comprising a flat radiopaque marker. The radiopaque marker may be rectangular. The catheter may comprise a needle aperture. The catheter may comprise needle configured to extend through the needle aperture.

The distal portion of the catheter may be curved. The marker may not follow the curvature of the distal portion of the catheter. The needle aperture may be proximal to the marker. The needle aperture may be distal to the marker. The needle aperture may at least partially overlap the marker.

The needle aperture may be on a first side of the distal portion of the catheter. The marker may be on a second side of the distal portion of the catheter. The first side may be the same as the second side. The first side may be opposite the second side. A distal end of the needle extended out of the needle aperture may be longitudinally aligned with the radiopaque marker. The needle may comprise a profile. The needle may slide through a needle lumen. The needle lumen may comprise a complementary shape to the profile (e.g., to reduce longitudinal movement of the needle during advancement of the needle).

The marker may comprise a first radiolucent material and a second radiopaque material coupled to the first radiolucent material. The second radiopaque material may be coupled to the first radiolucent material by one or more of cladding, plating, chemical vapor deposition, atomic layer deposition, screen printing, coating, adhesion, or sputtering. The second radiopaque material may be polished or flattened after being coupled to the first radiolucent material.

A ratio of a length of the marker to a width of the marker may be between 1/1 and 5/1.

The marker may have a thickness between 0.001 mm and 1 mm. The marker may have a thickness between 1 nm and 10 µm.

A kit may comprise the launching catheter and a target catheter. The target catheter may comprise an expandable member. The expandable member may comprise a snare. The expandable member may comprise a mesh. The expandable member may comprise a radiopaque material. The target catheter may comprise a first radiopaque marker. The target catheter may comprise a second radiopaque marker longitudinally spaced from the first radiopaque marker.

In some examples, a launching catheter for targeting a second vessel from a first vessel comprises a catheter comprising a proximal portion and a distal portion comprising a needle aperture and a flat rectangular radiopaque marker. The flat rectangular radiopaque marker disappears under fluoroscopy upon rotation to provide information about rotational alignment of the launching catheter. The launching catheter further comprises a needle configured to extend through the needle aperture.

In some examples, a catheter comprises a flat radiopaque marker. The catheter may be a launching catheter for targeting a second vessel from a first vessel. The catheter may comprise a distal portion comprising the flat radiopaque marker. The radiopaque marker may be rectangular. The catheter may comprise a needle aperture. The catheter may comprise needle configured to extend through the needle aperture. The distal portion of the catheter may be curved. The marker may not follow the curvature of the distal portion of the catheter. The needle aperture may be proximal to the marker. The needle aperture may be distal to the marker. The needle aperture may at least partially overlap the marker. The needle aperture may be on a first side of the distal portion of the catheter. The marker may be on a second side of the distal portion of the catheter. The first side may be the same as the second side. The first side may be opposite the second side. A distal end of the needle extended out of the needle aperture may be longitudinally aligned with the radiopaque marker. The needle may comprise a profile. The needle may slide through a needle lumen. The needle lumen may comprise a complementary shape to the profile (e.g., to reduce longitudinal movement of the needle during advancement of the needle). A kit may comprise the launching catheter and a target catheter. The target catheter may comprise an expandable member. The expandable member may comprise a snare. The expandable member may comprise a mesh. The expandable member may comprise a radiopaque material. The target catheter may comprise a first radiopaque marker. The target catheter may comprise a second radiopaque marker longitudinally spaced from the first radiopaque marker.

In some examples, a method of aligning a catheter comprises rotating a catheter in a first blood vessel. The catheter comprises a flat radiopaque marker. The rotating is until the marker has a thickness that indicates rotational alignment of the catheter. The thickness may be visible under fluoroscopy. The thickness may be less than a certain value. The thickness may be indicated by a thin (e.g., minimum thickness) line. The radiopaque marker may be rectangular.

The method may comprise rotating the catheter in the first blood vessel until the marker has the thickness (e.g., minimal thickness) under fluoroscopy and is on a side of the catheter. The method may further comprise longitudinally advancing the catheter until the marker is proximate a second catheter in a second blood vessel. The second catheter may comprise a radiopaque feature visible under fluoroscopy. The radiopaque feature of the second catheter visible under fluoroscopy may comprise an expandable member. The expandable member may comprise a snare. The expandable member comprise a mesh.

The method may further comprise, after rotating the catheter, extending a needle out of the catheter. Extending the needle out of the catheter may comprise exiting the first vessel and entering a second vessel different than the first vessel. Aligning the catheter may comprise aligning the needle. Extending the needle out of the catheter may comprise traversing interstitial tissue between the first vessel and the second vessel.

The method may further comprise extending a guidewire through the needle and into the second vessel. The method may further comprise entangling the guidewire in a second catheter in the second vessel. Entangling the guidewire may comprise closing an expandable member of the second catheter. The method may further comprise moving the second catheter to detect corresponding movement of the guidewire. The method may further comprise moving the second catheter to move the guidewire through the second vessel.

A catheter system can include a tubular body, and at least one of a targeting system coupled to the tubular body, an expandable member, or a fluid injection port.

In some embodiments, a catheter system for identifying a bifurcation in a vessel comprises, or alternatively consists essentially of, a tubular body, a targeting system coupled to the tubular body, an expandable member configured to appose sidewalls of a vessel to occlude the vessel in an expanded state, and a fluid injection port configured to inject radiopaque fluid into a vessel proximal to the expandable member in the expanded state such that the radiopaque fluid pools proximate to the expandable member and provides visualization of the vessel and branch vessels.

The expandable member may be coupled to the tubular body. The tubular body may comprise the fluid injection port. The catheter system may further comprise a second tubular body. The expandable member may be coupled to the second tubular body. The second tubular body may comprise the fluid injection port. The targeting system may comprise an ultrasound transducer. The targeting system may comprise an omnidirectional ultrasound transducer.

In some embodiments, a catheter system comprises, or alternatively consists essentially of, a tubular body, a targeting system coupled to the tubular body, and an expandable member.

The expandable member may be coupled to the tubular body. The catheter system may further comprise a second tubular body. The expandable member may be coupled to the second tubular body. The expandable member may be configured to appose sidewalls of a vessel to occlude the vessel. The catheter system may further comprise a fluid injection port. The tubular body may comprise the fluid injection port. The catheter system may further comprise a second tubular body comprising the fluid injection port. The targeting system may comprise an ultrasound transducer. The targeting system may comprise an omnidirectional ultrasound transducer.

In some embodiments, a catheter system comprises, or alternatively consists essentially of, a tubular body, a targeting system coupled to the tubular body, and a fluid injection port.

The tubular body may comprise the fluid injection port. The catheter system may further comprise a second tubular body comprising the fluid injection port. The catheter system may further comprise an expandable member. The expandable member may be coupled to the tubular body. The catheter system may further comprise a second tubular body. The expandable member may be coupled to the second tubular body. The expandable member may be configured to appose sidewalls of a vessel to occlude the vessel. The targeting system may comprise an ultrasound transducer. The targeting system may comprise an omnidirectional ultrasound transducer.

In some embodiments, a catheter system comprises, or alternatively consists essentially of, a tubular body, a fluid injection port, and an expandable member.

The tubular body may comprise the fluid injection port. The catheter system may further comprise a second tubular body comprising the fluid injection port. The expandable member may be coupled to the tubular body. The catheter system may further comprise a second tubular body. The expandable member may be coupled to the second tubular body. The expandable member may be configured to appose sidewalls of a vessel to occlude the vessel. The catheter system may further comprise a targeting system. The targeting system may comprise an ultrasound transducer. The targeting system may comprise an omnidirectional ultrasound transducer. A method of identifying a bifurcation may comprise inserting the catheter system into a first vessel, positioning the catheter system at a first location, expanding the expandable member to occlude the first vessel, and delivering contrast material into the first vessel. The contrast material may pool proximate to the expandable member. The method may further comprise reviewing a shape of the contrast material in the first vessel under fluoroscopy.

In some embodiments, a method of identifying a bifurcation comprises, or alternatively consists essentially of, inserting a catheter system into a first vessel and positioning the catheter system at a first location. The catheter system comprises an expandable member and a fluid injection port. The method further comprises expanding the expandable member to occlude the first vessel and delivering contrast material out of the fluid injection port. The contrast material pools proximate to the expandable member. The method further comprises reviewing a shape of the contrast material in the first vessel under fluoroscopy.

A single catheter may comprise the expandable member and the fluid injection port. A first catheter may comprise the expandable member and a second catheter may comprise the fluid injection port. Expanding the expandable member may comprise providing fluid flow through an inflation lumen in fluid communication with the expandable member. Expanding the expandable member may comprise expanding the first vessel. The contrast material may comprise at least one of iodine-based contrast and barium sulfate-based contrast. Delivering the contrast material may comprise expanding the first vessel. Reviewing the shape of the contrast material may comprise identifying the presence of at least one of a bifurcation and a branch vessel. The method may further comprise repositioning the catheter system if at least one of the bifurcation and the branch vessel is present. The method may further comprise extending a needle from another catheter in a second vessel if at least one of the bifurcation and the branch vessel is not present. Extending the needle may comprise exiting the second vessel, traversing interstitial tissue between the second vessel and the first vessel, and entering the first vessel. The method may further comprise advancing a guidewire through the needle. The catheter system may comprise a capture element configured to guide the guidewire into a guidewire lumen.

The catheter system may comprise a targeting system. Positioning the catheter system at the first location may comprise targeting the targeting system from a complementary targeting system on another catheter in a second vessel. The targeting system may comprise an ultrasound receiver. The complementary targeting system may comprise an ultrasound emitter. The ultrasound receiver may comprise an omnidirectional ultrasound transducer. The ultrasound emitter may comprise a directional ultrasound transducer. The method may further comprise dilating the fistula.

The method may further comprise deploying a prosthesis at least partially in a fistula between the second vessel and the first vessel. After deploying the prosthesis, blood may be diverted from the first vessel to the second vessel through the prosthesis. The method may further comprise, after deploying the prosthesis, lining the first vessel with a stent-graft including covering the collateral vessels of the first vessel. Lining the first vessel with the stent-graft may comprise lining the first vessel with a plurality of stent grafts. Lining the first vessel with the plurality of stent-grafts may comprise first deploying a distal-most stent-graft of the plurality of stent-grafts and last deploying a proximal-most stent-graft of the plurality of stent-grafts. After lining the first vessel with the plurality of stent-grafts, a proximal edge of a distal-most stent-graft of the plurality of stent-grafts may overlap a distal edge of a next distal-most stent-graft of the plurality of stent-grafts. After lining the first vessel with the plurality of stent-grafts, a proximal edge of a proximal-most stent-graft of the plurality of stent-grafts may overlap a distal edge of the prosthesis.

The method may further comprise making a valve in the first vessel incompetent. Making the valve in the first vessel incompetent may be after lining the vessel with a stent-graft. Making the valve in first the vessel incompetent may comprise advancing a reverse valvulotome through the prosthesis and distally advancing the reverse valvulotome in the first vessel to disable the valve. Making the valve in the first vessel incompetent may comprise advancing a two-way valvulotome proximate to the valve in a radially compressed state, radially expanding the two-way valvulotome to a radially expanded state, and in the radially expanded state, at least one of distally advancing the two-way valvulotome and proximally retracting the two-way valvulotome in the first vessel to disable the valve. Radially expanding the two-way valvulotome may comprise at least one of proximally retracting a sheath and distally advancing the two-way valvulotome. A method of making a valve in a vessel incompetent may comprise advancing the two-way valvulotome proximate to the valve in the radially compressed state, radially expanding the two-way valvulotome to the radially expanded state, and in the radially expanded state, at least one of distally advancing the two-way valvulotome and proximally retracting the two-way valvulotome in the vessel to disable the valve.

In some embodiments, a method of modifying a vessel including making valves in the vessel incompetent and covering collateral vessels of the vessel comprises, or alternatively consists essentially of, lining the vessel with a stent-graft including covering the collateral vessels of the vessel and after lining the vessel with the stent-graft, making a valve in the vessel incompetent.

The method may further comprise deploying a prosthesis at least partially in a fistula between a second vessel and the vessel. After deploying the prosthesis, blood may be diverted from the second vessel to the vessel through the prosthesis. Lining the vessel with the stent-graft may be after deploying the prosthesis. The method may further comprise dilating the fistula. The method may further comprise advancing a needle from the second vessel to the vessel to form the fistula. Advancing the needle may comprise targeting a first catheter in the vessel with a second catheter in the second vessel. The second catheter may comprise an ultrasound emitter. The first catheter may comprise an ultrasound receiver. Targeting the catheter in the vessel with the catheter in the second vessel may comprise targeting the ultrasound receiver with the ultrasound emitter. The method may further comprise advancing a guidewire through the needle. A catheter system in the vessel may comprise a capture element configured to guide the guidewire into a guidewire lumen. Lining the vessel with the stent-graft may comprise lining the vessel with a plurality of stent grafts. Lining the vessel with the plurality of stent-grafts may comprise first deploying a distal-most stent-graft of the plurality of stent-grafts and last deploying a proximal-most stent-graft of the plurality of stent-grafts. After lining the vessel with the plurality of stent-grafts, a proximal edge of a distal-most stent-graft of the plurality of stent-grafts may overlap a distal edge of a next distal-most stent-graft of the plurality of stent-grafts. After lining the vessel with the plurality of stent-grafts, a proximal edge of a proximal-most stent-graft of the plurality of stent-grafts may overlap a distal edge of a prosthesis in the fistula. Making the valve in the vessel incompetent may comprise distally advancing a reverse valvulotome in the vessel to disable the valve. Making the valve in the vessel incompetent may comprise advancing a two-way valvulotome proximate to the valve in a radially compressed state, radially expanding the two-way valvulotome to a radially expanded state and in the radially expanded state, at least one of distally advancing the two-way valvulotome and proximally retracting the two-way valvulotome in the vessel to disable the valve. Radially expanding the two-way valvulotome may comprise at least one of proximally retracting a sheath and distally advancing the two-way valvulotome. The method may further comprise promoting retroperfusion of blood into toes. Promoting retroperfusion of blood into toes may comprise inflating a first expandable member in a medial plantar vein to occlude the medial plantar vein. Promoting retroperfusion of blood into toes may comprise inflating a second expandable member in a lateral plantar vein to occlude the lateral plantar vein. Promoting retroperfusion of blood into toes may comprise increasing hydrostatic pressure in a deep plantar venous arch. Increasing the hydrostatic pressure in the deep plantar venous arch may comprise disabling venous valves and enabling reversal of blood flow into metatarsal veins.

In some embodiments, a method of promoting retroperfusion of blood into toes comprises, or alternatively consists essentially of, inflating a first expandable member in a medial plantar vein to occlude the medial plantar vein and increasing hydrostatic pressure in a deep plantar venous arch. Increasing the hydrostatic pressure in the deep plantar venous arch may comprise disabling venous valves and enabling reversal of blood flow into metatarsal veins. The method may further comprise inflating a second expandable member in a lateral plantar vein to occlude the lateral plantar vein.

In some embodiments, a catheter system for promoting retroperfusion of blood into toes comprises, or alternatively consists essentially of, a first catheter comprising a first expandable member configured to be expanded in a medial plantar vein to occlude the medial plantar vein and a second catheter comprising a second expandable member configured to be expanded in a lateral plantar vein to occlude the lateral plantar vein.

The first catheter may be longitudinally movable through the second catheter and the second expandable member. The first catheter may comprise an inflation lumen in fluid communication with the first expandable member. The second catheter may comprise an inflation lumen in fluid communication with the second expandable member. The first catheter may be configured to curve around a lateral plantar vein into a medial plantar vein.

In some embodiments, a two-way valvulotome comprises, or alternatively consists essentially of, a proximal portion, a distal portion, and an intermediate portion longitudinally between the proximal portion and the distal portion. The intermediate portion comprises a distally facing blade and a proximally facing blade.

The intermediate portion may comprise a strut comprising the distally facing blade and the proximally facing blade. The intermediate portion may comprise a plurality of struts. One strut of the plurality of struts may comprise the distally facing blade and the proximally facing blade. Each strut of the plurality of struts may comprise a distally facing blade and a proximally facing blade. At least one strut of the plurality of struts may comprise a distally facing blade. At least one strut of the plurality of struts may comprise a proximally facing blade. The intermediate portion may comprise three struts. The three struts may be evenly circumferentially spaced. The intermediate portion may be radially expandable. The intermediate portion may be self-expanding upon release from a sheath. The proximal portion may be coupled to a pusher element. The intermediate portion may be laser cut (e.g., from a hypotube or a sheet). At least one of the distally facing blade and the proximally facing blade may be rotated relative to a circumference of the intermediate portion.

In some embodiments, a method of making a valve in a vessel incompetent comprises, or alternatively consists essentially of, advancing a two-way valvulotome proximate to the valve in a radially compressed state, radially expanding the two-way valvulotome to a radially expanded state, and in the radially expanded state, at least one of distally advancing the two-way valvulotome and proximally retracting the two-way valvulotome in the vessel to disable the valve.

Advancing the two-way valvulotome proximate to the valve may comprise advancing the two-way valvulotome in a direction opposite native fluid flow. Advancing the two-way valvulotome proximate to the valve may comprise advancing the two-way valvulotome in a direction of native fluid flow. Advancing the two-way valvulotome proximate to the valve may comprise advancing the two-way valvulotome proximal to the valve. Advancing the two-way valvulotome proximate to the valve may comprise advancing the two-way valvulotome distal to the valve.

In some embodiments, a catheter for capturing a guidewire comprises, or alternatively consists essentially of, a catheter body, a capture element, and a guidewire lumen in communication with the capture element.

The capture element may be configured to deploy from a distal end of the catheter body. The capture element may be configured to deploy from a side of the catheter body. The capture element may have a collapsed state and an expanded state. The capture element may comprise shape memory material configured to change to the expanded state at body temperature. The capture element may have an angle between 110° and 150° in the expanded state. The guidewire lumen may comprise an expanded portion proximate to the capture element. The catheter may further comprise an expandable element configured to expand the capture element. The expandable element may comprise an inflatable member. The catheter body may comprise an inflation lumen in fluid communication with the inflatable member. The expandable element may be movable relative to the catheter body.

In some embodiments, a method of making valves incompetent comprises, or alternatively consists essentially of, forming a fistula between a first vessel and a second vessel. The first vessel may be an artery. The second vessel may be a vein. Forming the fistula comprises inserting a first catheter into the first vessel. The first catheter comprises an ultrasound emitting transducer and a needle configured to radially extend from the first catheter. Forming the fistula further comprises inserting a second catheter into the second vessel. The second catheter comprises an ultrasound receiving transducer. Forming the fistula further comprises emitting an ultrasound signal from the ultrasound emitting transducer and after the ultrasound signal is received by the ultrasound receiving transducer, extending the needle from the first catheter. Extending the needle comprises exiting the first vessel, traversing interstitial tissue between the first vessel and the second vessel, and entering the second vessel. The method further comprises deploying a prosthesis at least partially in the fistula. After deploying the implantable prosthesis, blood is diverted from the first vessel to the second vessel through the prosthesis. The method further comprises making valves in the second vessel incompetent. Making the valves in the second vessel incompetent comprises using a reverse valvulotome to cut the valves and lining the second vessel with a stent.

The stent may comprise a covering or a graft. Lining the second vessel may comprise covering collateral vessels of the second vessel. The stent may be separate from the prosthesis. The stent may be spaced from the prosthesis along a length of the second vessel. The stent may be integral with the prosthesis.

In some embodiments, a method of making valves incompetent comprises, or alternatively consists essentially of, forming a fistula between a first vessel and a second vessel. Forming the fistula comprises inserting a catheter into the first vessel. The catheter comprises a needle configured to radially extend from the first catheter. Forming the fistula further comprises extending the needle from the first catheter. Extending the needle comprises exiting the first vessel, traversing interstitial tissue between the first vessel and the second vessel, and entering the second vessel. The method further comprises deploying a prosthesis at least partially in a fistula between a first vessel and a second vessel. After deploying the implantable prosthesis, blood is diverted from the first vessel to the second vessel through the prosthesis. The method further comprises making valves in the second vessel incompetent. Making the valves in the second vessel incompetent comprises at least one of using a reverse valvulotome to cut the valves, inflating a balloon, expanding a temporary stent, and lining the second vessel with an implantable stent.

The implantable stent may comprise a covering or a graft. Lining the second vessel may comprise covering collateral vessels of the second vessel. The implantable stent may be separate from the prosthesis. The implantable stent may be integral with the prosthesis. The first catheter may comprise an ultrasound emitting transducer. Forming the fistula may comprise inserting a second catheter into the second vessel, the second catheter comprising an ultrasound receiving transducer, emitting an ultrasound signal from the ultrasound emitting transducer, and extending the needle from the first catheter after the ultrasound signal is received by the ultrasound receiving transducer.

In some embodiments, a method of making valves incompetent comprises, or alternatively consists essentially of, deploying a prosthesis at least partially in a fistula between a first vessel and a second vessel. After deploying the implantable prosthesis, blood is diverted from the first vessel to the second vessel through the prosthesis. The method further comprises making valves in the second vessel incompetent.

Making the valves in the second vessel incompetent may comprise using a reverse valvulotome to cut the valves. Making the valves in the second vessel incompetent may comprise lining the second vessel with a stent. The stent may comprise a covering or a graft. Lining the second vessel may comprise covering collateral vessels of the second vessel. The stent may be separate from the prosthesis. The stent may be spaced from the prosthesis along a length of the second vessel. A proximal segment of the stent may longitudinally overlap a distal segment of the prosthesis. The stent may be integral with the prosthesis. Making the valves in the second vessel incompetent may comprise using a reverse valvulotome to cut the valves and lining the second vessel with a stent. Making the valves in the second vessel incompetent may comprise at least one of inflating a balloon and expanding a temporary stent. Making the valves in the second vessel incompetent may comprise inflating a balloon. Making the valves in the second vessel incompetent may comprise expanding a temporary stent.

In some embodiments, an implantable prosthesis for treating an occlusion in a first vessel comprises, or alternatively consists essentially of, a plurality of filaments woven together into a woven structure, a proximal end, a distal end, sidewalls between the proximal end and the distal end, a lumen defined by the sidewalls, and a porosity sufficient to direct fluid flow through the lumen substantially without perfusing through the sidewalls.

The porosity may be between about 0% and about 50%. The porosity may be between about 5% and about 50%. The prosthesis may be substantially free of graft material. The prosthesis may comprise a first longitudinal segment having the porosity and a second longitudinal segment having a second porosity different than the porosity. The second longitudinal segment may have a parameter different than the first longitudinal segment. The parameter may comprise at least one of braid angle, filament diameter, filament material, woven structure diameter, woven structure shape, and supplemental support structure. The prosthesis may further comprise a third longitudinal segment between the first longitudinal segment and the second longitudinal segment. The third longitudinal segment may have a parameter different than at least one of the first longitudinal segment and the second longitudinal segment. The parameter may comprise at least one of braid angle, filament diameter, filament material, woven structure diameter, woven structure shape, and supplemental support structure. The prosthesis may further comprise a supplemental support structure. The supplemental support structure may comprise a second plurality of filaments woven together into a second woven structure, the second plurality of filaments having a parameter different than the plurality of filaments. The parameter may comprise at least one of braid angle, filament diameter, woven structure diameter, and filament material. The supplemental support structure may comprise a cut hypotube. The plurality of filaments may comprise a filament comprising a shape memory material (e.g., nitinol) and a prosthesis comprising a biocompatible polymer (e.g., Dacron®, Kevlar®).

In some embodiments, an implantable prosthesis for treating an occlusion in a first vessel comprises, or alternatively consists essentially of, a proximal end, a distal end, sidewalls between the proximal end and the distal end, a lumen defined by the sidewalls, a first longitudinal section configured to anchor in a first cavity, a second longitudinal section configured to anchor in a second cavity, and a third longitudinal section between the first longitudinal section and the second longitudinal section. At least one of the first longitudinal section and the third longitudinal section comprises a porosity sufficient to direct fluid flow through the lumen substantially without perfusing through the sidewalls.

The porosity may be between about 0% and about 50%. The porosity may be between about 5% and about 50%. The prosthesis may be substantially free of graft material. The second longitudinal segment may have a parameter different than the first longitudinal segment. The parameter may comprise at least one of braid angle, filament diameter, filament material, diameter, shape, and supplemental support structure. The third longitudinal segment may comprise a second porosity different than the porosity. The first longitudinal segment may be balloon expandable. The second longitudinal segment may be self expanding. The prosthesis may comprise a plurality of filaments woven together into a woven structure. The plurality filaments may comprise a filament comprising a shape memory material (e.g., nitinol) and a prosthesis comprising a biocompatible polymer (e.g., Dacron®, Kevlar®). The third longitudinal section may have a parameter different than at least one of the first longitudinal section and the second longitudinal section. The parameter may comprise at least one of braid angle, filament diameter, filament material, diameter, shape, and supplemental support structure. The prosthesis may further comprise a supplemental support structure. The first longitudinal section may be substantially cylindrical and may have a first diameter, the second longitudinal section may be substantially cylindrical and may have a second diameter larger than the first diameter, and the third longitudinal section may be frustoconical and may taper from the first diameter to the second diameter. The first longitudinal section may be substantially cylindrical and may have a first diameter and the second longitudinal section and the third longitudinal section may be frustoconical and taper from the first diameter to a second diameter larger than the first diameter.

In some embodiments, an implantable prosthesis for treating an occlusion in a first vessel comprises a plurality of filaments woven together into a woven structure, a proximal end, a distal end, sidewalls between the proximal end and the distal end, a lumen defined by the sidewalls, and a porosity between about 5% and about 50%.

The porosity may be configured to direct fluid flow substantially through the lumen. The prosthesis may comprise a first longitudinal segment having the porosity and a second longitudinal segment having a second porosity different than the porosity.

In some embodiments, a kit comprises the prosthesis and a fistula formation system. The kit may further comprise a valve disabling device. In some embodiments, a kit comprises the prosthesis and a valve disabling device. The kit may comprising a prosthesis delivery system including the prosthesis. In some embodiments, a method comprises deploying the prosthesis in a fistula between the first vessel and a second vessel. The valve disabling device may comprise a reverse valvulotome. The valve disabling device may comprise a balloon. The valve disabling device may comprise a venous stent. The venous stent may comprise a covering or graft. The venous stent may be integral with the prosthesis.

In some embodiments, a method of diverting fluid flow from a first vessel to a second vessel in which the first vessel comprises an occlusion comprises deploying a prosthesis at least partially in a fistula between the first vessel and the second vessel. The prosthesis comprises a plurality of filaments woven together into a woven structure comprising a porosity less than about 50%. After deploying the implantable prosthesis, blood may be diverted from the first vessel to the second vessel through the prosthesis.

The first vessel may be an artery. The vessel passage may be a vein. The method may comprise dilating the fistula. The first vessel may be substantially parallel to the second vessel. Deploying the prosthesis may comprise allowing the prosthesis to self-expand. Deploying the prosthesis may comprise balloon expanding the prosthesis. Deploying the prosthesis may comprise deploying the woven structure and deploying a supplemental support structure. Deploying the supplemental support structure may be before deploying the woven structure. Deploying the supplemental support structure may be after deploying the woven structure. The supplemental support structure may comprise a second plurality of filaments woven into a second woven structure. The supplemental support structure may comprise cut hypotube. The method may further comprise forming the fistula. Forming the fistula may comprise inserting a launching catheter into the first vessel and inserting a target catheter into the second vessel. The launching catheter may comprise an ultrasound emitting transducer and a needle configured to radially extend from the launching catheter. The target catheter may comprise an ultrasound receiving transducer. Forming the fistula may comprise emitting an ultrasound signal from the ultrasound emitting transducer, during emitting the ultrasound signal and until the ultrasound signal may be received by the ultrasound receiving transducer, at least one of rotating the launching catheter and longitudinally moving the launching catheter, and after the ultrasound signal is received by the ultrasound receiving transducer, extending the needle from the launching catheter, wherein extending the needle comprises exiting the first vessel, traversing interstitial tissue between the first vessel and the second vessel, and entering the second vessel. The method may further comprise making valves in the second vessel incompetent. Making valves in the second vessel incompetent may comprise using a reverse valvulotome to cut the valves. Making valves in the second vessel incompetent may comprise inflating a balloon. Making valves in the second vessel incompetent may comprise expanding a stent. Making valves in the second vessel incompetent may comprise lining the second vessel with a stent. The stent may comprise a covering or a graft. Lining the second vessel may comprise covering collateral vessels of the second vessel. The stent may be separate from the prosthesis. The stent may be spaced from the prosthesis along a length of the second vessel. An end of the stent may abut an end of the prosthesis. A portion of the stent may longitudinally overlap a portion of the prosthesis. The portion of the stent may be radially inward of the portion of the prosthesis. The method may comprise expanding the stent after deploying the prosthesis. The portion of the prosthesis may be radially inward of the portion of the stent. The method may comprise expanding the stent before deploying the prosthesis. The stent may be integral with the prosthesis.

In some embodiments, an implantable prosthesis for maintaining patency of an anastomosis between an artery and a vein in a lower extremity comprises a first section configured to reside in a lower extremity artery, a second section configured to reside in a lower extremity vein, and a third section longitudinally between the first section and the second section. The third section is configured to maintain patency of an anastomosis between the artery and the vein.

The first section may be configured to appose the walls of the lower extremity artery. The first section may comprise barbs. The second section may be configured to appose the walls of the lower extremity vein. The second section may comprise barbs. At least one of the first section, the second section, and the third section may be self-expanding. At least one of the first section, the second section, and the third section may be balloon expandable. A length of the second section may be greater than a length of the first section. The second section may be configured to disable valves the lower extremity vein. The second section may be configured to cover collateral vessels of the lower extremity vein.

In some embodiments, a method of diverting fluid flow from a first vessel to a second vessel in a lower extremity comprises forming an aperture between the first vessel and the second vessel, and expanding the aperture to form an anastomosis.

Forming the aperture may comprise forcing a wire from the first blood vessel into the second blood vessel. Forming the aperture may comprise traversing a needle from the first blood vessel into the second blood vessel. Expanding the aperture may comprise dilating the aperture using at least one balloon. Dilating the aperture may comprise using a plurality of balloons having progressively higher diameters. A first balloon of the plurality of balloons may have a diameter of about 1.5 mm and wherein a last balloon of the plurality of balloons may have a diameter of about 3 mm. The plurality of balloons may comprise a first balloon having a diameter of about 1.5 mm, a second balloon having a diameter of about 2.0 mm, a third balloon having a diameter of about 2.5 mm, and a third balloon having a diameter of about 3.0 mm. Dilating the aperture using the plurality of balloons may comprise using progressively higher balloon inflation pressures. The method may not include (e.g., be devoid of or free from) placing a prosthesis (e.g., without use of a stent, graft, scaffolding, or other prosthesis). Positions of the first vessel and the second vessel may be substantially maintained by anatomy surrounding the first vessel and the second vessel. The method may further comprise placing a prosthesis in the anastomosis. Placing the prosthesis in the anastomosis may comprise anchoring the prosthesis in at least one of the first vessel and the second vessel. The first vessel may comprise a lateral plantar artery. The second vessel may comprise a lateral plantar vein.

In some embodiments, a catheter for capturing a guidewire comprises, or alternatively consists essentially of, a sheath and an expandable element. The expandable element has a collapsed state when in the sheath and an expanded state when out of the sheath. The expandable element comprises a plurality of cells configured to snare a guidewire.

The catheter may further comprise a guidewire sheath extending through the sheath and the expandable element. A proximal end of the expandable element may be coupled to the guidewire sheath. The expandable element may be configured to expand a vessel upon deployment. The expandable element may be visible under fluoroscopy. The expandable element may comprise struts defining the plurality of cells. The struts may be deflectable if contacted by a needle. The catheter may further comprise an ultrasound receiving transducer. The ultrasound receiving transducer may be distal to the expandable element. The ultrasound receiving transducer may be longitudinally between a proximal end of the expandable element and a distal end of the expandable element. The ultrasound receiving transducer may be proximal to the expandable element. A method of capturing a guidewire may comprise inserting the catheter into a first vessel, expanding the expandable element to the expanded state in the first vessel, and extending a needle from a second vessel, through interstitial tissue, and into the first vessel between the proximal end of the expandable element and the distal end of the expandable element. Extending the needle may comprise extending through a cell of the plurality of cells. The method may further comprise extending a guidewire through the needle and into the expandable element and collapsing the expandable element towards the collapsed state. Collapsing the expandable element may comprise snaring the guidewire.

In some embodiments, a method of capturing a guidewire comprises, or alternatively consists essentially of, expanding an expandable element to an expanded state in a first vessel, and extending a needle from a second vessel, through interstitial tissue, and into the first vessel between a proximal end of the expandable element and a distal end of the expandable element. The expandable element comprises a plurality of cells. Extending the needle comprises extending through a cell of the plurality of cells. The method further comprises extending a guidewire through the needle and into the expandable element and collapsing the expandable element towards a collapsed state. Collapsing the expandable element comprises snaring the guidewire.

Collapsing the expandable element may comprise twisting the expandable element. Expanding the expandable element may comprise expanding the first vessel. Extending the needle may comprise targeting the expandable element under fluoroscopy. The method may further comprise proximally retracting the expandable element. Proximally retracting the expandable element may comprise routing the guidewire through the first vessel.

In some embodiments, a device for deploying a tubular structure comprises, or alternatively consists essentially of, a handle body, a knob, and a slider. The handle body comprises a first segment comprising threads, a second segment longitudinally adjacent and proximal to the first segment, and a longitudinal slot. The second segment is free of threads. The knob comprises threads. The knob is at a distal end of the first segment in a starting position. The slider is operably connected to the knob. The slider is coupled to a sheath. The knob is configured to rotate proximally about the handle body for the first segment and is configured to proximally slide along the handle body for the second segment. The slider is configured to proximally retract the sheath a first amount during rotating the knob and is configured to proximally retract the sheath a second amount during sliding the knob. The device is configured to fully deploy the tubular structure after the sheath is retracted the second amount.

The first amount may be less than the second amount. The first amount may be between 10% and 50% of the second amount. The tubular structure may comprise a stent. The tubular structure may comprise a stent-graft.

In some embodiments, a method of deploying a tubular structure comprises, or alternatively consists essentially of, rotating a knob about a handle body. Rotating the knob about the handle body comprises proximally retracting a sheath and deploying a first amount of the tubular structure. The method further comprises, after rotating the knob about the handle body, proximally sliding the knob along the handle body. Proximally sliding the knob along the handle body comprises proximally retracting the sheath deploying a second amount of the tubular structure. The first amount and the second amount are the full amount of the tubular structure.

The first amount may be less than the second amount. The first amount may be between 10% and 50% of the second amount. The tubular structure may comprise a stent. The tubular structure may comprise a stent-graft.

In some embodiments, a device for deploying a tubular structure comprises, or alternatively consists essentially of, a sheath, a handle body, a knob comprising a worm gear comprising teeth, and a slider coupled to the sheath. The slider comprises a first portion in the handle body, a second portion outside the handle body; and a worm screw comprising teeth configured to interact with the teeth of the worm gear. The slider is configured to proximally retract the sheath a first amount during rotating the knob and is configured to proximally retract the sheath a second amount during sliding the slider. The device is configured to fully deploy the tubular structure after the sheath is retracted the second amount.

The first amount may be less than the second amount. The first amount may be between 10% and 50% of the second amount. The tubular structure may comprise a stent. The tubular structure may comprise a stent-graft. The handle body may comprise a longitudinal slot. The slider may comprise a third portion extending through the longitudinal slot. The handle body may comprise a second longitudinal slot. The slider may comprise a fourth portion outside the handle body and a fifth portion extending through the second longitudinal slot. The fourth portion may be on an opposite side of the handle body than the second portion. The handle body may comprise a shell at least partially covering the second portion of the slider until the sheath may be proximally retracted the first amount.

In some embodiments, a method of deploying a tubular structure comprises, or alternatively consists essentially of, rotating a knob. Rotating the knob comprises proximally retracting a sheath and deploying a first amount of the tubular structure. The method further comprises, after rotating the knob, proximally sliding a slider along a handle body. Proximally sliding the slider along the handle body comprises proximally retracting the sheath a second distance and deploying a second amount of the tubular structure. The first amount and the second amount are the full amount of the tubular structure.

The first amount may be less than the second amount. The first amount may be between 10% and 50% of the second amount. The tubular structure may comprise a stent. The tubular structure may comprise a stent-graft. The knob may comprise a worm gear comprising teeth. The slider may comprise a worm screw comprising teeth configured to interact with the teeth of the worm gear. The handle body may comprise a longitudinal slot. The slider may comprise a first portion in the handle body, a second portion outside the handle body, and a third portion extending through the longitudinal slot. The handle body may comprise a second longitudinal slot. The slider may comprise a fourth portion outside the handle body and a fifth portion extending through the second longitudinal slot. The fourth portion may be on an opposite side of the handle body than the second portion. Proximally retracting the slider may comprise gripping the second portion and the fourth portion. The handle body may comprise a shell at least partially covering the second portion of the slider until the sheath may be proximally retracted the first amount. An axis of rotation of the knob may be transverse to a longitudinal axis of the handle body.

In some embodiments, a method of accessing a tibial vein of a subject comprises, or alternatively consists essentially of, positioning a first tourniquet above a knee of a leg, positioning a second tourniquet above an ankle of the leg, injecting a quantity of contrast through a metatarsal vein, and using fluoroscopy to prepare a venogram to image veins of a foot of the leg.

The first tourniquet may be a different type than the second tourniquet. The first tourniquet may be a same type as the second tourniquet. The first tourniquet may be a same size as the second tourniquet. The first tourniquet may be a different size than the second tourniquet. The method may further comprise positioning the subject in a reverse Trendelenburg position. The method may further comprise, after injecting the quantity of contrast through the metatarsal vein, flattening the subject. The contrast may comprise non-ionic contrast. The contrast may comprise a mixture of contrast material and saline. The contrast may comprise a 50/50 dilution of the contrast material and the saline. The quantity of contrast may comprise between 5 mL and 50 mL. The metatarsal vein may be a dorsal metatarsal vein. The metatarsal vein may be a plantar metatarsal vein. The method may further comprise palpating the metatarsal vein. The method may further comprise selecting the tibial vein using the venogram. The method may further comprise advancing a guidewire to the target tibial vein. The method may further comprise removing the second tourniquet. The method may further comprise tracking a functional catheter over the guidewire. The functional catheter may comprise a catheter for forming a fistula (e.g., a target catheter, a launching catheter). The functional catheter may comprise snare.

In some embodiments, a method of accessing a lateral plantar vein of a subject comprises, or alternatively consists essentially of, positioning a first tourniquet above an ankle of a leg, placing a needle in a dorsal medial marginal vein towards toes of a foot of the leg, advancing a first guidewire into a first metatarsal vein of the foot, injecting a quantity of contrast, and using fluoroscopy to prepare a venogram to image veins of a foot of the leg.

The contrast may comprise non-ionic contrast. The contrast may comprise a mixture of contrast material and saline. The contrast may comprise a 50/50 dilution of the contrast material and the saline. The quantity of contrast may comprise between 5 mL and 50 mL. The method may further comprise selecting a larger to two lateral plantar veins using the venogram. The method may further comprise advancing the first guidewire to at least one of a crossing point or above the ankle and using ultrasound to survey veins on a bottom of the foot to view a position of the first guidewire. The method may further comprise advancing the first guidewire to at least one of a crossing point or above the ankle, using ultrasound to survey veins on a bottom of the foot to view a position of the first guidewire, and accessing a lateral plantar vein containing the first guidewire of the foot as distal as possible in a plantar arch of the foot at a second access site. The method may further comprise advancing a second guidewire into the lateral plantar vein. The method may further comprise advancing the second guidewire into a posterior tibial vein and up to a crossing point. The method may further comprise removing the first guidewire. The method may further comprise removing the tourniquet. The method may further comprise tracking a functional catheter over the guidewire. The functional catheter may comprise a catheter for forming a fistula (e.g., a target catheter, a launching catheter). The functional catheter may comprise a snare.

In some embodiments, a method of performing an ascending venogram procedure comprises, or alternatively consists essentially of, injecting a quantity of contrast into venous vasculature from a first metatarsal vein.

In some embodiments, a method of performing a descending venogram procedure comprises, or alternatively consists essentially of, injecting a quantity of contrast into venous vasculature from a great saphenous vein towards a foot.

In some embodiments, a method of aligning a catheter for a venous arterialization procedure comprises inserting a first catheter in a first vessel. The first catheter comprises a needle aperture on a first side of the needle, a radiopaque marker being distal to the needle aperture and being on a second side of the first catheter opposite the first side, and a needle configured to extend through the needle aperture. The radiopaque marker is visible under fluoroscopy. The method further comprises inserting a second catheter in a second vessel. The second catheter comprises a balloon. The method further comprises expanding the balloon. Expanding the balloon comprises inflating the balloon with radiopaque material visible under fluoroscopy. The method further comprises longitudinally advancing the first catheter until the radiopaque marker is proximate the second catheter in the second vessel, and aligning the needle aperture of the first catheter with the second catheter. Aligning the needle aperture comprising rotating the first catheter in the first vessel such that the radiopaque marker transitions between a first position and a second position. The method further comprises monitoring rotation of the radiopaque marker towards the second position to confirm rotational alignment of the needle aperture with the second catheter, and after confirming rotational alignment, extending the needle out of the needle aperture of the first catheter. Extending the needle comprises exiting the first vessel, traversing interstitial tissue between the first vessel and the second vessel, and entering the second vessel.

The method may further comprise extending a guidewire through the needle and into the second vessel, and entangling the guidewire in the second catheter in the second vessel. Entangling the guidewire may comprise closing an expandable member of the second catheter. The method may further comprise, after extending the guidewire, moving the second catheter to detect corresponding movement of the guidewire to confirm entanglement of the guidewire in the second catheter. The method may further comprise moving the second catheter to move the guidewire through the second vessel. Moving the second catheter to move the guidewire through the second vessel may comprise exiting the second vessel at a location in a foot.

In some embodiments, a method of aligning a catheter for a venous arterialization procedure comprises inserting a first catheter in a first vessel. The first catheter comprises a radiopaque marker, and a needle extendable along an extension path. The method further comprises inserting a second catheter in a second vessel. The second catheter comprises an expandable member. The expandable member comprises a radiopaque material visible under fluoroscopy. The method further comprises expanding the expandable member, and aligning the needle of the first catheter with the second catheter. Aligning the needle comprises rotating the first catheter in the first vessel such that the radiopaque marker transitions between a first position and a second position. The method further comprises monitoring the rotation of the radiopaque marker towards the second position to confirm rotational alignment of the needle extension path with the second catheter, and after confirming rotational alignment, extending the needle out of the first catheter and along the extension path. Extending the needle comprises exiting the first vessel, traversing interstitial tissue between the first vessel and the second vessel, and entering the second vessel.

The method may further comprise extending a guidewire through the needle and into the second vessel. Extending the guidewire may comprise entangling the guidewire in the expandable member of the second catheter. The method may further comprise retracting the expandable member through the second vessel. Retracting the expandable member may comprise advancing the guidewire through the second vessel. Entangling the guidewire may comprise closing an expandable member of the second catheter. The radiopaque marker may be on a side of the first catheter opposite the needle extension path. The radiopaque marker may be distal to a needle exit aperture. The second catheter may comprise a balloon. The balloon may be inflated with the radiopaque material.

In some embodiments, a method of aligning a catheter for a venous arterialization procedure comprises inserting a first catheter in a first vessel. The first catheter comprises a radiopaque marker, and a needle. The method further comprises inserting a second catheter in a second vessel. The second catheter comprises an expandable member. The method further comprises expanding the expandable member. The expanded expandable member comprises radiopaque material. The method further comprises aligning an extension path of the needle with the second vessel using the radiopaque marker and the radiopaque material, and extending the needle out of the first vessel, through interstitial tissue between the first vessel and the second vessel, and into the second vessel.

The method may further comprise extending a guidewire through the needle and into the second vessel, and entangling the guidewire in the second catheter. Entangling the guidewire may comprise closing the expandable member. The method may further comprise moving the second catheter to move the guidewire through the second vessel. Aligning the extension path of the needle with the second vessel may comprise rotating the first catheter in the first vessel such that the radiopaque marker transitions between a first position and a second position. The first position may comprise a first thickness visible under fluoroscopy. The second position may comprise a second thickness visible under fluoroscopy. The first thickness may be different than the second thickness. The first catheter may comprise a needle aperture on a first side. The radiopaque marker may be on a second side of the first catheter opposite the first side. The first catheter may comprise a needle aperture proximal to the radiopaque marker. The expandable member may comprise a balloon. Expanding the expandable member may comprise inflating the balloon with the radiopaque material.

In some embodiments, a method of accessing a tibial vein of a subject comprises positioning the subject in a reverse Trendelenburg position, positioning a first tourniquet above a knee of a leg, positioning a second tourniquet above an ankle of the leg, injecting a quantity of contrast through a metatarsal vein, after injecting the quantity of contrast through the metatarsal vein, flattening the subject, using fluoroscopy to prepare a venogram to image veins of a foot of the leg, selecting the tibial vein using the venogram, advancing a guidewire to the selected tibial vein, removing the second tourniquet, tracking a functional catheter over the guidewire, snaring a second guidewire extending from an artery using the functional catheter, retracting the second guidewire out of the foot, and tracking a second functional catheter over the second guidewire. The metatarsal vein may be a dorsal metatarsal vein. The metatarsal vein may be a plantar metatarsal vein. The functional catheter may comprise a catheter for forming a fistula (e.g., a target catheter, a launching catheter). The second functional catheter may comprise a valve disabling device. The valve disabling device may comprise a valvulotome. The valve disabling device may comprise a cutting balloon. The valve disabling device may comprise an atherectomy device.

In some embodiments, a method of accessing a tibial vein of a subject comprises injecting a quantity of contrast through a metatarsal vein, using fluoroscopy to prepare a venogram to image veins of a foot of the leg, selecting the tibial vein using the venogram, advancing a guidewire to the selected tibial vein, tracking a functional catheter over the guidewire, extending a second guidewire from an artery into the tibial vein, snaring the second guidewire using the functional catheter, retracting the second guidewire out of the foot, and tracking a second functional catheter over the second guidewire.

The metatarsal vein may be a dorsal metatarsal vein. The metatarsal vein may be a plantar metatarsal vein. The functional catheter may comprise a catheter for forming a fistula (e.g., a target catheter, a launching catheter). The second functional catheter may comprise a valve disabling device. The valve disabling device may comprise a valvulotome. The valve disabling device may comprise a cutting balloon. The valve disabling device may comprise an atherectomy device.

In some embodiments, a method of accessing a tibial vein of a subject comprises injecting a quantity of contrast through a metatarsal vein, using fluoroscopy to prepare a venogram to image veins of a foot of the leg, selecting the tibial vein using the venogram, advancing a guidewire to the selected tibial vein, and tracking a functional catheter over the guidewire.

The metatarsal vein may be a dorsal metatarsal vein. The metatarsal vein may be a plantar metatarsal vein. The functional catheter may comprise an element configured to snare a guidewire. The method may further comprise snaring a second guidewire extending from an artery using the functional catheter, and retracting the second guidewire. The method may further comprise tracking a second functional catheter over the second guidewire. The functional catheter may comprise a catheter for forming a fistula (e.g., a target catheter, a launching catheter). The second functional catheter may comprise a valve disabling device. The valve disabling device may comprise a valvulotome. The valve disabling device may comprise a cutting balloon. The valve disabling device may comprise an atherectomy device.

In some embodiments, a cutting snare system comprises or consists essentially of a snaring structure, and a valvulotome structure.

The system may further comprise an outer sheath. The snaring structure and the valvulotome structure may be exchangeable in the outer sheath. The valvulotome structure may be proximal to the snaring structure. The snaring structure may be configured to extend from a distal end of the outer sheath. The valvulotome structure may be monolithic with the snaring structure. The outer sheath may comprise a plurality of apertures. The valvulotome structure may be configured to extend from the outer sheath laterally through the plurality of apertures. The snaring structure may comprise a plurality of cells configured to receive a guidewire. The snaring structure may comprise a plurality of struts configured to snare a guidewire. The snaring structure may comprise a plurality of wires configured to snare a guidewire. The valvulotome structure may be proximal to the snaring structure. The valvulotome structure may be distal to the snaring structure. The valvulotome structure may be monolithic with the snaring structure. The snaring structure may have a first diameter and the valvulotome structure may have a second diameter smaller than the first diameter. The snaring structure may be configured to evert into the valvulotome structure upon application of a longitudinal force to the snaring structure. The valvulotome structure may be separate from the snaring structure. The valvulotome structure may be configured to telescope in the snaring structure. The snaring structure may be configured to telescope in the valvulotome structure. The valvulotome structure may comprise an expandable member configured to apply radially outward force to the snaring structure. The valvulotome structure may comprise a plurality of blades. The plurality of blades may comprise between two blades and eight blades. The plurality of blades may comprise three blades. The plurality of blades may comprise four blades. The plurality of blades may face proximally. The plurality of blades may face distally. The plurality of blades may face proximally and distally.

In some embodiments, a cutting snare system comprises or consists essentially of a snaring structure comprising a plurality of cells configured to receive a guidewire, a valvulotome structure comprising between two proximally facing blades and eight proximally facing blades, and an outer sheath. The snaring structure and the valvulotome structure are expandable from the outer sheath. The valvulotome structure may be monolithic with the snaring structure.

In some embodiments, a method of accessing a plantar vein of a subject comprises positioning the subject in a reverse Trendelenburg position, positioning a first tourniquet above a knee of a leg, positioning a second tourniquet above an ankle of the leg, injecting a quantity of contrast through a metatarsal vein, after injecting the quantity of contrast through the metatarsal vein, flattening the subject, using fluoroscopy to prepare a venogram to image veins of a foot of the leg, selecting the plantar vein using the venogram, advancing a guidewire to the selected plantar vein, removing the second tourniquet, tracking a functional catheter over the guidewire, snaring a second guidewire extending from an artery using the functional catheter, retracting the second guidewire out of the foot, and tracking a second functional catheter over the second guidewire.

The metatarsal vein may be a dorsal metatarsal vein. The metatarsal vein may be a plantar metatarsal vein. The functional catheter may comprise a catheter for forming a fistula (e.g., a target catheter, a launching catheter). The second functional catheter may comprise a valve disabling device. The valve disabling device may comprise a valvulotome. The valve disabling device may comprise a cutting balloon. The valve disabling device may comprise an atherectomy device.

In some embodiments, a method of accessing a plantar vein of a subject comprises injecting a quantity of contrast through a metatarsal vein, using fluoroscopy to prepare a venogram to image veins of a foot of the leg, selecting the plantar vein using the venogram, advancing a guidewire to the selected plantar vein, tracking a functional catheter over the guidewire, extending a second guidewire from an artery into the plantar vein, snaring the second guidewire using the functional catheter, retracting the second guidewire out of the foot, and tracking a second functional catheter over the second guidewire.

The metatarsal vein may be a dorsal metatarsal vein. The metatarsal vein may be a plantar metatarsal vein. The functional catheter may comprise a catheter for forming a fistula (e.g., a target catheter, a launching catheter). The second functional catheter may comprise a valve disabling device. The valve disabling device may comprise a valvulotome. The valve disabling device may comprise a cutting balloon. The valve disabling device may comprise an atherectomy device.

In some embodiments, a method of accessing a plantar vein of a subject comprises injecting a quantity of contrast through a metatarsal vein, using fluoroscopy to prepare a venogram to image veins of a foot of the leg, selecting the plantar vein using the venogram, advancing a guidewire to the selected plantar vein, and tracking a functional catheter over the guidewire.

The metatarsal vein may be a dorsal metatarsal vein. The metatarsal vein may be a plantar metatarsal vein. The functional catheter may comprise an element configured to snare a guidewire. The method may further comprise snaring a second guidewire extending from an artery using the functional catheter, and retracting the second guidewire. The method may further comprise tracking a second functional catheter over the second guidewire. The functional catheter may comprise a catheter for forming a fistula (e.g., a target catheter, a launching catheter). The second functional catheter may comprise a valve disabling device. The valve disabling device may comprise a valvulotome. The valve disabling device may comprise a cutting balloon. The valve disabling device may comprise an atherectomy device.

In some embodiments, a method of accessing a plantar vein of a subject comprises positioning the subject in a reverse Trendelenburg position, positioning a first tourniquet above a knee of a leg, positioning a second tourniquet above an ankle of the leg, injecting a quantity of contrast through a metatarsal vein, after injecting the quantity of contrast through the metatarsal vein, flattening the subject, using fluoroscopy to prepare a venogram to image veins of a foot of the leg, selecting the plantar vein using the venogram, advancing a guidewire to the selected plantar vein, removing the second tourniquet, tracking a functional catheter over the guidewire, snaring a second guidewire extending from a vein using the functional catheter, retracting the second guidewire out of the foot, and tracking a second functional catheter over the second guidewire.

The metatarsal vein may be a dorsal metatarsal vein. The metatarsal vein may be a plantar metatarsal vein. The functional catheter may comprise a catheter for forming a fistula. The second functional catheter may comprise a valve disabling device. The valve disabling device may comprise a valvulotome.

In some embodiments, a method of accessing a tibial vein of a subject comprises positioning a first tourniquet above a knee of a leg, positioning a second tourniquet above an ankle of the leg, injecting a quantity of contrast through a metatarsal vein, using fluoroscopy to prepare a venogram to image veins of a foot of the leg, selecting the tibial vein using the venogram, comprising advancing a guidewire to the selected tibial vein, removing the second tourniquet, and tracking a functional catheter over the guidewire. The first tourniquet may be a different type than the second tourniquet.

In some embodiments, a method of aligning a catheter comprises positioning a first catheter in a first vessel and positioning the catheter in a second vessel. The first catheter comprises radiopaque material. The catheter comprises a flat rectangular radiopaque marker. The method further comprises rotating an imaging system until the first catheter and the catheter are in an imaging plane. Rotating the imaging system comprises drawing a first centerline over the first catheter, drawing a second centerline over the catheter, maximizing a distance between the first centerline and the second centerline, and creating a signal that the first catheter and the catheter are in the imaging plane. The method further comprises rotating the catheter until a thickness of the flat rectangular radiopaque marker is at a minimum. Rotating the catheter comprises drawing a first line along a first long edge of the flat rectangular radiopaque marker, drawing a second line along a second long edge of the flat rectangular radiopaque marker opposite the first long edge, minimizing a distance between the first long line and the second line, and creating a signal that the thickness is at the minimum. The method further comprises extending a needle the imaging plane from the catheter in the second vessel, out of the second vessel, and into the first vessel.

In some embodiments, a method of aligning a catheter comprises positioning a first catheter in a first vessel and positioning the catheter in a second vessel. The first catheter comprises radiopaque material. The catheter comprises a radiopaque marker. The method further comprises rotating an imaging system until the first catheter and the catheter are in an imaging plane and rotating the catheter until a thickness of the radiopaque marker is at a minimum. Rotating the catheter comprises creating a signal that the thickness is at the minimum.

In some embodiments, a method of aligning a catheter comprises positioning the catheter comprising a radiopaque marker in a vessel and rotating the catheter until a thickness of the radiopaque marker is at a minimum. Rotating the catheter may comprise creating a signal that the thickness is at the minimum.

In some embodiments, a method of aligning a first vessel and a second vessel in an imaging plane comprises a first catheter in the first vessel and positioning a second catheter in the second vessel. The first catheter comprises radiopaque material. The second catheter comprises a radiopaque marker. The method further comprises rotating an imaging system until the first catheter and the second catheter are in an imaging plane. Rotating the imaging system comprises drawing a first centerline over the first catheter, drawing a second centerline over the second catheter, maximizing a distance between the first centerline and the second centerline, and creating a signal that the first catheter and the catheter are in the imaging plane.

In some embodiments, a method of aligning a catheter comprises injecting contrast into a first vessel, injecting contrast into a second vessel, and rotating an imaging system until the first vessel and the second vessel are in an imaging plane. Rotating the imaging system comprises drawing a first line along the first vessel, drawing a second line along the second vessel, maximizing an area between the first line and the second line, and creating a signal that the first vessel and the second vessel are in the imaging plane. The method further comprises positioning the catheter in the second vessel. The catheter comprises a flat rectangular radiopaque marker. The method further comprises rotating the catheter until a thickness of the flat rectangular radiopaque marker is at a minimum. Rotating the second catheter comprises drawing a first line along a first long edge of the flat rectangular radiopaque marker, drawing a second line along a second long edge of the flat rectangular radiopaque marker opposite the first long edge, minimizing a distance between the first long line and the second line, and creating a signal that the thickness is at the minimum. The method further comprises extending a needle the imaging plane from the catheter in the second vessel, out of the second vessel, and into the first vessel.

In some embodiments, a method of aligning a catheter comprises injecting contrast into a first vessel, injecting contrast into a second vessel, and rotating an imaging system until the first vessel and the second vessel are in an imaging plane. Rotating the imaging system comprises drawing a first line along the first vessel, drawing a second line along the second vessel, maximizing an area or distance between the first line and the second line, and creating a signal that the first vessel and the second vessel are in the imaging plane. The method further comprises positioning the catheter in the second vessel.

In some embodiments, a method of aligning a first vessel and a second vessel in an imaging plane comprises injecting contrast into the first vessel, injecting contrast into the second vessel, and rotating an imaging system until the first vessel and the second vessel are in the imaging plane.

In some embodiments, a method of aligning a catheter comprises positioning a first catheter in a first vessel and positioning the catheter in a second vessel. The catheter comprises a radiopaque marker. The method further comprises rotating the catheter until a thickness of the radiopaque marker is at a minimum, and creating a signal that the thickness is at the minimum.

In some embodiments, a method of aligning a catheter comprises positioning a first catheter in a first vessel and positioning the catheter in a second vessel. The catheter comprises a radiopaque marker. The method further comprises rotating the catheter until a thickness of the radiopaque marker is less than a value and creating a signal that the thickness is less than the value. The value may be less than 3 mm. The value may be less than 1 mm. The value may be less than 10 µm.

In some embodiments, a method of increasing blood perfusion to a distal extremity through retrograde flow through a venous system comprises diverting blood from an artery to a first vein and establishing a blood flow loop between the first vein and a second vein.

The distal extremity may comprise a foot. The distal extremity may comprise a hand. The distal extremity may comprise toes. The distal extremity may comprise fingers. The artery may be a posterior tibial artery. The first vein may be a medial plantar vein. The second vein may be an anterior tibial vein. The second vein may be a lateral plantar vein. The first vein may be on a first side of a dorsal venous arch and the second vein may be on a second side of the dorsal venous arch.

Establishing the blood flow loop may comprise disabling valves in at least one of the first vein or the second vein. Disabling the valves in the at least one of the first vein or the second vein may comprise using a valvulotome. Disabling the valves in the at least one of the first vein or the second vein may comprise using a balloon. Disabling the valves in the at least one of the first vein or the second vein may comprise using a stent. The stent may inhibit perfusion through sidewalls into branch vessels.

The method may comprise establishing a second blood flow loop between either the first vein or the second vein and a third vein. The third vein may be a lateral plantar vein. Establishing the second blood flow loop may comprise disabling valves in the third vein. Disabling the valves in the third vein may comprise using a valvulotome. Disabling the valves in the third vein may comprise using a balloon. Disabling the valves in the third vein may comprise using a stent. The stent may inhibit perfusion through sidewalls into branch vessels. Establishing the second blood flow loop may be during a same interventional procedure. Establishing the second blood flow loop may be during a later interventional procedure.

The method may further comprise limiting an outflow in the venous system. Limiting the outflow in the venous system may comprise channeling blood past bifurcating veins or side branches.

The method may further comprise embolizing bifurcating veins or side branches. Embolizing the bifurcating veins or side branches may comprise using at least one of coils, microspheres, liquid embolics, or laser.

The method may further comprise applying external pressure to increase blood pressure in the distal extremity by limiting venous outflow. Applying the external pressure may comprise using at least one of a cuff, a tourniquet, or a wrap. Applying the pressure may be continuous. Applying the pressure may be intermittent.

The method may further comprise diverting blood from a second artery to at least one of the second vein, a third vein, or a fourth vein. Diverting the blood from the artery to the first vein does not include reentering the artery. The method may further comprise creating a fistula between an artery in the distal extremity and a vein in the distal extremity.

The method may further comprise creating flow loops for multiple vein targets. The multiple vein targets may include at least one vein in a first level the distal extremity and at least one vein in a second level of the distal extremity. The multiple vein targets may include veins between at least one vein in a first level the distal extremity and at least one vein in a second level of the distal extremity. The multiple vein targets may include perforators.

Establishing the blood flow loop may increase pressure in the blood flow loop. Increasing pressure in the blood flow loop may increase distality of blood perfusion to a limb comprising the distal extremity.

In some embodiments, a method of increasing blood perfusion to toes of a foot through retrograde flow through a venous system comprises diverting blood from an artery to a first vein. Diverting the blood from the artery to the first vein does not include reentering the artery. The method further comprises establishing a blood flow loop between the first vein and a second vein. The first vein is on a first side of a dorsal venous arch and the second vein is on a second side of the dorsal venous arch. Establishing the blood flow loop comprises disabling valves in at least one of the first vein or the second vein using at least one of a valvulotome, a balloon, or a stent. The method further comprises limiting an outflow in the venous system by channeling blood past bifurcating veins or side branches. The method further comprises embolizing bifurcating veins or side branches using at least one of coils, microspheres, liquid embolics, or laser. The method further comprises applying external pressure to increase blood pressure in the distal extremity by limiting venous outflow using at least one of a cuff, a tourniquet, or a wrap.

In some embodiments, a device, system, kit, etc. for increasing blood perfusion to toes of a foot through retrograde flow through a venous system comprises, or alternatively consists essentially of, a first prosthesis configured to divert blood from an artery to a first vein, at least one of a valvulotome, a balloon, or a stent configured to disable valves to create a blood flow loop between the first vein and a second vein, a flow diverting stent configured to limit an outflow in the venous system by channeling blood past bifurcating veins or side branches, at least one of coils, microspheres, liquid embolics, or laser configured to embolize bifurcating veins or side branches, and at least one of a cuff, a tourniquet, or a wrap configured to apply external pressure to increase blood pressure in the foot by limiting venous outflow.

In some embodiments, devices, systems, kits, and methods for increasing blood perfusion to toes of a foot through retrograde flow through a venous system are described herein.

In some embodiments, devices, systems, kits, and methods for increasing blood perfusion to a distal extremity through retrograde flow through a venous system are described herein.

In some embodiments, a method of increasing blood perfusion to a distal extremity through retrograde flow through a venous system comprises establishing a blood flow loop between a first vein and a second vein.

In some embodiments, a device for diverting blood flow from a first vessel to a second vessel and maintaining blood flow in the first vessel comprises, or alternatively consists essentially of, a first segment and a second segment. The first segment is configured to anchor in the first vessel. The first segment comprises a window to allow blood to flow into the first segment, through the window, and distal in the first vessel. The second segment is configured to anchor in the second vessel. The second segment is configured to allow blood to flow into the first segment, through the second segment, and into the second vessel.

The first segment may comprise a stent structure. At least part of the stent structure may be uncovered. The second segment may comprise the stent structure. At least one parameter of the stent structure may be different between the first segment and the second segment. The parameter may comprise a cell pattern. The second segment may comprise a graft covering. The graft covering may be generally perpendicular to a longitudinal axis of the device. The graft covering may be at an angle to a longitudinal axis of the device. The angle may be between about 10° and about 70°. The first segment may comprise a graft covering. The graft covering of the first segment may comprise a V-shaped cutout. The first segment may be separately deployable from the second segment. The window may be formed during the manufacturing process. The window may be formed in situ. The first segment may comprise a puncturable graft. The first segment may comprise a stent structure configured to facilitate puncturing. The first segment may comprise a flap configured to open radially outward. The first segment may comprise a plurality of flaps configured to open radially outward. The first segment may comprise a branch configured to be positioned in a branch vessel of the first vessel. The first segment may comprise a plurality of slits configured to open upon bending of the first segment. The device may comprise a woven braid having variable porosity along its length. The first segment may comprise a portion having a first porosity configured to permit perfusion of blood through the portion. The second segment may comprise a portion having a second porosity configured to divert blood through the portion. The first porosity may be less than 75%. The second porosity may be greater than 60%. The device may further comprise an occlusive implant. The occlusive implant may comprise a tether configured to anchor in the second segment. The second segment may comprise a third segment configured to limit fluid flow through the device. The third segment may comprise a narrower diameter than the second segment. The first segment may comprise a flange.

In some embodiments, a method of forming a window in a device for diverting blood flow from a first vessel to a second vessel and maintaining blood flow in the first vessel comprises, or alternatively consists essentially of, implanting the device in the first vessel, extending through interstitial tissue, and into the second vessel, and inserting a guidewire through a bend in the device in the first vessel. The guidewire punctures graft material to form an opening.

The method may further comprise tracking a dilator over the guidewire to widen the opening. The dilator may have a curved tip. Inserting the guidewire through the bend may comprise exiting a catheter having an angled ramp surface. The catheter further may comprise a straight path. The method may further comprise tracking a balloon over the guidewire. The balloon may extend through the opening. The method may further comprise expanding the balloon. The expanded balloon may enlarge the opening. The method may further comprise anchoring the guidewire. Anchoring the guidewire may comprise expanding an anchoring balloon in the first vessel. Inserting the guidewire through the bend may comprise forming a plurality of openings. The method may further comprise positioning a radiopaque target outside the device and downstream of the device in the first vessel. The method may further comprise deploying a stent through the opening.

In some embodiments, a device for diverting blood flow from a first vessel to a second vessel and maintaining blood flow in the first vessel comprises, or alternatively consists essentially of, a first section comprising a stent structure including pores configured to allow blood to flow into the first section, through the pores, and distal in the first vessel and/or into the first section, through the first section, and distal in the first vessel, and a second section configured to allow blood to flow from the first vessel into the second section, through the second section, and into the second vessel.

A proximal end of the first section may be configured to be placed in the first vessel. A distal end of the first section may be configured to be placed in the second vessel. A proximal end of the first section may be configured to be placed in the first vessel. A distal end of the first section may be configured to be placed in the first vessel. A proximal end of the second section may be configured to be placed in the first vessel. A distal end of the second section may be configured to be placed in the second vessel. A length of the first section may be about the same as a length of the second section. A length of the first section may be different than a length of the second section. A diameter of the first section may be about the same as a diameter of the second section. A diameter of the first section may be different than a diameter of the second section. The second section may taper from a proximal end to a distal end. A proximal section of the first section may have a crescent shape. A distal section of the first section may have a round shape. A proximal end of the first section may be configured to anchor in the first vessel and may taper inwardly towards the distal end. The second section may extend from the distal end of the first section. The second segment may comprise a third segment configured to limit fluid flow through the device. The third segment may comprise a narrower diameter than the second segment. The first segment may comprise a flange.

In some embodiments, an implant comprises, or alternatively consists essentially of, a first part comprising an occlusive implant configured to occlude blood flow in a vessel and a second part tethered to the first part. The second part comprises an anchor configured to be coupled to a stent.

The occlusive implant may comprise at least one of an expandable mesh, a sponge, a plug, a coil, a plurality of coils, an embolic liquid, a hydrogel, microspheres, or an implantable balloon. The anchor may comprise a wire configured to form a coil upon release from a catheter.

In some embodiments, a device for diverting blood flow from a first vessel to a second vessel and maintaining blood flow in the first vessel comprises, or alternatively consists essentially of, a flare to be anchored in the first vessel and an elongate section extending from the flare. The elongate section is configured to be anchored in the second vessel.

The flare may be configured to minimally extend into the first vessel. The device may comprise a plurality of flares including the flare. The flares of the plurality of flares may be symmetrical. The flares of the plurality of flares may be asymmetrical. At least one flare of the plurality of flares may be longer than other flares of the plurality of flares. The at least one flare may be configured to be downstream of other flares in the first vessel. The flare may be covered. The flare may be uncovered. The elongate section may comprise a third segment configured to limit fluid flow through the device. The third segment may comprise a narrower diameter than the second segment.

In some embodiments, a device for diverting flow from branch vessels to perfuse a distal vessel comprises, or alternatively consists essentially of, a plurality of wires woven together to form a mesh structure. The mesh structure may have an expanded diameter between about 4 mm and about 8 mm. The mesh structure may have a porosity between about 60% and about 75%. The mesh structure may have a length between about 50 mm and about 150 mm. The expanded structure may have a braid angle between about 120° and about 179°. The mesh structure may have a compression resistance between about 0.4 N/mm and about 1.1 N/mm.

The mesh structure may have a frustoconical shape. The mesh structure may taper from the expanded diameter to a second expanded diameter. The second expanded diameter may be configured to be downstream of the expanded diameter. The mesh structure may have a chronic outward force between about 0.25 N/mm and about 0.6 N/mm. Each of the plurality of wires may have a diameter between about 50 µm and about 100 µm. Each of the plurality of wires may comprise shape memory material. The mesh structure may have a PPI between about 50 and about 150.

In some embodiments, a device for reducing turbulence in a vessel comprises, or alternatively consists essentially of, a first segment having a first diameter and configured to overlap a stent graft that may be stretching the vessel and a second segment tapering from the first diameter to a second diameter. The device is configured to stretch the vessel in a tapered manner to provide laminar flow through the device.

The diameter may be between about 2 mm and about 10 mm. The second diameter may be between about 1 mm and about 8 mm. The second segment may have a length between about 5 mm and about 100 mm. The second segment may have a porosity between about 60% and about 75%. The device may further comprise a first radiopaque marker at a proximal end of the first segment. The device may further comprise a second radiopaque marker at a transition between the first segment and the second segment.

In some embodiments, a device for limiting fluid flow through the device comprises, or alternatively consists essentially of, a first segment having a first diameter and configured to be anchored in a first vessel, a second segment, a third segment, a fourth segment, and a fifth segment having a second diameter and configured to be anchored in a second vessel. The third segment has a third diameter less than the first diameter and the second diameter. The third diameter is configured to limit fluid flow through the device. The second segment tapers from the first diameter to the third diameter. The fourth segment tapers from the third diameter to the second diameter.

The first segment may be configured to divert fluid flow from the first vessel into the second vessel. The first segment may be configured to allow fluid to continue to flow through the first vessel. The first segment may comprise a window. The first diameter may be less than the second diameter. The first diameter may be the same as the second diameter. The first segment may comprise a flange having a fourth diameter larger than the first diameter. The device may comprise a stent structure and a graft. At least part of the first segment may be devoid of the graft. The graft may have the third diameter in the third segment. The stent structure may have a fourth diameter larger than the third diameter in the third segment. The graft in the third segment may be configured to flex inwardly in response to changes in pressure. The graft in the third segment may be configured to flex outwardly in response to changes in pressure. The first segment may be configured to anchor in a P3 segment of a popliteal artery. The first segment may be configured to anchor in a tibioperoneal trunk. The first diameter may be between about 5 mm and about 7 mm. The first diameter may be between about 4 mm and about 6 mm. The second diameter may be between about 5 mm and about 7 mm. The third diameter may be between about 2.5 mm and about 5 mm. At least one of the second segment or the third segment may be configured to provide laminar flow in the fifth segment.

In some embodiments, a device for limiting fluid flow through the device comprises, or alternatively consists essentially of, a first segment having a first diameter and configured to be anchored in a first vessel, a second segment, and a third segment having a second diameter and configured to be anchored in a second vessel. The first diameter is configured to limit fluid flow through the device. The second segment tapers from the first diameter to the second diameter.

The first segment may be configured to divert fluid flow from the first vessel into the second vessel. The first segment may be configured to allow fluid to continue to flow through the first vessel. The first segment may comprise a window. The first segment may comprise a flange having a third diameter larger than the first diameter. The device may comprise a stent structure and a graft. At least part of the first segment may be devoid of the graft. The graft may have the first diameter in the first segment. The stent structure may have a third diameter larger than the first diameter in the first segment. The graft in the first segment may be configured to flex inwardly in response to changes in pressure. The graft in the first segment may be configured to flex outwardly in response to changes in pressure. The first diameter may be between about 2.5 mm and about 5 mm. The second diameter may be between about 5 mm and about 7 mm.

In some embodiments, a device for limiting fluid flow through the device comprises, or alternatively consists essentially of, a first segment having a first diameter and configured to be anchored in a first vessel, a second segment extending transverse to the first segment, a third segment, and a fourth segment having a second diameter and configured to be anchored in a second vessel. The second segment has a third diameter less than the first diameter and the second diameter. The third diameter is configured to limit fluid flow through the device. The third segment tapers from the third diameter to the second diameter.

The first segment may be configured to divert fluid flow from the first vessel into the second vessel. The first segment may be configured to allow fluid to continue to flow through the first vessel.

In some embodiments, an implant for limiting fluid flow through a lumen comprises, or alternatively consists essentially of, a first segment, a second segment, and a third segment. The second segment has a first diameter configured to limit fluid flow through the implant and to limit fluid flow through the lumen when the implant is positioned in the lumen. The first segment tapers from a second diameter configured to anchor the implant in the lumen to the first diameter. The second segment tapers from the first diameter to a third diameter configured to anchor the implant in the lumen.

The first diameter may be between about 2.5 mm and about 5 mm. The graft in the first segment may be configured to flex inwardly in response to changes in pressure. The graft in the first segment may be configured to flex outwardly in response to changes in pressure. The lumen may be a flow diverting device. The lumen may be a vein. A system may comprise the implant and a flow diverting device configured to divert fluid flow from a first vessel to a second vessel. The implant may be configured to be position in the flow diverting device. The implant may be configured to be position in the second vessel.

The methods summarized above and set forth in further detail below describe certain actions taken by a practitioner; however, it should be understood that they can also include the instruction of those actions by another party. Thus, actions such as "making valves in the first vessel incompetent" include "instructing making valves in the first vessel incompetent."

For purposes of summarizing the invention and the advantages that may be achieved, certain objects and advantages are described herein. Not necessarily all such objects or advantages need to be achieved in accordance with any particular embodiment. In some embodiments, the invention may be embodied or carried out in a manner that can achieve or optimize one advantage or a group of advantages without necessarily achieving other objects or advantages.

All of these embodiments are intended to be within the scope of the invention herein disclosed. These and other embodiments will be apparent from the following detailed description having reference to the attached figures, the invention not being limited to any particular disclosed embodiment(s). Optional and/or preferred features described with reference to some embodiments may be combined with and incorporated into other embodiments. All references cited herein, including patents and patent applications, are incorporated by reference in their entirety.

BRIEF DESCRIPTION OF THE DRAWINGS

These and other features, aspects, and advantages of the present disclosure are described with reference to the drawings of certain embodiments, which are intended to illustrate certain embodiments and not to limit the invention, in which like reference numerals are used for like features, and in which:

FIGS. 26A and 26B schematically illustrate another example embodiment of a method for effecting retroperfusion.

FIG. 27 schematically illustrates another example embodiment of a prosthesis and a method for effecting retroperfusion.

FIG. 31A schematically illustrates an example embodiment of an arteriovenous fistula stent separate from an example embodiment of a venous stent.

FIG. 31B schematically illustrates an example embodiment of an arteriovenous fistula stent comprising an integrated venous stent.

FIG. 31C schematically illustrates an example embodiment of a fistula stent comprising an integrated venous stent.

FIGS. 37Ki through 37Nii illustrate example procedures that can be performed using the valve disabling device of FIG. 37A.

FIGS. 38Ei and 38Eii illustrates an example of a distal end of a catheter.

FIG. 38F illustrates an example of a portion of a catheter.

FIG. 38G illustrates another example of a portion of a catheter.

FIG. 41A is a perspective view of an example handle for deploying a tubular structure.

FIG. 41B is an expanded perspective partially transparent view of a portion of the handle of FIG. 41A.

FIGS. 41C to 41Eiii show an example method of operating the handle of FIG. 41A.

FIG. 42Bi is a schematic side view of an example radiopaque marker.

FIGS. 42Ci-42Ciii illustrate an example catheter including a profile attached to the needle.

FIG. 42D is a schematic side view of the distal portion of the launching device of FIG. 42A.

FIGS. 46A-46K show example procedures for performing an ascending venogram.

FIG. 47A is a perspective view of a portion of an example cutting snare system.

FIGS. 47Bi and 47Bii are side views of another example cutting snare system.

FIGS. 47Ci-47Ciii are side views of another example cutting snare system.

FIG. 47Civ is a side view of yet another example cutting snare system.

FIGS. 47Di-47Dv are side views of still another example cutting snare system.

FIGS. 47Ei-47Eiii are side views of still yet another example cutting snare system.

FIG. 47Eiv is a side view of another example cutting snare system.

FIGS. 47Fi and 47Fii are side views of yet another example cutting snare system.

FIGS. 47Gi-47Giii are side views of still another example cutting snare system.

FIG. 52Bii is an example cross-sectional view of the device of FIG. 52Bi across the line 52Bx-52Bx.

FIG. 52Biii is another example cross-sectional view of the device of FIG. 52Bi across the line 52Bx-52Bx.

FIG. 52Ci is a side view of another example device providing fluid flow from a first vessel to a second vessel and through the first vessel.

FIG. 52Cii is a cross-sectional view of the device of FIG. 52Ci across the line 52Cii-52Cii.

FIG. 52D is a side view of yet another example device providing fluid flow from a first vessel to a second vessel and through the first vessel.

FIG. 53A is a side view of still another example device providing fluid flow from a first vessel to a second vessel and through the first vessel.

FIGS. 53Bi-53Biii illustrate an example method of in situ formation of an example device providing fluid flow from a first vessel to a second vessel and through the first vessel.

FIG. 53Ci shows an example cell pattern for a stent structure of a fenestrated device.

FIG. 53Cii shows an example of the stent structure of FIG. 53Ci partially covered in graft and including a window.

FIG. 53Di illustrates an example method of in situ formation of an example device providing fluid flow from a first vessel to a second vessel and through the first vessel.

FIG. 53Dii shows an example tapered segment usable with the device of FIG. 53Di.

FIG. 53Diii shows another example tapered segment usable with the device of FIG. 53Di.

FIGS. 53Ei and 53Eii illustrate an example method of aligning a puncturer for in situ formation of an example device providing fluid flow from a first vessel to a second vessel and through the first vessel.

FIG. 54A is a side view of yet still another example device providing fluid flow from a first vessel to a second vessel and through the first vessel.

FIG. 54Bi is a side view of still yet another example device providing fluid flow from a first vessel to a second vessel and through the first vessel.

FIG. 54Bii is a side view of another example device providing fluid flow from a first vessel to a second vessel and through the first vessel.

FIG. 54C is a side view of yet another example device providing fluid flow from a first vessel to a second vessel and through the first vessel.

FIG. 55A is a side view of still another example device providing fluid flow from a first vessel to a second vessel and through the first vessel.

FIG. 55B shows the device of FIG. 55A positioned in a first vessel, extending through interstitial tissue, and into a second vessel.

FIG. 55C shows yet still another example device providing fluid flow from a first vessel to a second vessel and through the first vessel.

FIG. 55D is a distal end view of the device of FIG. 55C implanted in the first vessel and the second vessel.

FIG. 55Ei is a top view of a device sharing features of the device of FIGS. 55C and 55D.

FIG. 55Eii is a top view of another device sharing features of the device of FIGS. 55C and 55D.

FIG. 55F shows yet still another example device providing fluid flow from a first vessel to a second vessel and through the first vessel.

FIG. 55G is a top view of the device of FIG. 55F.

FIG. 56A is a side view of still another example device providing fluid flow from a first vessel to a second vessel and through the first vessel.

FIG. 56B is a graph showing flow through a parent vessel and a side branch with and without a device of FIG. 56A for different values of porosity of the device.

FIG. 57A illustrates an example device for directing flow below an ankle.

FIG. 57Bi illustrates a first example of blood flow through a vein proximate to an ankle.

FIG. 57Bii illustrates a second example of blood flow through a vein proximate to an ankle.

FIGS. 57Ci-57Ciii illustrate example variations on woven flow diverting devices sharing features with the device of FIG. 57A.

FIG. 57Di illustrates a device in which a portion of the graft covering is perforated with a plurality of openings.

FIG. 57Dii is a schematic side view of the device of FIG. 57Di showing the effect of the porous region on fluid flow.

FIG. 57E is a schematic spectrum of porosity showing the effect of porosity on steal.

FIG. 57Fi is a side view of another example device configured to provide fluid flow from a first vessel to a second vessel and through the first vessel.

FIG. 57Fii is an expanded view of the device of 57Fi in the area 57Fii.

FIG. 57Fiii shows the device positioned in a first vessel, extending through interstitial tissue, and into a second vessel.

FIG. 57Fiv is an expanded view of the device of 57Fiii in the area 57Fiv.

FIG. 58A is a side view of an example occlusive implant.

FIGS. 58Bi-58Biii illustrate an example method of in situ coupling of the occlusive implant of FIG. 58A and an example device providing fluid flow from a first vessel to a second vessel and through the first vessel.

FIG. 58C is a side view of an example occlusive implant system comprising the occlusive implant of FIG. 58A.

FIG. 59Ai illustrates a third example of blood flow through a vein proximate to an ankle.

FIG. 59Aii illustrates a fourth example of blood flow through a vein proximate to an ankle.

FIG. 59B illustrates the device of FIG. 59Aii overlapping a stent graft.

Figure 60:
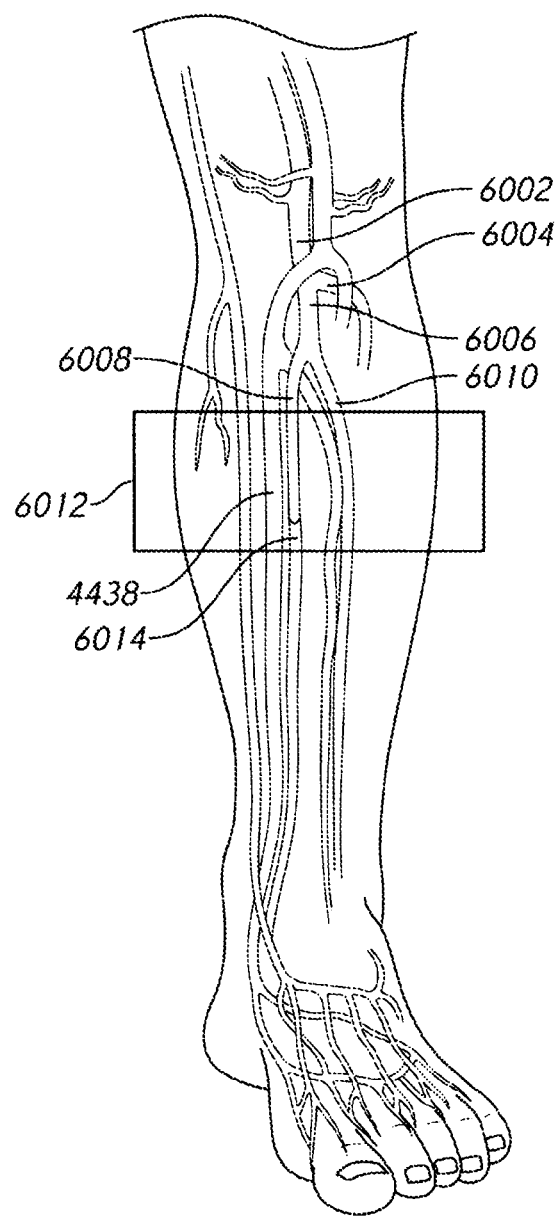

FIG. 60 is a partially transparent view showing certain vasculature of a left lower leg.

Figure 61A:
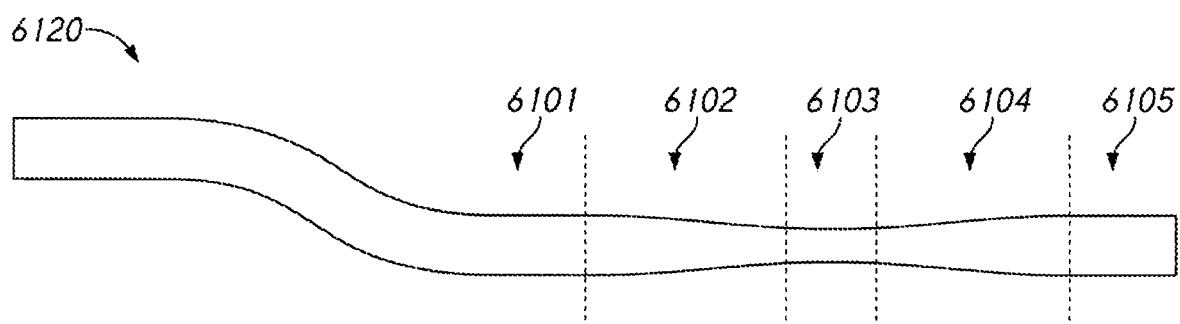

FIG. 61A illustrates an example of a prosthesis that can be placed upstream of an occlusion.

Figure 61B:
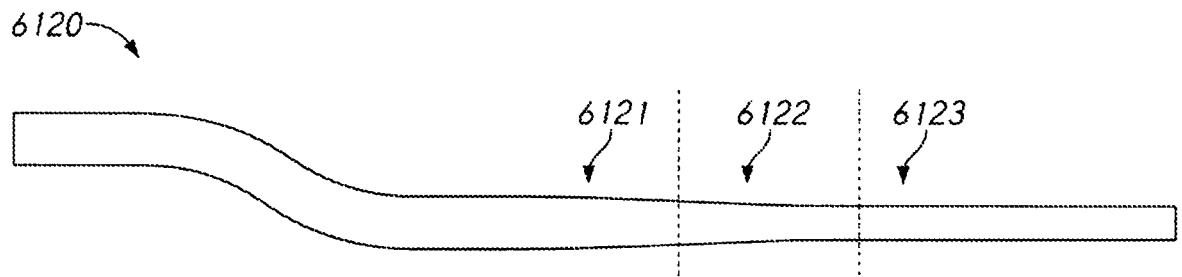

FIG. 61B illustrates another example of a prosthesis that can be placed upstream of an occlusion.

Figure 61C:
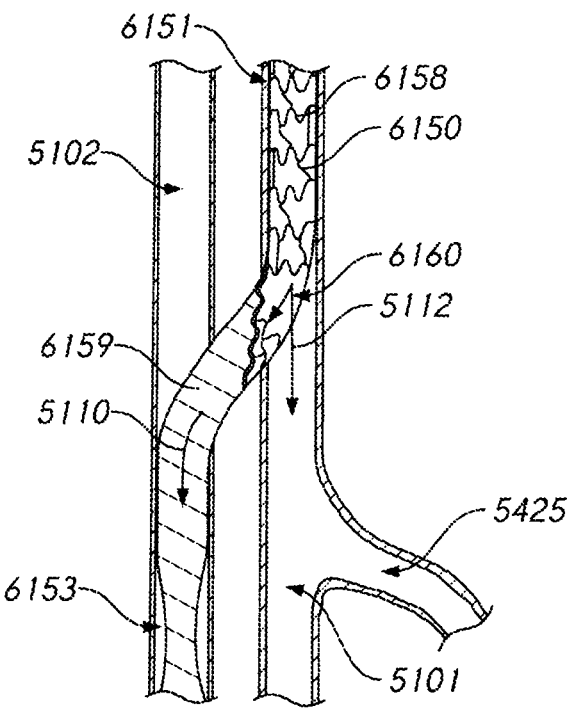

FIG. 61C illustrates yet another example of a prosthesis that can be placed upstream of an occlusion.

Figure 61D:
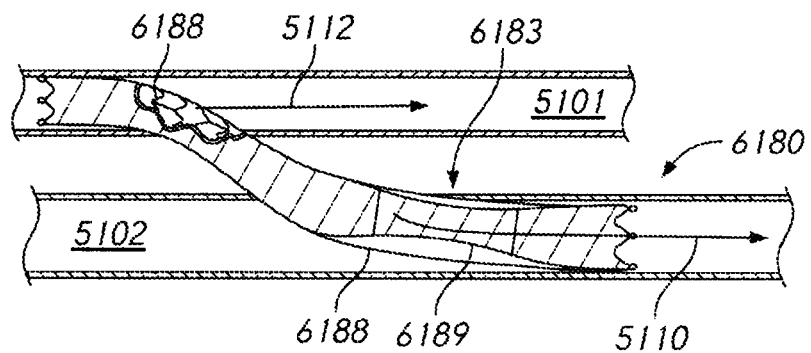

FIG. 61D illustrates still another example of a prosthesis that can be placed upstream of an occlusion.

Figure 62A:
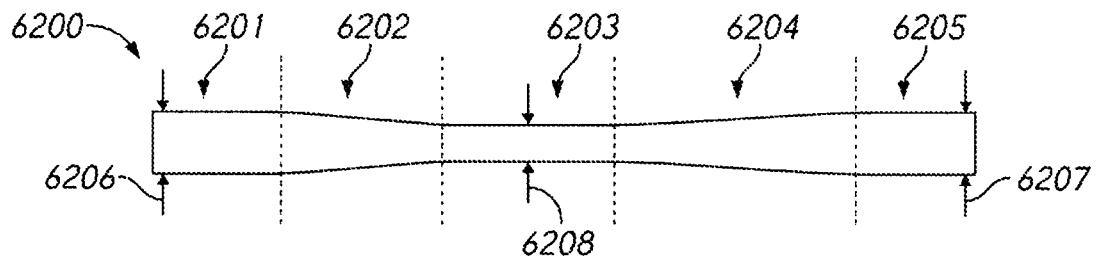

FIG. 62A illustrates an example of a prosthesis that can be placed upstream of an occlusion.

Figure 62B:
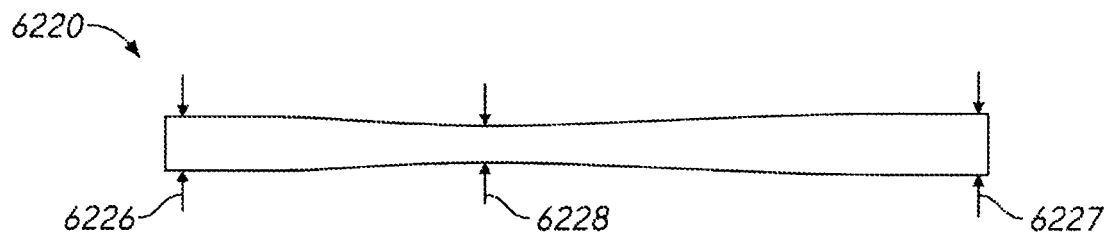

FIG. 62B illustrates another example of another prosthesis that can be placed upstream of an occlusion.

Figure 62C:
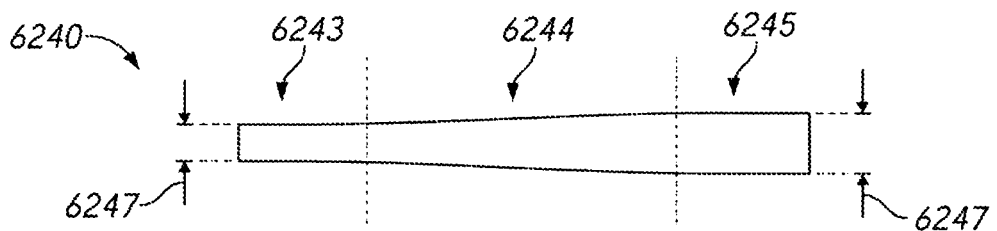

FIG. 62C illustrates yet another example of a prosthesis that can be placed upstream of an occlusion.

Figure 62D:
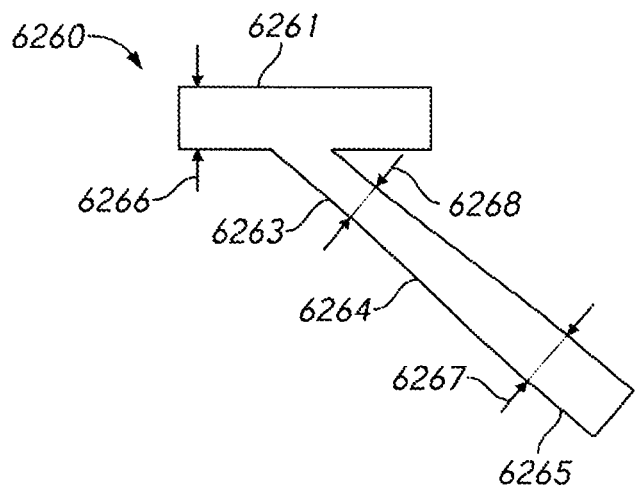

FIG. 62D illustrates still another example of a prosthesis that can be placed upstream of an occlusion.

Figure 63A:
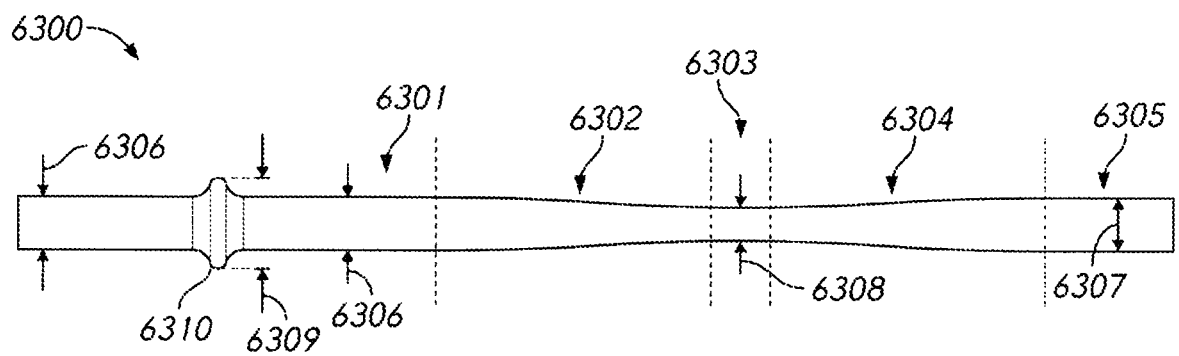

FIG. 63A illustrates an example of a prosthesis that can be placed upstream of an occlusion.

Figure 63B:
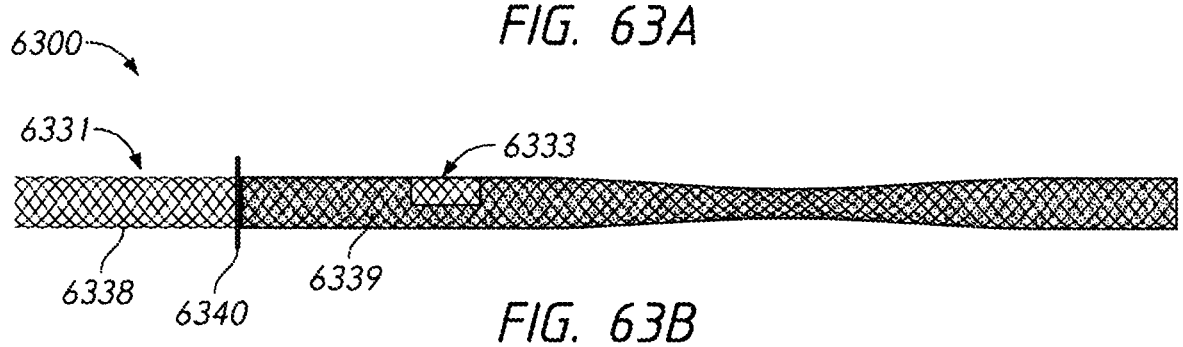

FIG. 63B illustrates another example of a prosthesis that can be placed upstream of an occlusion.

Figure 63C:
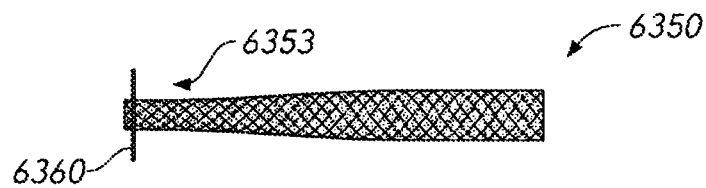

FIG. 63C illustrates yet another example of a prosthesis that can be placed upstream of an occlusion.

Figure 64:
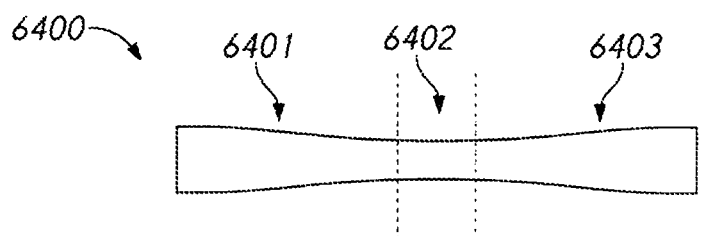

FIG. 64 illustrates an example of a flow limiting implant.

Figure 65:
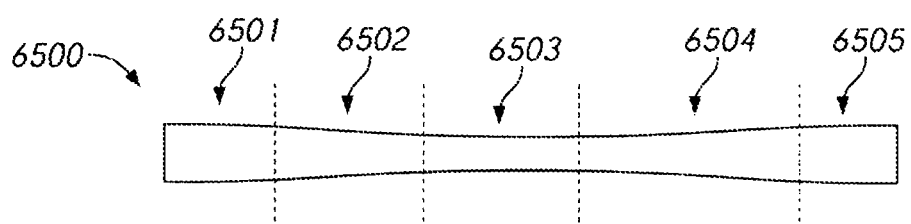

FIG. 65 illustrates still another example of a prosthesis that can be placed upstream of an occlusion.

DETAILED DESCRIPTION

Although certain embodiments and examples are described below, the invention extends beyond the specifically disclosed embodiments and/or uses and obvious modifications and equivalents thereof. The scope of the invention herein disclosed should not be limited by any particular embodiment(s) described below.

Minimally invasive surgery could provide a means for treating a broader range of patients, including those currently excluded from standard surgical techniques. One such procedure is percutaneous in situ coronary venous arterialization (PICVA), which is a catheter-based coronary bypass procedure in which the occlusion in the diseased artery is "bypassed" by creation of a channel between the coronary artery and the adjacent coronary vein. In this way, the arterial blood is diverted into the venous system and can perfuse the cardiac tissue in a retrograde manner (retroperfusion) and restores blood supply to ischemic tissue. Some example devices and methods for performing procedures like PICVA are described in PCT Pub. No. WO 99/049793 and U.S. Patent Pub. No. 2004/0133225, which are hereby incorporated by reference in their entirety.

Successfully performing a minimally invasive procedure of diverting blood flow from the coronary artery to the adjacent vein heretofore has had a low success rate, most often due to inability to properly target the vein from the artery. Without the proper systems and methods, such procedures (e.g., attempting to target the vein by combination of X-ray fluoroscopy and an imaging ultrasound probe located on the distal tip of the catheter e.g., as described in U.S. Patent Pub. No. 2004/0133225) are often doomed to failure before even starting. Indeed, such an arrangement can be difficult to navigate, and localization of the adjacent vein can require considerable skill on the part of the clinician. Improvements in the systems and methods for targeting, such as those using the catheters described herein, can enable procedures such as PICVA and transvascular surgery in general. Without such improvements, such percutaneous techniques will remain peripheral to conventional surgical open-heart and other types of bypass operations.

The present application, according to several embodiments, describes methods and systems usable in minimally invasive surgical procedures, which can reduce performance of conventional surgery to treat conditions such as coronary heart disease and critical limb ischemia. For example, patients who might otherwise be unable to receive surgery such as coronary bypass surgery or peripheral arterial bypass surgery can be treated, and the amount of surgical trauma, the risk of infection, and/or the time to recovery may be reduced or significantly reduced in comparison to conventional surgery.

Figure 1:
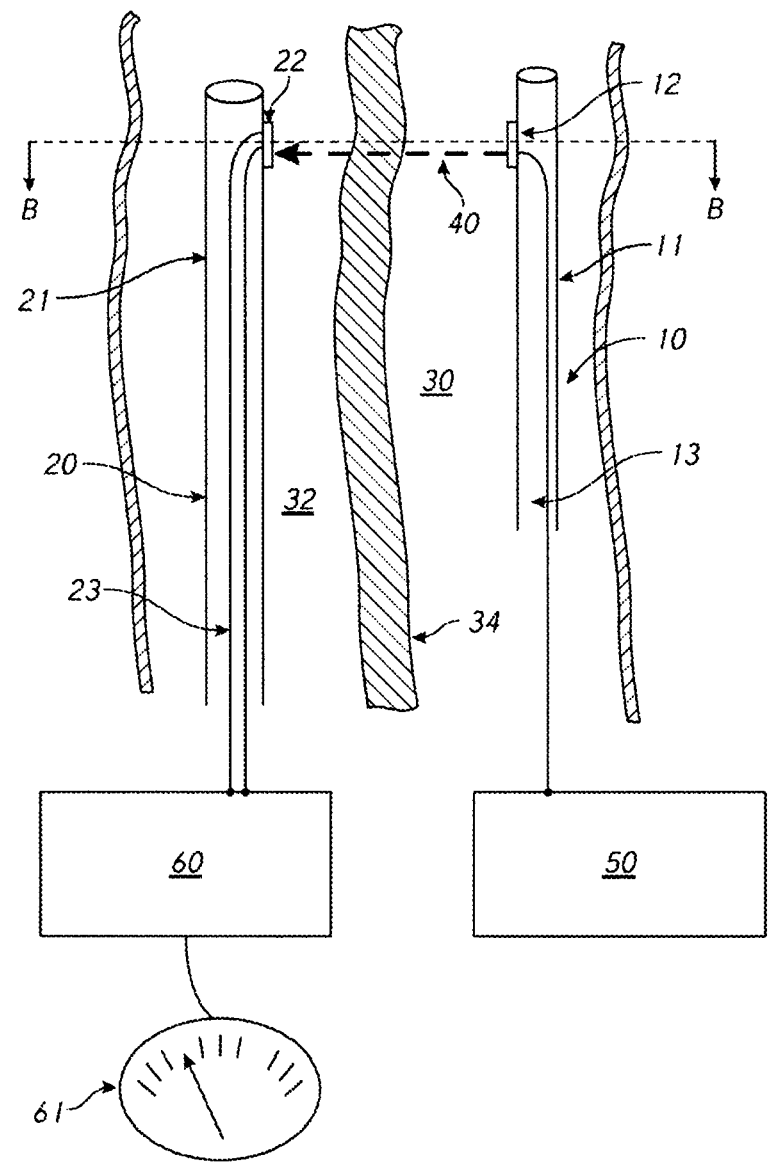
FIG. 1 schematically illustrates an example embodiment of a launching device directing a signal from a first body cavity to a target device in a second body cavity.

FIG. 1 schematically illustrates an example embodiment of a launching device 10 directing a signal from a first body cavity 30 to a target device 20 in a second body cavity 35. The launching device 10 comprises a signal transmitter 12. The launching device 10 may comprise, for example, a catheter including an elongate flexible rod-like portion and a tip portion, and may provides a conduit for administering therapy within the body of a patient. The launching device 10 may be suitable for location and movement through a first cavity or vessel 30 (e.g., heart chamber, coronary artery, coronary vein, peripheral artery, peripheral vein) within a patient's body. The elongate portion of the launching device 10 comprises an outer sheath 11 that encloses a space, defining a lumen 13. The space within the lumen 13 may be suitably partitioned or subdivided as necessary so as to define channels for administering therapy, controlling the positioning of the launching device 10, etc. Such subdivision may, for example, be achieved either longitudinally or concentrically in an axial fashion.

The launching device 10 comprises a signal transducer 12. The signal transducer 12 is configured to provide or emit a signal 40 that is directed outwards from the launching device 10. In the embodiment shown in FIG. 1, the signal 40 is directed radially outward from the launching device 10 in a direction that is perpendicular to the longitudinal axis of the launching device 10. As mentioned in greater detail below, in some embodiments, the direction of the signal 40 need not be perpendicular and can be directed at an angle to the longitudinal axis of the launching device 10. The signal transducer 12 may thereby form at least a portion of a signal generating means.

The signal transducer 12 is connected to signal transmitter 50. The signal transmitter 50 can be suitably selected from ultrasound or appropriate electromagnetic sources such as a laser, microwave radiation, radio waves, etc. In some embodiments, as described in further detail below, the signal transmitter 50 is configured to generate an ultrasound signal, which is relayed to the signal transducer 12, which in turn directs the signal 40 out of the first body cavity 30 into the surrounding tissue.

A target device 20 is located within an adjacent second body cavity or vessel 32 (e.g., heart chamber, coronary artery, coronary vein, peripheral artery, peripheral vein) within a patient's body. The first and second body cavities 30, 32 are separated by intervening tissue 34, sometimes referred to as interstitial tissue or a septum. The first and second body cavities 30, 32 are located next to each other in a parallel fashion for at least a portion of their respective lengths. For example, many of the veins and arteries of the body are known to run in parallel with each other for at least a portion of their overall length.

The target device 20 can assume a similar arrangement to that of the launching device 10. For example, the target device 20 can comprise a catheter including an elongate flexible rod-like portion and a tip portion. For another example, fine movement and positioning of the target device 20 within the body cavity 32 can be achieved. For yet another example, the target device 20 may comprise an outer sheath 21 that encloses a space, defining a lumen 23. The lumen 23 can be suitably partitioned, for example as with the launching device 10.

The target device 20 comprises a receiving transducer 22 configured to receive the signal 40 from the transducer 12 of the launching device 10. The receiving transducer 22 makes up at least a portion of a signal detection means. In use, when the receiving transducer 22 receives the signal 40 transmitted from the signal transducer 12, the receiving transducer 22 transmits the received signal to a signal detector 60. The signal detector 60 is configured to provide an output reading to the user of the system, for example via an output display 61. The output display 61 may be a visual display, an audio display (e.g., beeping or emitting some other sound upon receipt of a signal), etc.

In this way, the transmission and detection of the directed signal 40 can allow for the navigation and positioning of the launching device 10 relative to the target device 20. In use, the launching device 10 and the target device 20 can be maneuvered by the user of the system until the output display 61 indicates that signal 40 is being received by the target device 40.

In some embodiments, the signal 40 comprises or is an ultrasound signal. The signal 40 is directional and is emitted by the signal transducer 12 in the shape of a narrow cone or arc (e.g., with the width of the signal band increasing as the distance from the signal transducer 12 increases). As such, the precision of alignment between the launching device 10 and the target device 20 depends not only upon signal detection, but also upon the distance between the two devices, as the signal beam width is greater at greater distances. This level of error is referred to as "positional uncertainty." A certain level of tolerance can exist for positional uncertainty; however, if therapy is to be directed with precision, the amount of uncertainty should be reduced or minimized. For example, if the diameter d of the signal transducer 12 is 1 mm and the frequency of the ultrasound signal is 30 MHz, then the positional uncertainty x (e.g., the margin of error on either side of a center line) is 1 mm at a perpendicular separation of 5 mm between the launching device 10 and the target device 20. For clinical applications, the positional uncertainty generally should not exceed around ±5 mm (for a total signal beam width of 10 mm at the point of reception). In some embodiments, the positional uncertainty is between about ±0.01 mm and about ±4.50 mm or between about ±0.1 mm and about ±2 mm. In some embodiments, the positional uncertainty does not exceed about ±1 mm.

The strength of the signal 40 can be a factor in detection, and signal strength generally diminishes as the distance between the launching device 10 and the target device 20 increases. This distance is in part determined by the amount of intervening tissue 34 between the devices 10, 20. By way of example, if the signal 40 is an ultrasound signal, significant deterioration of signal can be expected when the launching device 10 and the target device 20 a separated by more than about 20 mm of solid tissue (e.g., the intervening tissue 34). The density of the intervening tissue 34 may also have an effect upon the deterioration of signal 40 over distance (e.g., denser tissue deteriorating the signal more than less dense tissue).

The frequency of the ultrasound signal may also affect the thickness of the signal transducer, which for a standard ultrasound ceramic transducer (e.g., a piezoelectric transducer (PZT)) is 0.075 mm at 30 MHz.

Figure 2:
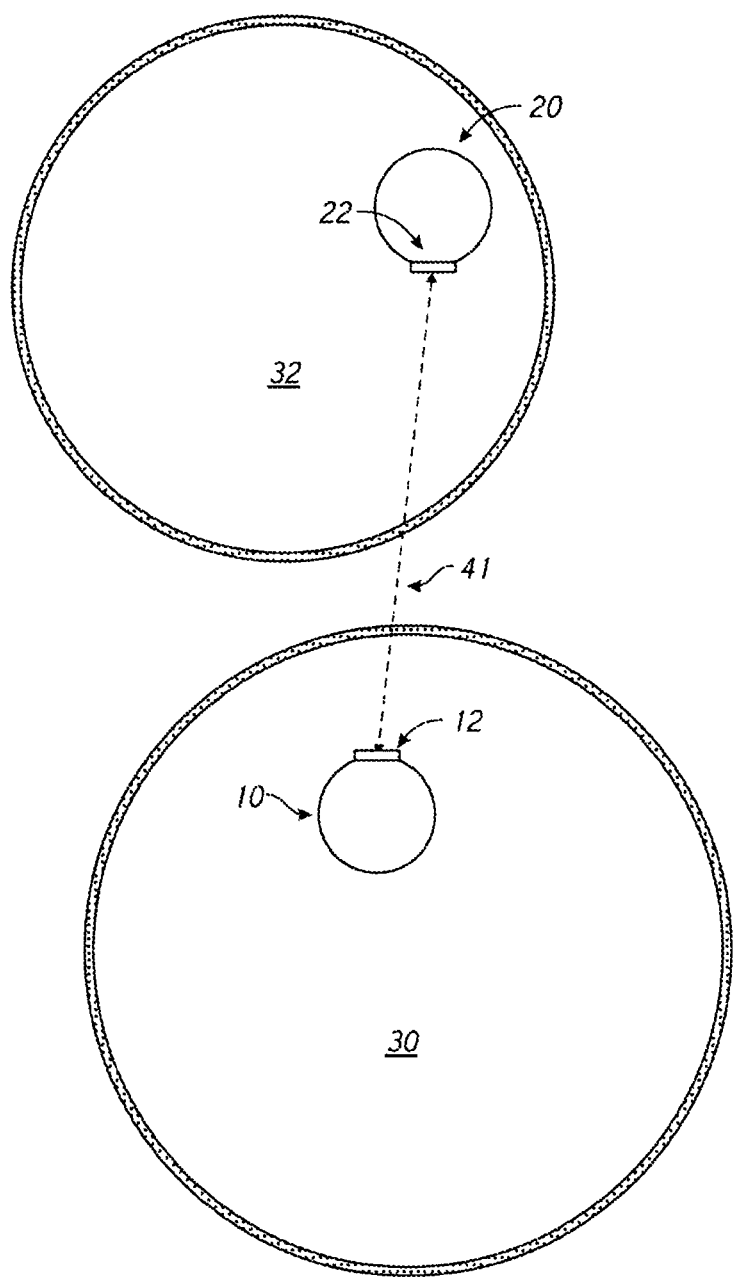
FIG. 2 is a cross-sectional representation along the dotted line B-B of FIG. 1.

FIG. 2 is a cross-sectional representation along the dotted line B-B of FIG. 1. The correct orientation of the launching device relative to the target device can be a factor in detection, as the line of orientation 41 can determine where the therapy is to be applied. The clinical need for precisional placing of therapy in a patient may function better if the directional signal 40 is linked to the means for delivering therapy (e.g., being parallel and longitudinally offset). For example, in this way the user of the system can administer therapy to the correct location by ensuring that the launching device 10 and the target device 20 are correctly positioned via transmission and reception of the signal 40. The orientation line 41 in FIG. 2 denotes not only the direction of signal travel but also the path along which therapy can be administered to the patient.

Figure 3:
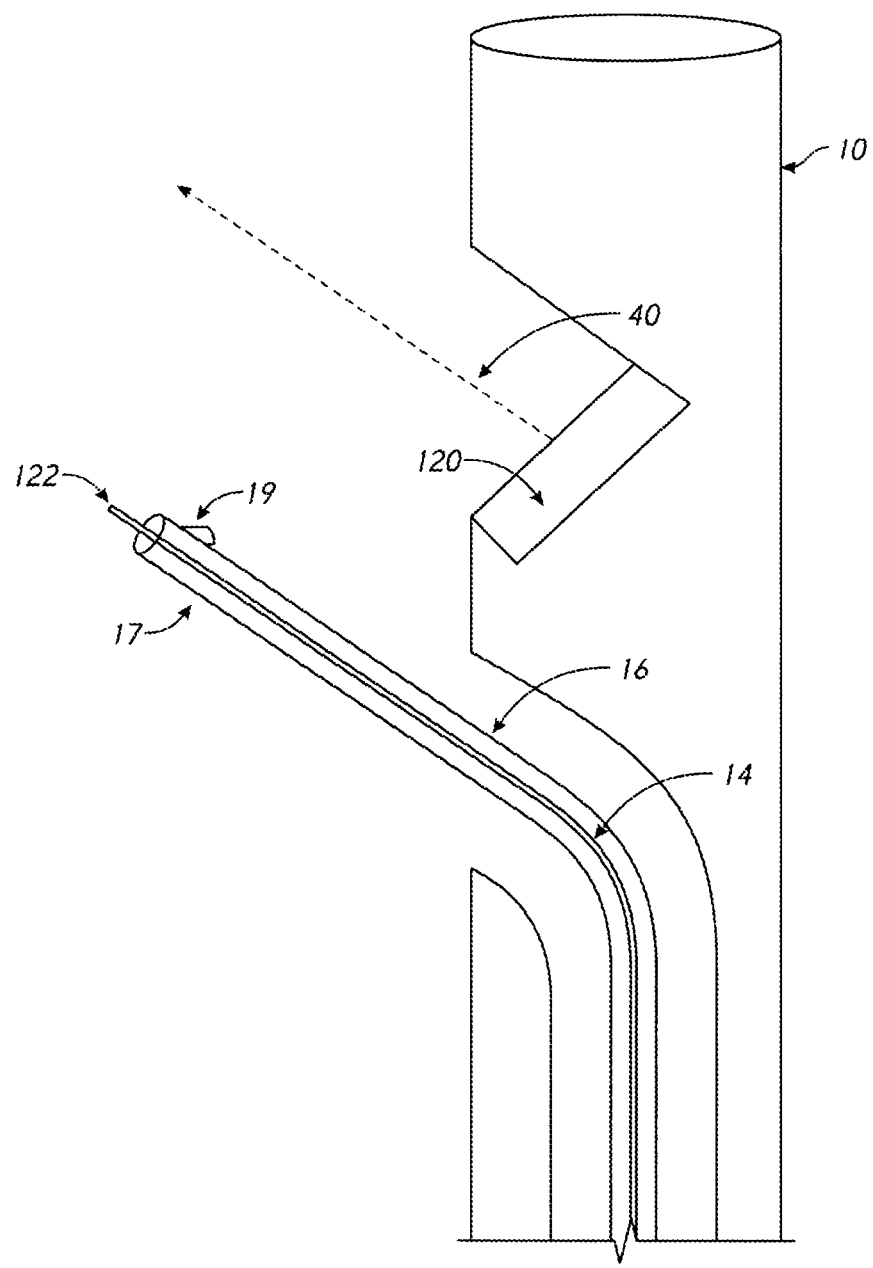
FIG. 3 schematically illustrates an example embodiment of a launching device.

FIG. 3 schematically illustrates an example embodiment of a launching device 10. The launching device 10 comprises a signal transducer 120 that is oriented at an oblique angle relative to the longitudinal axis of the launching device 10. The signal 40 is transmitted at an angle that is in the direction of travel (e.g., forward travel, transverse travel) of the launching device 10 as the launching device enters a body cavity 30 (FIGS. 1 and 2). In some embodiments, the beam angle is about perpendicular to the longitudinal axis of the launching device 10. In some embodiments, the beam angle is between about 20° and about 60° to the perpendicular, between about 30° and about 50° to the perpendicular, or about 45° to the perpendicular, when 0° corresponds to the longitudinal axis of the launching device 10 in the direction of travel.

The launching device 10 comprises a hollow needle or cannula 17, which is an example means for administering therapy. During travel of the launching device 10, the hollow needle 17 is located in an undeployed or retracted state within the lumen 13 of launching device 10. The hollow needle 17 may be deployed/extended from the launching device 10 via an aperture 16 in the outer sheath 11 at a time deemed appropriate by the user (e.g., upon detection of the signal 40 by the target device 20). The aperture 16 can allow fluid communication between the lumen 13 and the body cavity 30 (FIG. 1). As illustrated by the example embodiment of FIG. 3, the hollow needle 17 may travel along a path that is parallel to the direction of the signal 40. The hollow needle 17 may be used to pierce the intervening tissue 34 (FIG. 1). In some embodiments, the hollow needle 17 makes a transit across the entirety of the intervening tissue 34, and in doing so allows the launching device 10 to access the second body cavity 32 (FIG. 2). If desired, the pathway made by the hollow needle 17 through the intervening tissue 34 can be subsequently widened to allow fluid communication between the first body cavity 30 and the second body cavity 32.

Therapeutic means suitable for use in several embodiments can comprise, for example, devices and/or instruments selected from the group consisting of a cannula, a laser, a radiation-emitting device, a probe, a drill, a blade, a wire, a needle, appropriate combinations thereof, and the like.

In some embodiments, the hollow needle 17 comprises a sensor 19, which may assist in further determining positional information of the tip of the hollow needle 17 relative to the launching device 10. In some embodiments, the sensor 19 is configured to detect changes in hydrostatic pressure. Other sensors that are suitable for use in the systems and methods described herein can include temperature sensors, oxygenation sensors, and/or color sensors.

Optionally, the hollow needle 17 can comprise an additional signal transducer 122. In the embodiment shown in FIG. 3, the signal transducer 122 is located near the tip of the hollow needle 17 on the end of a guidewire 14. The signal transducer 122 can also or alternatively located on the hollow needle 17 if desired. In use, the signal transducer 122 is driven with a short transmit pulse that produces a directional signal or a non-directional signal pulse. The signal pulse can be detected by the receiving transducer 22 mounted on the target device 20. The distance from the guidewire 14 or hollow needle 17 to the receiving transducer 22 and hence the target device 20 can be at least partially determined time based on the delay between the transmission of the signal pulse from the signal transducer 122 and receipt of the signal pulse on the receiving transducer 22.

Figure 4:
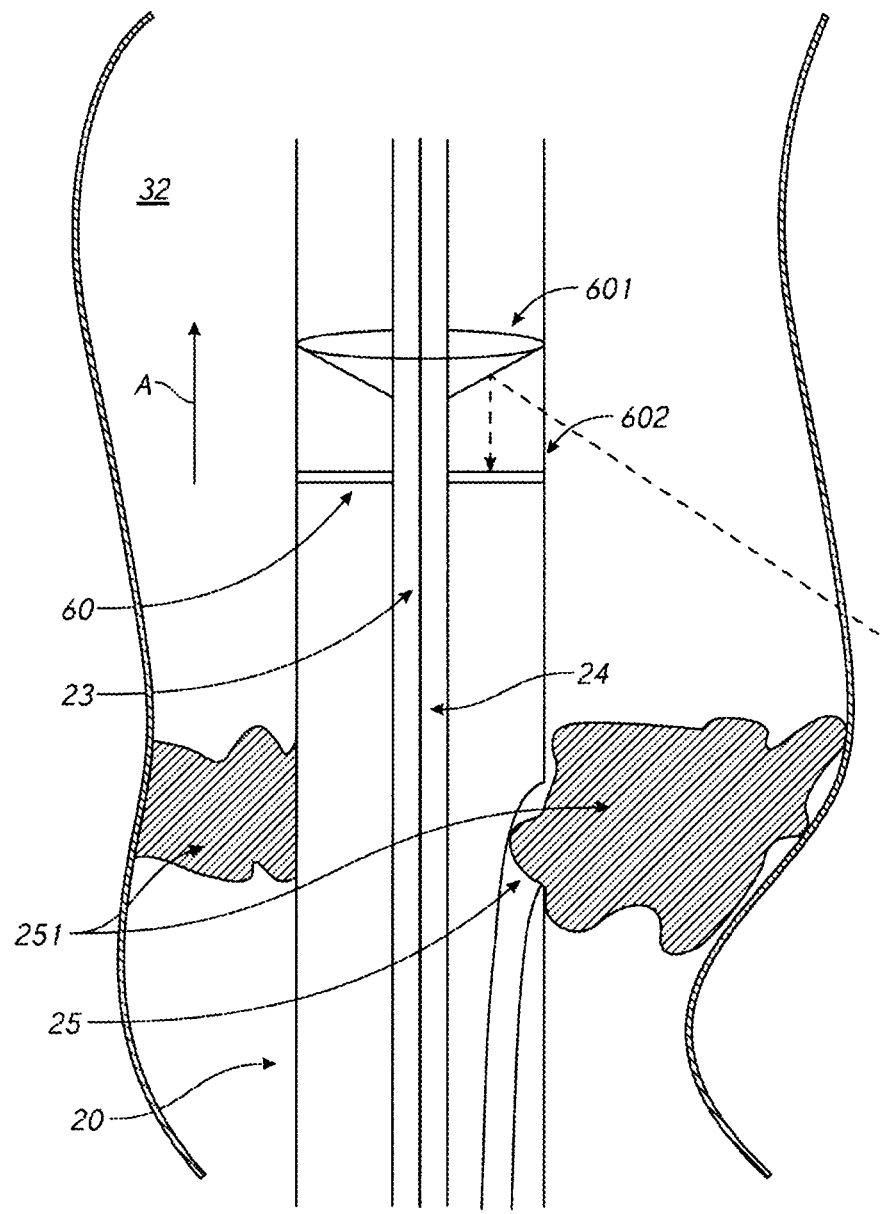
FIG. 4 schematically illustrates an example embodiment of a target device.

FIG. 4 schematically illustrates an example embodiment of a target device 20. In the embodiment shown in FIG. 4, the target device 20 is located within a body cavity 32. As mentioned above, the target device 20 comprises a receiving transducer 22 for receiving the signal 40. The receiving transducer 22 can be unidirectional (e.g., capable of receiving a signal from one direction only) or omnidirectional (e.g., capable of receiving a signal from any direction). Arrow A shows the reversed direction of blood flow after an arterial-venous arterialization (also called PICVA) has been effected. The target device 20 comprises an omnidirectional ultrasound signal receiving transducer 60. An optional reflecting cone 601 can direct the signal 40 onto a disc-shaped receiving transducer 60. An acoustically transparent window 602 can separate the reflecting cone 601 from the receiving transducer 60. In some embodiments, an omnidirectional ultrasound signal receiving transducer can be obtained by locating a cylinder of a flexible piezoelectric material such as polyvinyldifluoride (PVDF) around the outer sheath of the target device 20. In such a way, the cylinder can act in a similar or equivalent manner to the receiving transducer 60.

In the embodiment illustrated in FIG. 4, the target device 20 comprises an optional channel 25 for administering an agent, such as a therapeutic agent, to a patient. In some embodiments, the channel 25 functions as a conduit to allow application of a blocking material 251 that serves to at least partially obstruct or occlude the body cavity 32. The blocking material 251 can be suitably selected from a gel-based substance. The blocking material 251 can also or alternatively include embolization members (e.g., balloons, self-expanding stents, etc.). The placement of the blocking material 251 can be directed by movement of the target device 20. The presence of a guide member 24 within the lumen 23 of the target device 20 can allow the user to precisely manipulate the position of the target device 20 as desired.

Figure 5:
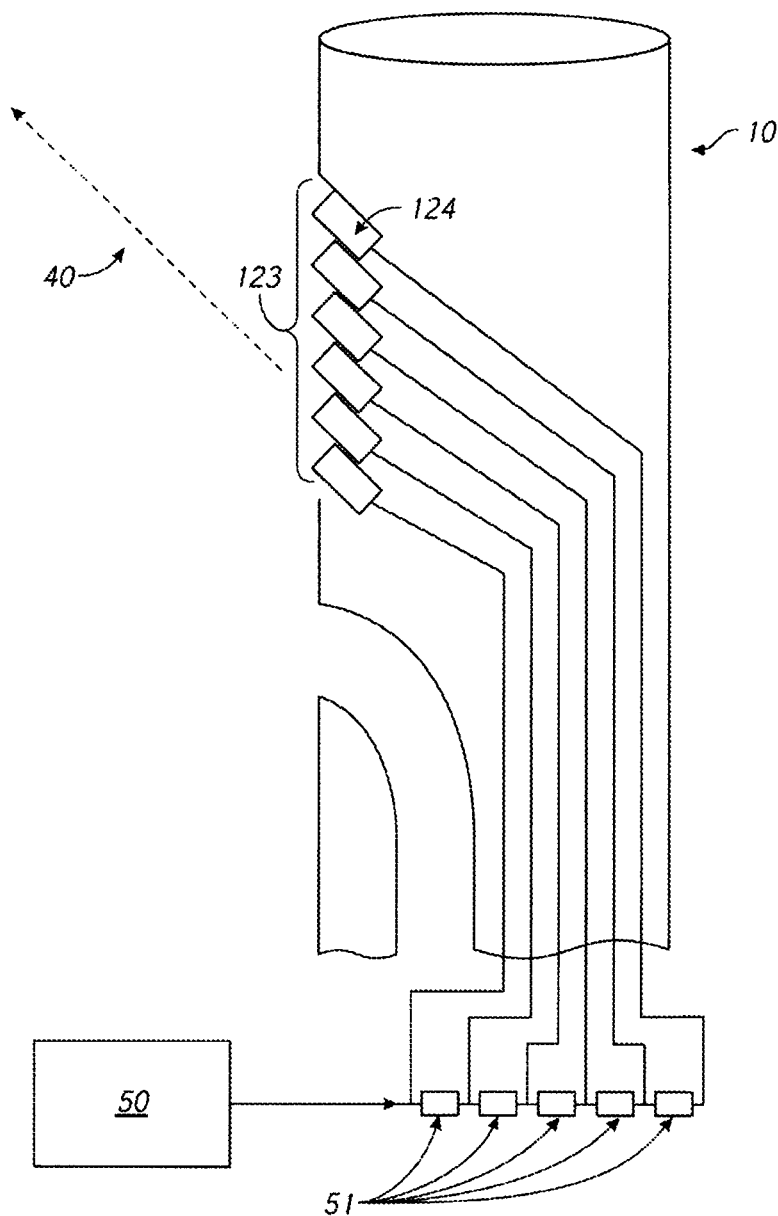
FIG. 5 schematically illustrates another example embodiment of a launching device.

Referring again to FIG. 2, the launching device 10 comprises a signal transducer 12 that may optionally be oriented so that the signal 40 is transmitted at an angle other than perpendicular to the signal transducer 12. FIG. 5 schematically illustrates another example embodiment of a launching device 10. In some embodiments, for example the launching device 10 shown in FIG. 5, the signal transducer is in the form of a signal transducer array 123. The signal transducer array 123 comprises a plurality of signal transducer elements 124, which can be oriented collectively to at least partially define a signal beam width and angle relative to the launching device 10. Smaller size of the elements 124 can allow the signal transducer 123 to not occupy a significant proportion the lumen 13 of the launching device 10.

The embodiment shown in FIG. 5 may be useful for ultrasound beam-forming signaling. FIG. 5 shows an array of signal transducer elements 124 that are separately connected to a transmitter 50 via delays 51, which allows the signals to each element 124 to be delayed relative to each other. The delays can provide or ensure that the ultrasound wavefronts from each element 124 are aligned to produce a beam of ultrasound 40 at the desired angle. In some embodiments, for example in which the signal 40 comprises visible light, an array of LEDs can also or alternatively be used.

Figure 6:
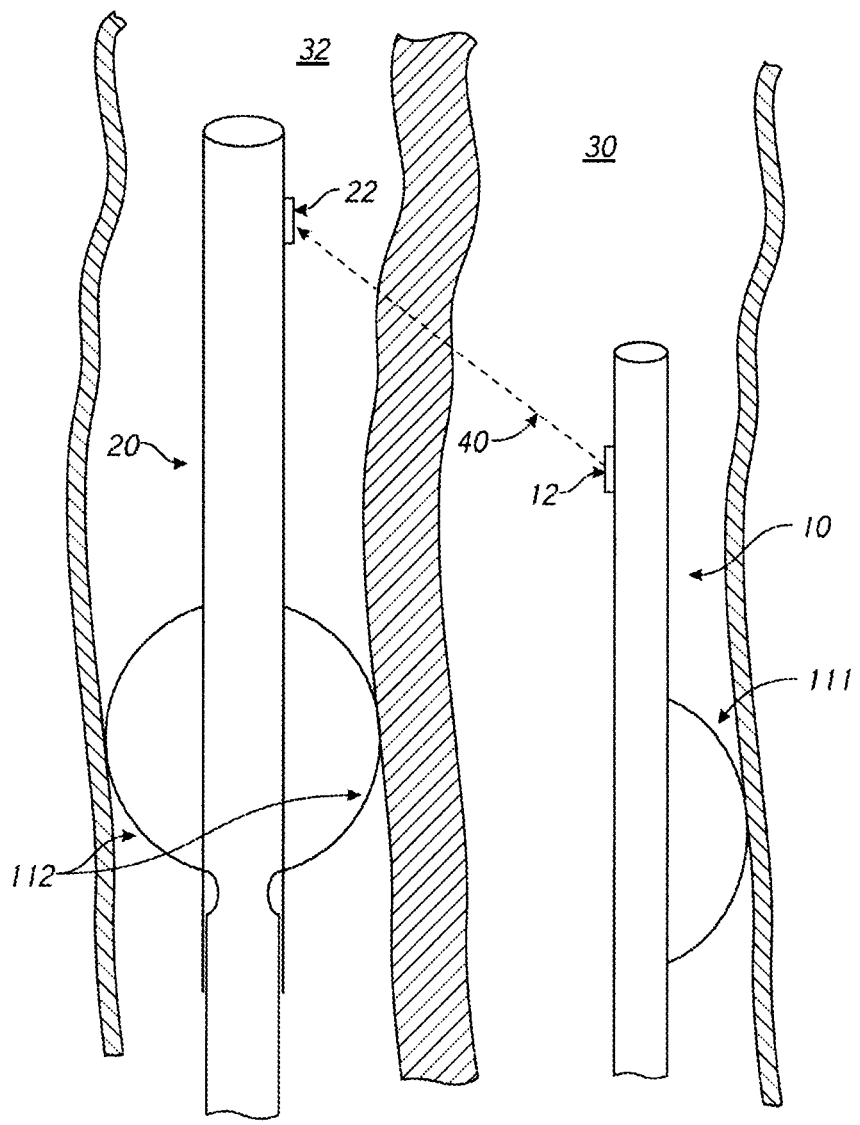
FIG. 6 schematically illustrates an example embodiment of centering devices for launching and/or target devices.

FIG. 6 schematically illustrates an example embodiment of centering devices for launching and/or target devices 10, 20. To assist in the process of alignment between the launching device 10 in the first body cavity 30 and the target device 20 in the second body cavity 32, one or both of the devices 10, 20 may comprise means for centering the respective devices within their body cavities.

In some embodiments, the centering means comprises an inflatable bladder or balloon 111 that is located in the lumen 13, 23 when in an undeployed state and, when the device 10, 20 reaches the desired location within the patient, can be inflated. The balloon 111 can be disposed on an outer surface of the outer sheath 11, 21. The balloon 111 can be annular in shape such that it at least partially surrounds the device 10, 20 in a toroidal or doughnut-like fashion. The balloon 111 can be arranged such that it inflates on only one side or only on two opposite sides of the device 10, 20. As illustrated in FIG. 6, the balloon 111 is deployed on one side of the launching device 10.

In some embodiments, the centering means comprises one or more loop structures 112 located either in the lumen 13, 23 or within recesses made in the outer sheath 11, 21 when in an undeployed or retracted state. When the device 10, 20 reaches the desired location within the patient, the one or more loop structures 112 can be expanded radially outwardly from the device 10, 20, thereby centering the device 10, 20 within the body cavity 30, 32. Outward expansion of the loop structures 112 can be suitably effected by compression of a length of wire, for example, such that it bows outwardly from the outer sheath 11, 21. A centering device that adopts this conformation may comprise a plurality of compressible lengths of wire or other suitable flexible material arranged in parallel at radially spaced intervals around the periphery of the outer sheath 11, 21. Compression of the plurality of wires can be induced by way of a sliding member (not shown) located proximally and/or distally near to the ends of the plurality of wires. The sliding member is capable of translational movement along the longitudinal axis of the device 10, 20. As illustrated in FIG. 6, the target device 20 comprises fully deployed centering means 112 that has allowed the target device 20 to be centered within the body cavity 32.

Other possible means for centering the devices 10, 20 within the body cavities 30, 32 include, but are not limited to, expandable Chinese-lantern type devices, reversibly expandable stents, coils, helices, retractable probes or legs, combinations thereof, and the like.

In some embodiments, the centering means or other means (e.g., balloons, metal stand-offs having differing lengths, etc.) can be used to orient the devices 10, 20 within the body cavities 30, 32 other than in the center or substantially the center of the body cavities. For example, the device 10 may be oriented proximate to the wall of the body cavity 30 where the needle 17 will exit the body cavity 30, which can, for example, provide a shorter ultrasound signal path and/or reduce error due to the needle 17 traversing intraluminal space. For another example, the device 10 may be oriented proximate to the wall of the body cavity 30 opposite the wall of the body cavity 30 where the needle 17 will exit the body cavity 30, which can, for example, provide a firm surface for the needle 17 to push against. For yet another example, the device 20 may be oriented proximate to the wall of the body cavity 32 where the needle 17 will enter the body cavity 32, which can, for example, provide a shorter ultrasound signal path. Other device orientations that are neither centered nor proximate to a vessel wall are also possible (e.g., some fraction of the diameter away from the wall and/or the center of the lumen, such as ½, ⅓, ¼, etc.).

Example

The methods and systems described herein demonstrate particular utility in cardiovascular surgery according to several embodiments. Certain aspects are further illustrated by the following non-limiting example, in which the system is used by a clinician to perform the procedure of arterial-venous connection (PICVA) so as to enable retroperfusion of cardiac tissue following occlusion of a coronary artery.

The launching catheter 10 is inserted into the occluded coronary artery by standard keyhole surgical techniques (e.g., tracking over a guidewire, tracking through a guide catheter). The target catheter 20 is inserted into the coronary vein that runs parallel to the coronary artery by standard keyhole surgical techniques (e.g., tracking over a guidewire, tracking through a guide catheter). The coronary vein is not occluded and, therefore, provides an alternative channel for blood flow to the cardiac muscle, effectively allowing the occlusion in the coronary artery to be bypassed.

The launching catheter 10 comprises a PZT ultrasound transducer 12 (e.g., available from CTS Piezoelectric Products of Albuquerque, New Mexico) that is oriented such that a directional ultrasound beam is transmitted in this example at a 45° angle (relative to the longitudinal axis of the launching device), preferably in the direction of blood flow in the artery 30, although other angles including about 90° are also possible. The ultrasound transducer 12 is activated, and in this example a 30 MHz directional ultrasound signal 40 is transmitted from the launching catheter 10, although other frequencies are also possible. The target catheter 20 comprises an omnidirectional ultrasound receiving transducer 60. To assist with localization of both the launching catheter 10 and the target catheter 20, both catheters 10, 20 comprise centering or orienting means, in this example in the form of an annular inflatable balloon 111, although other or absence of centering or orienting means are also possible. The centering means 111 on the launching catheter 10 is deployed by the clinician when the launching catheter 10 is deemed to be in an appropriate location close to the site of the occlusion within the coronary artery 30. This may be determined via standard fluoroscopic imaging techniques and/or upon physical resistance. The target catheter 20 is then moved within the adjacent coronary vein 32 until the directed ultrasound signal 40 is detected by the signal receiving transducer 60. To enable more precise alignment between the launching catheter 10 and the target catheter 20, the centering means 111 on the target catheter 20 can be deployed either before or after the signal 40 is detected.

Upon reception of the transmitted signal 40, the clinician can be certain that the launching catheter 10 and the target catheter 20 are correctly located, both rotationally and longitudinally, within their respective blood vessels 30, 32 to allow for the arterial-venous connection procedure to commence. The target catheter 20 may be used to block blood flow within the coronary vein 32 via administration of a gel blocking material 251 though a channel 25 in the target catheter 20. The blocking material 251 may be administered at a position in the coronary vein 32 that is downstream in terms of the venous blood flow relative to the location of the receiving signal transducer 60.

The clinician may then initiate arterial-venous connection by deploying a hollow needle 17 from the launching catheter 10 substantially along a path that is parallel and close to the path taken by the ultrasound signal 40 though the intervening tissue 34 between the coronary artery 30 and the coronary vein 32, or the hollow needle 17 may traverse a path that intercepts the path of the ultrasound signal at a point within the coronary vein 32. The hollow needle 17 optionally comprises a sensor 19 near its tip that is configured to detect changes in hydrostatic pressure or Doppler flow such that the user can monitor the transition from arterial pressure to venous pressure as the hollow needle 17 passes between the two vessels 30, 32. The hollow needle 17 optionally comprises a guidewire 14 in a bore or lumen of the hollow needle 17 during deployment. Once the hollow needle 17 and guidewire 14 have traversed the intervening tissue 34, the hollow needle 17 may be retracted back into the lumen 13 of the launching catheter 10, leaving the guidewire 14 in place. In some embodiments, once the hollow needle 17 has traversed the intervening tissue 34, the user can separately pass the guidewire 14 through the bore or lumen of the hollow needle 17 and then retract the needle 17 into the launching catheter 10.

Figure 7:
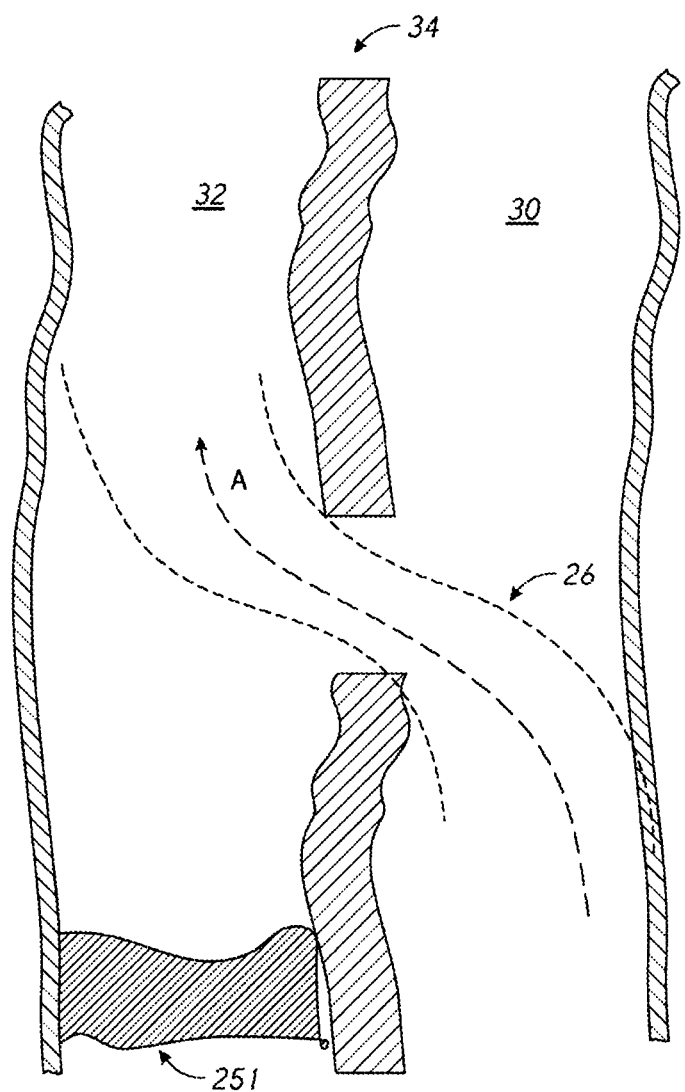
FIG. 7 schematically illustrates a prosthesis in place following a procedure such as arterial-venous arterialization.

The clinician withdraws the launching catheter 10 from the patient, leaving the guidewire 14 in place. A further catheter device is then slid along the guidewire 14. FIG. 7 schematically illustrates a prosthesis 26 such as an expandable stent 26 in place following a procedure such as arterial-venous arterialization. Further detail about possible prostheses including stents and stent-grafts are provided below. The stent 26 may be deployed to widen the perforation in the intervening tissue 34 between the coronary artery 30 and the coronary vein 32, in which the interrupted arrow A shows the direction of blood flow through the stent 26 between the first and second body cavities 30, 32 (e.g., arterial blood is thereby diverted into the venous system and is enabled to retroperfuse the cardiac muscle tissue). The stent 26 can block flow upwards in the cavity 32, forcing blood flow in the cavity 32 to be in the same direction as blood flow in the cavity 30. Graft material of the stent 26 can form a fluid-tight lumen between the cavity 30 and the cavity 32. The target catheter 20 is withdrawn from the patient, leaving the blocking material 251 in position. Optionally, a further block or suture may be inserted into the coronary vein to inhibit or prevent reversal of arterial blood flow, as described in further detail herein.

Whilst the specific example described above is with respect to cardiovascular surgery, the methods and systems described herein could have far reaching applications in other forms of surgery. For example, any surgery involving the need to direct therapy from one body cavity (e.g., for treatment of peripheral artery disease) towards another adjacent body cavity could be considered. As such, applications in the fields of neurosurgery, urology, and general vascular surgery are also possible. The type of therapy need not be restricted to formation of channels between body cavities. For instance, the methods and systems described herein may also be used in directing techniques such as catheter ablation, non-contact mapping of heart chambers, the delivery of medicaments to precise areas of the body, and the like.

Certain techniques for effectively bypassing an occlusion in an artery by percutaneous surgery are described above. These techniques include creating a channel or passage between a first passage, such as an artery upstream of an occlusion, a vein, or a heart chamber, and a second passage, such as an artery, vein, or heart chamber, proximate to the first passage to interconnect the first and second passages by a third passage. Fluid such as blood may be diverted from the first passage into the second passage by way of the interconnecting third passage. In embodiments in which the first passage includes an artery and the second passage includes a vein, the arterial blood can perfuse into tissue in a retrograde manner (retroperfusion).

As described above, an interconnecting passage between first and second body passages can be created by, for example, deploying a needle outwards from a first catheter located within the first passage, so that the needle traverses the interstitial tissue or septum between the first and second passages. A second catheter may be located in the second passage, so as to provide a target device which receives a signal, for example an ultrasound signal, transmitted from the first catheter. By monitoring the received signal, the position of the first catheter with respect to the second catheter can be determined so as to ensure that the needle is deployed in the correct position and orientation to create a passage for fluid flow between the first and second passages.

In order to provide or maintain the flow of blood thorough the interconnecting passage or channel, a structure including a lumen may be inserted in the passage to support the interstitial tissue and/or to inhibit or prevent the passage from closing. The tube may, for example, include a stent expanded in the channel using a balloon catheter or self-expansion, as described herein. A catheter to deliver the structure, for example a balloon catheter or catheter that allows self-expansion, may be guided to the channel by a guidewire deployed in the passage by the first catheter.

Passages such as arteries, veins, and heart chambers can pulsate as the heart beats, for example due to movement of heart walls, peripheral limbs, and/or fluctuations in pressure within the passages themselves. This pulsation can cause movement of the passages relative to each another, which can impose stress on a structure within an interconnecting passage therebetween. This stress may be large in comparison to stress experienced by a structure within a single passage. Stress can lead to premature failure of the structure, for example by fatigue failure of the stent struts. Failure of the structure may result in injury to the interstitial tissue and/or occlusion of the interconnecting passage, which could lead to significant complications or complete failure of the therapy.

Figure 8:
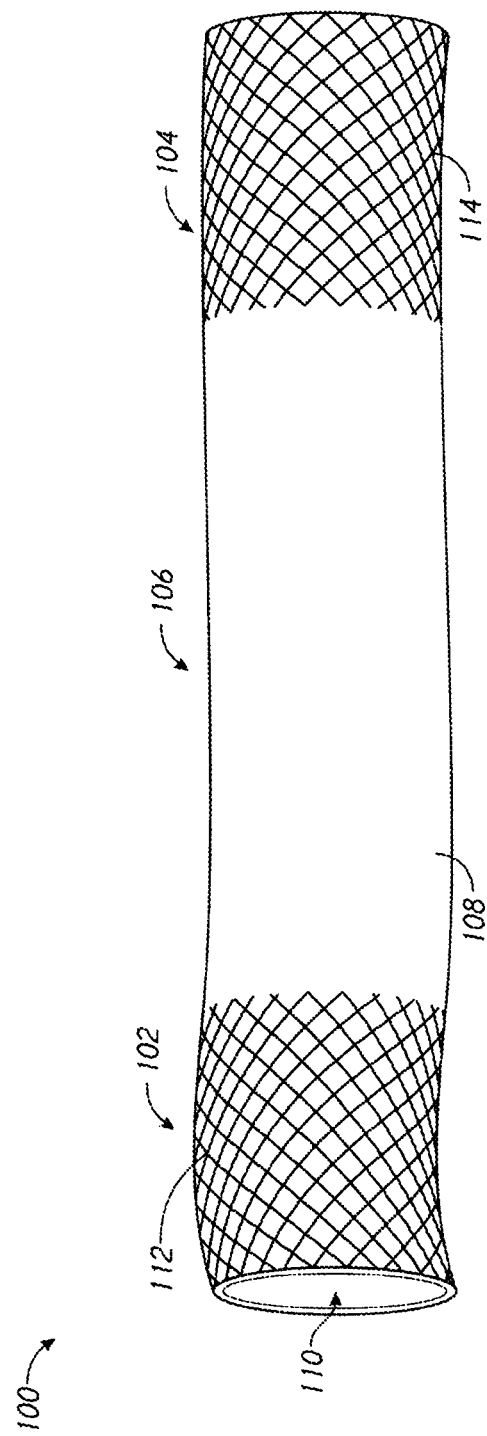
FIG. 8 is a side perspective view of an example embodiment of a device for providing fluid flow.

FIG. 8 illustrates a device or implant or prosthetic 100 for providing or maintaining fluid flow through at least one passage. The device 100 includes a first or proximal end portion 102, a second or distal end portion 104, and an intermediate portion 106 between the proximal end portion 102 and the distal end portion 104. The device includes a bore or lumen 110 for passage of fluid through the device 100. The device 100, for example at least the intermediate portion 106 of the device 100, includes a flexible polymer tube 108. The flexible polymer tube 108 may at least partially define the lumen 110.

The device 100 includes a support structure (e.g., at least one stent) including a mesh 112 and a mesh 114. In some embodiments, at least a portion of the mesh 112 is embedded in the outside wall of the tube 108 proximate to the proximal end portion 102 of the device 100. In some embodiments, at least a portion of the mesh 114, for example a wire or a strut, is embedded in the outside wall of the tube 108 proximate to the distal end portion 104 of the device 100. The meshes 112, 114 may include biocompatible metal such as stainless steel and/or shape memory material such as nitinol or chromium cobalt.

The wire meshes 112, 114 can stiffen the end portions 102, 104, respectively. In some embodiments in which the intermediate portion 106 does not include a mesh, the intermediate portion 106 may be relatively flexible in comparison to the end portions 102, 104, and/or the end portions 102, 104 may have a relatively high radial stiffness.

In some embodiments, the end portions 102, 104 of the device 100 are diametrically expandable. For example, the wire meshes 112, 114 may have a smaller diameter after formation or manufacture than the passages, for example blood vessels, into which the device 100 will be deployed. When the device 100 is in position in the passages, the end portions 102, 104 can be expanded or deformed outwardly so that the respective diameters of the end portions 102, 104 increase, for example to abut the interior sidewalls of the passages. The end portions 102, 104 are configured to maintain the expanded diameter indefinitely, for example by plastic deformation of the material (e.g., wires, struts) of the meshes 112, 114 and/or by provision of a locking mechanism arranged to mechanically lock the meshes 112, 114 in the expanded position. The intermediate portion 106 of the device 100 may be diametrically expandable, for example by way of plastic deformation of the tube 108.

Figure 9:
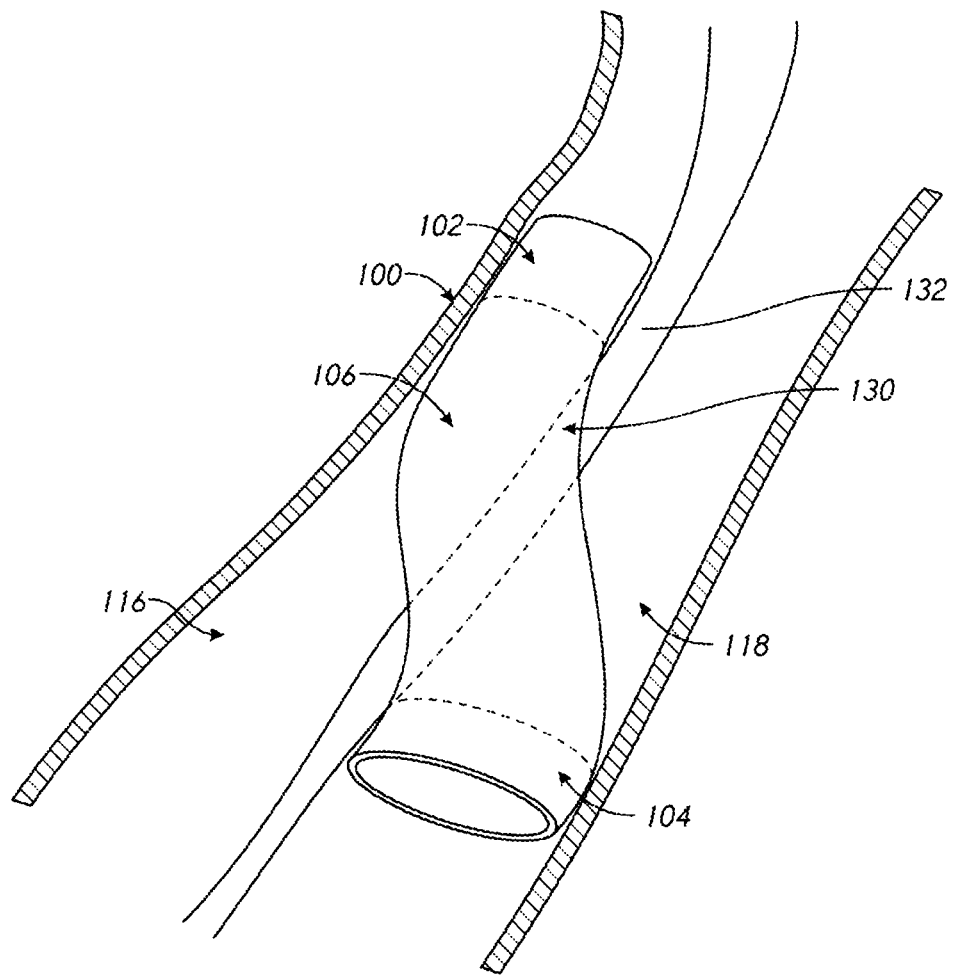
FIG. 9 shows the device of FIG. 8 in use as a shunt between two blood vessels.

FIG. 9 shows the device 100 of FIG. 8 deployed to provide a fluid flow path between a first passage 116 and a second passage 118. The passages 116, 118 may include coronary blood vessels, for example a coronary artery 116 and a coronary vein 118, or vice versa. The passages 116, 118 may include peripheral blood vessels (e.g., blood vessels in limbs), for example a femoral or other peripheral artery 116 and a femoral or other peripheral vein 118, or vice versa. The end portions 102, 104 and the intermediate portion 106 of the device 100 have been expanded to meet with and push against the inner walls of the passages 116, 118. The distal end portion 104 of the device 100 is located within the second passage 118, and the proximal end portion 102 of the device 100 is located within the first passage 116. The intermediate portion 106 extends through an opening or interconnecting passage 130 surgically formed between the passages 116, 118.

The expanded end portions 102, 104 of the device 100 are resilient, and impart an outward radial force on the inner walls of the passages 116, 118. By virtue of the radial stiffness of the end portions 102, 104 of the device 100, the end portions 102, 104 are held or anchored in place within the respective passages 116, 118. Slippage of the device 100 within the passages 116, 118 is thereby prevented or reduced. In this way, the end portions 102, 104 of the device 100 can anchor or fix the device 100 in position, in use, while providing or maintaining fluid flow through the lumen 110 of the tube 108 (FIG. 8). In this way, the device 100 can act as a shunt between the first passage 116 and the second passage 118.

The intermediate portion 106 of the device 100 may be flexible, for example allowing the intermediate portion 106 to form an 'S' shape formed by the combination of the first passage 116, the second passage 118, and the interconnecting passage 130 (FIG. 9). The flexible intermediate portion 106 can allow the end portions 102, 104 of the device 100 to move with respect to one another in response to relative movement of the passages 116, 118.

In embodiments in which the intermediate portion 106 does not include a wire mesh but includes the flexible polymer material of the tube 108, the intermediate portion 106 may not be susceptible to damage due to mesh fatigue, for example upon cyclic or other stress imparted by relative movement of the passages 116, 118.

The intermediate portion 106 of the device 100 has sufficient resilience to maintain dilatation of the interconnecting passage 130, so that the interconnecting passage 130 remains open to provide or maintain a path for blood flow from the artery 116 to the vein 118 by way of the lumen 110 of the tube 108 (FIG. 8). Blood flow from the artery 116 to the vein 118, by way of the interconnecting passage 130, may thereby be provided or maintained through the lumen 110 of the tube 108. The device 100 at least partially supports the artery 116, the vein 118, and the interconnecting passage 130 to provide a pathway for fluid communication through the device 100.

The proximal end portion 102 and the distal end portion 104 of the device 100 are arranged so that, when the device 100 is deployed with the distal end portion 104 in a vein 118 and the proximal end portion 102 in an artery 116, for example as shown in FIG. 9, the diameter of the expanded distal end portion 104 is sufficient to hold the distal end portion 104 within the vein 118, and the diameter of the expanded proximal end portion 102 is sufficient to hold the proximal end portion 102 within the artery 116. The diameter of the proximal end portion 102 may therefore differ from the diameter of the distal end portion 104. By selecting appropriate diameters for the end portions 102, 104 and the intermediate portion 106, the device 100 can be tailored to a certain anatomy and/or the anatomy of an individual patient.

An example procedure for positioning the device 100 of FIG. 8 to provide a shunt between an occluded artery 116 and a vein 118 (e.g., a coronary artery 116 and a coronary vein 118, or a peripheral artery 116 and a peripheral vein 118) to achieve retroperfusion of arterial blood, for example as shown in FIG. 9, will now be described.

A catheter may be inserted into the patient's arterial system by way of a small aperture cut, usually in the patient's groin area. The catheter is fed to the artery 116 and guided to a position upstream of the site of the occlusion, for example at a site proximate and parallel or substantially parallel to a vein 118. A hollow needle is deployed from the catheter, through the wall of the artery 116, through the interstitial tissue 132 that separates the artery 116 and vein 118, and through the wall of the vein 118. The path of the needle creates an interconnecting passage or opening 130, which allows blood to flow between the artery 116 and the vein 118. Deployment of the needle may be guided by a transmitter (e.g., a directional ultrasound transmitter) coupled to a catheter in the artery 116 and a receiver (e.g., an omnidirectional ultrasound receiver) coupled to a catheter in the vein 118, or vice versa, for example as described herein and in U.S. patent application Ser. No. 11/662,128. Other methods of forming the opening 130 are also possible (e.g., with or without directional ultrasound guidance, with other types of guidance such as described herein, from vein to artery, etc.).

Before the needle is withdrawn from the passage 130, a guidewire (e.g., as described with respect to the guidewire 14 of FIG. 3) is inserted through the hollow needle and into the vein 118. The needle is then retracted, leaving the guidewire in place in the artery 116, the passage 130, and the vein 118. The catheter carrying the needle can then be withdrawn from the patient's body. The guidewire can be used to guide further catheters to the interconnecting passage 130 between the artery 116 and the vein 118.

A catheter carrying the device 100 in a non-expanded state is advanced towards the interconnecting passage 130, guided by the guidewire, for example by a rapid exchange lumen or through the lumen 110. The catheter may include, for example, a balloon catheter configured to expand at least a portion of the device 100 and/or a catheter configured to allow self-expansion of at least a portion of the device 100. The distal end portion 104 of the device 100 is passed through the interconnecting passage 130 and into the vein 118, leaving the proximal end portion 102 in the artery 116. The intermediate portion 106 of the device 100 is at least partially in the passage 130, and is at least partially within the artery 116 and the vein 118. The intermediate portion 106 flexes to adopt a curved or "S"-shaped formation, depending on the anatomy of the site. Adoption of such curvature may conform the shape of an intermediate portion 106 extending through the interconnecting passage 130, and optionally into at least one of the passages 116, 118, to the shape of at least the interconnecting passage 130.

The distal end portion 104 of the device 100 is expanded, for example upon inflation of a balloon or by self-expansion, so as to increase the diameter of the distal end portion 104 and anchor the distal end portion 104 against the inner wall of the vein 118. The catheter may be adapted to expand the intermediate portion 106 of the device 100, for example by inflation of a balloon, so that the interconnecting passage 130 can be widened or dilated to obtain blood flow (e.g., sufficient blood flow) from the artery 116 to the vein 118. The proximal end portion 102 of the device 100 is expanded, for example upon inflation of a balloon or by self-expansion, so as to increase the diameter of the proximal end portion 102 and anchor the proximal end portion 102 against the inner wall of the artery 116.

After the end portions 102, 104 of the device 100 are expanded, for example due to self-expansion and/or balloon expansion, and with or without improving expansion after deployment, the catheter and the guidewire are withdrawn from the patient's body. In this way, the device 100 is anchored or fixed in position within the vein 118, the artery 116, and the interconnecting passage 130 as shown in FIG. 9. In embodiments in which the device 100 comprises a stent-graft, the graft, which can form a fluid-tight passage between the artery 116 and the vein 118, can inhibit or prevent blood from flowing antegrade in the vein 118 because such passageway is blocked, which can be in addition to or instead of a blocking agent in the vein 118.

The catheter may be adapted to selectively expand the proximal end portion 102, the distal end portion 104, and/or the intermediate portion 106 of the device 100 individually or in combination, for example by the provision of two or more separately inflatable balloons or balloon portions, a single balloon configured to expand all of the portions of the device 100 simultaneously, or a single balloon configured to expand one or more selected portions of the device 100. For example, the end portions 102, 104 may be self-expanding, and the intermediate portion 106 may be expanded by a balloon to dilate the passage 130. In some embodiments including balloon expansion, all or selected parts of the device 100 may be expanded, for example, simultaneously by a balloon across the entire length of the device 100 or by a plurality of balloons longitudinally spaced to selectively inflate selected parts of the device 100, and/or sequentially by a balloon or plurality of balloons. In some embodiments including at least partial self-expansion, all or selected parts of the device 100 may be expanded, for example, by proximal retraction of a sheath over or around the device 100, which can lead to deployment of the device 100 from distal to proximal as the sheath is proximally retracted. Deployment of the device 100 proximal to distal and deployment of the device 100 intermediate first then the ends are also possible. In some embodiments, for example embodiments in which the device 100 is at least partially conical or tapered, a conical or tapered balloon may be used to at least partially expand the device 100. In certain such embodiments, a portion of the balloon proximate to the vein 118 may have a larger diameter than a portion of the balloon proximate to the artery 116, for example such that the device 100 can adapt to changing vein diameters due to any increase in pressure or blood flow in the vein 118.

Other steps may be included in the procedure. For example, before the device 100 is deployed, a balloon catheter may be guided to the interconnecting passage 130 and positioned so that an inflatable balloon portion of the catheter lies in the interconnecting passage 130. Upon inflation of the balloon, the balloon pushes against the walls of the interconnecting passage 130 to widen or dilate the interconnecting passage 130 to ease subsequent insertion of the device 100.

Figure 10:
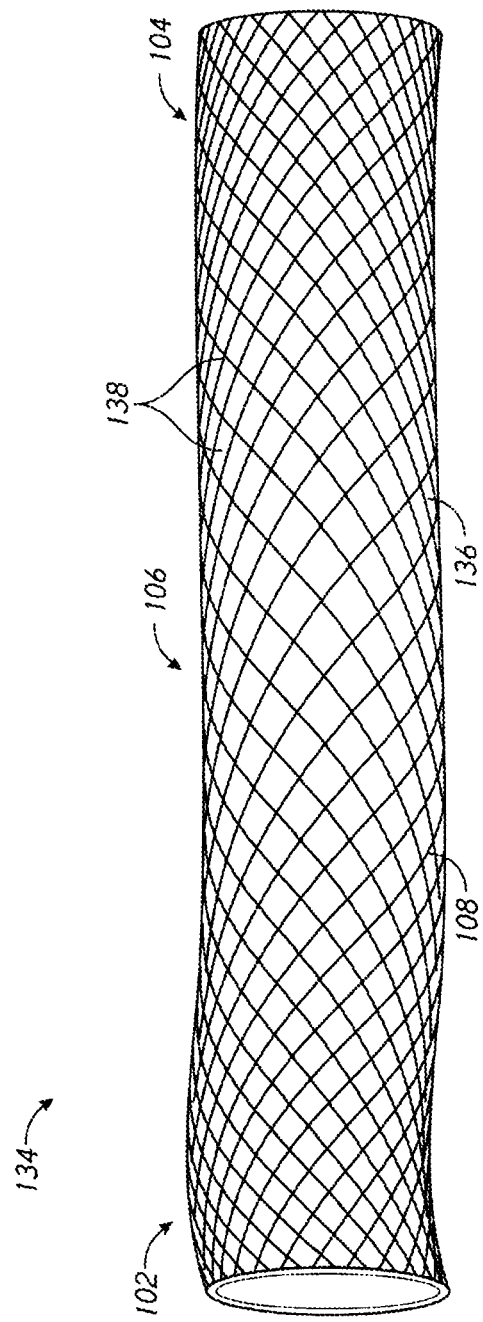
FIG. 10 is a side perspective view of another example embodiment of a device for providing fluid flow.

FIG. 10 illustrates another device 134 for providing fluid flow through at least one passage. The device 134 includes a mesh 136 and a polymer tube 108. The mesh 136 is shown as being on the outside of the polymer tube 108, but as described herein could also or alternatively be on an inside of the polymer tube and/or within the polymer tube 108. As described with respect to the device 100, the device 134 includes a proximal end portion 102, a distal end portion 104, and an intermediate portion 106. In the embodiment illustrated in FIG. 10, the mesh 136 extends along the entire length of the device 134, including along the intermediate portion 106.

In some embodiments, the spacing of filaments or struts of the mesh 136 varies along the length of the device 134. For example, winding density of a woven or layered filamentary mesh may be varied and/or a window size pattern of a cut mesh may be varied.

In some embodiments, the spacing may be relatively small in the proximal end portion 102 and the distal end portions 104, and the spacing may be relatively large in the intermediate portion 106. In other words, the density or window size of the mesh 136 may be relatively low in the intermediate portion 106, and the density or window size of the mesh 136 may be relatively high in the end portions 102, 104. In certain such embodiments, the intermediate portion 106 may be flexible in comparison to the end portions 102, 104. The relatively rigid end portions 102, 104 may engage and anchor in passages. Although the mesh 136 in the intermediate portion 106 may be subject to stress such as cyclic stress, in use, the relatively high flexibility of the intermediate portion 106 due to the low density or window size allows the impact of the stress to be low because the intermediate portion 106 can flex in response to the stress. The risk of fatigue failure of the device 134, and particularly the filaments or struts 138 of the mesh 136, may therefore be reduced in comparison to a device having uniform flexibility along its entire length.

In some embodiments, the spacing may be relatively large in the proximal end portion 102 and the distal end portions 104, and the spacing may be relatively small in the intermediate portion 106. In other words, the density of the mesh 136 may be relatively high (or the window size of the mesh 136 may be relatively low) in the intermediate portion 106, and the density of the mesh 136 may be relatively low (or the window size of the mesh 136 may be relatively high) in the end portions 102, 104. In certain such embodiments, the intermediate portion 106 may have radial strength sufficient to inhibit or prevent collapse of the passage 130, yet still, flexible enough to flex in response to stress such as cyclic stress. The end portions 102, 104 may engage and anchor in passages.

Figure 11:
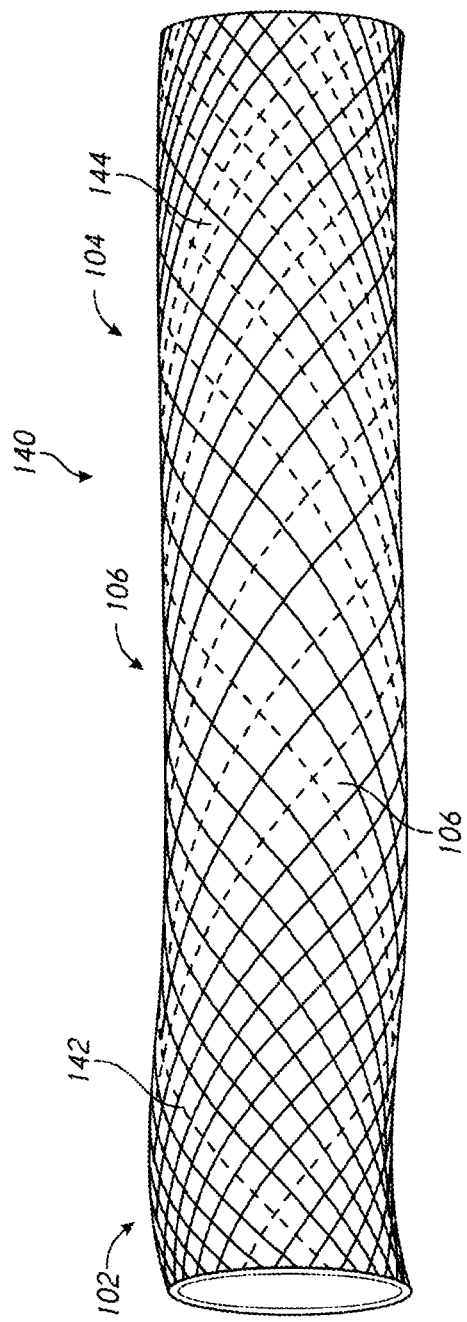
FIG. 11 is a side perspective view of still another example embodiment of a device for providing fluid flow.

FIG. 11 illustrates another device or implant or prosthetic 140 for providing fluid flow through at least one passage. As described with respect to the device 100, the device 140 includes a proximal end portion 102, a distal end portion 104, and an intermediate portion 106. The device 140 includes a polymer tube 108 and a support structure including a first mesh 142 and a second mesh 144. The first mesh 142 extends from the proximal end portion 102 toward (e.g., into) the intermediate portion 106 and optionally into the distal end portion 104. The second mesh 144 extends from the distal end portion 104 toward (e.g., into) the intermediate portion 106 and optionally into the proximal end portion 102. The meshes 142, 144 thereby overlap each other at least in the intermediate portion 106. Both meshes 142, 144 may be on the outside of the tube 108, on the inside of the tube 108, or embedded within the tube 108, or one mesh may be on the outside of the tube 108, on the inside of the tube 108, or embedded within the tube 108 while the other mesh is differently on the outside of the tube 108, on the inside of the tube 108, or embedded within the tube 108 (e.g., one mesh inside the tube 108 and one mesh outside the tube 108). The meshes 142, 144 may be formed, for example, by winding wire in a lattice configuration around or inside the polymer tube 108, by placing a cut tube around or inside the polymer tube 108, by being embedded in the polymer tube 108, combinations thereof, and the like.

In some embodiments, the density of the meshes 142, 144 is relatively high (or the window size of the meshes 142, 144 is relatively low) in their respective end portions 102, 104 and decreases in density (or increases in window size) towards the intermediate portion 106. The total winding density (e.g., the winding density of both meshes 142, 144, taken together) may be lower in the intermediate portion 106 than in the end portions 102, 104, or the total window size (e.g., the window size of both meshes 142, 144, taken together) may be higher in the intermediate portion 106 than in the end portions 102, 104. In certain such embodiments, the intermediate portion 106 is relatively flexible in comparison to the end portions 102, 104. In some embodiments, the meshes 142, 144 do not extend into the intermediate portion, and absence of a mesh could cause the intermediate portion 106 to be relatively flexible in comparison to the end portions 102, 104. In some embodiments, as window size increases (e.g., longitudinally along a tapered portion of the device 140), the density decreases, the mesh coverage decreases, and/or the porosity increases because the width of the struts and/or filaments remains substantially constant or constant or does not increase in the same proportion as the window size, which could provide a change in flexibility along a longitudinal length.

The first and second meshes 142, 144 may include different materials, which can allow optimization of the properties of each of the respective distal and proximal end portions 102, 104 of the device 140 for a particular application of the device 140. For example, the second mesh 144 at the distal end portion 104 of the device 140 may include a relatively flexible metallic alloy for ease of insertion through an interconnecting passage between two blood vessels, while the first mesh 142 at the proximal end portion 102 of the device 140 may include a relatively inelastic metallic alloy to provide a high degree of resilience at the proximal end portion 104 to anchor the device 140 firmly in position. The first and second meshes 142, 144 could include the same material composition (e.g., both including nitinol) but different wire diameters (gauge) or strut thicknesses.

Figure 12:
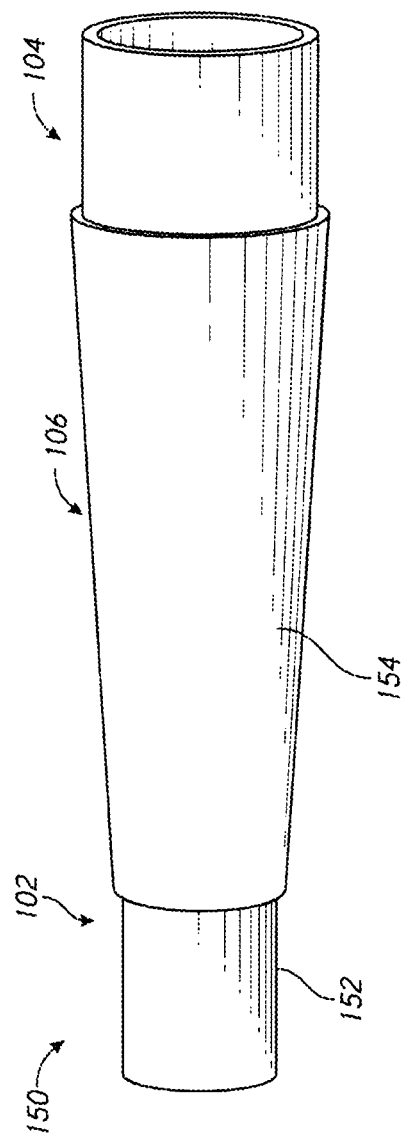
FIG. 12 is a side perspective view of yet another example embodiment of a device for providing fluid flow.

FIG. 12 illustrates another device or implant or prosthetic 150 for providing fluid flow through at least one passage. The device 150 includes a support structure (e.g., stent) 152 and a graft 154. As described with respect to the device 100, the device 150 includes a proximal end portion 102, a distal end portion 104, and an intermediate portion 106. The proximal end portion 102 includes a cylindrical or substantially cylindrical portion and the distal end portion 104 includes a cylindrical or substantially cylindrical portion. The diameter of the proximal end portion 102 is smaller than the diameter of the distal end portion 104. In some embodiments, the diameter of the proximal end portion 102 is larger than the diameter of the distal end portion 104. The intermediate portion 106 has a tapered or frustoconical shape between the proximal end portion 102 and the distal end portion 104. The stent 152 may include filaments (e.g., woven, layered), a cut tube or sheet, and/or combinations thereof.

Parameters of the stent 152 may be uniform or substantially uniform across a portion and/or across multiple portions, or may vary within a portion and/or across multiple portions. For example, the stent 152 at the proximal end portion 102 may include a cut tube or sheet, the stent 152 at the distal end portion 102 may include a cut tube or sheet, and the stent 152 at the intermediate portion 106 may include filaments (e.g., woven or layered). Certain such embodiments may provide good anchoring by the proximal end portion 102 and the distal end portion 104 and good flexibility (e.g., adaptability to third passage sizes and dynamic stresses) of the intermediate portion 106.

The stent 152 may include different materials in different portions. For example, the stent 152 at the proximal end portion 102 may include chromium cobalt and/or tantalum, the stent 152 at the distal end portion 104 may include nitinol, and the stent 152 at the intermediate portion 106 may include nitinol. Certain such embodiments may provide good anchoring and/or wall apposition by the device 150 in each deployment areas (e.g., the proximal end portion 102 engaging sidewalls of an artery, the distal end portion 104 engaging sidewalls of a vein, and the intermediate portion 106 engaging sidewalls of the passage between the artery and the vein). In some embodiments in which the distal end portion 104 is self-expanding, the distal end portion 104 can adapt due to changing vessel diameter (e.g., if vein diameter increases due to an increase in pressure or blood flow), for example by further self-expanding.

Combinations of support structure materials and types are also possible. For example, the stent 152 at the proximal portion may include a cut tube or sheet including chromium cobalt and/or tantalum, the stent 152 at the distal end portion 104 may include a cut tube or sheet including nitinol, and the stent 152 at the intermediate portion 106 may include filaments including nitinol.

In embodiments in which the stent 152 includes at least one portion including a cut tube or sheet, the cut pattern may be the same. For example, the cut pattern may be the same in the proximal end portion 102 and the distal end portion 104, but proportional to the change in diameter. In some embodiments, the window size or strut density is uniform or substantially uniform within a portion 102, 104, 106, within two or more of the portions 102, 104, 106, and/or from one end of the stent 152 to the other end of the stent 152. In embodiments in which the stent 152 includes at least one portion including filaments, the winding may be the same. For example, the winding may be the same in the proximal end portion 102 and the distal end portion 104, but changed due to the change in diameter. In some embodiments, the winding density or porosity is uniform or substantially uniform within a portion 102, 104, 106, within two or more of the portions 102, 104, 106, and/or from one end of the stent 152 to the other end of the stent 152. In embodiments in which the stent 152 includes at least one portion including a cut tube or sheet and at least one portion including filaments, the cut pattern and winding may be configured to result in a uniform or substantially uniform density. Non-uniformity is also possible, for example as described herein.

The graft 154 may include materials and attachment to the stent 152 as described with respect to the tube 108. The graft 154 generally forms a fluid-tight passage for at least a portion of the device 150. Although illustrated as only being around the intermediate portion 106, the graft 154 may extend the entire length of the device 150, or may partially overlap into at least one of the cylindrical end portions 102, 104.

Figure 13:
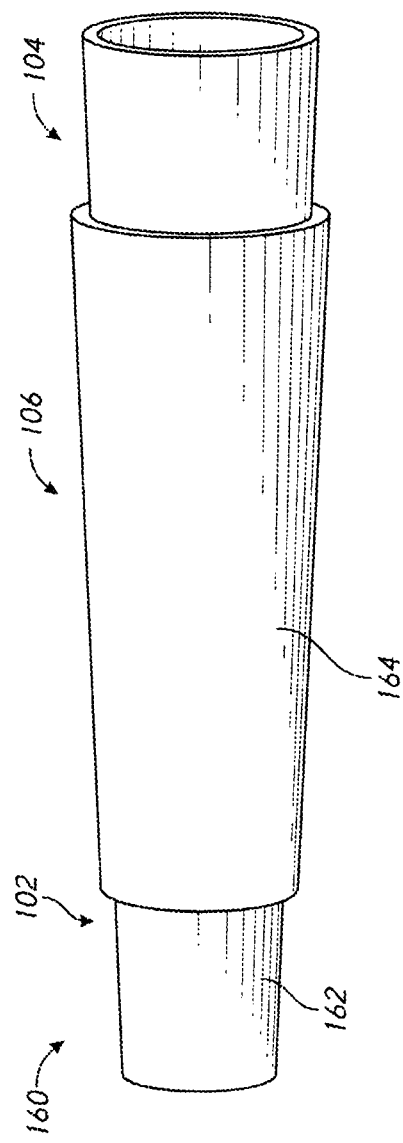
FIG. 13 is a side perspective view of yet still another example embodiment of a device for providing fluid flow.

FIG. 13 illustrates another device 160 for providing fluid flow through at least one passage. The device 160 includes a support structure (e.g., stent) and a graft 164. As described with respect to the device 100, the device 160 includes a proximal end portion 102, a distal end portion 104, and an intermediate portion 106. The proximal end portion 102 includes a tapered or frustoconical portion and the distal end portion 104 includes a tapered or frustoconical portion. The diameter of the proximal end of the proximal end portion 102 is smaller than the diameter of the distal end of the distal end portion 104. In some embodiments, the diameter of the proximal end of the proximal end portion 102 is larger than the diameter of the distal end of the distal end portion 104. The intermediate portion 106 has a tapered or frustoconical shape between the proximal end portion 102 and the distal end portion 104. In some embodiments, the angle of inclination of the portions 102, 104, 106 is the same or substantially the same (e.g., as illustrated in FIG. 13). In some embodiments, the angle of inclination of at least one portion is sharper or narrower than at least one other portion. The frustoconical proximal end portion 102 and distal end portion 104 may allow better anchoring in a body passage, for example because arteries tend to taper with distance from the heart and veins tend to taper with distance towards the heart, and the end portions 102, 104 can be configured to at least partially correspond to such anatomical taper.

FIG. 12 illustrates a device 150 comprising a first cylindrical or straight portion, a conical or tapered portion, and second cylindrical or straight portion. FIG. 13 illustrates a device 160 comprising one or more conical or tapered sections (e.g., the entire device 160 being conical or tapered or comprising a plurality of conical or tapered sections). In some embodiments, combinations of the devices 150, 160 are possible. For example, a device may comprise a cylindrical or straight portion and a conical or tapered portion for the remainder of the device. In certain such embodiments, the device may have a length between about 1 cm and about 10 cm (e.g., about 5 cm), which includes a cylindrical or straight portion having a diameter between about 1 mm and about 5 mm (e.g., about 3 mm) and a length between about 0.5 cm and about 4 cm (e.g., about 2 cm) and a conical or tapered portion having a diameter that increases from the diameter of the cylindrical or straight portion to a diameter between about 3 mm and about 10 mm (e.g., about 5 mm) and a length between about 1 cm and about 6 cm (e.g., about 3 cm). Such a device may be devoid of another cylindrical or conical portion thereafter.

As described above with respect to the support structure 152, the support structure 162 may include filaments (e.g., woven, layered), a cut tube or sheet, the same materials, different materials, and combinations thereof.

The graft 164 may include materials and attachment to the stent 162 as described with respect to the tube 108. The graft 164 generally forms a fluid-tight passage for at least a portion of the device 160. Although illustrated as only being around the intermediate portion 106, the graft 164 may extend the entire length of the device 160, or may partially overlap into at least one of the frustoconical end portions 102, 104.

In some embodiments, a combination of the device 150 and the device 160 are possible. For example, the proximal end portion 102 can be cylindrical or substantially cylindrical (e.g., as in the device 150), the distal end portion 104 can be tapered or frustoconical (e.g., as in the device 160), with the proximal end portion 102 having a larger diameter than the distal end of the distal end portion 104. For another example, the proximal end portion 102 can be tapered or frustoconical (e.g., as in the device 160), the distal end portion 104 can be cylindrical or substantially cylindrical (e.g., as in the device 150), with the proximal end of the proximal end portion 102 having a larger diameter than the distal end portion 104. In each example, the intermediate portion 106 can have a tapered or frustoconical shape between the proximal end portion 102 and the distal end portion 104.

An example deployment device for the implantable devices described herein is described in U.S. patent application Ser. No. 12/545,982, filed Aug. 24, 2009, and U.S. patent application Ser. No. 13/486,249, filed Jun. 1, 2012, the entire contents of each of which is hereby incorporated by reference. The device generally includes a handle at the proximal end with a trigger actuatable by a user and a combination of tubular member at the distal end configured to be pushed and/or pulled upon actuation of the trigger to release the device. Other delivery devices are also possible. The delivery device may include a portion slidable over a guidewire (e.g., a guidewire that has been navigated between the artery and the vein via a tissue traversing needle) and/or may be trackable through a lumen of a catheter.

Although certain embodiments and examples are shown or described herein in detail, various combinations, sub-combinations, modifications, variations, substitutions, and omissions of the specific features and aspects of those embodiments are possible, some of which will now be described by way of example only.

The device, for example a stent of the device, a mesh of the device, a support structure of the device, etc., may be self-expanding. For example, a mesh may include a shape-memory material, such as nitinol, which is capable of returning to a pre-set shape after undergoing deformation. In some embodiments, the stent may be manufactured to a shape that is desired in the expanded configuration, and is compressible to fit inside a sleeve for transport on a catheter to a vascular site. To deploy and expand the stent, the sleeve is drawn back from the stent to allow the shape memory material to return to the pre-set shape, which can anchor the stent in the passages, and which may dilate the passages if the stent has sufficient radial strength. The use of a balloon catheter is not required to expand a fully self-expanding stent, but may be used, for example, to improve or optimize the deployment.

A device may include one or more self-expanding portions, and one or more portions which are expandable by deformation, for example using a balloon catheter. For example, in the embodiment shown in FIG. 11, the first mesh 142 may include stainless steel expandable by a balloon catheter, and the second mesh 144 may include nitinol for self-expansion upon deployment.

With respect to any of the embodiments described herein, the polymer tube 108, including the grafts 154, 164, may include any suitable compliant or flexible polymer, such as PTFE, silicone, polyethylene terephthalate (PET), polyurethane such as polycarbonate aromatic biodurable thermoplastic polyurethane elastomer (e.g., ChronoFlex C® 80A and 55D medical grade, available from AdvanSource Biomaterials of Wilmington, Massachusetts), combinations thereof, and the like. The polymer tube 108 may include biodegradable, bioabsorbable, or biocompatible polymer (e.g., polylactic acid (PLA), polyglycolic acid (PGA), polyglycolic-lactic acid (PLGA), polycaprolactone (PCL), polyorthoesters, polyanhydrides, combinations thereof, etc. The polymer may be in tube form before interaction with a support structure (e.g., stent), or may be formed on, in, and/or around a support structure (e.g., stent). For example, the polymer may include spun fibers, a dip-coating, combinations thereof, and the like. In some embodiments, for example when the device is to be deployed within a single blood vessel, the device may omit the tube. In certain such embodiments, the intermediate portion of the stent may include a mesh with a low winding density or high window size, while the end portions of the stent include a mesh with a higher winding density or lower window size, the mesh being generally tubular to define a pathway for fluid flow through the center of the mesh. In some embodiments, the polymer tube 108 includes a lip (e.g., comprising the same or different material), which can help form a fluid-tight seal between the polymer tube 108 and the body passages. The seal may be angled, for example to account for angled positioning of the polymer tube 108 between body passages. In some embodiments, the polymer tube 108 may extend longitudinally beyond the support structure in at least one direction, and the part extending beyond is not supported by the support structure.

The mesh may include any suitable material, such as nickel, titanium, chromium, cobalt, tantalum, platinum, tungsten, iron, manganese, molybdenum, combinations thereof (e.g., nitinol, chromium cobalt, stainless steel), and the like. The mesh may include biodegradable, bioabsorbable, or biocompatible polymer (e.g., polylactic acid (PLA), polyglycolic acid (PGA), polyglycolic-lactic acid (PLGA), polycaprolactone (PCL), polyorthoesters, polyanhydrides, combinations thereof, etc.) and/or glass, and may lack metal. Different materials may be used for portions of the mesh or within the same mesh, for example as previously described with reference to FIG. 11. For example, the mesh 114 at the distal end portion 104 and the mesh 112 at the proximal end portion 102 of the device 100 may include different materials. For another example, the mesh 112, and/or the mesh 114, may include a metallic alloy (e.g., comprising cobalt, chromium, nickel, titanium, combinations thereof, and the like) in combination with a different type of metallic alloy (e.g., a shape memory alloy in combination with a non-shape memory alloy, a first shape memory alloy in combination with a second shape memory alloy different than the first shape memory alloy, a clad material (e.g., comprising a core including a radiopaque material such as titanium, tantalum, rhenium, bismuth, silver, gold, platinum, iridium, tungsten, etc.)) and/or a non-metallic material such as a polymer (e.g., polyester fiber), carbon, and/or bioabsorbable glass fiber. In some embodiments, at least one mesh 112, 114 comprises nitinol and stainless steel. The nitinol may allow some self-expansion (e.g., partial and/or full self-expansion), and the mesh could then be further expanded, for example using a balloon.

Although generally illustrated in FIGS. 8, 10, and 11 as a woven filament mesh, any other structure that can provide the desired degree of resilience may be used. For example, layers of filaments wound in opposite directions may be fused at the filament ends to provide an expandable structure. For another example, a metal sheet may be cut (e.g., laser cut, chemically etched, plasma cut, etc.) to form perforations and then heat set in a tubular formation or a metal tube (e.g., hypotube) may be cut (e.g., laser cut, chemically etched, plasma cut, etc.) to form perforations. A cut tube (including a cut sheet rolled into a tube) may be heat set to impart an expanded configuration.

Filaments or wires or ribbons that may be woven or braided, or layered or otherwise arranged, are generally elongate and have a circular, oval, square, rectangular, etc. transverse cross-section. Example non-woven filaments can include a first layer of filaments wound in a first direction and a second layer of filaments wound in a second direction, at least some of the filament ends being coupled together (e.g., by being coupled to an expandable ring). Example braid patterns include one-over-one-under-one, a one-over-two-under-two, a two-over-two-under-two, and/or combinations thereof, although other braid patterns are also possible. At filament crossings, filaments may be helically wrapped, cross in sliding relation, and/or combinations thereof. Filaments may be loose (e.g., held together by the weave) and/or include welds, coupling elements such as sleeves, and/or combinations thereof. Ends of filaments can be bent back, crimped (e.g., end crimp with a radiopaque material such as titanium, tantalum, rhenium, bismuth, silver, gold, platinum, iridium, tungsten, etc. that can also act as a radiopaque marker), twisted, ball welded, coupled to a ring, combinations thereof, and the like. Weave ends may include filament ends and/or bent-back filaments, and may include open cells, fixed or unfixed filaments, welds, adhesives, or other means of fusion, radiopaque markers, combinations thereof, and the like. Parameters of the filaments may be uniform or substantially uniform across a portion and/or across multiple portions, or may vary within a portion and/or across multiple portions. For example, the proximal end portion 102 may include a first parameter and the distal end portion 104 may include a second parameter different than the first braid pattern. For another example, the proximal end portion 102 and the distal end portion 104 may each include a first parameter and the intermediate portion 106 may include a second parameter different than the parameter. For yet another example, at least one of the proximal end portion 102, the distal end portion 104, and the intermediate portion 106 may include both a first parameter and a second parameter different than the first parameter. Filament parameters may include, for example, filament type, filament thickness, filament material, quantity of filaments, weave pattern, layering, wind direction, pitch, angle, crossing type, filament coupling or lack thereof, filament end treatment, weave end treatment, layering end treatment, quantity of layers, presence or absence of welds, radiopacity, braid pattern, density, porosity, filament angle, braid diameter, winding diameter, and shape setting.

Tubes or sheets may be cut to form strut or cell patterns, struts being the parts of the tube or sheet left after cutting and cells or perforations or windows being the parts cut away. A tube (e.g., hypotube) may be cut directly, or a sheet may be cut and then rolled into a tube. The tube or sheet may be shape set before or after cutting. The tube or sheet may be welded or otherwise coupled to itself, to another tube or sheet, to filaments, to a graft material, etc. Cutting may be by laser, chemical etchant, plasma, combinations thereof, and the like. Example cut patterns include helical spiral, weave-like, coil, individual rings, sequential rings, open cell, closed cell, combinations thereof, and the like. In embodiments including sequential rings, the rings may be coupled using flex connectors, non-flex connectors, and/or combinations thereof. In embodiments including sequential rings, the rings connectors (e.g., flex, non-flex, and/or combinations thereof) may intersect ring peaks, ring valleys, intermediate portions of struts, and/or combinations thereof (e.g., peak-peak, valley-valley, mid-mid, peak-valley, peak-mid, valley-mid, valley-peak, mid-peak, mid-valley). The tube or sheet or sections thereof may be ground and/or polished before or after cutting. Interior ridges may be formed, for example to assist with fluid flow. Parameters of the cut tube or sheet may be uniform or substantially uniform across a portion and/or across multiple portions, or may vary within a portion and/or across multiple portions. For example, the proximal end portion 102 may include a first parameter and the distal end portion 104 may include a second parameter different than the first parameter. For another example, the proximal end portion 102 and the distal end portion 104 may each include a first parameter and the intermediate portion 106 may include a second parameter different than the parameter. For yet another example, at least one of the proximal end portion 102, the distal end portion 104, and the intermediate portion 106 may include both a first parameter and a second parameter different than the first parameter. Cut tube or sheet parameters may include, for example, radial strut thickness, circumferential strut width, strut shape, cell shape, cut pattern, cut type, material, density, porosity, tube diameter, and shape setting.

In some embodiments, the perforations may provide the mesh with a relatively flexible intermediate portion and relatively stiff end portions. The supporting structure may instead be an open-cell foam disposed within the tube.

Filaments of a stent, stent-graft, or a portion thereof, and/or struts of a cut stent, stent-graft, or a portion thereof, may be surface modified, for example to carry medications such as thrombosis modifiers, fluid flow modifiers, antibiotics, etc. Filaments of a stent, stent-graft, or a portion thereof, and/or struts of a cut stent, stent-graft, or a portion thereof, may be at least partially covered with a coating including medications such as thrombosis modifiers, fluid flow modifiers, antibiotics, etc., for example embedded within a polymer layer or a series of polymer layers, which may be the same as or different than the polymer tube 108.

Thickness (e.g., diameter) of filaments of a stent, stent-graft, or a portion thereof, and/or struts of a cut stent, stent-graft, or a portion thereof, may be between about 0.0005 inches and about 0.02 inches, between about 0.0005 inches and about 0.015 inches, between about 0.0005 inches and about 0.01 inches, between about 0.0005 inches and about 0.008 inches, between about 0.0005 inches and about 0.007 inches, between about 0.0005 inches and about 0.006 inches, between about 0.0005 inches and about 0.005 inches, between about 0.0005 inches and about 0.004 inches, between about 0.0005 inches and about 0.003 inches, between about 0.0005 inches and about 0.002 inches, between about 0.0005 inches and about 0.001 inches, between about 0.001 inches and about 0.02 inches, between about 0.001 inches and about 0.015 inches, between about 0.001 inches and about 0.01 inches, between about 0.001 inches and about 0.008 inches, between about 0.001 inches and about 0.007 inches, between about 0.001 inches and about 0.006 inches, between about 0.001 inches and about 0.005 inches, between about 0.001 inches and about 0.004 inches, between about 0.001 inches and about 0.003 inches, between about 0.001 inches and about 0.002 inches, between about 0.002 inches and about 0.02 inches, between about 0.002 inches and about 0.015 inches, between about 0.002 inches and about 0.01 inches, between about 0.002 inches and about 0.008 inches, between about 0.002 inches and about 0.007 inches, between about 0.002 inches and about 0.006 inches, between about 0.002 inches and about 0.005 inches, between about 0.002 inches and about 0.004 inches, between about 0.002 inches and about 0.003 inches, between about 0.003 inches and about 0.02 inches, between about 0.003 inches and about 0.015 inches, between about 0.003 inches and about 0.01 inches, between about 0.003 inches and about 0.008 inches, between about 0.003 inches and about 0.007 inches, between about 0.003 inches and about 0.006 inches, between about 0.003 inches and about 0.005 inches, between about 0.003 inches and about 0.004 inches, between about 0.004 inches and about 0.02 inches, between about 0.004 inches and about 0.015 inches, between about 0.004 inches and about 0.01 inches, between about 0.004 inches and about 0.008 inches, between about 0.004 inches and about 0.007 inches, between about 0.004 inches and about 0.006 inches, between about 0.004 inches and about 0.005 inches, between about 0.005 inches and about 0.02 inches, between about 0.005 inches and about 0.015 inches, between about 0.005 inches and about 0.01 inches, between about 0.005 inches and about 0.008 inches, between about 0.005 inches and about 0.007 inches, between about 0.005 inches and about 0.006 inches, between about 0.006 inches and about 0.02 inches, between about 0.006 inches and about 0.015 inches, between about 0.006 inches and about 0.01 inches, between about 0.006 inches and about 0.008 inches, between about 0.006 inches and about 0.007 inches, between about 0.007 inches and about 0.02 inches, between about 0.007 inches and about 0.015 inches, between about 0.007 inches and about 0.01 inches, between about 0.007 inches and about 0.008 inches, between about 0.008 inches and about 0.02 inches, between about 0.008 inches and about 0.015 inches, between about 0.008 inches and about 0.01 inches, between about 0.01 inches and about 0.02 inches, between about 0.01 inches and about 0.015 inches, or between about 0.015 inches and about 0.02 inches. Other thicknesses are also possible, including thicknesses greater than or less than the identified thicknesses. Filaments and/or struts comprising certain materials (e.g., biodegradable material, materials with less restoring force, etc.) may be thicker than the identified thicknesses.

Thicknesses of filaments and/or struts may be based, for example, on at least one of device or device portion size (e.g., diameter and/or length), porosity, radial strength, material, quantity of filaments and/or struts, cut pattern, weave pattern, layering pattern, and the like. For example, larger filament and/or strut thicknesses (e.g., greater than about 0.006 inches) may be useful for large devices or device portions used to treat large vessels such as coronary vessels, mid-sized filament and/or strut thicknesses (e.g., between about 0.003 inches and about 0.006 inches) may be useful for mid-sized used to treat mid-sized vessels such as peripheral vessels, and small filament and/or strut thicknesses (e.g., less than about 0.003 inches) may be useful for small devices or device portions used to treat small vessels such as veins and neurological vessels.

The internal or external diameter of a stent, a stent-graft, or a first end portion, second end portion, intermediate portion, or subportion thereof, for example taking into account filament or strut thickness, may be between about 1 mm and about 12 mm, between about 1 mm and about 10 mm, between about 1 mm and about 8 mm, between about 1 mm and about 6 mm, between about 1 mm and about 4 mm, between about 1 mm and about 2 mm, between about 2 mm and about 12 mm, between about 2 mm and about 10 mm, between about 2 mm and about 8 mm, between about 2 mm and about 6 mm, between about 2 mm and about 4 mm, between about 4 mm and about 12 mm, between about 4 mm and about 10 mm, between about 4 mm and about 8 mm, between about 4 mm and about 6 mm, between about 6 mm and about 12 mm, between about 6 mm and about 10 mm, between about 6 mm and about 8 mm, between about 8 mm and about 12 mm, between about 8 mm and about 10 mm, or between about 10 mm and about 12 mm. Certain such diameters may be suitable for treating, for example, coronary vessels. The internal or external diameter of a stent, a stent-graft, or a portion thereof, for example taking into account filament or strut thickness, may be between about 1 mm and about 10 mm, between about 1 mm and about 8 mm, between about 1 mm and about 6 mm, between about 1 mm and about 4 mm, between about 1 mm and about 2 mm, between about 2 mm and about 10 mm, between about 2 mm and about 8 mm, between about 2 mm and about 6 mm, between about 2 mm and about 4 mm, between about 4 mm and about 10 mm, between about 4 mm and about 8 mm, between about 4 mm and about 6 mm, between about 6 mm and about 10 mm, between about 6 mm and about 8 mm, or between about 8 mm and about 10 mm. Certain such diameters may be suitable for treating, for example, veins. The internal or external diameter of a stent, a stent-graft, or a portion thereof, for example taking into account filament or strut thickness, may be between about 6 mm and about 25 mm, between about 6 mm and about 20 mm, between about 6 mm and about 15 mm, between about 6 mm and about 12 mm, between about 6 mm and about 9 mm, between about 9 mm and about 25 mm, between about 9 mm and about 20 mm, between about 9 mm and about 15 mm, between about 9 mm and about 12 mm, between about 12 mm and about 25 mm, between about 12 mm and about 20 mm, between about 12 mm and about 15 mm, between about 15 mm and about 25 mm, between about 15 mm and about 20 mm, or between about 20 mm and about 25 mm. Certain such diameters may be suitable for treating, for example, peripheral vessels. The internal or external diameter of a stent, a stent-graft, or a portion thereof, for example taking into account filament or strut thickness, may be between about 20 mm and about 50 mm, between about 20 mm and about 40 mm, between about 20 mm and about 35 mm, between about 20 mm and about 30 mm, between about 30 mm and about 50 mm, between about 30 mm and about 40 mm, between about 30 mm and about 35 mm, between about 35 mm and about 50 mm, between about 35 mm and about 40 mm, or between about 40 mm and about 50 mm. Certain such diameters may be suitable for treating, for example, aortic vessels. Other diameters are also possible, including diameters greater than or less than the identified diameters. The diameter of the device may refer to the diameter of the first end portion, the second end portion, or the intermediate portion, each of which may be in expanded or unexpanded form. The diameter of the device may refer to the average diameter of the device when all of the portions of the device are in either expanded or unexpanded form.

The length of a stent, a stent-graft, or a first end portion, second end portion, intermediate portion, or subportion thereof may be between about 5 mm and about 150 mm, between about 5 mm and about 110 mm, between about 5 mm and about 70 mm, between about 5 mm and about 50 mm, between about 5 mm and about 25 mm, between about 5 mm and about 20 mm, between about 5 mm and about 10 mm, between about 10 mm and about 150 mm, between about 10 mm and about 110 mm, between about 10 mm and about 70 mm, between about 10 mm and about 50 mm, between about 10 mm and about 25 mm, between about 10 mm and about 20 mm, between about 20 mm and about 150 mm, between about 20 mm and about 110 mm, between about 20 mm and about 70 mm, between about 20 mm and about 50 mm, between about 20 mm and about 25 mm, between about 25 mm and about 150 mm, between about 25 mm and about 110 mm, between about 25 mm and about 70 mm, between about 25 mm and about 50 mm, between about 50 mm and about 150 mm, between about 50 mm and about 110 mm, between about 50 mm and about 70 mm, between about 70 mm and about 150 mm, between about 70 mm and about 110 mm, or between about 110 mm and about 150 mm. Other lengths are also possible, including lengths greater than or less than the identified lengths.

The porosity of a stent, a stent-graft, or a first end portion, second end portion, intermediate portion, or subportion thereof may be between about 5% and about 95%, between about 5% and about 50%, between about 5% and about 25%, between about 5% and about 10%, between about 10% and about 50%, between about 10% and about 25%, between about 25% and about 50%, between about 50% and about 95%, between about 50% and about 75%, between about 50% and about 60%, between about 60% and about 95%, between about 75% and about 90%, between about 60% and about 75%, and combinations thereof. The density of a stent may be inverse to the porosity of that stent. The porosity of a portion of a stent covered by a graft may be about 0%. The porosity may vary by objectives for certain portions of the stent. For example, the intermediate portion may have a low porosity to increase fluid flow through the device, while end portions may have lower porosity to increase flexibility and wall apposition.

Figure 25B:
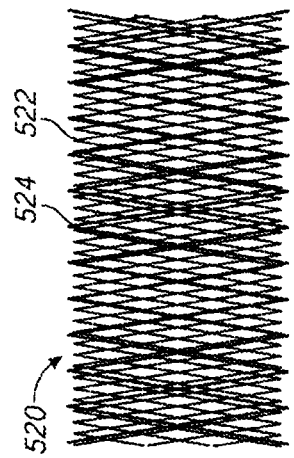
FIG. 25B is a schematic side elevational view of still another example embodiment of a prosthesis.
Figure 25A:
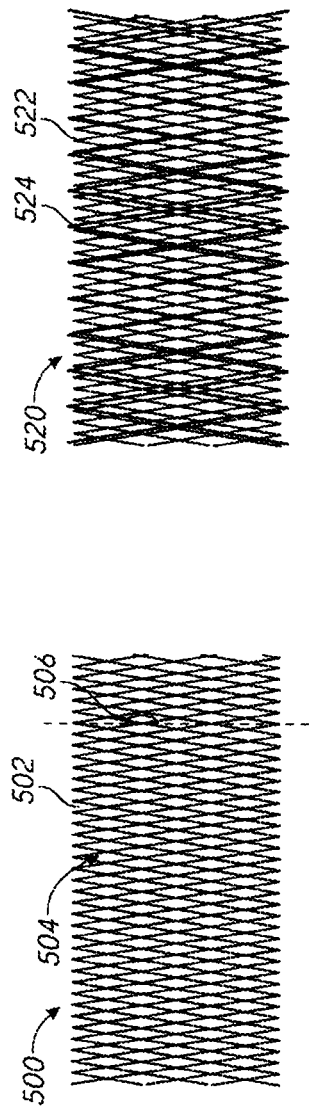
FIG. 25A is a schematic side elevational view of yet another example embodiment of a prosthesis.

FIG. 25A is a schematic side elevational view of yet another example embodiment of a prosthesis 500. The prosthesis or stent or device 500 includes and/or consist essentially of a plurality of filaments 502 woven together into a woven structure. The stent 500 may be devoid of graft material, as described in further detail below.

The filaments 502, which may also be described as wires, ribbons, strands, and the like, may be woven, braided, layered, or otherwise arranged in a crossing fashion. The filaments 502 are generally elongate and have a circular, oval, square, rectangular, etc. transverse cross-section. Example non-woven filaments can include a first layer of filaments wound in a first direction and a second layer of filaments wound in a second direction, at least some of the filament ends being coupled together (e.g., by being coupled to an expandable ring). Example weave patterns include one-over-one-under-one (e.g., as shown in FIG. 25A), a one-over-two-under-two, a two-over-two-under-two, and/or combinations thereof, although other weave patterns are also possible. At crossings of the filaments 502, the filaments 502 may be helically wrapped, cross in sliding relation, and/or combinations thereof. The filaments 502 may be loose (e.g., held together by the weave) and/or include welds, coupling elements such as sleeves, and/or combinations thereof. Ends of filaments 502 can be bent back, crimped (e.g., end crimp with a radiopaque material such as titanium, tantalum, rhenium, bismuth, silver, gold, platinum, iridium, tungsten, etc. that can also act as a radiopaque marker), twisted, ball welded, coupled to a ring, combinations thereof, and the like. Weave ends may include filament 502 ends and/or bent-back filaments 502, and may include open cells, fixed or unfixed filaments 502, welds, adhesives, or other means of fusion, radiopaque markers, combinations thereof, and the like.

The stent 500 includes pores 504 or open, non-covered areas between the filaments 502. The porosity of the stent 500 may be computed as the outer surface area of the pores 504 divided by the total outer surface area of the stent 500. The porosity may be affected by parameters such as, for example, the number of filaments 502, the braid angle 506, the size (e.g., diameter) of the filaments 502, and combinations thereof.

The porosity of the stent 500 may be less than about 50% (e.g., slightly more covered than open), between about 0% (e.g., almost no open area) and about 50%, between about 0% and about 45%, between about 0% and about 40%, between about 0% and about 35%, between about 0% and about 30%, between about 0% and about 25%, between about 0% and about 20%, between about 0% and about 15%, between about 0% and about 10%, between about 0% and about 5%, between about 5% and about 50%, between about 5% and about 45%, between about 5% and about 40%, between about 5% and about 35%, between about 5% and about 30%, between about 5% and about 25%, between about 5% and about 20%, between about 5% and about 15%, between about 5% and about 10%, between about 10% and about 50%, between about 10% and about 45%, between about 10% and about 40%, between about 10% and about 35%, between about 10% and about 30%, between about 10% and about 25%, between about 10% and about 20%, between about 10% and about 15%, between about 15% and about 50%, between about 15% and about 45%, between about 15% and about 40%, between about 15% and about 35%, between about 15% and about 30%, between about 15% and about 25%, between about 15% and about 20%, between about 20% and about 50%, between about 20% and about 45%, between about 20% and about 40%, between about 20% and about 35%, between about 20% and about 30%, between about 20% and about 25%, between about 25% and about 50%, between about 25% and about 45%, between about 25% and about 40%, between about 25% and about 35%, between about 25% and about 30%, between about 30% and about 50%, between about 30% and about 45%, between about 30% and about 40%, between about 30% and about 35%, between about 35% and about 50%, between about 35% and about 45%, between about 35% and about 40%, between about 40% and about 50%, between about 40% and about 45%, between about 45% and about 50%, and combinations thereof.

In some embodiments in which the porosity is less than about 50%, blood may be unable to perfuse through the sidewalls of the stent 500 under normal vascular pressures (e.g., a pressure drop across a vessel, a pressure drop from an afferent vessel to an efferent vessel). In certain such embodiments, blood flowing into a proximal end of the stent 500 can be directed through a lumen of the stent 500 to a distal end of the stent 500 without (e.g., substantially without, free of, substantially free of) graft material, but still without loss or substantial loss of blood through the sidewalls of the stent 500. By contrast, in certain so-called "flow diverting stents," the porosity is specifically designed to be greater than about 50% in order to ensure perfusion to efferent vessels.

The density of the stent 500 may be inverse to the porosity (e.g., the outer surface area of the filaments 502 divided by the total outer surface area of the stent 500). The density of the stent 500 may be 100% minus the porosity values provided above.

The filaments 502 are at a braid angle 506 relative to an axis perpendicular to the longitudinal axis of the stent 500 (e.g., as illustrated by the example dashed line in FIG. 25A). The braid angle 506 can range from just more than 90° to just under 180°. The braid angle 506 can be acute or obtuse. In some embodiments, the braid angle 506 is between about 90° and about 180°, between about 120° and about 180°, between about 150° and about 180°, between about 160° and about 180°, between about 170° and about 180°, between about 160° and about 170°, between about 165° and about 175°, combinations thereof, and the like. In some embodiments, the closer the braid angle 506 is to 180°, the greater the radial strength of the stent 500. Devices 500 with greater radial strength may aid in keeping a fistula (e.g., formed as described herein) open or patent. Other factors can also influence radial strength such as filament 502 diameter, filament 502 material, number of filaments 502, etc.

The filaments 502 may all be the same or some of the filaments 502 may have a different parameter (e.g., material, dimensions, combinations thereof, and the like). In some embodiments, some of the filaments 502 comprise shape memory material (e.g., comprising nitinol) and others of the filaments 502 comprise another material (e.g., comprising aramid fiber (e.g., Kevlar®), Dacron®, biocompatible polymer, etc.). The shape memory material may provide the mechanical structure and the other material may provide low porosity (e.g., by being thick in the dimension of the sidewalls).

FIG. 25B is a schematic side elevational view of still yet another example embodiment of a prosthesis 520. The prosthesis or stent or device 520 includes and/or consist essentially of a first plurality of filaments 522 woven together into a first woven structure and a second plurality of filaments 524 woven together into a second woven structure. The stent 520 may be devoid of graft material, as described in further detail herein. The first plurality of filaments 522 may be similar to the filaments 502 of the stent 500 described with respect to FIG. 25A. In some embodiments, the filaments 522 may lack sufficient radial force to keep a fistula open and/or to appose sidewalls of an artery and/or a vein. In certain such embodiments, the filaments 524 may act as a supplemental support structure to provide the radial force. The filaments 524 may be radially outward of the filaments 522 (e.g., as illustrated in FIG. 25B), radially inward of the filaments 522, and/or integrated with the filaments 522 (e.g., such that the first and second woven structures are not readily separable. The filaments 524 may be the same or different material as the filaments 522, the same or different thickness as the filaments 522, etc., and/or the filaments 524 may be braided with the same or different parameters (e.g., braid angle) than the filaments 522, resulting in filaments 524 having greater radial force. The filaments 524 may be coupled to the filaments 522 (e.g., in a single deployable stent 520) or separately deployed. For example, if the filaments 524 are deployed and then the filaments 522 are deployed, the filaments 524 can prop open a fistula and allow the filaments 522 to expand within the lumen created by the filaments 524 without substantial opposing force. For another example, if the filaments 522 are deployed and then the filaments 524 are deployed, the filaments 524 can act as an expansion force on the portions of the filaments 522 in need of an expansive force.

Although illustrated in FIG. 25B as comprising a second woven structure, the supplemental support structure may additionally or alternatively comprise a helical coil, a cut hypotube, combinations thereof, and the like. Determination of the porosity of the prosthesis 520 may be primarily based on the porosity of the first woven structure such that the supplemental support structure may be designed primarily for providing radial force (e.g., sufficient to keep a fistula open or patent).

Figure 25C:
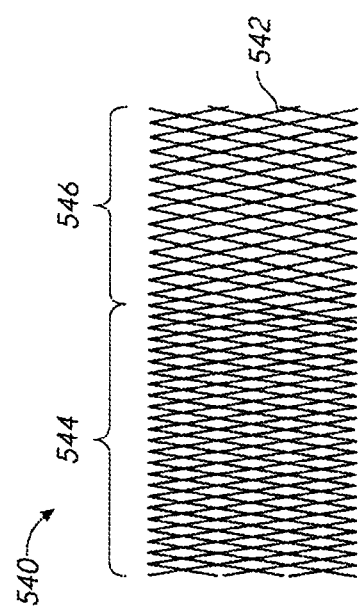
FIG. 25C is a schematic side elevational view of still yet another example embodiment of a prosthesis.

Although illustrated as being uniform or substantially uniform across the length of the stent 500, parameters of the stent 500 and the filaments 502 may vary across the stent 500, for example as described with respect to FIG. 25C. Uniformity may reduce manufacturing costs, reduce a demand for precise placement, and/or have other advantages. Non-uniformity may allow specialization or customization for specific properties and/or functions along different lengths and/or have other advantages.

FIG. 25C is a schematic side elevational view of still another example embodiment of a prosthesis 540. The prosthesis or stent or device 540 includes and/or consist essentially of a plurality of filaments 542 woven together into a woven structure. The stent 540 may be devoid of graft material, as described in further detail herein. The stent 540 comprises a first longitudinal section or segment or portion 544 and a second longitudinal section or segment or portion 546. Parameters such as porosity (e.g., as illustrated in FIG. 25B), braid angle, braid type, filament 542 parameters (e.g., diameter, material, etc.), existence of a supplemental support structure (e.g., the supplemental support structure 544), stent diameter, stent shape (e.g., cylindrical, frustoconical), combinations thereof, and the like may be different between the first longitudinal section 544 and the second longitudinal section 546. The porosity may vary by objectives for certain portions of the stent 540. For example, the first longitudinal section 544, which may be configured for placement in an artery and a fistula, may have low porosity (e.g., less than about 50% as described with respect to the stent 500 of FIG. 25A) to increase fluid flow through the stent 500, while the second longitudinal section, which may be configured for placement in a vein, may have higher porosity to increase flexibility and wall apposition.

In some embodiments, a stent comprises a first longitudinal section comprising and/or consisting essentially of a low porosity weave configured to divert flow from an artery into a fistula and no supplemental support structure, a second longitudinal section comprising and/or consisting essentially of a low porosity weave configured to divert blood flow through a fistula and comprising a supplemental support structure configured to prop open the fistula, and a third longitudinal section comprising and/or consisting essentially of low porosity weave configured to divert flow from a fistula into a vein. In certain such embodiments, the first longitudinal section may be configured as the stent 500 of FIG. 25A and the third longitudinal section may be configured as the stent 500 of FIG. 25A or as the stent 540 of FIG. 25C.

The difference between the first longitudinal section 544 and the second longitudinal section 546 may be imparted during manufacturing (e.g., due to braid parameters, shape setting, etc.) and/or in situ (e.g., during and/or after deployment (e.g., by stent packing)).

Other variations between the first longitudinal section 544 and the second longitudinal section 546 (e.g., including laser-cut portions, additional longitudinal sections, etc.), for example as described herein, are also possible. In some embodiments, a stent comprises a first longitudinal section comprising and/or consisting essentially of a low porosity weave configured to divert flow from an artery into a fistula, a second longitudinal section comprising and/or consisting essentially of a low porosity laser cut portion configured to be placed in a fistula, to divert blood through the fistula, and/or to prop open the fistula, and a third longitudinal section comprising and/or consisting essentially of low porosity weave configured to divert flow from a fistula into a vein. In certain such embodiments, the first longitudinal section may be configured as the stent 500 of FIG. 25A and the third longitudinal section may be configured as the stent 500 of FIG. 25A or as the stent 540 of FIG. 25C.

FIG. 27 schematically illustrates an example embodiment of a prosthesis 720, which is described with respect to the anatomy in FIG. 27 in further detail below. The prosthesis 720 comprises a first longitudinal section 722, a second longitudinal section 724, and a third longitudinal section 726 between the first longitudinal section 722 and the second longitudinal section 724. The porosity of the prosthesis 720 may allow the fluid to flow substantially through the lumen of the prosthesis 720 substantially without perfusing through the sidewalls, even when substantially lacking graft material, for example due to a low porosity woven structure.

In embodiments in which the prosthesis 720 is used in peripheral vasculature, the first longitudinal section 722 may be described as an arterial section, the second longitudinal section 724 may be described as a venous section, and the third longitudinal section 726 may be described as a transition section. The first longitudinal section 722 is configured to appose sidewalls of an artery 700 or another cavity. For example, for some peripheral arteries, the first longitudinal section 722 may have an expanded diameter between about 2 mm and about 4 mm (e.g., about 3 mm). The second longitudinal section 724 is configured to appose sidewalls of a vein 702 or another cavity. For example, for some peripheral veins, the second longitudinal section 724 may have an expanded diameter between about 5 mm and about 7 mm (e.g., about 6 mm). In some embodiments, rather than being substantially cylindrical as illustrated in FIG. 27, the second longitudinal section 724 and the third longitudinal section 726 may have a shape comprising frustoconical, tapering from the smaller diameter of the first longitudinal section 722 to a larger diameter.

The length of the prosthesis 720 may be configured or sized to anchor the prosthesis 720 in the artery 700 and/or the vein 702 (e.g., enough to inhibit or prevent longitudinal movement or migration of the prosthesis 720) and to span the interstitial tissue T between the artery 700 and the vein 702. For example, for some peripheral arteries, the length of the first longitudinal section 722 in the expanded or deployed state may be between about 20 mm and about 40 mm (e.g., about 30 mm). For another example, for some peripheral veins, the length of the second longitudinal section 724 in the expanded or deployed state may be between about 10 mm and about 30 mm (e.g., about 20 mm). For yet another example, for some peripheral vasculature, the length of the third longitudinal section 726 in the expanded or deployed state may be between about 5 mm and about 15 mm (e.g., about 10 mm). The total length of the prosthesis 720 in the expanded or in a deployed state may be between about 30 mm and about 100 mm, between about 45 mm and about 75 mm (e.g., about 60 mm). The interstitial tissue T is illustrated as being about 2 mm thick, although other dimensions are possible depending on the specific anatomy of the deployment site. Other dimensions of the prosthesis 720, the first longitudinal section 722 and/or the second longitudinal section 724, for example as described herein, are also possible.

The third longitudinal section 726 comprises a frustoconical or tapered shape, expanding from the smaller diameter of the first longitudinal section 722 to the second longitudinal section 724. Transition points between the longitudinal sections 722, 724, 726 may be distinct or indistinct. For example, the transition section may be said to include a portion of the first longitudinal section 722 and the third longitudinal section 726, or the third longitudinal section 726 may be said to include a cylindrical portion having the same diameter as the first longitudinal section 722. The longitudinal sections 722, 724, 726 may differ in shape and dimensions as described above, and/or in other ways (e.g., materials, pattern, etc.). For example, one or more portions may be cylindrical, frustoconical, etc., as illustrated in FIGS. 12, 13, and 27 and described herein.

The first longitudinal section 722 and/or the third longitudinal section 726 may comprise a relatively high radial force, for example configured to keep a fistula patent, and the second longitudinal section 724 may comprise a relatively low radial force. In some embodiments, the first longitudinal section 722 and/or the third longitudinal section 726 comprise a balloon-expandable stent, a woven stent with a high braid angle, and/or the like. In some embodiments, the second longitudinal section 724 comprises a self-expanding stent, a woven stent with a low braid angle, and/or the like. Combinations of laser-cut stents, woven stents, different cut patterns, different weave patterns, and the like are described in further detail herein. In some embodiments, the longitudinal sections 722, 724, 726 may be integral or separate. The second longitudinal section 724 may be relatively flexible, for example comprising relatively low radial force, which may help the second longitudinal section 724 flex with the anatomy during pulses of blood flow.

In some embodiments, the second longitudinal section 724 and/or the third longitudinal section 726 may comprise some graft material (e.g., comprising silicone). The graft material may inhibit or prevent flow through sidewalls of the prosthesis 720 and/or may be used to carry medicaments. For example, graft material may or may not occlude or substantially occlude the pores of the portions of the prosthesis 720 depending on the purpose of the graft material.

The proximal and/or distal ends of the prosthesis 720 may be atraumatic, for example comprising an end treatment, low braid angle, small filament diameter, combinations thereof, and the like.

The radial strength or compression resistance of a stent, a stent-graft, or a first end portion, second end portion, intermediate portion, or subportion thereof may be between about 0.1 N/mm and about 0.5 N/mm, between about 0.2 N/mm and about 0.5 N/mm, between about 0.3 N/mm and about 0.5 N/mm, between about 0.1 N/mm and about 0.3 N/mm, between about 0.1 N/mm and about 0.2 N/mm, between about 0.2 N/mm and about 0.5 N/mm, between about 0.2 N/mm and about 0.3 N/mm, or between about 0.3 N/mm and about 0.5 N/mm.

The values of certain parameters of a stent, a stent-graft, or a first end portion, second end portion, intermediate portion, or subportion thereof may be linked (e.g., proportional). For example, a ratio of a thickness of a strut or filament to a diameter of a device portion comprising that strut or filament may be between about 1:10 and about 1:250, between about 1:25 and about 1:175, or between about 1:50 and about 1:100. For another example, a ratio of a length of a device or portion thereof to a diameter of a device or a portion thereof may be between about 1:1 and about 50:1, between about 5:1 and about 25:1, or between about 10:1 and about 20:1.

Portions of the device may include radiopaque material. For example, filaments and/or struts a stent, a stent-graft, or a first end portion, second end portion, intermediate portion, or subportion thereof may comprise (e.g., be at least partially made from) titanium, tantalum, rhenium, bismuth, silver, gold, platinum, iridium, tungsten, combinations thereof, and the like. For another example, filaments and/or struts of a stent, stent-graft, or a portion thereof may comprise (e.g., be at least partially made from) a material having a density greater than about 9 grams per cubic centimeter. Separate radiopaque markers may be attached to certain parts of the device. For example, radiopaque markers can be added to the proximal end of the device or parts thereof (e.g., a proximal part of the intermediate portion, a proximal part of the distal portion), the distal end of the device or parts thereof (e.g., a distal part of the intermediate portion, a distal part of the proximal portion), and/or other parts. A radiopaque marker between ends of a device may be useful, for example, to demarcate transitions between materials, portions, etc. Radiopacity may vary across the length of the device. For example, the proximal portion could have a first radiopacity (e.g., due to distal portion material and/or separate markers) and the distal portion could have a second radiopacity (e.g., due to distal portion material and/or separate markers) different than the first radiopacity. Inflatable members such as balloons may be filled with radiopaque fluid. Inflatable members such as balloons may comprise a radiopaque marker coupled and/or integrated thereto (e.g., on an outer surface of the inflatable member).

In some embodiments, the device includes a polymer tube, and no supporting structure is provided. The intermediate portion of such a device may be relatively more flexible than the end portions by, for example, decreasing the wall thickness of the polymer tube within the intermediate portion.

When a mesh or other supporting structure is provided in combination with a polymer tube, the supporting structure may be located around the outside of the tube, in the inner bore of the tube, or embedded within a wall of the tube. More than one supporting structure may be provided, in which case each supporting structure may have a different location with respect to the tube.

One or both of the end portions of the device may include anchoring elements such as hooks, protuberances, or barbs configured to grasp or grip inner sidewalls of a blood vessel. The radial force of the end portions after expansion may be sufficient to grasp or grip inner sidewalls of a blood vessel without anchoring elements.

There need not be a well-defined transition between the intermediate and end portions. For example, mesh type, material, wall thickness, flexibility, etc. may gradually change from an end portion toward an intermediate portion or from an intermediate portion toward an end portion.

The flexibility of the device may increase gradually when moving from an end portion towards the intermediate portion, for example as described with respect to the devices 134, 140. The change in flexibility may be due to change in mesh density (e.g., winding density, window size), tube thickness, or other factors. The flexibility of the device may be uniform or substantially uniform along the entire length of the support structure (e.g., stent), or along certain portions of the support structure (e.g., along an entire end portion, along the entire intermediate portion, along one end portion and the intermediate portion but not the other end portion, etc.).

While the devices described herein may be particularly suitable for use as a transvascular shunt in percutaneous surgery, the devices could be used in many other medical applications. For example, the devices could be used in angioplasty for the treatment of occluded blood vessels with tortuous or kinked paths, or where the vessels may be subject to deflection or deformation at or near the position of the stent. The stent could also be used for the repair of damaged blood vessels, for example in aortic grafting procedures or after perforation during a percutaneous procedure. In certain such cases, the intermediate portion of the device can allow the device to conform to the shape of the blood vessel and to deform in response to movement of the vessel with reduced risk of fatigue failure while remaining fixed or anchored in position by the end portions. For another example, the devices could be used to form a shunt between a healthy artery and a healthy vein for dialysis access and/or access for administration of medications (e.g., intermittent injection of cancer therapy, which can damage vessels).

Referring again to FIGS. 4 and 7, blocking material 251 may be used to help inhibit or prevent reversal of arterial blood flow. As will now be described in further detail, additional or other methods and systems can be used to inhibit or prevent reversal of arterial blood flow, or, stated another way, to inhibit or prevent flow of arterial blood now flowing into the vein from flowing in the normal, pre-procedure direction of blood flow in the vein such that oxygenated blood bypasses downstream tissue such as the foot.

In the absence of treatment, Peripheral Vascular Disease (PVD) may progress to critical limb ischemia (CLI), which is characterized by profound chronic pain and extensive tissue loss that restricts revascularization options and frequently leads to amputation. CLI is estimated to have an incidence of approximately 50 to 100 per 100,000 per year, and is associated with mortality rates as high as 20% at 6 months after onset.

Interventional radiologists have been aggressively trying to treat CLI by attempting to open up chronic total occlusions (CTOs) or bypassing CTOs in the sub-intimal space using such products as the Medtronic Pioneer catheter, which tunnels a wire into the sub-intimal space proximal to the CTO and then attempts to re-enter the vessel distal to the occlusion. Once a wire is in place, a user can optionally create a wider channel and then place a stent to provide a bypass conduit past the occlusion. Conventional approaches such as percutaneous transluminal angioplasty (PTA), stenting, and drug eluting balloons (DEB) to treat PAD can also or alternatively be used in CLI treatment if a wire is able to traverse the occlusion.

From the amputee-coalition.org website, the following are some statistics regarding the CLI problem:
  There are nearly 2 million people living with limb loss in the United States.
  Among those living with limb loss, the main causes are:
    vascular disease (54%) (including diabetes and peripheral artery disease (PAD)),
    trauma (45%), and
    cancer (less than 2%).
  Approximately 185,000 amputations occur in the United States each year.
  Hospital costs associated with having a limb amputated totaled more than $6.5 billion in 2007.

Survival rates after an amputation vary based on a variety of factors. Those who have amputations due to vascular disease (including PAD and diabetes) face a 30-day mortality rate reported to be between 9% and 15% and a long-term survival rate of 60% at 1 year, 42% at 3 years, and 35%-45% at 5 years.

Nearly half of the people who lose a limb to dysvascular disease will die within 5 years. This is higher than the 5-year mortality rate experienced by people with colorectal, breast, and prostate cancer.

Of people with diabetes who have a lower-limb amputation, up to 55% will require amputation of the second leg within 2 to 3 years.

CLI has been surgically treated by open-leg venous arterialization since the early 1900's. Numerous small series of clinical trials have been published over the years using such an open-leg surgical approach, as summarized by a 2006 meta-analysis article by Lu et al. in the European Journal of Vascular and Endovascular Surgery, vol. 31, pp. 493-499, titled "Meta-analysis of the clinical effectiveness of venous arterialization for salvage of critically ischemic limbs." The article had the following results and conclusions:

Results:
A total of 56 studies were selected for comprehensive review. No randomized control trial (RCT) was identified. Seven patient series, comprising 228 patients, matched the selection criteria. Overall 1-year foot preservation was 71% (95% CI: 64%-77%) and 1-year secondary patency was 46% (95% CI: 39%-53%). The large majority of patients in whom major amputation was avoided experienced successful wound healing, disappearance of rest pain, and absence of serious complications.

Conclusions:
On the basis of limited evidence, venous arterialization may be considered as a viable alternative before major amputation is undertaken in patients with "inoperable" chronic critical leg ischemia.

Among other maladies as described herein, the methods and systems described herein may be used to create an ateriovenous (AV) fistula in the below-the-knee (BTK) vascular system using an endovascular, minimally invasive approach. Such methods may be appropriate for patients that (i) have a clinical diagnosis of symptomatic critical limb ischemia as defined by Rutherford 5 or 6 (severe ischemic ulcers or frank gangrene); (ii) have been assessed by a vascular surgeon and interventionist and it was determined that no surgical or endovascular treatment is possible; and/or (iii) are clearly indicated for major amputation.

In some embodiments, a system or kit optionally comprises one or more of the following components: a first ultrasound catheter (e.g., an arterial catheter, a launching catheter including a needle, etc.); a second ultrasound catheter (e.g., a venous catheter, a target catheter, etc.); and a prosthesis (e.g., a covered nitinol stent graft in a delivery system (e.g., a 7 Fr (approx. 2.3 mm) delivery system)). The system or kit optionally further comprises an ultrasound system, a control system (e.g., computer). Some users may already have an appropriate ultrasound system that can be connected to the ultrasound catheter(s). The catheters and prostheses described above may be used in the system or kit, and details of other, additional, and/or modified possible components are described below.

Figure 14A:
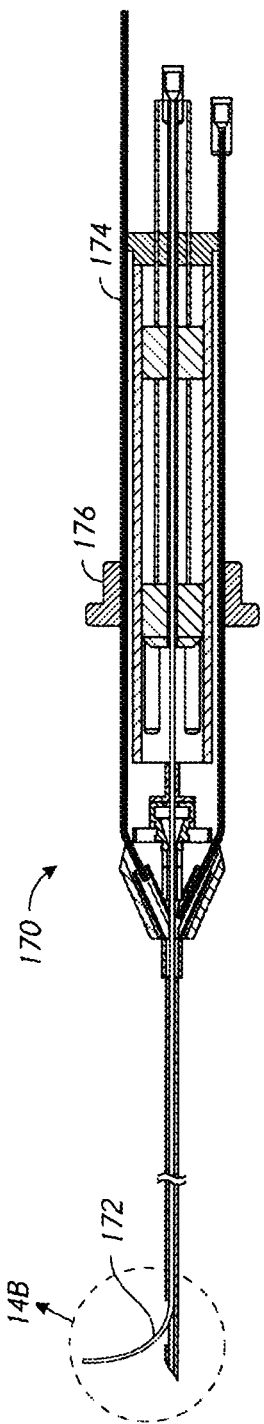
FIG. 14A is a schematic side cross-sectional view of an example embodiment of an ultrasound launching catheter.

FIG. 14A is a schematic side cross-sectional view of an example embodiment of an ultrasound launching catheter 170 comprising a needle 172 (e.g., a first ultrasound catheter, an arterial catheter (e.g., if extending a needle from artery into vein), a venous catheter (e.g., if extending a needle from vein into artery)). The catheter 170 is placed into an artery with the needle 172 in a retracted state inside a lumen of the catheter 170. The catheter 170 can be tracked over a guidewire (e.g., a 0.014 inch (approx. 0.36 mm) guidewire) and/or placed through a sheath in the artery (e.g., a femoral artery), and advanced up to the point of the total occlusion of the artery (in the tibial artery). The catheter 170 includes a handle 174 that includes a pusher ring 176. Longitudinal or distal advancement of the pusher ring 176 can advance the needle 172 from out of a lumen of the catheter 170, out of the artery and into a vein, as described herein. Other advancement mechanisms for the needle 172 are also possible (e.g., rotational, motorized, etc.). Before, after, and/or during after advancing the needle 172, a guidewire (e.g., a 0.014 inch (approx. 0.36 mm) guidewire) can be placed through the needle 172 (e.g., as described with respect to the guidewire 14 of FIG. 3), and this guidewire can be referred to as a crossing wire.

Figure 14B:
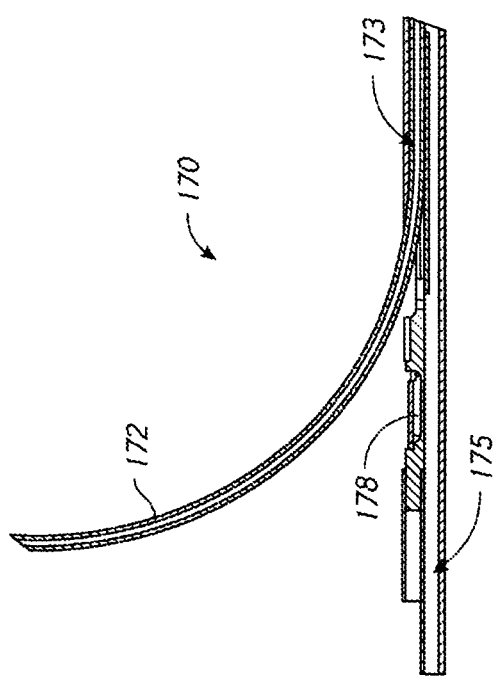
FIG. 14B is an expanded schematic side cross-sectional view of a distal portion of the ultrasound launching catheter of FIG. 14A within the circle 14B.

FIG. 14B is an expanded schematic side cross-sectional view of a distal portion of the ultrasound launching catheter 170 of FIG. 14A within the circle 14B. Upon advancing or launching, the needle 172 extends radially outwardly from a lumen 173 of the catheter 170. In some embodiments, the lumen 173 ends proximal to the ultrasound transmitting device 178. The needle 172 may extend along a path that is aligned with (e.g., parallel to) the path of the directional ultrasound signal emitted by the ultrasound transmitting device 178. FIG. 14B also shows the lumen 175, which can be used to house a guidewire for tracking the catheter 170 to the desired position.

Figure 15A:
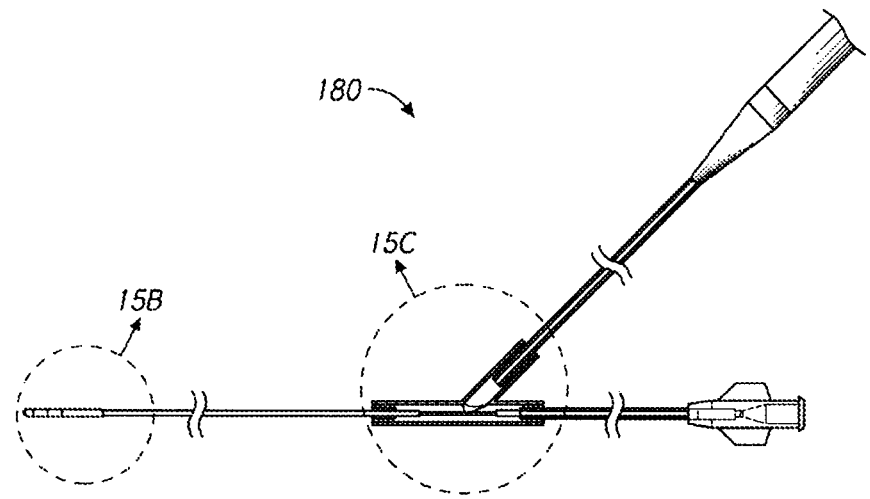
FIG. 15A is a schematic side elevational view of an example embodiment of an ultrasound target catheter.
Figure 15B:
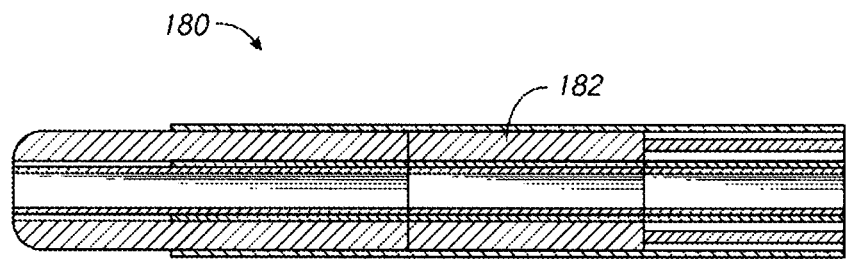
FIG. 15B is an expanded schematic side cross-sectional view of the ultrasound target catheter of FIG. 15A within the circle 15B.
Figure 15C:
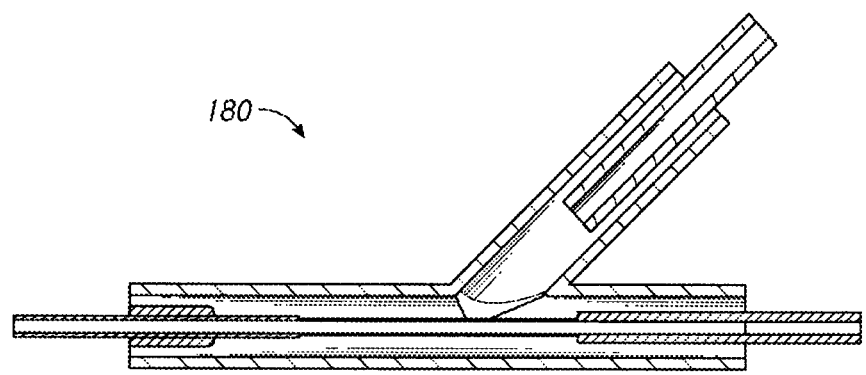
FIG. 15C is an expanded schematic side cross-sectional view of the ultrasound target catheter of FIG. 15A within the circle 15C.

FIG. 15A is a schematic side elevational view of an example embodiment of an ultrasound target catheter 180 (e.g., a second ultrasound catheter, an arterial catheter (e.g., if extending a needle from vein into artery), a venous catheter (e.g., if extending a needle from artery into vein)). FIG. 15B is an expanded schematic side cross-sectional view of the ultrasound target catheter 180 of FIG. 15A within the circle 15B. FIG. 15C is an expanded schematic side cross-sectional view of the ultrasound target catheter 180 of FIG. 15A within the circle 15C. The catheter 180 can be tracked over a guidewire (e.g., a 0.014 inch (approx. 0.36 mm) guidewire) and/or placed through a sheath in the vein (e.g., a femoral vein), and advanced up to a point (e.g., in the tibial vein) proximate and/or parallel to the distal end of the catheter 170 and/or the occlusion in the artery. The catheter 180 includes an ultrasound receiving transducer 182 (e.g., an omnidirectional ultrasound receiving transducer) that can act as a target in the vein for aligning the needle 172 of the catheter 170. The catheter 180 may be left in place or remain stationary or substantially stationary while the catheter 170 is rotated and moved longitudinally to obtain a good or optimal ultrasound signal indicating that the needle 172 is aligned with and in the direction of the catheter 180.

The catheters 170, 180 may be connected to an ultrasound transceiver that is connected to and controlled by a computer running transceiver software. As described in further detail herein, the catheter 170 includes a flat or directional ultrasound transmitter 178 configured to transmit an ultrasound signal having a low angular spread or tight beam (e.g., small beam width) in the direction of the path of the needle 172 upon advancement from the lumen 173 of the catheter 170. The catheter 180 includes an omnidirectional (360 degrees) ultrasound receiver 182 configured to act as a target for the ultrasound signal emitted by the directional transmitter 178 of the catheter 170. The catheter 170 is rotated until the peak ultrasound signal is displayed, indicating that the needle 172 is aligned to the catheter 180 such that, upon extension of the needle 172 (e.g., by longitudinally advancing the ring 176 of the handle 174), the needle 172 can pass out of the artery in which the catheter 170 resides, through interstitial tissue, and into the vein in which the catheter 180 resides.

Figure 16:
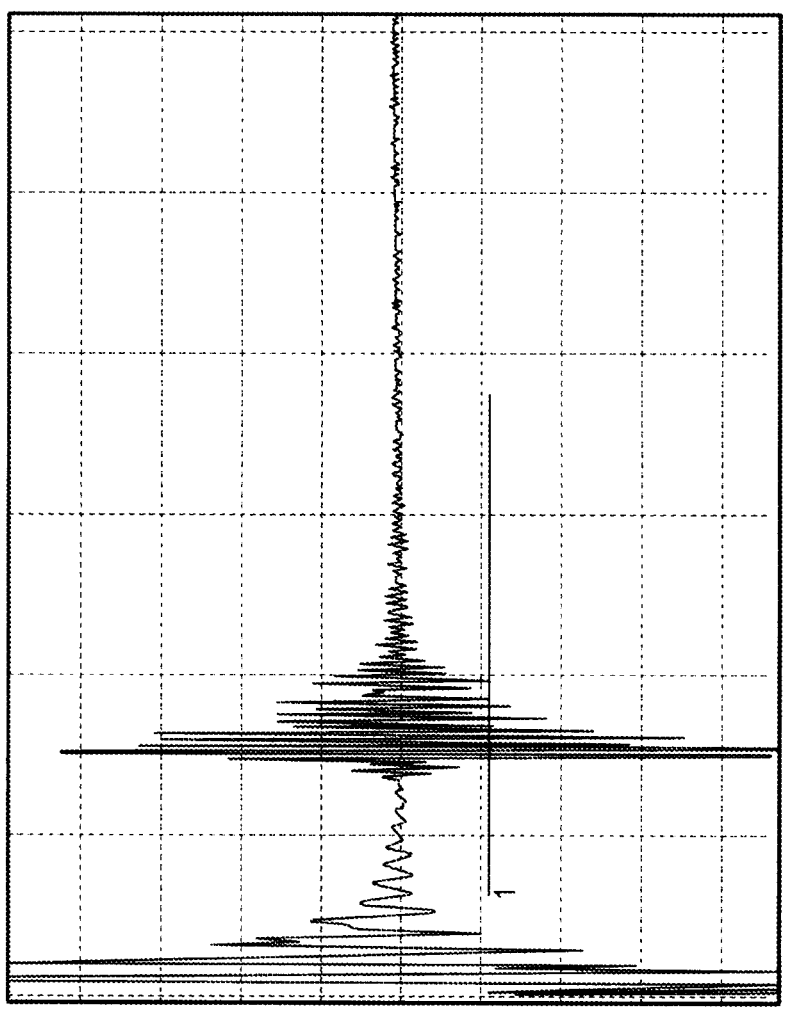
FIG. 16 is an example embodiment of a graph for detecting catheter alignment.

FIG. 16 is an example embodiment of a graph for detecting catheter alignment, as may be displayed on display device of an ultrasound system (e.g., the screen of a laptop, tablet computer, smartphone, combinations thereof, and the like). The graph in FIG. 16 shows that the signal originating from the transmitting catheter in the artery has been received by the receiving catheter in the vein. The second frequency envelope from the right is the received signal. The distance from the left side of the illustrated screen to the leading edge of the second frequency envelope may indicate the distance between the catheters. The operator can move the catheter in the artery both rotationally and longitudinally, for example until the second envelope is maximal, which indicates the catheters are correctly orientated.

Figure 17:
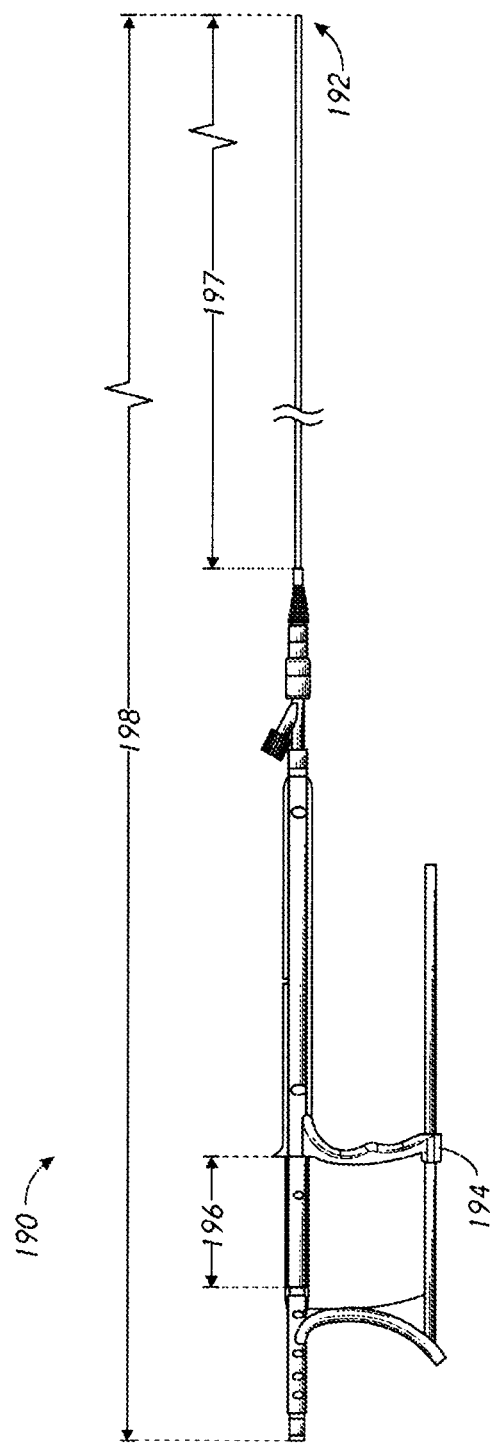
FIG. 17 is a schematic side elevational view of an example embodiment of a prosthesis delivery system.
Figure 18:
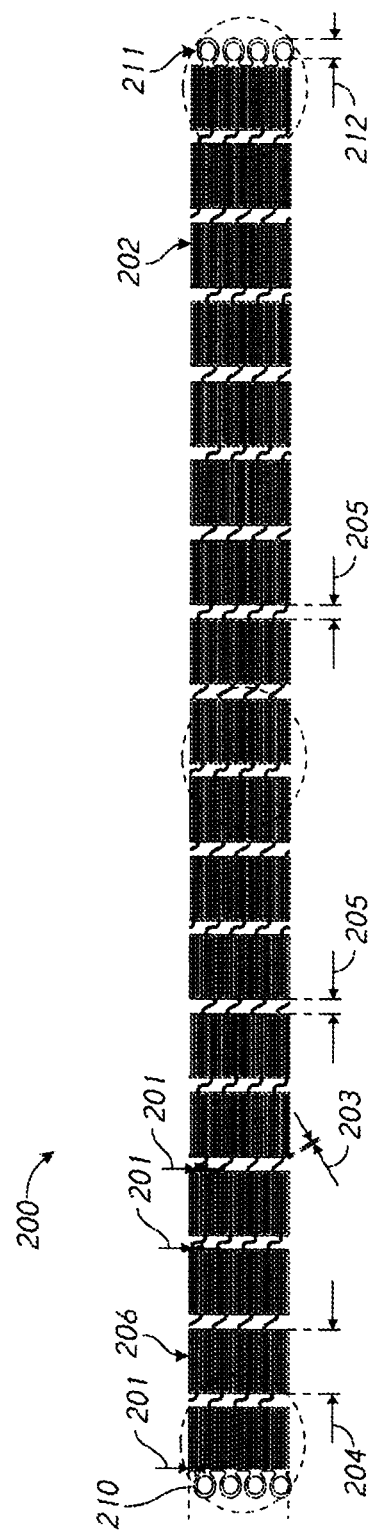
FIG. 18 is a schematic side elevational view of an example embodiment of a prosthesis.

FIG. 17 is a schematic side elevational view of an example embodiment of a prosthesis (e.g., stent, stent-graft) delivery system 190. In some embodiments, the delivery system 190 is a 7 Fr (approx. 2.3 mm) delivery system. FIG. 18 is a schematic side elevational view of an example embodiment of a prosthesis (e.g., stent, stent-graft) 200. In FIG. 17, a prosthesis (e.g., the prosthesis 200, other prostheses described herein, etc.) is in a compressed or crimped state proximate to the distal end 192 of the delivery system 190. In some embodiments, the prosthesis 200 comprises a shape-memory stent covered with a graft material, for example as described above. Once the crossing wire extends from the artery to the vein, for example as a result of being advanced through the needle 172 as described herein, the delivery system 190 can be advanced over the crossing wire. The prosthesis 200 may be deployed from the delivery system 190, for example by squeezing the trigger handle 194 of the delivery system 190, causing the outer cover sheath to proximally retract and/or distally advance the prosthesis 200. The prosthesis 200 can create a flow path between the artery and the vein and through the interstitial tissue. Other types of delivery systems and prostheses are also possible.

Referring again to FIG. 17, some non-limiting example dimensions of the delivery system 190 are provided. The distance 196 of travel of the trigger handle 194 may be, for example, between about 0.4 inches (approx. 1 cm) and about 12 inches (approx. 30 cm), between about 1 inch (approx. 2.5 cm) and about 8 inches (approx. 20 mm), or between about 2 inches (approx. 5 cm) and about 6 inches (approx. 15 mm) (e.g., about 2 inches (approx. 5 cm)). In some embodiments, the distance 196 of travel of the trigger handle 194 is at least as long as the length of the prosthesis 200 to be deployed (e.g., in the radially expanded state). In some embodiments, gearing or other mechanisms may be employed to reduce the distance 196 of travel of the trigger handle 194 be less than the length of the prosthesis 200 to be deployed (e.g., in the radially expanded state). The distance 196 may be adjusted for example, based on at least one of: the length of the prosthesis 200 to be deployed, the degree of foreshortening of the prosthesis 200 to be deployed, the mechanism of deployment (e.g., whether the outer sheath is proximally retracted, the prosthesis 200 is pushed distally forward, or both, whether the delivery system 190 includes gearing mechanism, etc.), combinations thereof, and the like. The length 197 of the outer sheath or catheter portion may be, for example, between about 40 inches (approx. 1,020 mm) and about 50 inches (approx. 1,270 mm), between about 46 inches (approx. 1,170 mm) and about 47 inches (approx. 1,190 mm), or between about 46.48 inches (approx. 1,180 mm) and about 46.7 inches (approx. 1,186 mm). The total length 198 of the delivery system 190 from proximal tip to distal tip may be, for example, between about 40 inches (approx. 1,000 mm) and about 60 inches (approx. 1,500 mm). The lengths 197, 198 may be adjusted, for example based on at least one of: length of the prosthesis 200 to be deployed, the degree of foreshortening of the prosthesis 200 to be deployed, the height of the patient, the location of the occlusion being treated, combinations thereof, and the like. In some embodiments, spacing the trigger handle 194 from the vascular access point, for example by between about 10 cm and about 30 cm (e.g., at least about 20 cm) may advantageously provide easier handling or management by the user. In certain such embodiments, the length 197 may be between about 120 cm and about 130 cm (e.g., for an antegrade approach) or between about 150 cm and about 180 cm (e.g., for a contralateral approach).

Referring again to FIG. 18, some non-limiting example dimensions of the prosthesis 200 are provided, depending on context at least in the compressed state. The thickness 201 of a structural strut may be, for example, between about 0.05 mm and about 0.5 mm or between about 0.1 mm and about 0.2 mm (e.g., about 0.143 mm). The spacing 202 between struts of a structural strut may be, for example, between about 0.005 mm and about 0.05 mm or between about 0.01 mm and about 0.03 mm (e.g., about 0.025 mm). The thickness 203 of a linking strut may be, for example, between about 0.05 mm and about 0.5 mm or between about 0.1 mm and about 0.2 mm (e.g., about 0.133 mm). The longitudinal length 204 of the structural components may be, for example, between about 1 mm and about 5 mm or between about 2.5 mm and about 3 mm (e.g., about 2.8 mm). The longitudinal length 205 between structural components may be, for example, between about 0.25 mm and about 1 mm or between about 0.5 mm and about 0.6 mm (e.g., about 0.565 mm). The length 206 of a strut within a structural component, including all portions winding back and forth, may be, for example, between about 25 mm and about 100 mm or between about 65 mm and about 70 mm (e.g., about 67.62 mm). The total longitudinal length of the prosthesis 200 may be, for example, between about 25 mm and about 150 mm or between about 50 mm and about 70 mm (e.g., about 62 mm). As described herein, a wide variety of laser-cut stents, woven stents, and combinations thereof, including various dimensions, are possible. The struts described herein may comprise wires or filaments or portions not cut from a hypotube or sheet.

The proximal and/or distal ends of the prosthesis 200 may optionally comprise rings 210. The rings 210 may, for example, help to anchor the prosthesis 200 in the artery and/or the vein. The circumferential width 211 of a ring 210 may be, for example, between about 0.25 mm and about 1 mm or between about 0.5 mm and about 0.75 mm (e.g., about 0.63 mm). The longitudinal length 212 of a ring 210 may be, for example, between about 0.25 mm and about 2 mm or between about 0.5 mm and about 1 mm (e.g., about 0.785 mm). In some embodiments, a ratio of the total length of the prosthesis 200 to the longitudinal length 212 of a ring 210 may be between about 50:1 and about 100:1 (e.g., about 79:1). The dimensions 211, 212 of the rings 210 may be adjusted, for example based on at least one of: strut thickness, diameter of the prosthesis (e.g., relative to the vessel), total length of the prosthesis, material, shape setting properties, combinations thereof, and the like.

Figure 19:
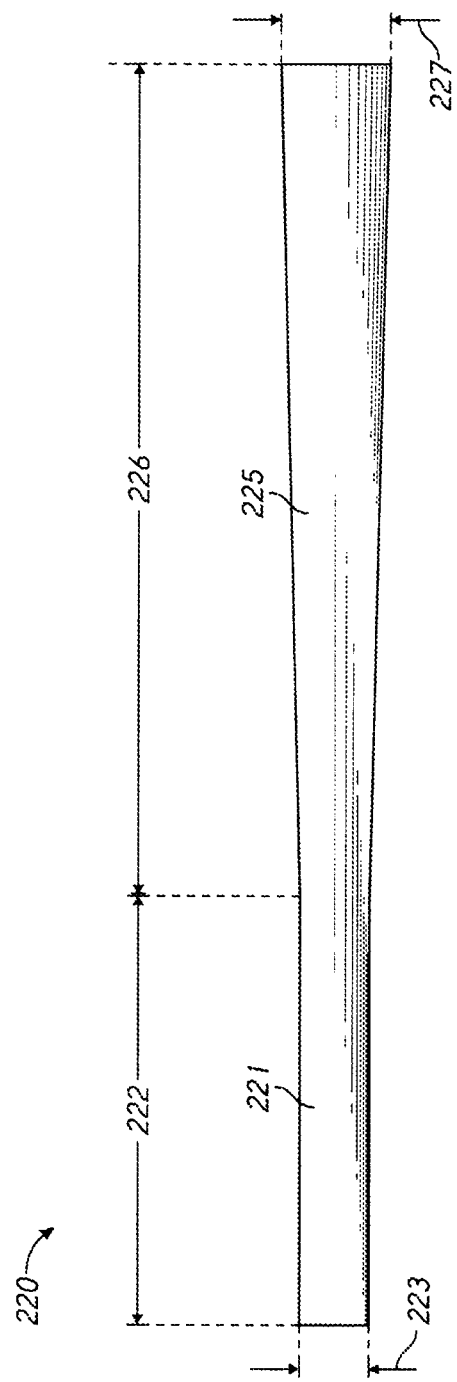
FIG. 19 is a schematic side elevational view of another example embodiment of a prosthesis.

FIG. 19 is a schematic side elevational view of another example embodiment of a prosthesis 220. The prosthesis 200 may have the shape of the prosthesis 220, for example in a radially expanded state (e.g., upon being deployed from the delivery system 190). FIG. 19 illustrates an example shape of the prosthesis 220 comprising a first portion 221 and a second portion 225. The first portion 221 has a substantially cylindrical or cylindrical shape having a length 222 between about 15 mm and about 25 mm (e.g., about 21 mm) and a diameter 223 between about 2.5 mm and about 5 mm (e.g., about 3.5 mm). The second portion 225 has a substantially frustoconical or frustoconical shape having a length 226 between about 30 mm and about 50 mm (e.g., about 41 mm) and a widest diameter 227 between about 4 mm and about 10 mm, between about 4 mm and about 7 mm (e.g., about 5.5 mm), etc. The angle of taper of the second portion 225 away from the first portion 221 may be between about 0.02 degrees and about 0.03 degrees (e.g., about 0.024 degrees).

Further details regarding prostheses that can be used in accordance with the methods and systems described herein are described in U.S. patent application Ser. No. 13/791,185, filed Mar. 8, 2013, which is hereby incorporated by reference in its entirety.

FIGS. 20A-20H schematically illustrate an example embodiment of a method for effecting retroperfusion. The procedure will be described with respect to a peripheral vascular system such as the lower leg, but can also be adapted as appropriate for other body lumens (e.g., cardiac, other peripheral, etc.). Certain steps such as anesthesia, incision specifics, suturing, and the like may be omitted for clarity. In some embodiments, the procedure can be performed from vein to artery (e.g., with the venous catheter coming from below).

Access to a femoral artery and a femoral vein is obtained. An introducer sheath (e.g., 7 Fr (approx. 2.3 mm)) is inserted into the femoral artery and an introducer sheath (e.g., 6 Fr (approx. 2 mm)) is inserted into the femoral vein, for example using the Seldinger technique. A guidewire (e.g., 0.014 inch (approx. 0.36 mm), 0.035 inch (approx. 0.89 mm), 0.038 inch (approx. 0.97 mm)) is inserted through the introducer sheath in the femoral artery and guided into the distal portion of the posterior or anterior tibial diseased artery 300. A second guidewire (e.g., 0.014 inch (approx. 0.36 mm), 0.035 inch (approx. 0.89 mm), 0.038 inch (approx. 0.97 mm)) or a snare is inserted through the introducer sheath in the femoral vein. In embodiments in which a snare is used, the described third guidewire, fourth guidewire, etc. described herein are accurate even though the numbering may not be sequential.

A venous access needle is percutaneously inserted into a target vein, for example a tibial vein (e.g., the proximal tibial vein (PTV)). In some embodiments, the venous access needle may be guided under ultrasound. In some embodiments, contrast may be injected into the saphenous vein towards the foot (retrograde), and then the contrast will flow into the PTV. This flow path can be captured using fluoroscopy such that the venous access needle can be guided by fluoroscopy rather than or in addition to ultrasound.

Figure 20A:
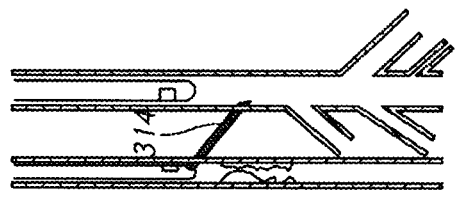
FIGS. 20A-20H schematically illustrate an example embodiment of a method for effecting retroperfusion.

The target vein may be accessed proximate to and distal to (e.g., a few inches or centimeters) below where the launching catheter 310 will likely reside. In some embodiments, the target vein may be in the ankle. Once the venous access needle is in the vein, a third guidewire (or "second" guidewire in the case that a snare is used instead of a second guidewire) is inserted into the venous access needle and advanced antegrade in the target vein up to the femoral vein. This access method can advantageously reduce issues due to advancing wires retrograde across venous valves, which are described in further detail below. The third guidewire is snared, for example using fluoroscopic guidance, and pulled through the femoral vein sheath. The target catheter 320 is inserted into the femoral vein sheath over the third guidewire, which has been snared. The target catheter 320 is advanced over the third guidewire into the venous system until the target catheter is proximate to and/or parallel with the guidewire in the distal portion of the posterior or anterior tibial diseased artery and/or proximate to the occlusion 304, as shown in FIG. 20A.

In some embodiments, the third guidewire may include an ultrasound receiving transducer (e.g., omnidirectional) mounted to provide the target for the signal emitted by the launching catheter 310 or the target catheter 320 could be tracked over the third guidewire, either of which may allow omission of certain techniques (e.g., femoral vein access, introducing vein introducer sheath, inserting second guidewire, antegrade advancing of the third guidewire up to the femoral vein, snaring the third guidewire, advancing the target catheter 320 over the third guidewire).

In some embodiments, the PTV may be accessed directly, for example using ultrasound, which can allow placement of the target catheter 320 directly into the PTV, for example using a small sheath. which may allow omission of certain techniques (e.g., femoral vein access, introducing vein introducer sheath, inserting second guidewire, antegrade advancing of the third guidewire up to the femoral vein).

In some embodiments, the catheter 320 is not an over-the-wire catheter, but comprises a guidewire and an ultrasound receiving transducer (e.g., omnidirectional). The catheter 320 may be inserted as the third guidewire, as discussed above, as the second guidewire, or as a guidewire through a small sheath when directly accessing the PTV.

Figure 21:
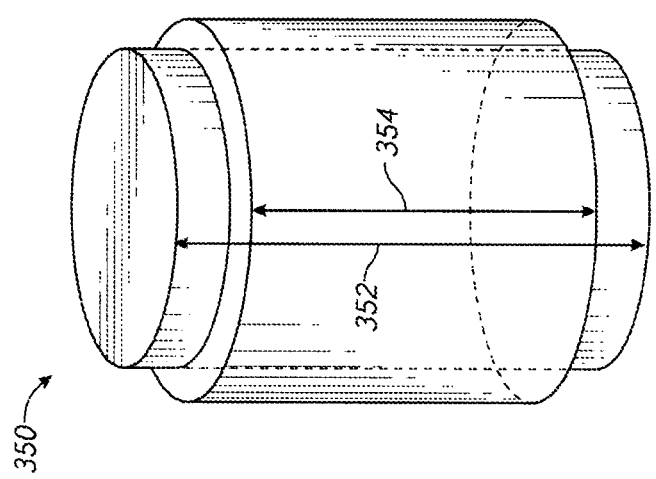
FIG. 21 is a schematic perspective view of an example embodiment of an ultrasound receiving transducer.

Ultrasound transducers generally include two electrodes including surfaces spaced by a ceramic that can vibrate. An incoming or received ultrasound signal wave can couple into a length extensional mode, as shown in FIG. 21. FIG. 21 is a schematic perspective view of an example embodiment of an ultrasound receiving transducer 350. If the proximal or top end 352 of the transducer 350 and the distal or bottom end 354 of the transducer are conductive and electrically connected to wires, the transducer can receive ultrasound signals. In some embodiments, the transducer 350 has a length 356 between about 0.1 mm and about 0.4 mm (e.g., about 0.25 mm). In some embodiments, the transducer 350 has an overlap length 358 between about 0.1 mm and about 0.3 mm (e.g., about 0.2 mm). In some embodiments, the transducer 350 has a diameter that is similar to, substantially similar to, or the same as the guidewire on which it is mounted. In some embodiments, an array or series of laminates may enhance the signal-receiving ability of the transducer 350.

Figure 22:
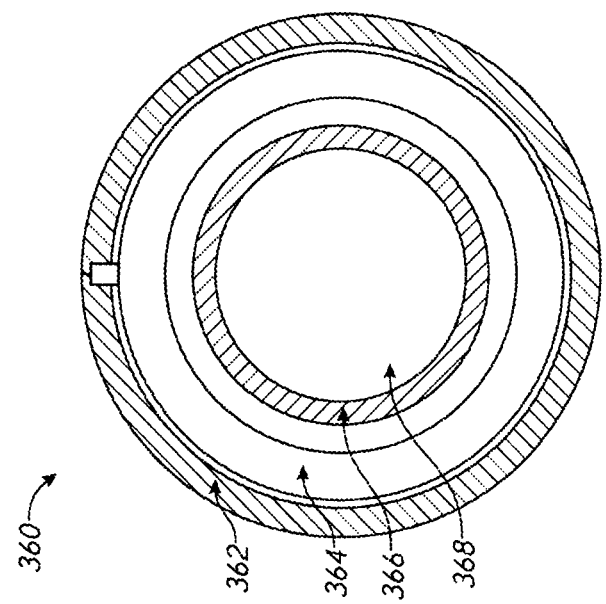
FIG. 22 is a schematic cross-sectional view of another example embodiment of an ultrasound receiving transducer.

In some embodiments, a guidewire comprising an ultrasound receiving transducer may comprise a piezoelectric film (e.g., comprising plastic), which could enhance the signal-receiving ability of the transducer. FIG. 22 is a schematic cross-sectional view of another example embodiment of an ultrasound receiving transducer 360. The ultrasound receiving transducer 360 shown in FIG. 22 includes an optional lumen 368. The ultrasound receiving transducer 360 includes a series of layers 362, 364, 366. The layer 362 may comprise a polymer (e.g., polyvinylidene fluoride (PVDF)) layer. The layer 364 may comprise an inorganic compound (e.g., tungsten carbide) layer. The layer 366 may comprise a polymer (e.g., polyimide) layer. The layer 366 may have a thickness between about 25 micrometers (μm or microns) and about 250 μm (e.g., at least about 50 μm).

Figure 20B:
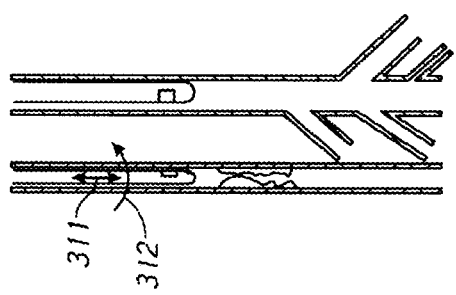
Figure 20C:
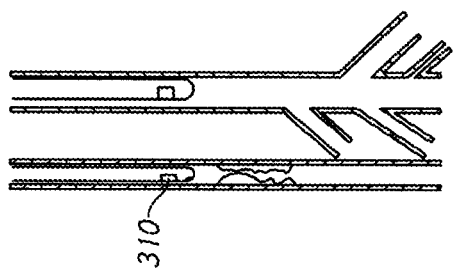

The launching catheter 310 is tracked over the guidewire in the femoral and tibial arteries proximate to and proximal to the occlusion 304, as shown in FIG. 20B. The catheter 310 may be more proximal to the occlusion 304 depending on suitability at that portion of the anatomy for the retroperfusion process. In some embodiments, the catheter 310 may be positioned in the distal portion of the posterior or anterior tibial artery, for example proximate to the catheter 320. In some embodiments, the catheter 310 may be positioned within a few inches or centimeters of the ankle.

Figure 20D:
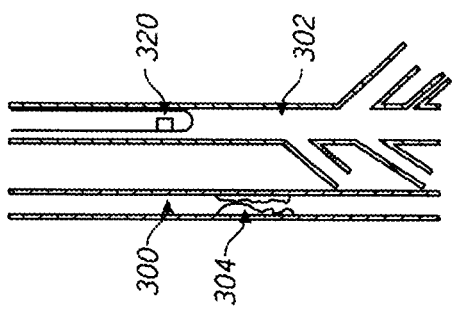

The launching catheter 310 emits a directional ultrasound signal. As shown by the arrow 311, 312 in FIG. 20C, the launching catheter 310 is rotated and moved longitudinally until the signal is received by the target catheter 320. Once the signal is received, which indicates alignment such that extension of the needle form the launching catheter 310 will result in successful access of the vein, a crossing needle 314 is advance out of the catheter 310, out of the tibial artery 300 and into the tibial vein 302, as shown in FIG. 20D. Accuracy of the placement of the crossing needle 314 to form a fistula between the artery 300 and the vein 302 may be confirmed, for example, using contrast and fluoroscopy.

In some embodiments, the ultrasound signal can be used to determine the distance between the artery 300 and the vein 302. Referring again to FIG. 16, the distance from the left side of the illustrated screen to the leading edge of the second frequency envelope can be used as an indicator of distance between the catheters.

Referring again to FIG. 16, a display device may graphically show signal alignment peaks to allow the user to determine the alignment position. In some embodiments, the signal alignment may change color above or below a threshold value, for example from red to green. In some embodiments, an audio signal may be emitted, for example when an alignment signal crosses over a threshold value, which can allow a user to maintain focus on the patient rather than substantially continuously monitoring a screen.

In some embodiments, a horizontal line on the screen may move up to indicate the maximum signal value or peak achieved to that point during the procedure. This line may be called "peak hold." If a greater signal value is achieved, the horizontal line moves to match that higher value. If no manipulation is able to raise the peak above the horizontal line, that can indicate maximum alignment. If the signal peak falls a certain amount below the horizontal line, the catheters may have moved and no longer be properly aligned. Since the level of alignment indicated by the horizontal line has previously been achieved during the procedure, the user knows that such a level of alignment can be achieved by further rotational and/or longitudinal manipulation.

Figure 20H:
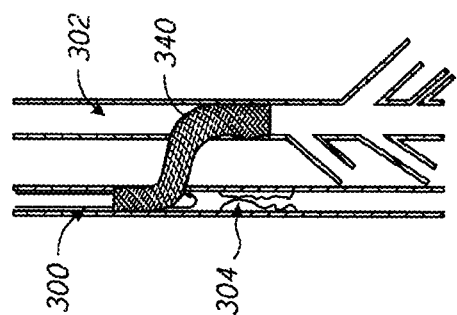
Figure 20G:
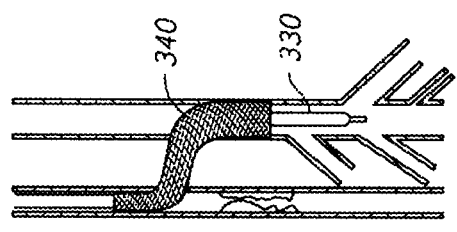
Figure 20F:
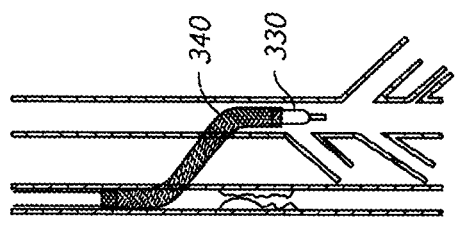
Figure 20E:
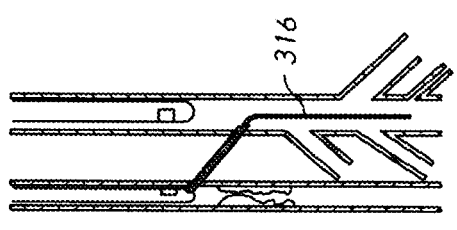

A fourth guidewire 316 (e.g., 0.014 inch (approx. 0.36 mm)) (or "third" guidewire in the case that a snare is used instead of a second guidewire) is placed through the lumen of the crossing needle 314 of the catheter 310 and into the tibial vein 302 in a retrograde direction (of the vein 302) towards the foot, as shown in FIG. 20E. External cuff pressure may be applied above the needle crossing point to reduce flow in the artery 300 to inhibit or prevent formation of a hematoma, and/or to engorge the vein to facilitate valve crossing. The catheters 310, 320 may be removed, leaving the guidewire 316 in place, extending from the introducer sheath in the femoral artery, through the arterial tree, and into the tibial vein 302.

Certain techniques for crossing a guidewire 316 from an artery 300 to a vein 302 may be used instead of or in addition to the directional ultrasound techniques described herein.

In some embodiments, a tourniquet can be applied to the leg, which can increase vein diameters. In some embodiments, a blocking agent (e.g., as discussed with respect to FIGS. 4 and 7, a blocking balloon, etc.) may be used to increase vein diameter. For example, venous flow could back up, causing dilation of the vein. A larger vein diameter can produce a larger target for the crossing needle 314, making the vein 300 easier to access with the crossing needle 314.

In some embodiments, a PTA balloon can be used in the target vein, and a needle catheter (e.g., Outback, available from Cordis) can target the PTA balloon under fluoroscopy. The crossing needle 314 can puncture the PTA balloon, and the reduction in pressure of the PTA balloon can confirm proper alignment of the crossing needle 314. The PTA balloon can increase vein diameter, producing a larger target for the crossing needle 314, making the vein 300 easier to access with the crossing needle 314. The guidewire 316 may be advanced through the crossing needle 314 and into the PTA balloon.

In some embodiments, the PTA balloon comprises a mesh (e.g., a woven mesh), for example embedded in the polymer of the balloon. When a balloon without such a mesh is punctured, the balloon material could rupture and cause emboli (e.g., pieces of the balloon floating downstream). The mesh can help to limit tearing of the balloon material, which can inhibit or prevent balloon material from causing emboli. In some implementations, a balloon without a mesh can be configured to snare a guidewire upon being collapsed (e.g., by entangling the guidewire in folds of the balloon), whether or not punctured.

In some embodiments, two PTA balloons spaced longitudinally along the axis of the catheter can be used in the target vein, and a needle catheter can target the one of the PTA balloons. Upon puncturing of one of the PTA balloons by the crossing needle 314, contrast in a well between the PTA balloons can be released because the punctured balloon no longer acts as a dam for the contrast. The release of contrast can be monitored using fluoroscopy. The PTA balloons can be on the same catheter or on different catheters.

In some embodiments, two PTA balloons spaced longitudinally along the axis of the catheter can be used in the target vein, and a needle catheter can target the space or well between the PTA balloons. Upon puncturing of the well by the crossing needle 314, contrast in the well can be disturbed. The disturbance of contrast can be monitored using fluoroscopy. The PTA balloons can be on the same catheter or on different catheters.

In some embodiments in which a PTA balloon may be used in combination with an ultrasound target in the target vein, a PTA balloon catheter includes a PTA balloon and an ultrasound receiving transducer (e.g., omnidirectional). In certain such embodiments, the launching catheter 310 can target the PTA balloon under fluoroscopy and/or can target the ultrasound receiving transducer as described herein. The crossing needle 314 can puncture the PTA balloon, and the reduction in pressure of the PTA balloon can confirm proper alignment of the crossing needle 314. The PTA balloon can increase vein diameter, producing a larger target for the crossing needle 314, making the vein 300 easier to access with the crossing needle 314. The guidewire 316 may be advanced through the crossing needle 314 and into the PTA balloon.

In some embodiments, a LeMaitre device (e.g., the UnBalloon™ Non-Occlusive Modeling Catheter, available from LeMaitre Vascular of Burlington, Massachusetts) can be used in the target vein. In some embodiments, a LeMaitre device can increase vein diameters. A larger vein diameter can produce a larger target for the crossing needle 314, making the vein 300 easier to access with the crossing needle 314. In some embodiments, the needle 314 can penetrate into the LeMaitre device. In certain such embodiments, the LeMaitre device can act as a mesh target (e.g., comprising radiopaque material visible under fluoroscopy) for the crossing needle 314. The mesh of the LeMaitre device can be radially expanded by distally advancing a proximal portion of the mesh and/or proximally retracting a distal portion of the mesh (e.g., pushing the ends together like an umbrella) and/or by allowing the mesh to self-expand (e.g., in embodiments in which at least some parts of the mesh comprise shape-memory material). In some embodiments, a LeMaitre device can grip a crossing wire to hold the crossing wire in the target vein as the LeMaitre device closes.

In some embodiments, the launching catheter 310 may comprise a first magnet having a first polarity and the target catheter 320 may comprise a second magnet having a second polarity. When the magnets are close enough for magnetic forces to move one or both of the catheters 310, 320, the crossing needle 314 may be advanced to create the fistula between the artery 300 and the vein 302. In some embodiments, the first magnet maybe circumferentially aligned with the crossing needle 314 and/or the launching catheter 310 may be magnetically shielded to provide rotational alignment. In some embodiments, the second magnet may be longitudinally relatively thin to provide longitudinal alignment. In some embodiments, the crossing needle 314 and/or the guidewire 316 may be magnetically pulled from the artery 300 to the vein 302, or vice versa. Some systems may include both ultrasound guidance and magnetic guidance. For example, ultrasound guidance could be used for initial alignment and magnetic guidance could be used for refined alignment.

Referring again to FIGS. 20A-20H, a prosthesis delivery system 330 carrying a prosthesis 340 is tracked over the guidewire 316 through the interstitial space between the artery 300 and the vein 300 and then into the vein 302, as shown in FIG. 20F. In some embodiments, a separate PTA balloon catheter (e.g., about 2 mm) can be tracked over the guidewire 316 to pre-dilate the fistula between the artery 300 and the vein 302 prior to introduction of the prosthesis delivery system 330. Use of a PTA balloon catheter may depend, for example, on the radial strength of the prosthesis 340.

The prosthesis 340 is deployed from the prosthesis delivery system 330, for example by operating a trigger handle 194 (FIG. 17). In some embodiments, for example if the prosthesis 340 is not able to expand and/or advance, the prosthesis delivery system 330 may be removed and a PTA catheter (e.g., about 2 mm) advanced over the guidewire 316 to attempt to dilate or further dilate the fistula the artery 300 and the vein 302. Deployment of the prosthesis 340 may then be reattempted (e.g., by self-expansion, balloon expansion, etc.). In some embodiments, deployment of the prosthesis 340 may remodel a vessel, for example expanding the diameter of the vessel by at least about 10%, by at least about 20%, by at least about 30%, or more, by between about 0% and about 10%, by between about 0% and about 20%, by between about 0% and about 30%, or more. In embodiments in which the prosthesis 340 is self-expanding, the degree of remodeling may change over time, for example the prosthesis 340 expanding as the vessel expands or contracting when the vessel contracts.

Once the prosthesis 340 is deployed, as shown in FIG. 20G, the fistula may be dilated with a PTA catheter. The diameter of the PTA catheter (e.g., about 3 mm to about 6 mm) may be selected based at least in part on: the diameter of the artery 300, the diameter of the vein 302, the composition of the interstitial tissue, the characteristics of the prosthesis 340, combinations thereof, and the like. In some embodiments, the prosthesis delivery system 330 may comprise a PTA balloon catheter (e.g., proximal or distal to the prosthesis 340) usable for one, several, or all of the optional PTA balloon catheter techniques described herein. In embodiments in which the prosthesis comprises a conical portion, the PTA balloon may comprise a conical portion. Once the prosthesis 340 is in place, the prosthesis delivery system 330 may be removed, as shown in FIG. 20H. An AV fistula is thereby formed between the artery 300 and the vein 302. Confirmation of placement of various catheters 310, 320, 330 and the prosthesis 340 may be confirmed throughout parts or the entire procedure under fluoroscopy using contrast injections.

In some embodiments, a marker (e.g., a clip a lancet, scissors, a pencil, etc.) may be applied (e.g., adhered, placed on top of, etc.) to the skin to approximately mark the location of the fistula formed between the artery 300 and the vein 302 by the crossing needle 314 prior to deployment of the prosthesis 340. In embodiments in which the user uses a sphygmomanometer inflated above the fistula to avoid bleeding, the lack of blood flow can render visualization or even estimation of the fistula site difficult, and the marker can provide such identification. In embodiments in which the transmitting and receiving catheters are removed after fistula formation, the cross-over point may be difficult for the user to feel or determine, and the marker can provide such identification. If the fistula is to be dilated, a midpoint of the dilation balloon may be preferably aligned with the midpoint of the fistula (e.g., to increase or maximize the hole-through interstitial space). In some embodiments, the marker may be visualized under fluoroscopy (e.g., comprising radiopaque material) to allow the user to see and remember the location of the fistula under fluoroscopy prior to deployment of the prosthesis 340.

Once the prosthesis 340 is in place, an obstacle to blood flowing through the vein 302 and into the foot are the valves in the veins. Steering a guidewire across venous valves can be a challenge, for example because pressure from the artery may be insufficient to extend the veins and make the valves incompetent. The Applicant has discovered that venous valves distal to the AV fistula can be disabled or made incompetent using one or more of a variety of techniques such as PTA catheters, stents (e.g., covered stents, stent-grafts, etc.), and a valvulotome, as described in further detail below. Disabling venous valves can allow blood to flow via retroperfusion from the femoral artery, retrograde in the vein 302, and retrograde in the vein to the venules and capillaries to the distal part of the venous circulation of the foot to provide oxygenated blood to the foot in CLI patients.

In some embodiments, a high-pressure PTA balloon catheter may be used to make venous valves incompetent (e.g., when inflated to greater than about 10 atm (approx. 1,013 kilopascals (kPa))).

In some embodiments, one or more stents can be placed across one or more venous valves to render those valves incompetent. For example, such stents should have sufficient radial force that the valves stay open. The stent may force-fully rupture the valves. In some embodiments, the stent comprises a covering or a graft. Certain such embodiments can cover venous collateral vessels. In some embodiments, the stent is bare or free of a covering or graft. Certain such embodiments can reduce costs. The venous stent may extend along a length (e.g., an entire length) of the vein. For example, in some embodiments, the entire length of the PTV is lined with a covered stent, covering the venous collaterals, disrupting venous valves.

In some embodiments, the venous stent is separate from the fistula prosthetic. A separate venous stent may allow more flexibility in properties such as dimensions (e.g., length, diameter), materials (e.g., with or without a covering or graft), and other properties. FIG. 31A schematically illustrates an example embodiment of an arteriovenous fistula stent 340 separate from an example embodiment of a venous stent 342. The venous stent 342 may be spaced from the fistula stent 340 (e.g., as illustrated in FIG. 31A), abutting the fistula stent 340, or overlapping, telescoping, or coaxial with the fistula stent 340 (e.g., a distal segment of the fistula stent 340 being at least partially inside a proximal segment of the venous stent 342 or a proximal segment of the venous stent 342 being at least partially inside a distal segment of the fistula stent 340). In embodiments in which the fistula stent 340 and the venous stent 342 overlap, placement of the venous stent 342 first can allow the proximal end of the venous stent 342, which faces the direction of retrograde blood flow, to be covered by the fistula stent 340 to reduce or eliminate blood flow disruption that may occur due the distal end of the venous stent 342. In embodiments in which the fistula stent 340 and the venous stent 342 overlap, placement of the venous stent 342 second can be through the fistula stent 340 such that both stents 340, 342 can share at least one deployment parameter (e.g., tracking stent deployment devices over the same guidewire). The venous stent 342 may be deployed before or after the fistula stent 340. The venous stent 342 may have a length between about 2 cm and about 30 cm (e.g., about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, about 20 cm, about 21 cm, about 22 cm, about 23 cm, about 24 cm, about 25 cm, about 26 cm, about 27 cm, about 28 cm, about 29 cm, about 30 cm, ranges between such values, etc.).

In some embodiments, the venous stent is integral with the fistula prosthetic. An integral venous stent may allow more flexibility in properties such as dimensions (e.g., length, diameter), materials (e.g., with or without a covering or graft), and other properties. FIG. 31B schematically illustrates an example embodiment arteriovenous fistula stent 344 comprising an integrated venous stent. FIG. 31C schematically illustrates an example embodiment of fistula stent 344 comprising an integrated venous stent. The stent 344 comprises a first portion 346 configured to anchor in an artery, a second portion 350 configured to anchor in and line a length of a vein, and a third portion 348 longitudinally between the first portion 346 and the second portion 350. In embodiments in which the first portion 346 and the second portion 350 have different diameters (e.g., as illustrated in FIG. 31C), the third portion 348 may be tapered. In some embodiments, a portion of the second portion 350 that is configured to line a vein has a different property (e.g., diameter, material, radial strength, combinations thereof, and the like) than other portions of the second portion 350. A length of the second section 350 may be greater than a length of the first section 346. For example, the second section 350 may have a length configured to line a vessel such as the PTV. The second section 350 may have a length between about between about 2 cm and about 30 cm (e.g., about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, about 20 cm, about 21 cm, about 22 cm, about 23 cm, about 24 cm, about 25 cm, about 26 cm, about 27 cm, about 28 cm, about 29 cm, about 30 cm, ranges between such values, etc.).

Figure 23A:
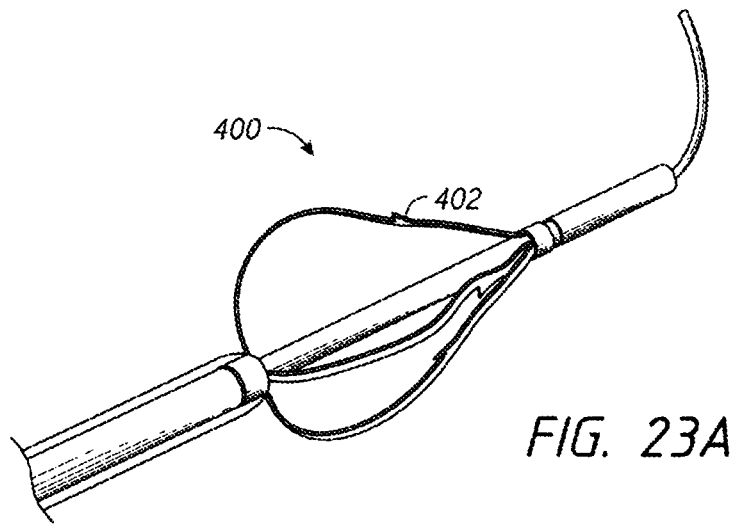
FIG. 23A is a schematic perspective view of an example embodiment of a valvulotome.

In some in situ bypass procedures, a saphenous vein is attached to an artery in the upper leg and another artery in the lower leg, bypassing all blockages in the artery. In certain such procedures, the vein is not stripped out of the patient, flipped lengthwise, and used as a prosthesis, but rather is left in place so that blood flow is retrograde (against the valves of the vein). A standard valvulotome may be placed into the saphenous vein from below and advanced to the top in a collapsed state, opened, and then pulled backwards in an open state, cutting venous valves along the way. Cutting surfaces of such valvulotomes face backwards so as to cut during retraction during these procedures. FIG. 23A is a schematic perspective view of an example embodiment of a valvulotome 400 that may be used with such procedures, including blades 402 facing proximally.

Figure 23B:
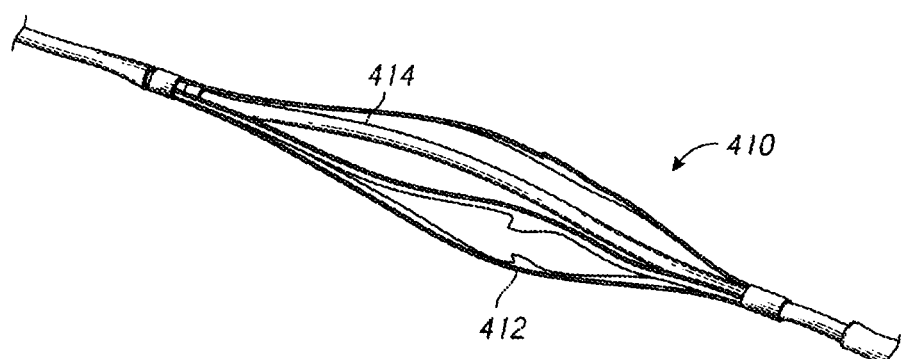
FIG. 23B is a schematic perspective view of an example embodiment of a reverse valvulotome.

In some embodiments of the methods described herein, access distal to the vein valves is not available such that pulling a valvulotome backwards is not possible, but pushing a reverse valvulotome as described herein forward is possible. FIG. 23B is a schematic perspective view of an example embodiment of a valvulotome 410 that may be used with such procedures. The reverse valvulotome 410 includes one or a plurality of blades 412 (e.g., two to five blades (e.g., three blades)) facing forward or distal such that valves can be cut as the reverse valvulotome 410 is advanced distally. At least because retrograde access to veins to be disabled has not previously been recognized as an issue, there has been no prior motivation to reverse the direction of the blades of a valvulotome to create a reverse valvulotome 410 such as described herein. The reverse valvulotome 410 may be tracked over a guidewire 414, which can be steered into the veins, for making the venous valves incompetent. After forming a fistula between an artery and a vein as described herein, the flow of fluid in the vein is in the direction opposite the native or normal or pre-procedure direction of fluid flow in the vein such that pushing the reverse valvulotome 410 is in a direction opposite native fluid flow but in the direction of post-fistula fluid flow.

Other systems and methods are also possible for making the valves in the vein incompetent (e.g., cutting balloons, atherectomy, laser ablation, ultrasonic ablation, heating, radio frequency (RF) ablation, a catheter with a tip that is traumatic or not atraumatic (e.g., an introducer sheath) being advanced and/or retracted, combinations thereof, and the like).

Figure 24:
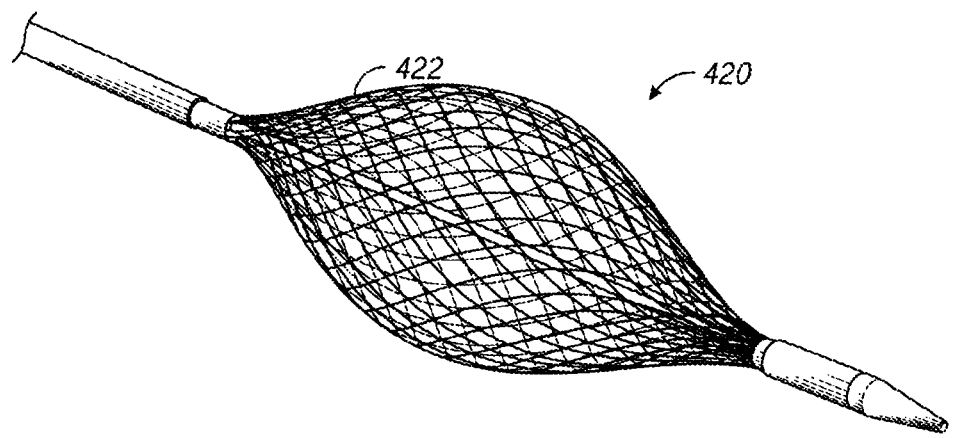
FIG. 24 is a schematic perspective view of an example embodiment of a LeMaitre device.

Crossing vein valves in a retrograde manner before such valves are made incompetent can also be challenging. FIG. 24 is a schematic perspective view of an example embodiment of a LeMaitre device 420 that may be used to radially expand the veins, and thus their valves. The LeMaitre device 420 includes an expandable oval or oblong leaf shape 422, for example a self-expanding nitinol mesh. In some embodiments, a PTA balloon catheter may be used to radially expand the veins, and thus their valves. In some embodiments, application of a tourniquet to the leg can radially expand the veins, and thus their valves. Upon radial expansion, a guidewire can be advanced through the stretched valve(s) (e.g., through an expansion device such as the LeMaitre device) and catheters (e.g., PTA, stent delivery, atherectomy (e.g., directional, orbital, laser, etc.), etc.) or other over-the-wire devices can be advanced over the guidewire.

FIGS. 26A and 26B schematically illustrate another example embodiment of a method for effecting retroperfusion. Referring again to FIG. 20E, a fistula may be created between an artery 600 including an occlusion 604 and a vein 602 with a guidewire 606 extending therethrough using one or more of the techniques described herein and/or other techniques. A prosthesis delivery system carrying a prosthesis 620 is tracked over the guidewire 606 through the interstitial space between the artery 600 and the vein 602 and then into the vein 602, as shown in FIG. 26A. In some embodiments, a separate PTA balloon catheter (e.g., about 2 mm) can be tracked over the guidewire 606 to pre-dilate the fistula between the artery 600 and the vein 602 prior to introduction of the prosthesis delivery system. Use of a PTA balloon catheter may depend, for example, on the radial strength of the prosthesis 620. The prosthesis 620 may be the stent 500, 520, 540 of FIGS. 25A-25C or variations thereof (e.g., as described with respect to FIG. 25C), which include uncovered and low porosity woven filaments configured to divert blood flow.

The flow diverting properties of uncovered woven filaments may depend on certain hemodynamic characteristics of the vascular cavities. For example, if the occlusion 604 is not total such that some pressure drop may occur between the lumen of the prosthesis 620 and the portion of the artery 600 between the occlusion 604 and the prosthesis 620, blood may be able to flow through the sidewalls of the prosthesis 620 rather than into the fistula. Referring again to FIG. 4 and the description of the blocking material 251, blocking material 608 may optionally be provided in the artery 600 to further occlude the artery 600, which can inhibit hemodynamic effects that might cause and/or allow blood to flow through the sidewalls of the prosthesis 620. For another example, a pressure drop between the artery 600 and the vein 602 might cause and/or allow blood to flow through the sidewalls of the prosthesis in the normal direction of venous blood flow rather than through the lumen of the prosthesis to effect retroperfusion. Referring again to FIG. 4 and the description of the blocking material 251, blocking material 610 may optionally be provided in the vein 602 to occlude the portion of the vein 602 downstream to the fistula under normal venous flow, which can inhibit hemodynamic effects that might cause and/or allow blood to flow through the sidewalls of the prosthesis 620.

The prosthesis 620 is deployed from the prosthesis delivery system, for example by operating a trigger handle 194 (FIG. 17). In some embodiments, for example if the prosthesis 620 is not able to expand and/or advance, the prosthesis delivery system may be removed and a PTA catheter (e.g., about 2 mm) advanced over the guidewire 620 to attempt to dilate or further dilate the fistula the artery 600 and the vein 602. Deployment of the prosthesis 620 may then be reattempted (e.g., by self-expansion, balloon expansion, etc.). In some embodiments, deployment of the prosthesis 620 may remodel a vessel, for example expanding the diameter of the vessel as described herein. In embodiments in which the prosthesis 620 is self-expanding, the degree of remodeling may change over time, for example the prosthesis 620 expanding as the vessel expands or contracting when the vessel contracts. The prosthesis 620 may be conformable to the anatomy in which the prosthesis 620 is deployed. For example, in an expanded state on a table or benchtop, the prosthesis 620 may be substantially cylindrical, but the prosthesis 620 may conform to the diameters of the vessels and fistula in which the prosthesis 620 is deployed such that the prosthesis may have different diameters in different longitudinal segments, tapers, non-cylindrical shapes, combinations thereof, and the like.

In some embodiments in which the prosthesis 620 comprises a supplemental support structure (e.g., as described with respect to FIG. 25B), deployment of the prosthesis may comprise deploying the first woven structure and, before, during, and/or after deploying the first woven structure, deploying the supplemental support structure.

The fistula may optionally be dilated with a PTA catheter before, during, and/or after deploying the prosthesis 620. The diameter of the PTA catheter (e.g., about 3 mm to about 6 mm) may be selected based at least in part on: the diameter of the artery 600, the diameter of the vein 602, the composition of the interstitial tissue, the characteristics of the prosthesis 620, combinations thereof, and the like.

Once the prosthesis 620 is in place, the prosthesis delivery system may be removed, as shown in FIG. 26B. An AV fistula is thereby formed between the artery 600 and the vein 602. Blood flows through the lumen of the prosthesis 620 even though the prosthesis lacks or is free from graft material due to the hemodynamic effects of the low porosity (e.g., less than about 50% porosity or other values described herein). FIG. 26B shows an implementation in which the blocking material 608, 610 was not used. Once the prosthesis 620 is in place, valves in the veins may be made incompetent, for example as described herein.

In embodiments in which the prosthesis 620 comprises two pluralities of filaments that may be deployed separately (e.g., as described with respect to certain embodiments of FIG. 25B), the pluralities of filaments may be deployed at least partially simultaneously, sequentially deployed without intervening steps, or sequentially with intervening steps such as the PTA steps described herein.

FIG. 27 schematically illustrates another example embodiment of a prosthesis 720 and a method for effecting retroperfusion. Although some dimensions and even an example scale of "10 mm" are provided, the shapes, dimensions, positional relationships, etc. of the features illustrated therein may vary. The prosthesis 720 is positioned in an artery 700 including an occlusion 704, in a vein 702, and spanning interstitial tissue T between the artery 700 and the vein 702. The prosthesis 720 may be positioned, for example, as described herein and/or using other methods. In some embodiments, the prosthesis 720 is delivered through a delivery system having a 5 Fr (1.67 mm) inner diameter over a guidewire having a 2 Fr (0.67 mm) outer diameter.

In some embodiments, the porosity of the first longitudinal section 722, the second longitudinal section 724, and/or the third longitudinal section 726, or one or more portions thereof may be between about 0% and about 50% and ranges therebetween, for example as described herein. Blood flow from the artery 700 may be diverted into the vein 702 through the prosthesis 720, for example due to hemodynamic forces such as a pressure difference between the artery 700 and the vein 702. The low porosity of the prosthesis 720 may allow the fluid to flow substantially through the lumen of the prosthesis 720 substantially without perfusing through the sidewalls of the prosthesis 720. In some embodiments, proximal and/or distal portions towards the ends of the prosthesis 720 may be configured to appose vessel sidewalls, for example having a lower porosity, since blood is not likely to flow through those portions.

Figures 28A, 28B:
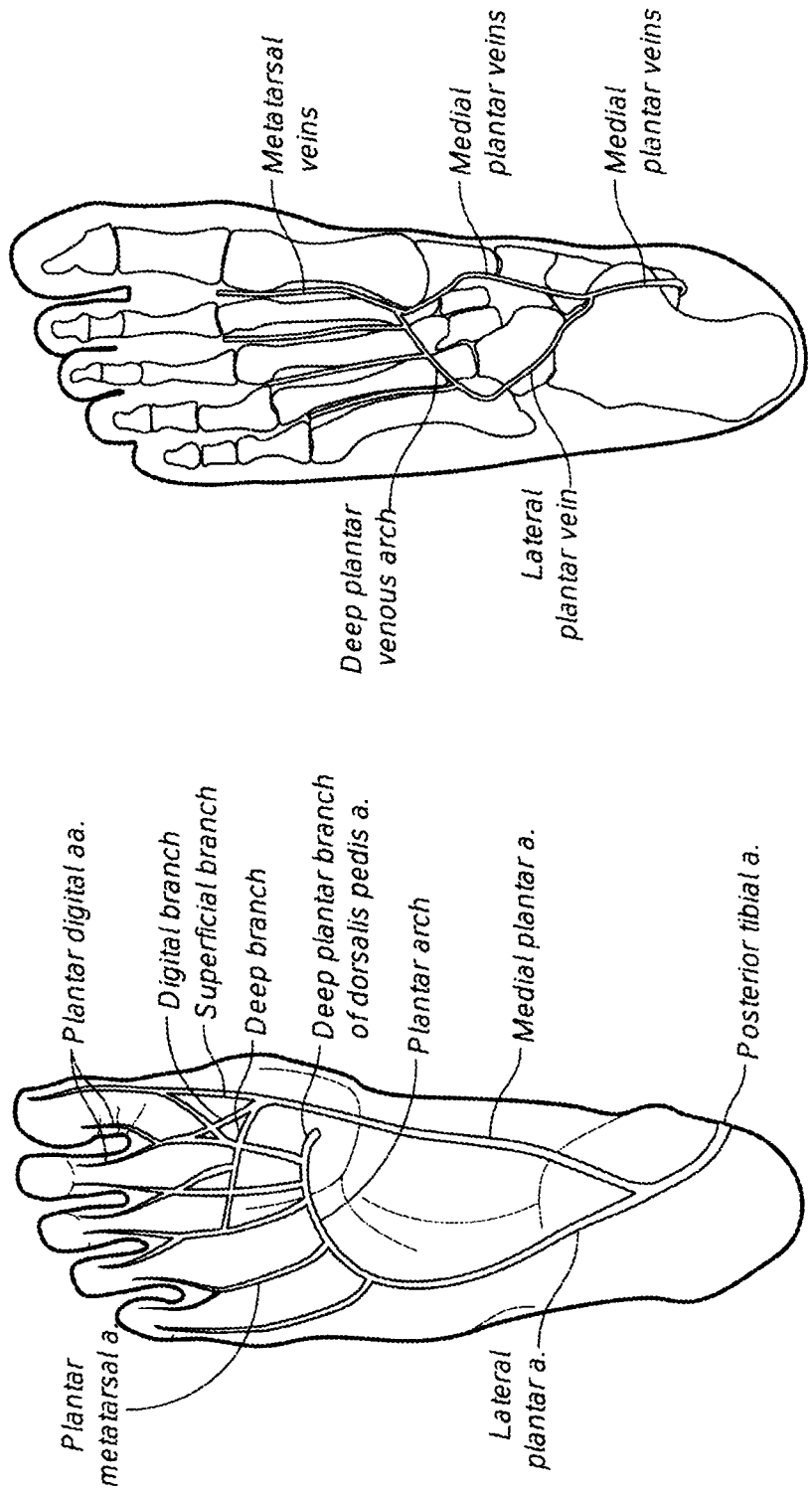
FIGS. 28A and 28B schematically illustrate arteries and veins of the foot, respectively.

The techniques described herein may be useful for forming a fistula between two body cavities near the heart, in the periphery, or even in the lower extremity such as the plantar arch. FIGS. 28A and 28B schematically illustrate arteries and veins of the foot, respectively. A fistula or anastomosis may be formed between two blood vessels in the foot. In one example, a passage from an artery to a vein was formed in the mid-lateral plantar, from the lateral plantar artery to the lateral plantar vein.

The artery supplying blood to the foot was occluded and the subintimal space was calcific. A wire was urged distally, and traversed into an adjacent vein. The hole between the artery and the vein was dilated with a 1.5 mm balloon, for example because a small arteriovenous fistula should not cause much if any damage for the patient at that position and in that position. After dilatation, blood started to flow from the artery to the vein without leakage. After such flow was confirmed, further dilatation of the space was performed using larger balloons (2.0 mm, 2.5 mm, 3.0 mm) at larger pressures (e.g., 20-30 atm). Leakage was surprisingly minimal or non-existent, even without placement of a stent, graft, scaffolding, or other type of device. Procedures not including a prosthesis may reduce costs, procedure time, complexity, combinations thereof, and/or the like. The lateral plantar vein goes directly into the vein arch of the forefoot, making it an excellent candidate for supplying blood to that portion of the foot. The patient had a lot of pain in the foot prior to the procedure and no pain in the foot after the procedure, indicating that blood was able to be supplied through the vein retrograde, as described herein. Fistula or anastomosis maintaining devices may optionally be omitted for certain situations, such as for hemodialysis in which a distal or lower extremity artery and vein may be described as "glued" in surrounding tissue (e.g., mid-lateral plantar artery and vein).

Figure 29:
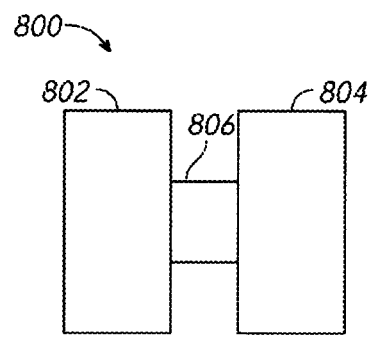
FIG. 29 schematically illustrates an example embodiment of an anastomosis device.

In some situations, a fistula or anastomosis maintaining device may be optionally used. Several fistula maintaining devices are described herein. FIG. 29 schematically illustrates an example embodiment of an anastomosis device 800. The anastomosis device includes a first section 802, a second section 804, and optionally a third section 806 longitudinally between the first section 802 and the second section 804. The first section 802 may be configured to anchor in a first body cavity (e.g., blood vessel such as an artery or vein). The first section 802 may include expandable members, barbs, etc. The second section 804 may be configured to anchor in a second body cavity (e.g., blood vessel such as an artery or vein, which may be the opposite type of the first body cavity). The third section 806 may be configured to span between the lumens of the first body cavity and the second body cavity. In some embodiments, the space between the lumens of the first body cavity and the second body cavity generally comprises the vessel walls such that the dimensions of the third section 806 may be small or even omitted.

Some anastomosis devices are available and/or have been developed for the treating holes in larger vessels (e.g., Spyder from Medtronic, CorLink from Johnson and Johnson, Symmetry from St. Jude Medical, PAS-Port from Cardica, and ROX Coupler from ROX Medical). Such devices may be appropriate for use in the periphery or the lower extremity, for example if resized and/or reconfigured. Other devices are also possible.

Figure 30:
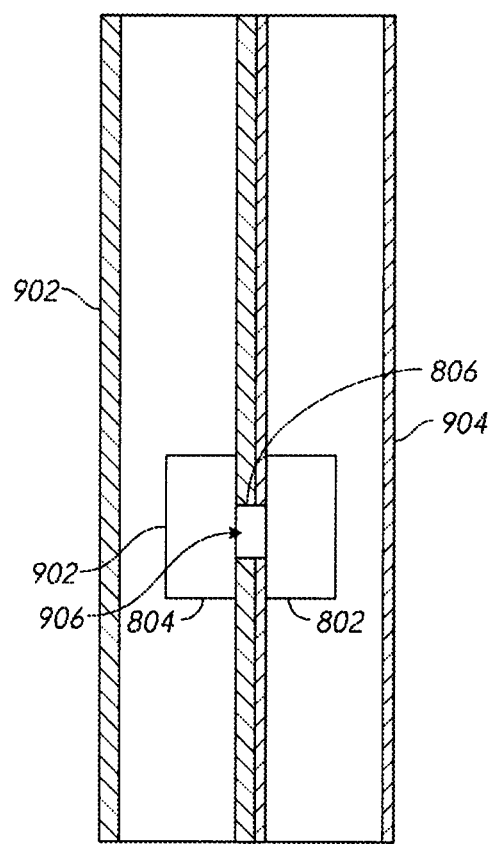
FIG. 30 schematically illustrates an example embodiment of two blood vessels coupled by an anastomosis device.

FIG. 30 schematically illustrates an example embodiment of two blood vessels 902 and 904 coupled together with an anastomosis device 800 spanning the walls of the blood vessels 902, 904. The blood vessel 902 is an artery, as schematically shown by having thick walls, and the blood vessel 904 is a vein. Other combinations of blood vessels and other body cavities are also possible. After a passage 906 is formed between the first blood vessel 902 and the second blood vessel 904, for example as described herein (e.g., using a wire, a deployable needle, one or more balloons, etc.), the anastomosis device 800 is deployed. For example, the distal end of an anastomosis device 800 deployment system may reside in the first blood vessel 902 and extend partially through the passage 906. The first section 802 of the anastomosis device 800 may be deployed through the passage 906 and in the second blood vessel 904. Upon deployment, the first section 802 may self-expand, for example to appose the walls of the second vessel 904. The third section 806 of the anastomosis device 800 may be deployed through the passage 906. Upon deployment, the third section 806 may self-expand, for example to appose the tissue surrounding the passage 906 and to maintain patency through the passage 906. The second section 804 of the anastomosis device 800 may be deployed in the first blood vessel 902. Upon deployment, the second section 804 may self-expand, for example to appose the walls of the first vessel 902. One or more of the first section 802, the second section 804, and the third section 806 may be expanded using a balloon. Different balloons or series of balloons can be used for different of the sections 802, 804, 806 of the anastomosis device 800.

FIGS. 32A through 32D illustrate an example method and device for identifying and avoiding a bifurcation 1104 in a percutaneous bypass procedure. A first vessel 1000 (e.g., an artery) is occluded by an occlusion 1008. The occlusion 1008 may be partial or complete (e.g., causing critical limb ischemia). A percutaneous procedure, for example as described herein, can use a second vessel 1002 (e.g., a vein) to bypass the occlusion 1008. A first catheter 1010 resides in the first vessel 1000. A second catheter 1020 resides in the second vessel 1002. The second vessel 1002 includes a bifurcation 1004 at a junction with a branch or collateral vessel 1006. The first catheter 1010 comprises ultrasound transmitter 1012 (e.g., a directional transmitter) configured to send a signal 1014 to an ultrasound receiver 1022 (e.g., an omnidirectional received) of the second catheter 1020 in the second vessel 1002, for example as described herein. A needle 1016 (FIG. 32D) may extend out of the first catheter 1010 towards the second vessel 1002. In the configuration shown in FIG. 32A, if the needle 1016 extends at the same angle as the signal 1014, for example as described herein (e.g., FIG. 3), then the needle 1016 may extend into the bifurcation 1004 and into the branch vessel 1006. Subsequent navigation of a guidewire through a lumen of the needle 1016 may disadvantageously be into the branch vessel 1006 rather than second vessel 1002. Navigation in the branch vessel 1006 rather than the second vessel 1002 may be difficult to detect by the user.

Figure 32A:
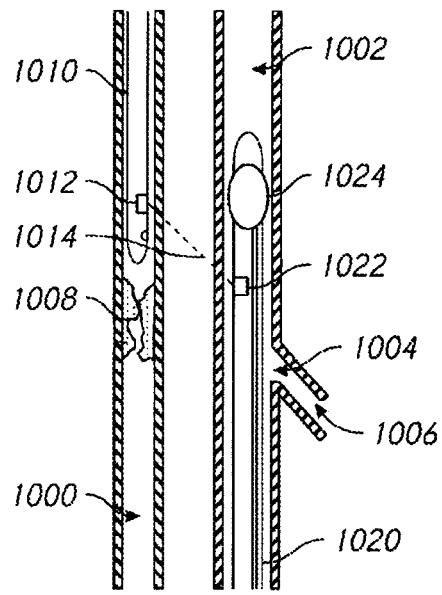
FIGS. 32A through 32D illustrate an example method and device for identifying and avoiding a bifurcation 1104 in a percutaneous bypass procedure.
Figure 32B:
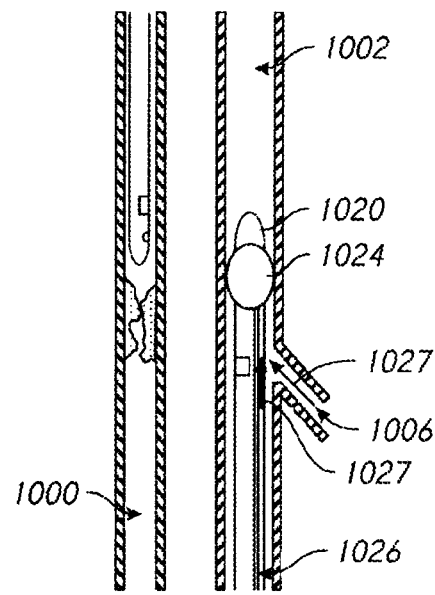

FIG. 32B illustrates a first step in an example method of diagnosing the existence and/or location of the bifurcation 1004. The expandable member 1024 is expanded, for example by providing fluid flow (e.g., saline, contrast materials, etc.) through an inflation lumen 1026 in fluid communication with the expandable member. In FIGS. 32A-32D, the second catheter 1020 comprises an integral expandable member 1024 (e.g., comprising a balloon) and an inflation lumen 1026. A separate catheter comprising an expandable member may be used in the second vessel 1002. Expansion of the expandable member 1024 occludes the second vessel 1002. As shown by the arrows 1027, blood is still flowing towards the expandable member 1020 from both from a proximal end of the second vessel 1002 and from the branch vessel 1006. The occlusion of the second vessel 1002 and the blood still flowing into the second vessel 1002 can cause the second vessel 1002 to expand. Expansion of the second vessel 1002 can make the second vessel easier to target and/or puncture with the needle 1016.

Figure 32C:
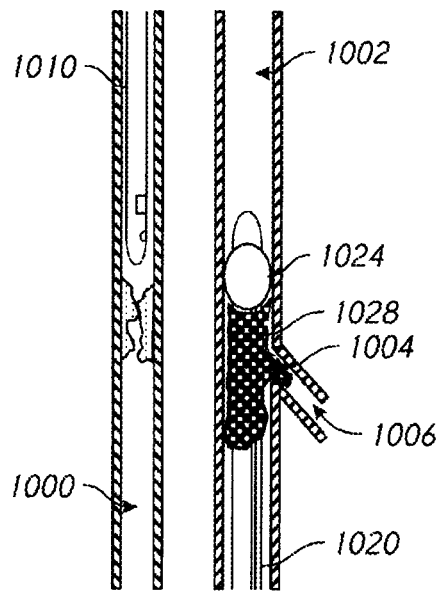

FIG. 32C shows the introduction of contrast material 1028 in the second vessel 1002. The contrast material 1028 maybe delivered through an infusion port integral with the second catheter 1020 and/or using a separate catheter in the second vessel 1002. The contrast material 1028 may comprise, for example contrast agents or contrast media configured to improve fluoroscopy including iodine-based, barium sulfate-based (e.g., for subjects with impaired kidney function), combinations thereof, and the like. The contrast material 1028 can contribute to expansion of the second vessel 1002. The contrast material 1028 flows until reaching the expandable member 1024, then begins to gather proximate to the expandable member 1024. A portion of the contrast material 1028 may gather in the bifurcation 1004, making the existence and location of the bifurcation 1004 and/or the branch vessel 1006 visible under fluoroscopy. Without the expandable member 1024, the contrast material 1028 would flow through the second vessel 1002 without showing the bifurcation 1004 and/or the branch vessel 1006. With knowledge of the angle of the needle 1016, and the position of the first catheter 1010, the user can determine whether the needle 1016 would extend into the bifurcation 1004 and/or the branch vessel 1006. Since this situation would generally result in ineffective bypass, a different puncture site for forming a fistula may be selected.

Figure 32D:
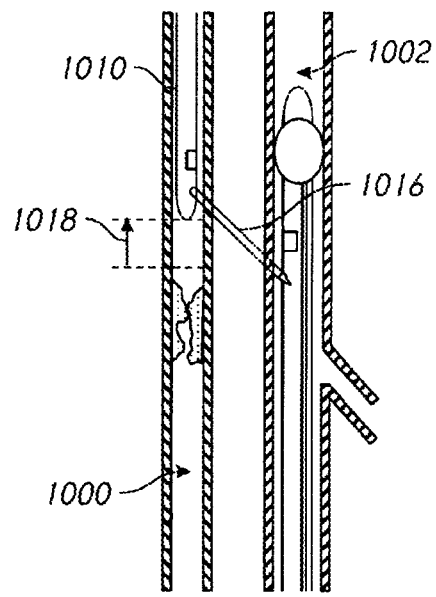

In FIG. 32D, the first catheter 1010 has been retracted by a distance 1018. The ultrasound signal 1014 (FIG. 32A) from the first catheter 1010 may be used to target the second catheter 1020. The procedure shown in FIGS. 32B and 32C may be repeated, for example looking for another bifurcation. Once the user is satisfied with that the needle 1016 will puncture the second vessel 1002 at a position free from a bifurcation to inhibit or prevent advancement into a branch vessel rather than the second vessel 1002, the needle 1016 may be extended from the first catheter 1010, out of the first vessel 1000, through interstitial tissue between the first vessel 1000 and the second vessel 1002, and into the second vessel 1002 at a position at which the second vessel 1002 does not include a bifurcation or branch vessel. The needle 1016 may be extended with the expandable member 1024 inflated or deflated, or even with the second catheter 1020 removed from the second vessel 1002. In some embodiments, a permanent occluder may be positioned in the second vessel 1002, for example as described herein (e.g., FIG. 4). A guidewire may be tracked through a lumen of the needle 1016, and other procedures as described herein, for example fistula dilation, deployment of a fistula prosthesis, deployment of a stent graft, use of a reverse valvulotome, etc., can be performed by tracking a catheter over guidewire (e.g., through the first vessel 1000, through the fistula, and then through the second vessel 1002). In some embodiments, the devices and methods described herein can be used to guide a needle into a bifurcation and/or a branch vessel if desired by the user.

Figure 33A:
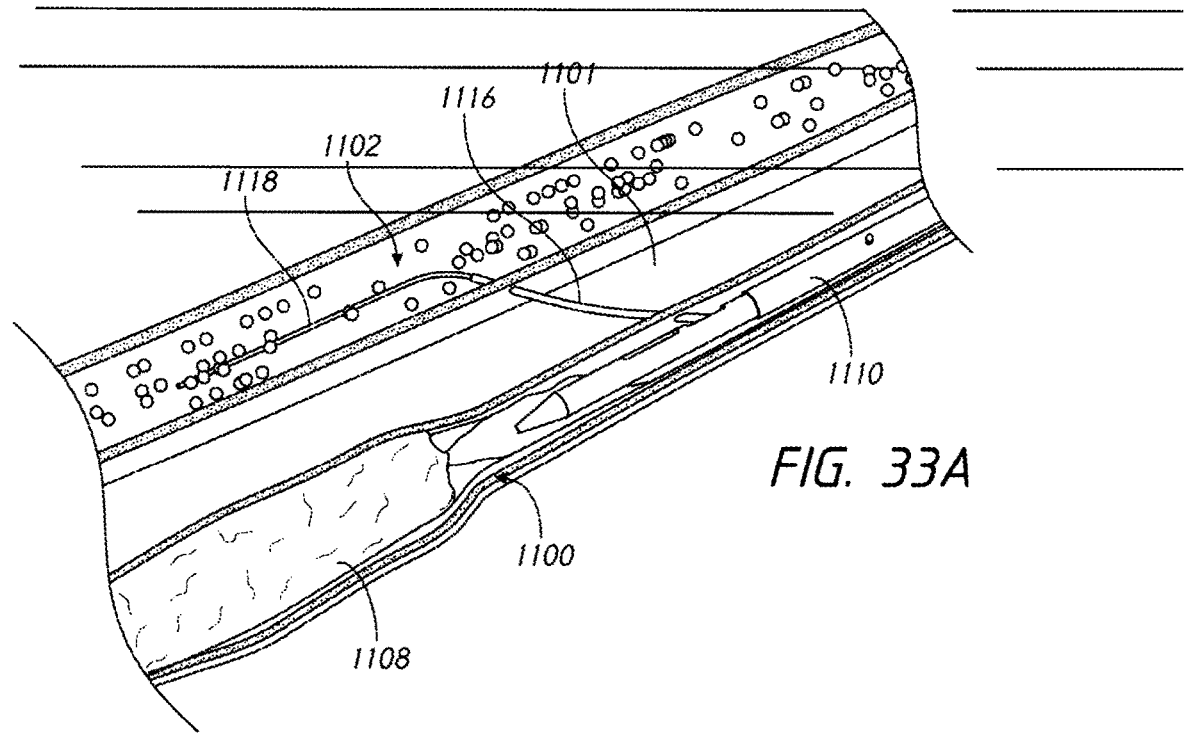
FIGS. 33A and 33B schematically illustrate an example procedure that can be performed the following connection of a first vessel and a second vessel with a needle traversing interstitial tissue.
Figure 33B:
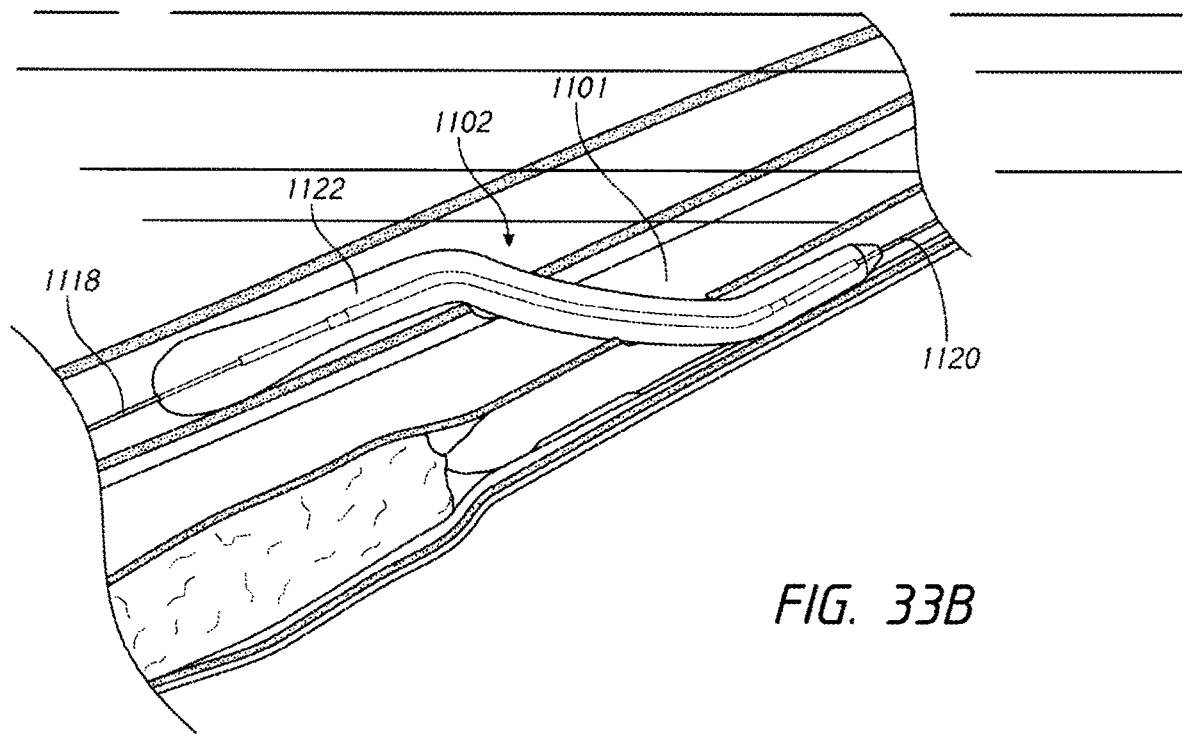

FIGS. 33A and 33B schematically illustrate an example procedure that can be performed the following connection of a first vessel 1100 (e.g., an artery) and a second vessel 1102 (e.g., a vein) with a needle 1116 traversing interstitial tissue 1101. The needle 1116 extends from a first catheter 1110 in the first vessel 1100. The first vessel 1100 is occluded by an occlusion 1108. In FIG. 33A, a guidewire 1118 extends through a lumen in the needle 1116, and can then be navigated through the second vessel 1102. The needle 1116 may be retracted upon placement of the guidewire 1118, and the first catheter 1110 may be retracted from the first vessel 1100. As illustrated in FIG. 33B, a second catheter 1120 maybe tracked over the guidewire 1118 through the first vessel 1100, through the interstitial tissue 1101, and into the second vessel 1102. In FIG. 33B, the second catheter 1120 comprises a balloon catheter comprising a balloon 1122 (e.g., a PTA balloon). Inflation of the balloon 1122 can dilate a fistula formed between the first vessel 1100 and the second vessel 1102. Dilation of the interstitial tissue 1101 and/or aperture in the vessels 1100, 1102 can enhance later procedures, such as placement of a prosthesis across the fistula.

Figure 34A:
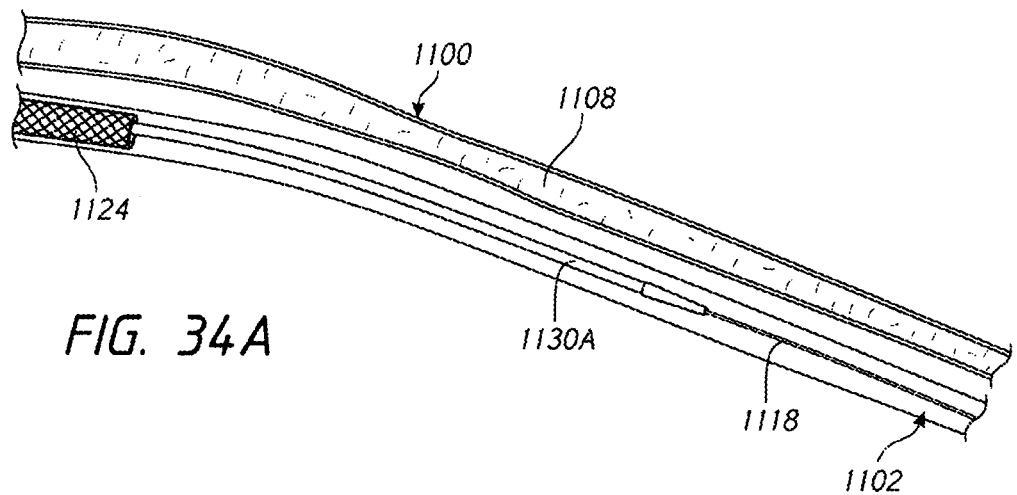
FIGS. 34A through 35F illustrate example procedures that can be performed when a guidewire is in a vessel.
Figure 34B:
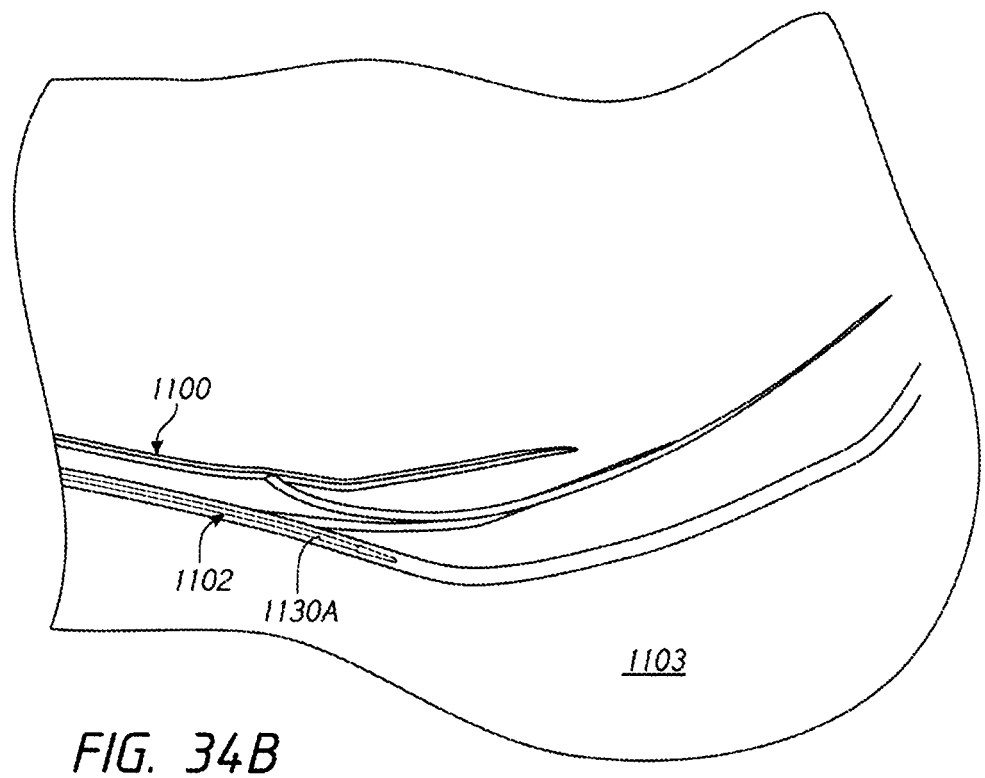

FIGS. 34A through 35F illustrate example procedures that can be performed when a guidewire 1118 is in a vessel 1102 (e.g., a vein). In FIG. 34A, a prosthesis 1124 has been placed across the interstitial tissue 1101 between the first vessel 1100 in the second vessel 1102. The deployment system for placing the prosthesis 1124 may have been tracked over the guidewire 1118. A catheter 1130A is tracked over the guidewire 1118 distal to the prosthesis 1124. As shown in FIG. 34B, the catheter 1130A may be tracked all the way towards a heel 1103 of the subject.

Figure 34C:
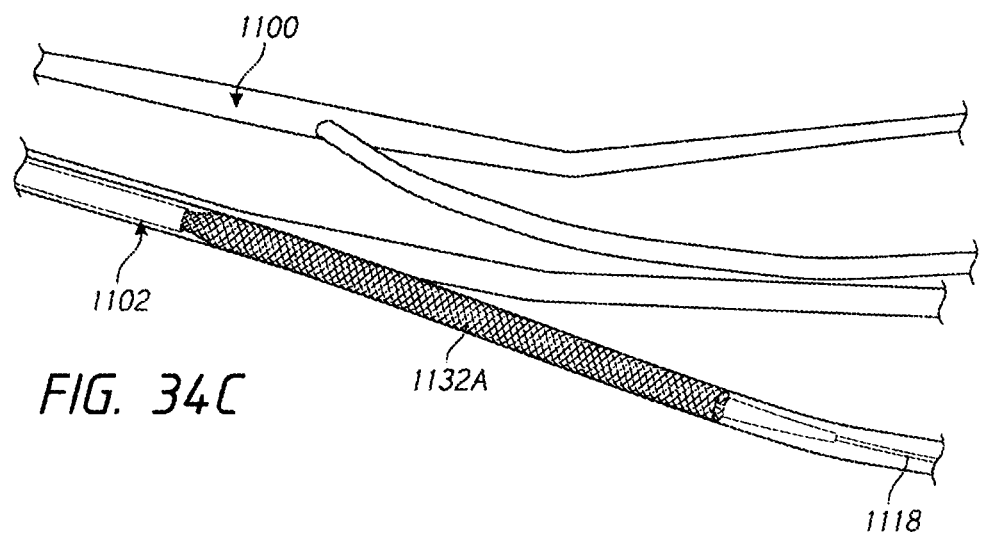
Figure 34D:
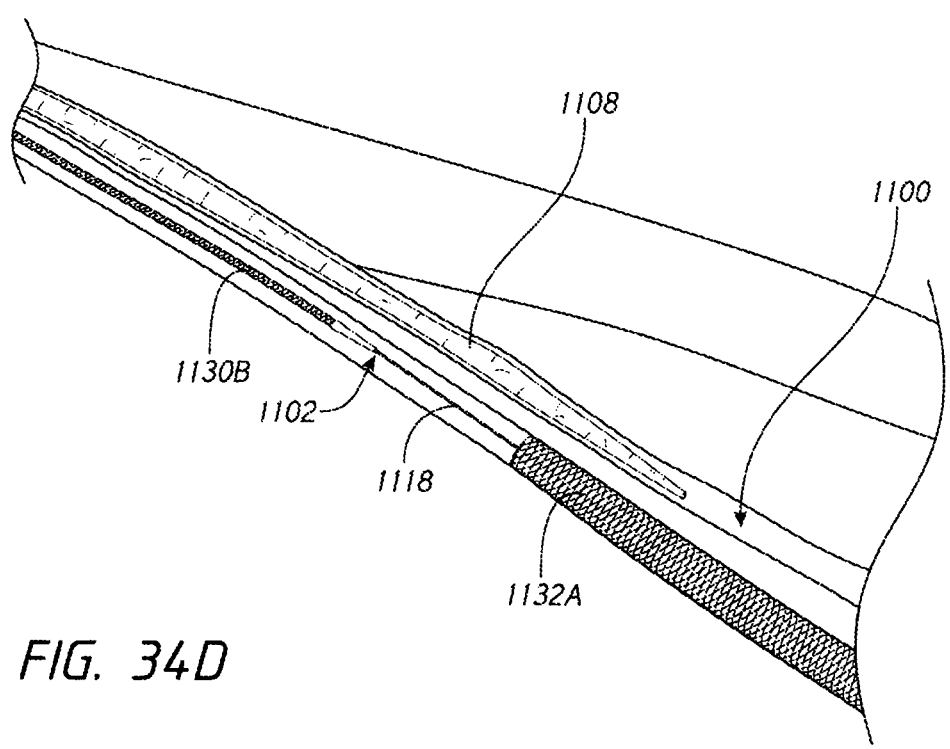
Figure 34E:
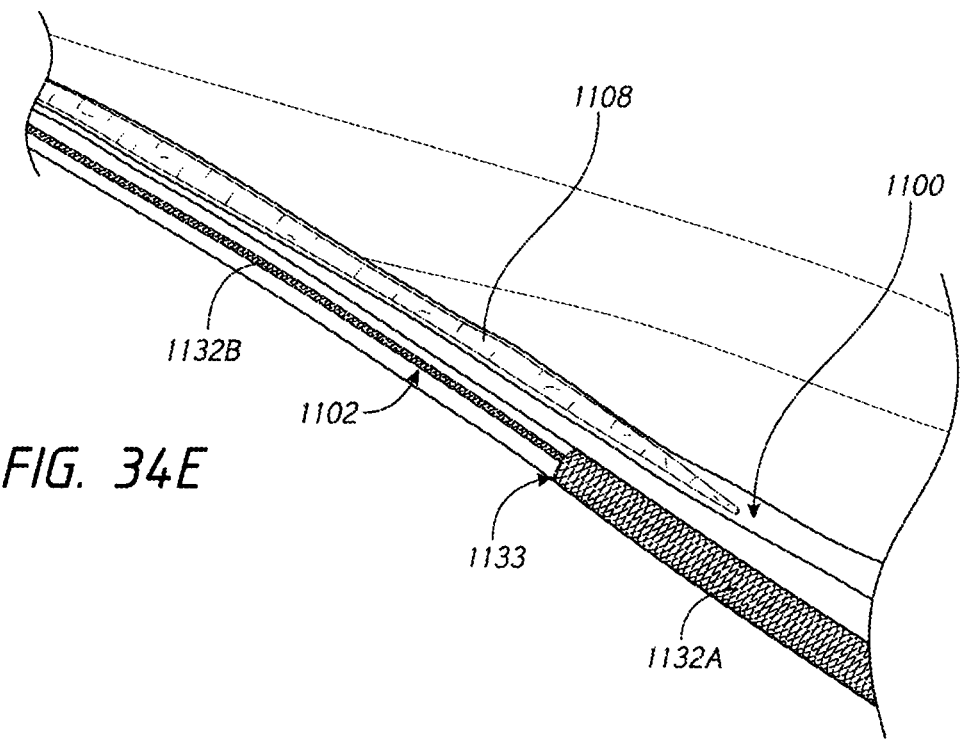

As shown in FIG. 34C, the catheter 1130A is configured to deliver a first stent graft 1132A, which can line the second vessel 1102, disabling valves in the second vessel 1102, occluding branch vessels of the second vessel 1102, etc., for example as described. In FIG. 34D, the catheter 1130A has been retracted and another catheter 1130B has been tracked over the guide wire 1118. FIG. 34D also shows an example of where the occlusion 1108 in the first vessel 1100 may terminate, which may be useful if another fistula was formed between the first vessel 1100 and the second vessel 1102 (e.g., to bypass the occlusion 1108). Forming a second fistula may be the same or different than forming the first fistula (e.g., using at least one of the ultrasound guidance, extending a needle, and prosthesis deployment described herein). In FIG. 34E, the catheter 1130B is delivering a second stent graft 1132B, which may at least partially overlap the first stent graft 1132A in an area 1133. In some embodiments, the distal end of the second stent graft 1132B may be configured to overlap the proximal end of the first stent graft 1132A. In some embodiments, the proximal end of the first stent graft 1132A may be configured to be overlapped by the distal end of the second stent graft 1132B. In some embodiments, for example if the second stent graft 1132B is placed first, the proximal end of the first stent graft 1132A may be configured to be overlapped by the distal end of the second stent graft 1132B. The second stent graft 1132B may be longitudinally spaced from the first stent graft 1132A, for example if the longitudinal spacing is small enough that there is unlikely to be a branch vessel and/or a valve in the location of the spacing.

Figure 34F:
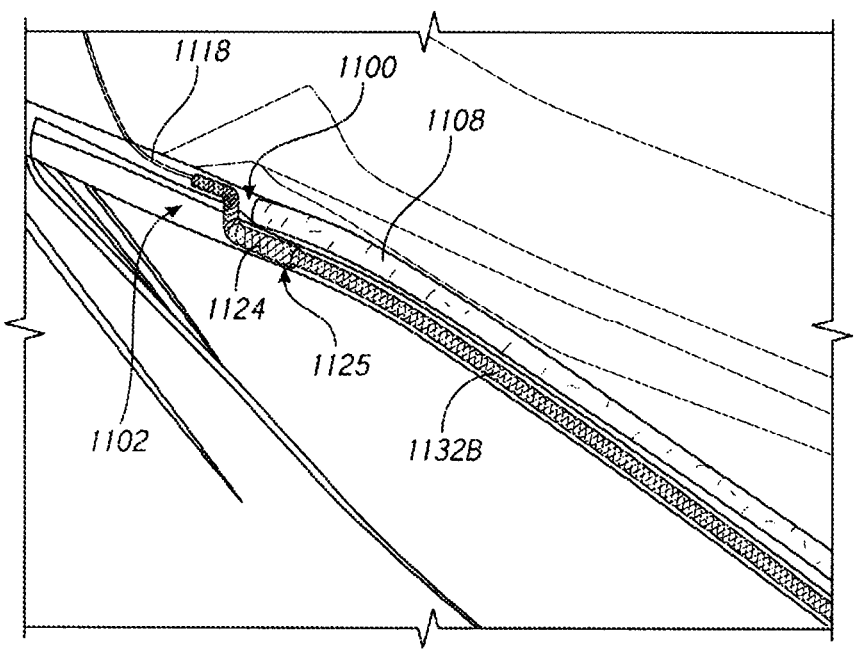

In FIG. 34F, the second stent graft 1132B at least partially overlaps the prosthesis 1124. In some embodiments, the proximal end of the second stent graft 1132A may be configured to overlap the distal end of the prosthesis 1124. In some embodiments, the distal end of the prosthesis may be configured to be overlapped by the proximal end of the second stent graft 1132B. The second stent graft 1132B may be longitudinally spaced from the prosthesis 1124, for example if the longitudinal spacing is small enough that there is unlikely to be a branch vessel and/or a valve in the location of the spacing. FIG. 34F also shows the catheter 1132B retracted out of the vasculature. Although two stent grafts 1132A, 1132B are described in this example, one, two, three, or more stent grafts may be used, for example depending on the length of the second vessel 1102 distal to the prosthesis 1124, the length(s) of the stent graft(s), the likelihood or existence of branch vessels, etc.

Figure 35A:
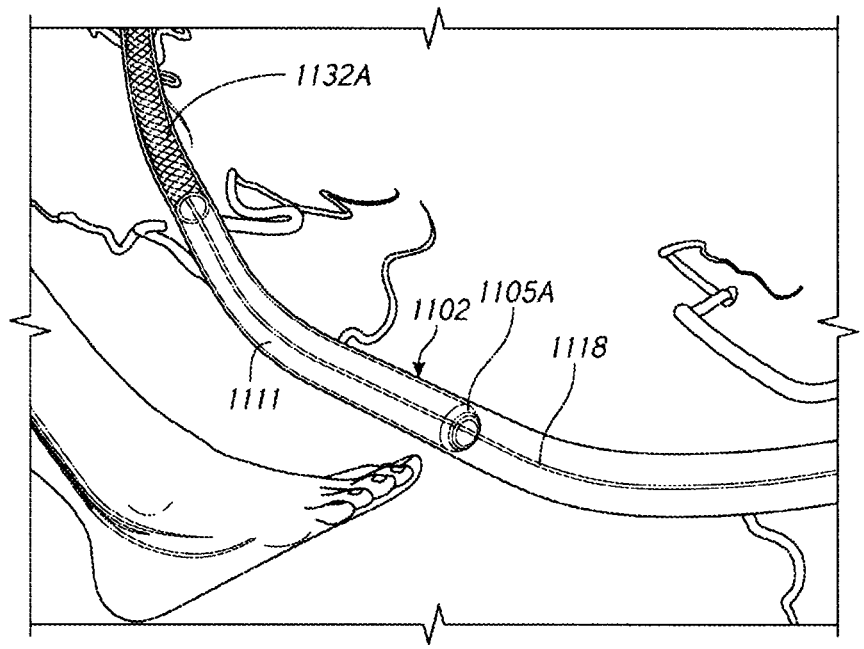
Figure 35B:
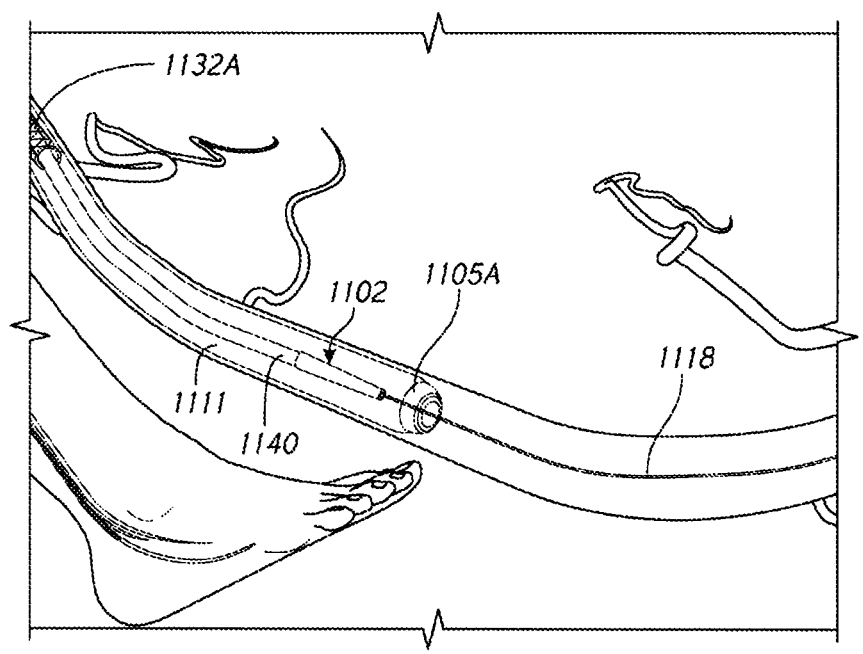
Figure 35C:
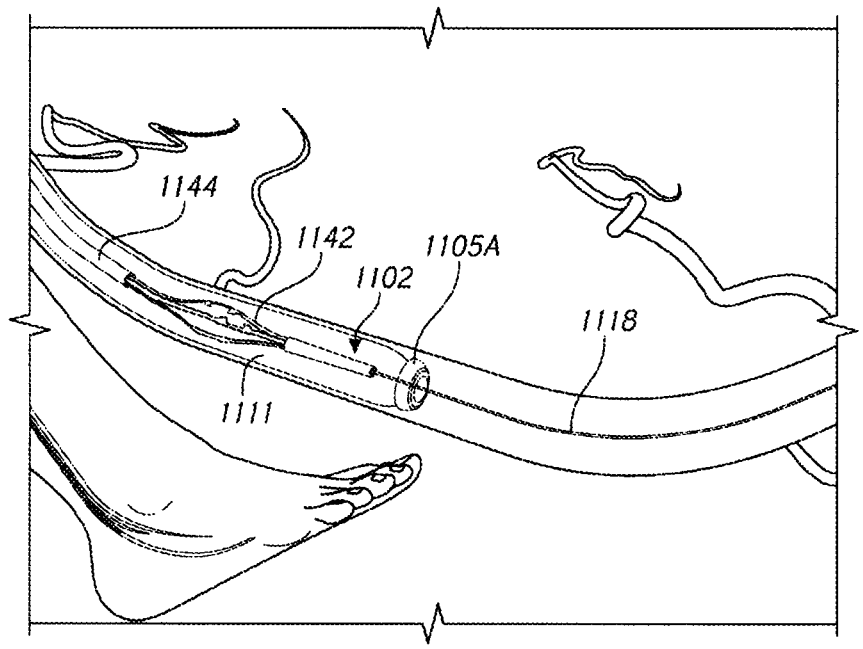
Figure 35D:
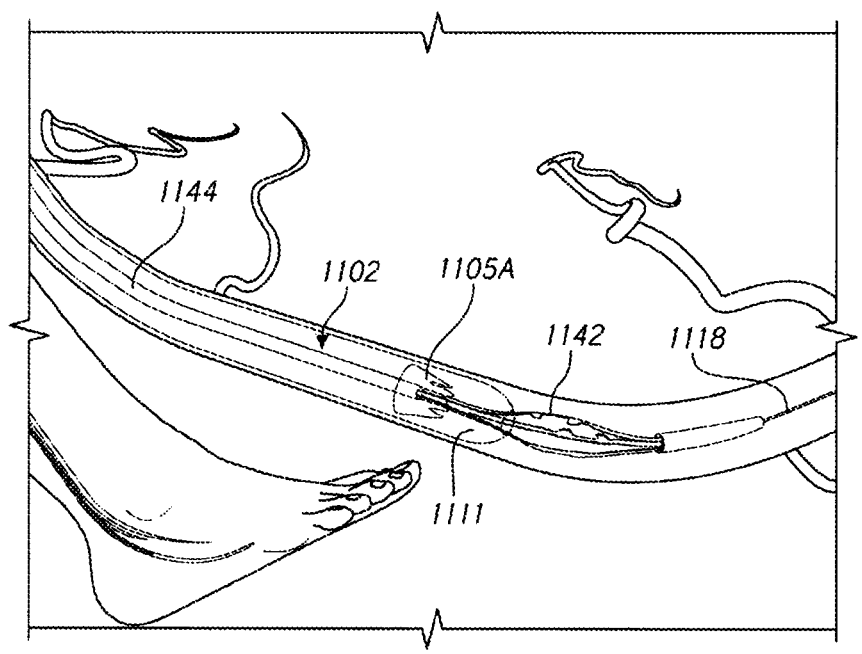

FIG. 35A shows the second vessel 1102 distal to the first stent graft 1132A. The second vessel 1102 comprises a first valve 1105A that inhibits or prevents blood 1111 from flowing distal to the first valve 1105A. In FIG. 35B, a catheter 1140 is tracked over the guidewire 1118 towards the first valve 1105A through the stent graft 1132A. The catheter 1140 comprises a valve disabling device. In FIG. 35C, the catheter 1140 is shown as comprising a reverse valvulotome 1142, for example as described herein, and a sheath 1144. Referring again FIG. 35B, when the reverse valvulotome 1142 is in the sheath 1144, the reverse valvulotome 1142 is in a radially contracted state. As shown in the FIG. 35C, when the sheath 1144 is proximally retracted and/or the reverse valvulotome 1142 is distally advanced, the reverse valvulotome 1142 radially expands to a state configured to cut valves upon distal advancement. In FIG. 35D, the blade or blades of the reverse valvulotome 1142 ablate or cut or sever the leaflets of the first valve 1105A, allowing blood 1111 to flow distal to the first valve 1105A.

Figure 35E:
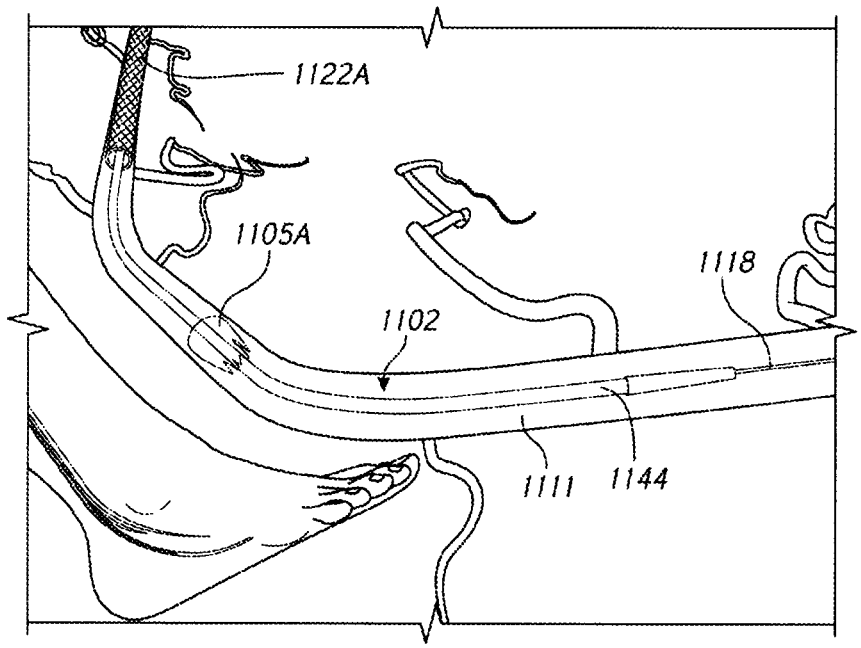
Figure 35F:
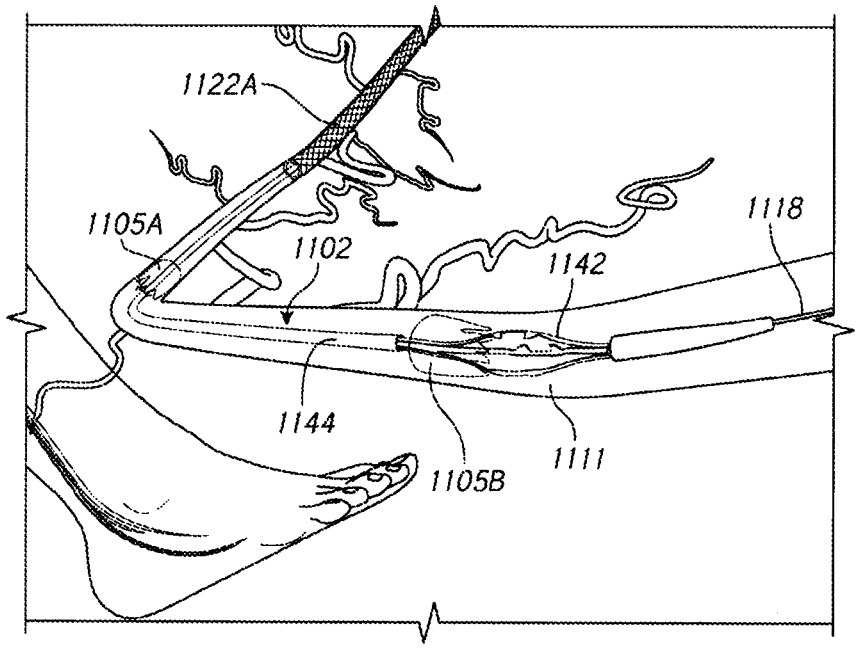

Referring to FIG. 35E, after the first valve 1105A has been disabled, the reverse valvulotome 1142 may be radially compressed in the outer sheath 1144 for further distal advancement without affecting the second vessel 1102. As shown in FIG. 35F, when a second valve 1105B is encountered, the reverse valvulotome 1142 may extend from the sheath 1144 and then distally advanced to disable the second valve 1105B, allowing the blood 1111 to flow distal to the second valve 1105B. The use of the reverse valvulotome 1142 may be repeated for as many valves in the second vessel 1102 as desired by the user. In some embodiments, a reverse valvulotome 1142 may be used before placement of stent grafts 1132A, 1132B. Valve disabling devices other than a reverse valvulotome, for example but not limited to the two-way valvulotome 1300 as described herein, may also or alternatively be used.

Figure 36A:
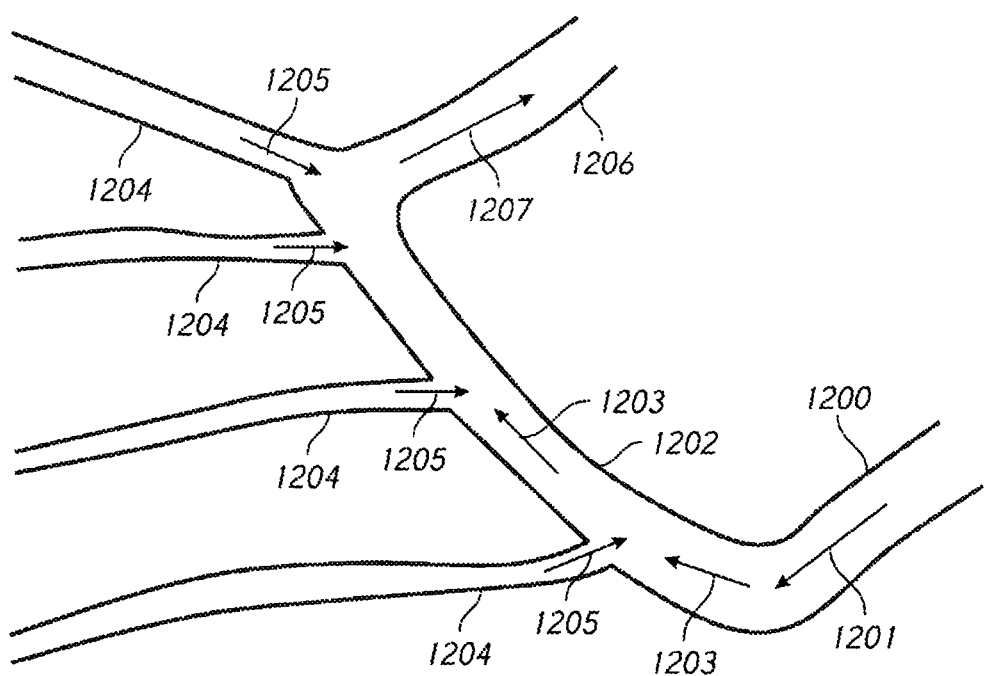
FIGS. 36A through 36D illustrate an example method of promoting retroperfusion of blood through a vein into toes.

FIGS. 36A through 36D illustrate method of promoting retroperfusion of blood through a vein into toes. In FIG. 36A, the vasculature illustrated includes a lateral plantar vein 1200, a deep plantar venous arch 1202, metatarsal veins 1204, and a medial plantar vein 1206. Blood flow through the lateral plantar vein 1200, as illustrated by the arrow 1201, is counter to the normal direction of blood flow, for example due to retroperfusion caused by percutaneous bypass from an artery into a vein upstream of the lateral plantar vein 1200. The blood continues to flow through the vasculature as shown by the arrows 1203, where the blood is joined by blood flowing away from the toes in the normal direction of blood flow through the metatarsal veins 1204, as indicated by the arrows 1205. The medial plantar vein 1206 is configured to return blood towards the heart, so normal blood flow, as indicated by the arrow 1207, is maintained. Blood may preferentially flow as illustrated in FIG. 36A, which is not desirable when the intended effect of the retroperfusion is to perfuse oxygenated blood to the toes.

Figure 36B:
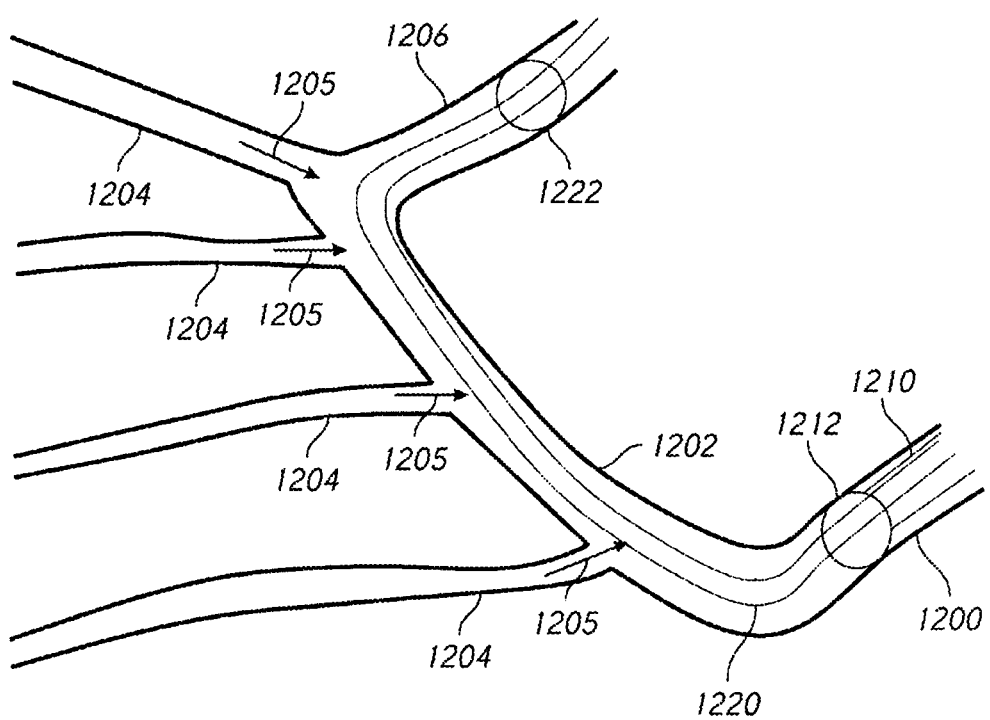

FIG. 36B illustrates an example embodiment of a device that can be used to promote blood flow to the toes through the metatarsal veins 1204. A first catheter 1210 comprising a first expandable member 1212 (e.g., balloon) may comprise a 6 French occlusion catheter comprising a three-way fitting. The expandable member 1212 is inflated in the lateral plantar vein 1200. A second catheter 1220 that is coaxial with the first catheter 1210 extends through the expandable member 1212, through the deep plantar venous arch 1202, and into the medial plantar vein 1206. The second catheter 1220 comprises an expandable member 1222 (e.g., balloon), which may be inflated in the medial plantar vein 1206. At that point, the medial planar vein 1206 is partially or fully occluded, and blood flow through the medial plantar vein 1206 is inhibited or prevented. Blood may continue to flow from the toes through the metatarsal veins 1204, as indicated by the persistence of the arrows 1205. The blood has no exit route, so hydrostatic pressure may build up in the deep plantar venous arch 1202, which can disable valves and/or other structures configured to promote normal blood flow. Optionally, the first expandable member 1212 may permit retroperfusion blood to flow, which can further build pressure in the deep plantar venous arch 1202. Blood flow would normally perfuse opposite to the direction of the retroperfusion in the lateral plantar vein 1200, but the expandable member 1212 can inhibit or prevent such flow.

In some embodiments, a device comprising a single catheter may be used to promote blood flow to the toes through the metatarsal veins 1204. The device may comprise a first expandable member and a second expandable member. For example, the device can comprise a double balloon catheter having a first balloon and a second balloon distal to the first balloon.

The device may allow one of the first and second expandable members to inflate independently of the other expandable member. For example, in some embodiments, the device may comprise at least a first lumen and a second lumen. The first lumen can be configured to inflate the first expandable member independently of the second expandable member. The second lumen can be configured to inflate the second expandable member independently of the first expandable member. The device may comprise a single lumen configured to inflate both the first and second expandable members. The device may include one or more inflation ports configured to inflate at least one of the first and second expandable members.

The device may be configured to adjust the distance between the expandable members prior to inflation of at least one of the expandable members. The device may permit the expandable members to isolate a patient-specific treatment area and promote retroperfusion of blood through a vein into toes, as described herein. For example, the device may permit the placement of the first expandable member in the lateral plantar vein 1200 and placement of the second expandable member in the medial plantar vein 1206, and/or vice versa. The device may comprise one or more handles configured to control the movement of various portions of the device. For example, the device may comprise a first handle to control the movement of both the first and second expandable members. In some embodiments, the device may comprise a second handle configured to control the movement of the first expandable member independently of the second expandable member. The second handle may allow the device to advance the first expandable member in a proximal direction relative to the second expandable member from a first position to a second position. After the first expandable member has been advanced to a second position, the second handle may allow the device to advance the first expandable member in a distal direction to the first position.

The device may comprise an infusion port configured to inject fluid into a treatment area defined by the first and second expandable members. For example, the treatment area may comprise the deep plantar venous arch 1202. After the first and second expandable members have been inflated, blood flow through the medial plantar vein 1206 is inhibited or prevented. The infusion port may then allow the device to inject fluid into the treatment area. The injection of fluid can increase hydrostatic pressure within the treatment area. The hydrostatic pressure increases due to the inflated first and second expandable members preventing the injected fluid from flowing outside the treatment area through the medial plantar vein 1206 and/or the lateral plantar vein 1200. The infusion port can be configured to sufficiently increase in hydrostatic pressure within the treatment area to allow the device to disable valves and/or other structures. For example, the infusion port may be sized to inject an amount of fluid sufficient to increase the hydrostatic pressure to promote blood flow to the toes.

Figure 36C:
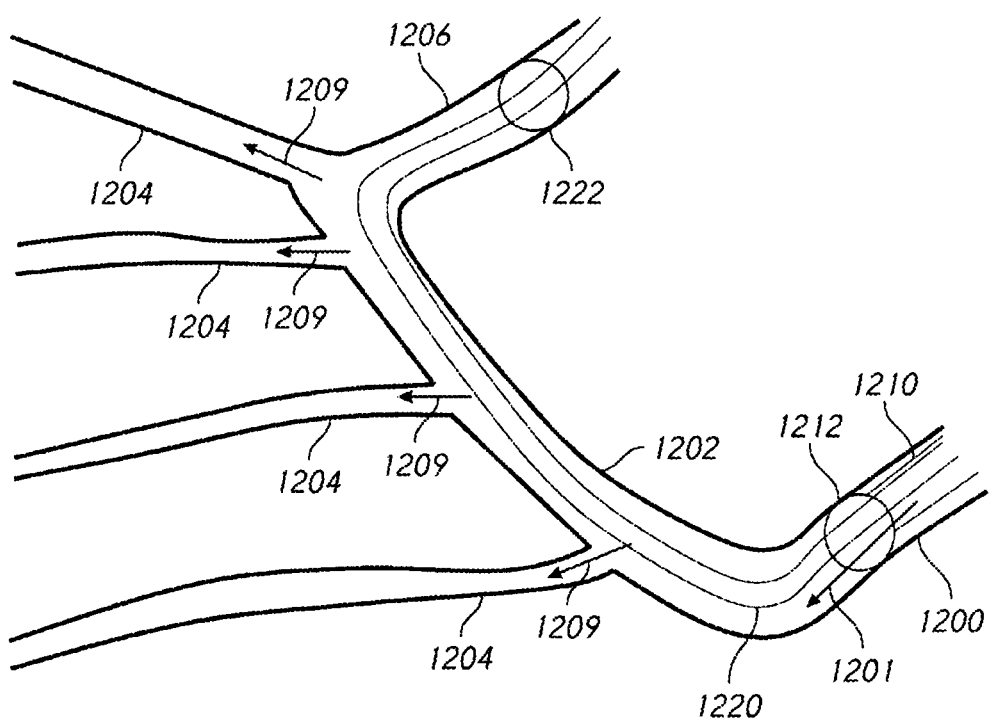

In FIG. 36C, blood flow is allowed through the expandable member 1212, as shown by the arrow 1201, but the inflatable member 1212 inhibits normal blood flow in the deep plantar venous arch 1202. Pressure due to the restricted flow builds up in the deep plantar venous arch 1202. The pressure buildup, optionally in combination with the flow of blood from the lateral plantar vein 1200, can causes reversal of blood flow into the metatarsal veins 1204, as shown by the arrows 1209.

Figure 36D:
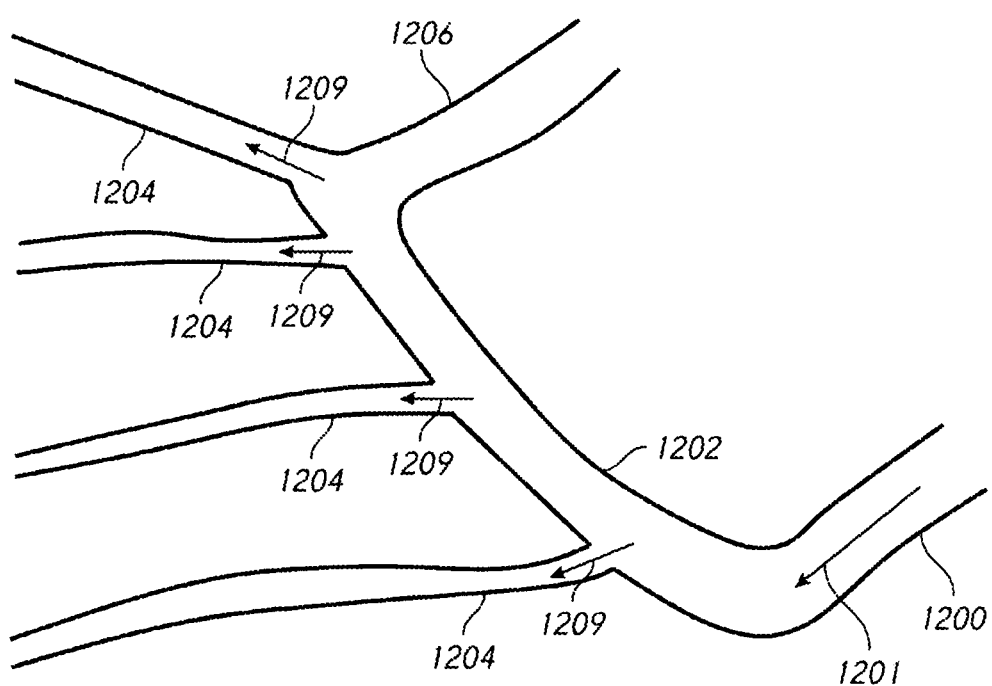

In FIG. 36D, the first catheter 1210 and the second catheter 1220 are removed. The disabling of the normal vasculature in the deep plantar venous arch 1202 causes continued retroperfusion of blood through the metatarsal veins 1204, as shown by the maintenance of the arrows 1209. A small amount of oxygenated blood may flow through the medial plantar vein 1206. In some embodiments, the medial plantar vein 1206 may remain occluded using the expandable member 1222 (e.g., detachable from the catheter 1220) or a different occluder. In some embodiments, blood may flow through the plantar vein 1206 in a direction opposite normal blood flow.

Figure 37A:
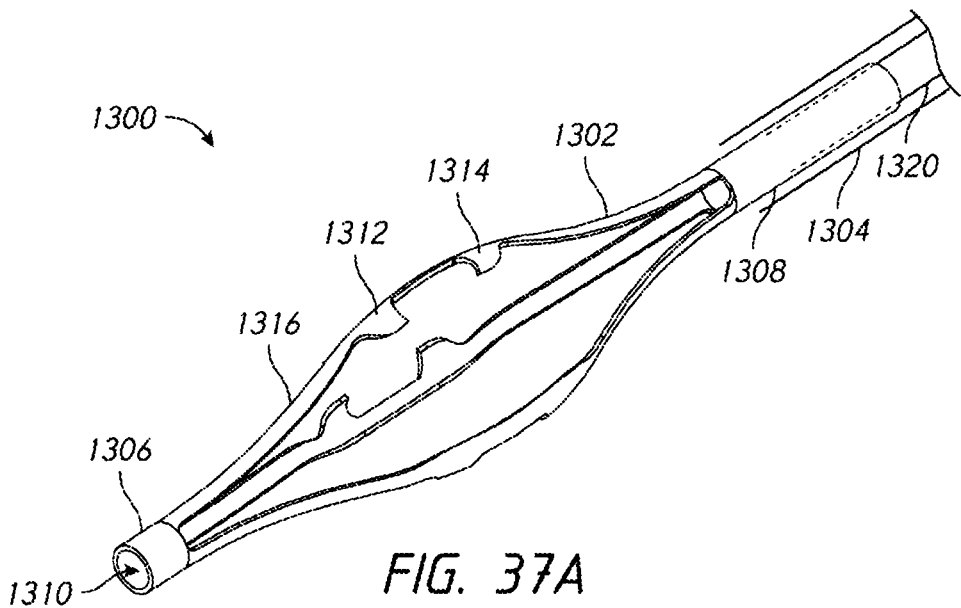
FIG. 37A illustrates an example of a valve disabling device in a radially expanded state.

FIG. 37A illustrates an example of a valve disabling device 1300 in a radially expanded state. The valve disabling device 1300 is configured to cut or ablate or sever or disable leaflets of a valve (e.g., a venous valve) upon retraction and/or advancement in a radially expanded state. The valve disabling device 1300 comprises a proximal portion 1308, a distal portion 1306, and intermediate portion 1302 between the proximal portion 1308 and the distal portion 1306. The proximal portion 1308 comprises a tubular element. The distal portion 1306 comprises a tubular portion. The device 1300 may be formed by cutting (e.g., laser cutting) a hypotube, cutting a flat sheet and rolling into a hypotube, forming parts of the device 1300 and then coupling the parts together, shape setting, combinations thereof, and the like. The tubular element of the distal portion 1306 and/or the tubular element of the proximal portion 1308 may comprise an uncut portion of a hypotube or sheet.

The proximal portion 1308 may be coupled to a pusher element 1320. The pusher element may comprise a lumen, for example configured to advance across a guidewire. The device 1300 may be in a radially compressed state when confined in a sheath 1304 and in a radially expanded state when not confined in the sheath 1304. The device 1300 may be radially expanded by proximally retracting the sheath 1304 and/or by distally advancing the pusher element 1320 and thereby the device 1300. The device 1300 may be radially compressed by distally advancing the sheath 1304 and/or by proximally retracting the pusher element 1320 and thereby the device 1300. In the radially expanded state, the intermediate portion 1302 may radially expand while the proximal portion 1308 and the distal portion 1306 do not radially expand (e.g., as shown in FIG. 37A).

The intermediate portion 1302 may comprise cut portions of a hypotube or sheet. The intermediate portion 1302 may comprise one or more struts 1316 extending between the proximal portion 1308 and the distal portion 1306. The intermediate portion 1302 may comprise between about one strut and about eight struts (e.g., one strut, two struts, three struts (e.g., as shown in FIG. 37A), four struts, five struts, six struts, seven struts, eight struts, ranges between such values, etc.). The struts 1316 may be approximately equally circumferentially spaced, for example to provide uniform cutting in any circumferential orientation. For example, three struts 1316 may be circumferentially spaced by about 120°. The struts 1316 may unequally circumferentially spaced, for example to provide more cutting in a certain circumferential area. For example, a first strut 1316 may be circumferentially spaced from a second strut 1316 by about 135° and spaced from a third strut 1316 by about 135°, and the second strut 1316 may be spaced from the third strut 1316 by about 90°.

The strut 1316 may comprise between about one and about four blades (e.g., one blade, two blades (e.g., as shown in FIG. 37A), three blades, four blades, ranges between such values, etc.). The strut 1316 shown in FIG. 37A comprises a first blade 1312 and a second blade 1314. The first blade 1312 faces proximally and is configured to cut as the device 1300 is proximally retracted. The second blade 1314 faces distally and is configured to cut as the device 1300 is distally advanced. The proximally facing blades 1312 and the distally facing blades 1314 allow the device 1300 to disable a valve when proximally retracted and/or when distally advanced, providing flexibility as a two-way valvulotome. Other configurations are also possible. For example, a first strut 1316 may comprise a proximally facing blade 1312 and a second strut 1316 may comprise a distally facing blade 1314. For another example, a first strut 1316 may comprise a plurality of proximally facing blades 1312 and a second strut 1316 may comprise a plurality of distally facing blades 1314. For another example, a first strut 1316 may comprise a proximally facing blade 1312 and a distally facing blade 1314 and a second strut 1316 may comprise zero blades or be free of or devoid of blades. For another example, a first strut 1316 may comprise a proximally facing blade 1312 and a distally facing blade 1314 and a second strut 1316 may comprise a distally facing blade 1314. For another example, a first strut 1316 may comprise two proximally facing blades 1312 and a distally facing blade 1314.

Figure 37B:
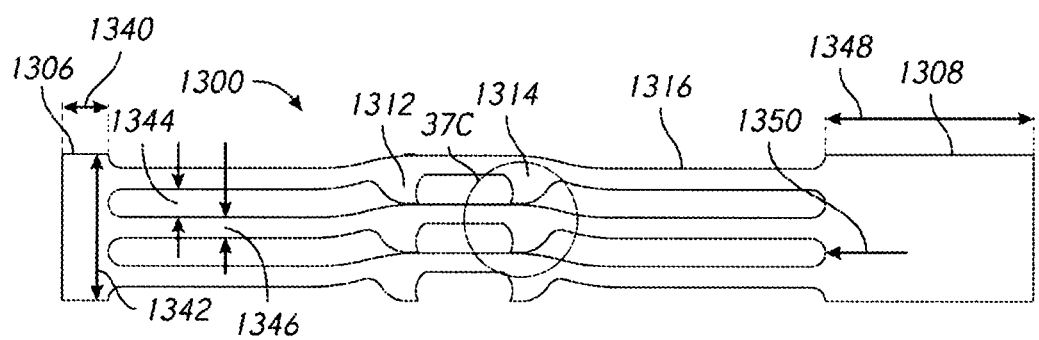
FIG. 37B is a flattened side view of the valve disabling device of FIG. 37A.

FIG. 37B is a flattened side view of the valve disabling device 1300 of FIG. 37A. The device 1300 may be cut from a flat sheet that is rolled into a hypotube. FIG. 37B provides an example cut pattern that may be used to form the device 1300. The cut pattern shown in FIG. 37B may also be on a round hypotube. FIG. 37B provides some example dimensions of the device 1300. The length 1340 of the distal portion 1306 may be between about 0.1 mm and about 3 mm (e.g., about 0.1 mm, about 0.5 mm, about 1 mm, about 1.5 mm, about 2 mm, about 3 mm, ranges between such values, etc.). The distal portion 1306 may have a length 1340 configured to provide a stable joint for the distal ends of the struts 1316. The circumferential length 1342 of the distal portion 1306 may be between about 1.5 mm and about 5 mm (e.g., about 1.5 mm, about 2 mm, about 2.5 mm, about 3 mm, about 3.5 mm, about 4 mm, about 5 mm, ranges between such values, etc.). The circumferential length 1342 of the distal portion 1306 may correspond to a circumference of a hypotube used to form the disabling device 1300 or an expansion thereof. The length 1344 of the space between struts 1316 may be between about 0.1 mm and about 1 mm (e.g., about 0.1 mm, about 0.2 mm, about 0.3 mm, about 0.4 mm, about 0.5 mm, about 0.7 mm, about 0.8 mm, about 0.9 mm, about 1 mm, ranges between such values, etc.). The length 1344 of the space between struts 1316 may be between about 2% and about 67% of the circumferential length 1340 of the distal portion 1306 (e.g., about 2%, about 5%, about 10%, about 15%, about 20%, about 25%, about 35%, about 50%, about 67%, ranges between such values, etc.). The circumferential thickness 1346 of the struts 1316 maybe between about 0.1 mm and about 1 mm (e.g., about 0.1 mm, about 0.2 mm, about 0.3 mm, about 0.4 mm, about 0.5 mm, about 0.7 mm, about 0.8 mm, about 0.9 mm, about 1 mm, ranges between such values, etc.). The circumferential thickness 1346 of the struts 1316 may be between about 2% and about 67% of the circumferential length 1340 of the distal portion 1306 (e.g., about 2%, about 5%, about 10%, about 15%, about 20%, about 25%, about 35%, about 50%, about 67%, ranges between such values, etc.). Thicker struts 1316 and/or less spacing between the struts 1316 may provide more rigidity and cutting than thinner struts 1316. Thinner struts 1316 and/or more spacing between the struts 1316 may use less force for radial expansion and/or retraction. If the spaces between the struts 1316 have rounded proximal edges, the radius of curvature 1350 at the interface between the proximal portion 1308 and the intermediate portion 1302 may be between about 0.1 mm and about 0.5 mm (e.g., about 0.1 mm, about 0.2 mm, about 0.3 mm, about 0.4 mm, about 0.5 mm, ranges between such values, etc.). If the spaces between the struts 1316 have rounded distal edges, the radius of curvature at the interface between the distal portion 1306 in the intermediate portion may be between about 0.1 mm and about 0.5 mm (e.g., about 0.1 mm, about 0.2 mm, about 0.3 mm, about 0.4 mm, about 0.5 mm, ranges between such values, etc.). The radii of curvature at the proximal and distal interfaces may be the same or different. Rather than a radius of curvature, the struts 1316 could meet the proximal portion 1308 and/or the distal portion 1306 at angle. The length 1348 of the proximal portion 1308 may be between about 0.1 mm and about 8 mm (e.g., about 0.1 mm, about 0.5 mm, about 1 mm, about 2 mm, about 3 mm, about 4 mm, about 5 mm, about 6 mm, about 8 mm, ranges between such values, etc.). The proximal portion 1308 may have a length 1348 configured to provide a stable joint for the proximal ends of the struts 1316. The proximal portion 1308 may have a length 1348 configured to be coupled to the pusher element 1320. The circumferential length of the proximal portion 1308 may correspond to a circumference of a hypotube used to form the disabling device 1300 or an expansion thereof. The circumferential length of the proximal portion 1308 may be the same or different then the circumferential length 1342 of the distal portion 1306. For example, if the device 1300 is cut from a hypotube and the proximal portion 1308 and the distal portion 1306 comprise uncut portions of the hypotube, the proximal portion 1308 and the distal portion 1306 may have the same circumferential length, or one may be expanded relative to the other (e.g., due to a shape setting process, expansion by outward force of a pusher element 1320, etc.).

Figure 37C:
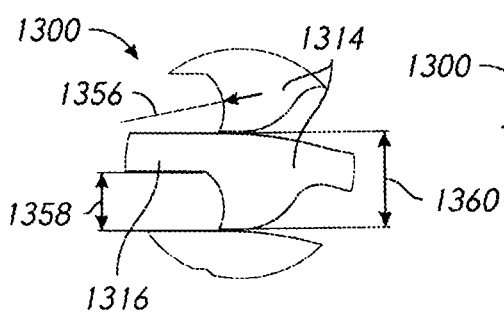
FIG. 37C is an expanded view of the flattened side view of the valve disabling device of FIG. 37A in the area identified by the circle 37C in FIG. 37B.

FIG. 37C is an expanded view of the flattened side view of the valve disabling device 1300 of FIG. 37A in the area identified by the circle 37C in FIG. 37B. FIG. 37C shows some example dimensions of the device 1300. The radius of curvature 1356 of the blade 1314 may be between about 0.1 mm and about 1 mm (e.g., about 0.1 mm, about 0.2 mm, about 0.3 mm, about 0.4 mm, about 0.5 mm, about 0.7 mm, about 0.8 mm, about 0.9 mm, about 1 mm, ranges between such values, etc.). The distance 1358 between an edge of the blade 1314 and a strut 1316 may be between about 0.1 mm and about 2 mm (e.g., about 0.1 mm, about 0.25 mm, about 0.5 mm, about 0.75 mm, about 1 mm, about 1.25 mm, about 1.5 mm, ranges between such values, etc.). The combined thickness 1360 of a strut 1316 and blade may be between about 0.1 mm and about 3 mm (e.g., about 0.1 mm, about 0.5 mm, about 1 mm, about 1.5 mm, about 2 mm, about 3 mm, ranges between such values, etc.). The dimensions of the blade 1312 on the strut 1316 of FIG. 37C maybe the same or different than the dimensions of the blade 1314 in FIG. 37C. The dimensions of the other blades 1314 may be the same or different than the dimensions of the blade 1314 in FIG. 37C.

Figure 37D:
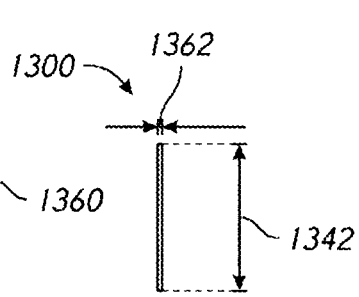
FIG. 37D is an end view of the valve disabling device of FIG. 37A flattened as shown in FIG. 37B.

FIG. 37D is an end view of the valve disabling device 1300 of FIG. 37A flattened as shown in FIG. 37B. FIG. 37D shows some example dimensions of the device 1300. The thickness 1362 may be between about 0.05 mm and about 0.25 mm (e.g., about 0.05 mm, about 0.1 mm, about 0.15 mm, about 0.2 mm, about 0.25 mm, ranges between such values, etc.). A greater thickness 1362 may provide more rigidity and cutting force. A smaller thickness 1362 may use less force for radial expansion and/or retraction. If the device 1300 is formed from a hypotube, the thickness 1362 maybe a difference between an inner diameter of the hypotube and an outer diameter of the hypotube, or the thickness of the hypotube wall. The circumferential distance 1342, as described above, may be about 1.5 mm and about 5 mm (e.g., about 1.5 mm, about 2 mm, about 2.5 mm, about 3 mm, about 3.5 mm, about 4 mm, about 5 mm, ranges between such values, etc.).

Figure 37E:
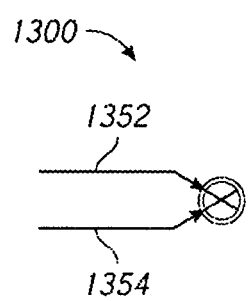
FIG. 37E is an end view of the valve disabling device of FIG. 37A in a radially contracted state.

FIG. 37E is an end view of the valve disabling device 1300 of FIG. 37A in a radially contracted state. FIG. 37 shows some example dimensions of the device 1300 in a radially contracted state. The outer diameter 1352 may be between 0.6 mm and about 1.5 mm (e.g., about 0.6 mm, about 0.8 mm, about 1 mm, about 1.2 mm, about 1.5 mm, ranges between such values, etc.). The outer diameter 1352 is greater than the inner diameter 1354. The inner diameter 1354 may be between about 0.5 mm and about 1.4 mm (e.g., about 0.5 mm, about 0.75 mm, about 1 mm, about 1.25 mm, about 1.4 mm, ranges between such values, etc.). Referring again to FIG. 37D, the thickness 1362 may correspond to the difference between the outer diameter 1352 and the inner diameter 1354, divided by two. For example, if the outer diameter 1352 is 1 mm and the inner diameter 1354 is 0.8 mm, the thickness 1362 would be: (1 mm−0.8 mm)/2=0.1 mm.

Figure 37F:
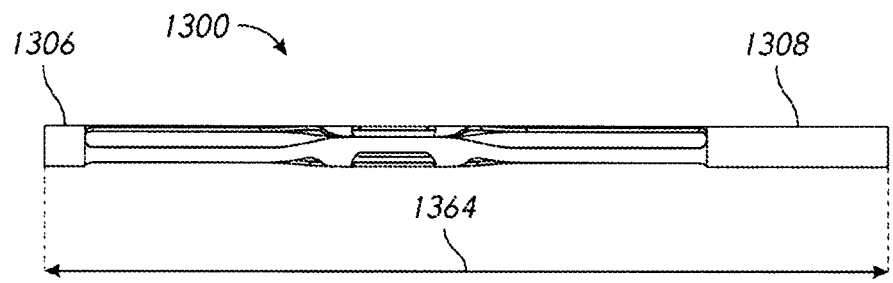
FIG. 37F is a side view of the valve disabling device of FIG. 37A in a radially contracted state.
Figure 37G:
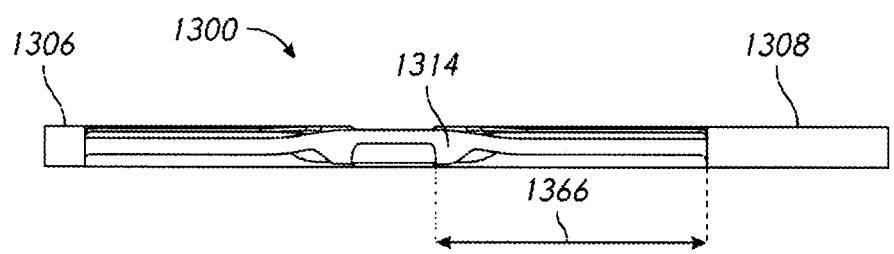
FIG. 37G is another side view of the valve disabling device of FIG. 37A in a radially contracted state and circumferentially rotated compared to FIG. 37F.

FIG. 37F is a side view of the valve disabling device 1300 of FIG. 37A in a radially contracted state. FIG. 37G is another side view of the valve disabling device 1300 of FIG. 37A in a radially contracted state and circumferentially rotated compared to FIG. 37F. FIGS. 37F and 37G show some example dimensions of the device 1300 in a radially contracted state. The length 1364 between a distal end of the distal portion 1306 and a proximal end of the proximal portion 1308 may be between about 15 mm and about 27 mm (e.g., about 15 mm, about 18 mm, about 21 mm, about 24 mm, about 27 mm, ranges between such values, etc.). Referring again to FIG. 37B, the length 1340 of the distal portion 1306 and the length 1348 of the proximal portion 1308 may be subtracted from the length 1364 to calculate the length of the intermediate portion 1302. The length 1366 between an edge of the blade 1314 and a distal end of the proximal portion 1308 may be between about 5 mm and about 10 mm (e.g., about 5 mm, about 6 mm, about 7 mm, about 8 mm, about 9 mm, about 10 mm, ranges between such values, etc.). The length 1366 may affect and/or be based on a diameter of the blade 1314 in a radially expanded state.

Figure 37H:
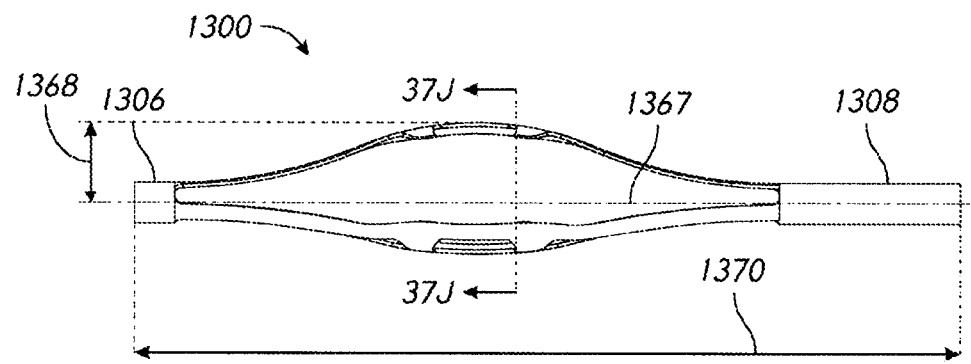
FIG. 37H is a side view of the valve disabling device of FIG. 37A in a radially expanded state.
Figure 37I:
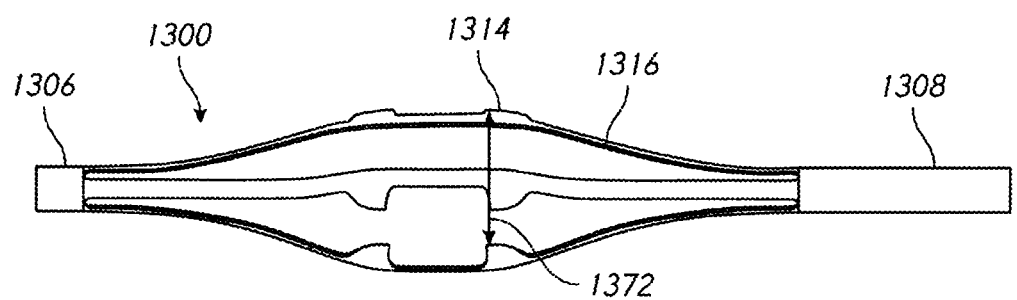
FIG. 37I is another side view of the valve disabling device of FIG. 37A in a radially expanded state and circumferentially rotated compared to FIG. 37H.

FIG. 37H is a side view of the valve disabling device 1300 of FIG. 37A in a radially expanded state. FIG. 37I is another side view of the valve disabling device 1300 of FIG. 37A in a radially expanded state and circumferentially rotated compared to FIG. 37H. FIGS. 37H and 37G show some example dimensions of the device 1300 in a radially expanded state. The radially expanded state shown in FIGS. 37H and 37G may be fully expanded (e.g., the shape of the device 1300 absent external forces) or a partially radially expanded state. The length or radius 1368 between a longitudinal axis 1367 through a center of the device 1300 and outer circumference of an expanded intermediate portion 1302 may be between about 0.5 mm and about 7 mm (e.g., about 0.5 mm, about 1 mm, about 1.5 mm, about 2 mm, about 2.5 mm, about 3 mm, about 4 mm, about 5 mm, about 6 mm, about 7 mm, ranges between such values, etc.). A length 1370 between a distal end of the distal portion 1306 and a proximal end of the proximal portion 1308 may be between 10 mm and about 25 mm (e.g., about 10 mm, about 15 mm, about 18 mm, about 20 mm, about 22 mm, about 25 mm, ranges between such values, etc.). Referring again to FIG. 37F, the length 1364 in a radially contracted state may be longer than the length 1370 in the radially expanded state. The difference between the length 1370 and the length 1364 may be between about 0.1 mm and about 1 mm (e.g., about 0.1 mm, about 0.2 mm, about 0.3 mm, about 0.4 mm, about 0.5 mm, about 0.6 mm, about 0.7 mm, about 0.8 mm, about 0.9 mm, about 1 mm, ranges between such values, etc.). Referring again to FIG. 37B, the length 1340 of the distal portion 1306 and the length 1348 of the proximal portion 1308 maybe subtracted from the length 1370 to calculate the length of the intermediate portion 1302 in a really expanded state. The length 1372 between a tip of a first blade 1314 and a second blade 1314, taken transverse to the longitudinal axis 1367 of the device 1300, may be between about 2 mm and about 4 mm (e.g., about 2 mm, about 2.5 mm, about 3 mm, about 3.5 mm, about 4 mm, ranges between such values, etc.).

Figure 37J:
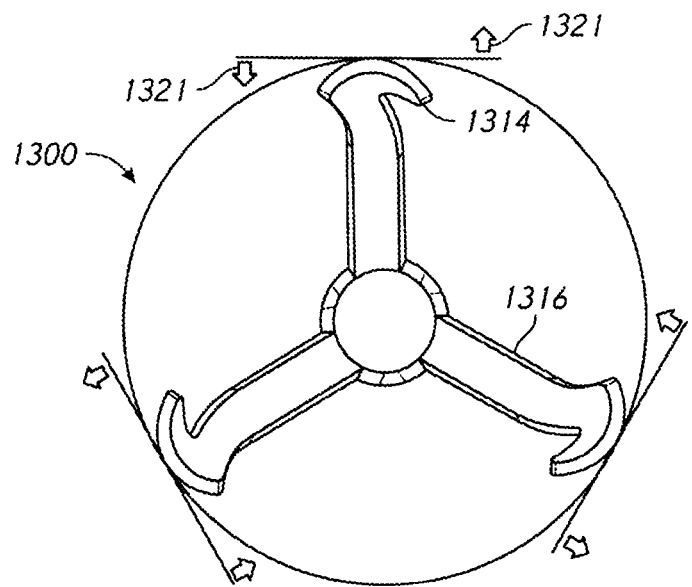
FIG. 37J is a cross-sectional end view of the valve disabling device of FIG. 37A in a radially expanded state taken along the line 37J-37J of FIG. 37H.

FIG. 37J is a cross-sectional end view of the valve disabling device 1300 of FIG. 37A in a radially expanded state taken along the line 37J-37J of FIG. 37H. FIG. 37J shows that the blades 1314 maybe rotated relative to the struts 1316, as indicated by the arrows 1321. Each blade 1314 may be rotated the same amount and in the same direction, or different blades 1314 may be rotated in different amounts and/or in different directions. The blades 1312 may also be rotated the same way and/or in a different way (e.g., opposite) than as shown for the blades 1314 in FIG. 37J.

FIGS. 37Ki through 37Nii illustrate example procedures that can be performed using the valve disabling device 1300 of FIG. 37A. The procedures are not mutually exclusive and maybe performed based on, for example, user preference, anatomy, vessel access point, other procedure(s) being performed, combinations thereof, and the like.

FIG. 37Ki shows a device 1300 being tracked through a vessel 1301 having a valve 1305. The device 1300 may be tracked over a guidewire 1318 that has been navigated through the valve 1305. The device 1300 may be advanced over the guidewire 1318 in a radially contracted state, with the intermediate portion 1302 collapsed in the sheath 1304. In FIG. 37Kii, the sheath 1304 is retracted, as indicated by the arrow 1323, which allows the intermediate portion 1302 to radially expand, as shown by the arrows 1325. The device 1300 may then be distantly advanced, as shown by the arrow 1327. The distally facing blades 1314 may interact with the valve 1305 to cut or ablate or disable the leaflets of the valve 1305. The intermediate portion 1302 may be really compressed by proximally retracting the device 1300 into the sheath 1304 and/or by distally advancing the sheath 1304 over the device 1300. The device 1300 may then be used to disable another valve or withdrawn as desired.

FIG. 37Li shows a device 1300 tracked through the cavity a vessel 1301 including a valve 1305. The device 1300 has been advanced distal to the valve 1305 in a radially contracted state over the guidewire 1318. In FIG. 37Lii, the sheath 1304 is proximally retracted, as indicated by the arrow 1323, which allows the intermediate portion 1302 of the device 1300 to radially expand, as shown by the arrows 1325. The device 1300 may then be proximally retracted, as shown by the arrow 1329, which allows the proximally facing blade 1312 to disable the valve 1305. The intermediate portion 1302 may be really compressed by proximally retracting the device 1300 into the sheath 1304 and/or by distally advancing the sheath 1304 over the device 1300. The device 1300 may then be used to disable another valve or withdrawn as desired.

FIG. 37Mi shows a device 1300 being tracked through a vessel 1301 having a valve 1305. The device 1300 may be tracked over a guidewire 1318 that has been navigated through the valve 1305. The device 1300 may be advanced over the guidewire 1318 in a radially contracted state, with the intermediate portion 1302 collapsed in the sheath 1304. In FIG. 37Mii, the sheath 1304 is retracted, as indicated by the arrow 1323, which allows the intermediate portion 1302 to radially expand, as shown by the arrows 1325. The device 1300 may then be distantly advanced, as shown by the arrow 1327. The distally facing blades 1314 may interact with the valve 1305 to cut or ablate or disable the leaflets of the valve 1305. The intermediate portion 1302 may be really compressed by proximally retracting the device 1300 into the sheath 1304 and/or by distally advancing the sheath 1304 over the device 1300. The device 1300 may then be used to disable another valve or withdrawn as desired. Compared to FIGS. 37Ki and 37Kii, the method shown in FIGS. 37Mi and 37Mii is from an opposite direction. One direction may be upstream and the other direction may be downstream. One direction may be in the direction of normal blood flow and the other direction may be the direction of blood flow after retroperfusion.

FIG. 37Ni shows a device 1300 tracked through the cavity a vessel 1301 including a valve 1305. The device 1300 has been advanced distal to the valve 1305 in a radially contracted state over the guidewire 1318. In FIG. 37Nii, the sheath 1304 is proximally retracted, as indicated by the arrow 1323, which allows the intermediate portion 1302 of the device 1300 to radially expand, as shown by the arrows 1325. The device 1300 may then be proximally retracted, as shown by the arrow 1329, which allows the proximally facing blade 1312 to disable the valve 1305. The intermediate portion 1302 may be really compressed by proximally retracting the device 1300 into the sheath 1304 and/or by distally advancing the sheath 1304 over the device 1300. The device 1300 may then be used to disable another valve or withdrawn as desired. Compared to FIGS. 37Li and 37Lii, the method shown in FIGS. 37Ni and 37Nii is from an opposite direction. One direction may be upstream and the other direction may be downstream. One direction may be in the direction of normal blood flow and the other direction may be the direction of blood flow after retroperfusion.

Figure 38A:
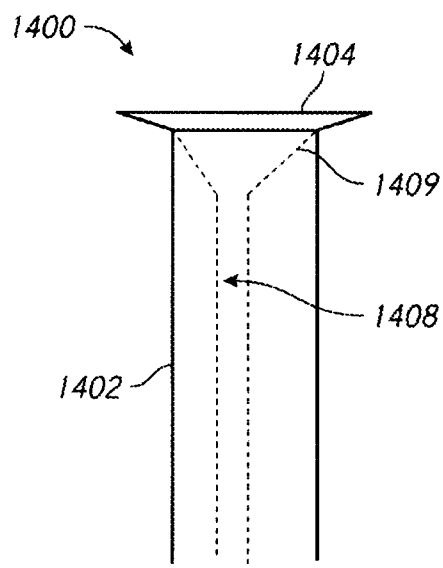
FIG. 38A schematically illustrates an example of a distal end of a catheter.

FIG. 38A schematically illustrates an example of a distal end of a catheter 1400. The catheter 1400 may include an ultrasound transducer or other targeting device. The catheter

1400 may be used in a second vessel (e.g. a vein) that can be targeted by another catheter (e.g., comprising an ultrasound transducer) in a first vessel. The distal end of the catheter 1400 comprises a capture element 1404 having a funnel shape extending distal to a tubular element 1402. The capture element 1404 may extend out the tubular element 1402, for example due to an actuation mechanism coupled to the handle and the capture element 1404, by comprising shape memory material configured to assume a predetermined shape upon undergoing a phase change due to temperature (e.g., due to body temperature versus room temperature), due to expansion by an expandable member (e.g., an inflatable balloon), and/or other mechanisms. The capture element 1404 may have an angle between about 90° and about 170° (e.g., about 90°, about 110°, about 130°, about 150°, about 170°, ranges between such values, etc.). The tubular member 1402 may comprise a lumen 1408 extending at least partially therethrough for guiding a guidewire captured by the capture element 1404 through the catheter 1400. Guiding a guidewire through the catheter 1400 can ensure that the guidewire is advanced through the same vessel(s) as the catheter 1400, rather than through unintended branch or collateral vessels. The lumen 1408 may comprise an expanded portion 1409 that is internal to the tubular member 1402.

Figure 38B:
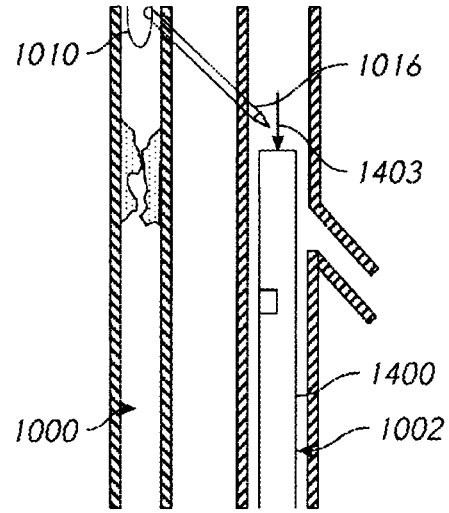
FIGS. 38B through 38D illustrate an example procedure that can be performed using the distal end of the catheter of FIG. 38A.
Figure 38C:
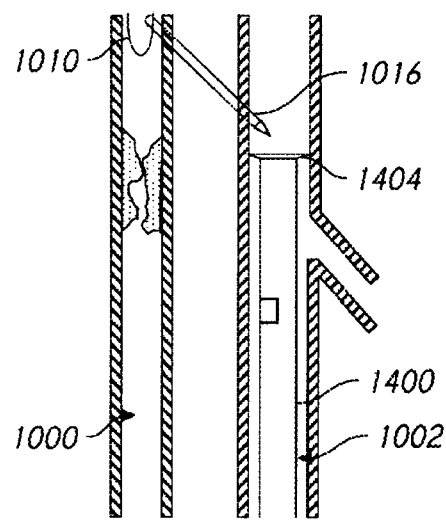
Figure 38D:
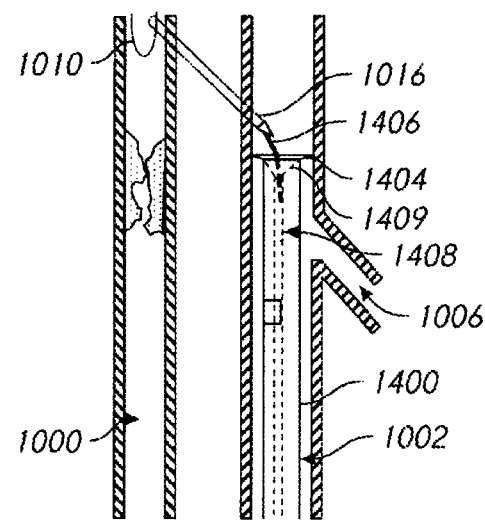

FIGS. 38B through 38D illustrate an example procedure that can be performed using the distal end of the catheter 1400 of FIG. 38A. FIG. 38B is similar to FIG. 32D in that a needle 1016 has passed from a first vessel 1000, through interstitial tissue, and into a second vessel 1002. The catheter 1400 of FIG. 38A is in the second vessel 1002. The catheter 1400 may have been proximally retracted, for example as indicated by the arrow 1403, after being successfully targeted by the catheter 1010 in the first vessel 1000. The distance of retraction of the catheter 1400 after successful targeting may be predetermined (e.g., based on a distance between the distal end of the catheter 1400 and a transducer of the catheter 1400) and/or maybe based on user experience, fluoroscopy, combinations thereof, and the like. In FIG. 38C, the capture element 1404 has expanded out of the distal end of the catheter 1400. The capture element 1404 can act as a funnel to guide a guidewire extending out of the needle 1016 into the catheter 1400. In FIG. 38D, a guidewire 1406 extends out of the needle 1016, for example as described herein, is captured by the capture element 1404, and then is guided by the portion 1409 into the lumen 1408. The guidewire 1406, further distally advanced, will extend further into the lumen 1408, as opposed to any chance of the guidewire 1406 extending through the branch vessel 1006 and/or other branch vessels. Procedures performed by tracking over the guidewire 1406 (e.g., valve disabling, graft placement, balloon expansion, etc.), can ensure that such procedure will be performed in the intended vessels, which can provide better and more predictable retroperfusion.

FIGS. 38Ei and 38Eii illustrate an example of a distal end of a catheter 1440. The catheter 1440 may be similar to the catheter 1400. The catheter 1440 includes an inflation lumen 1445 and an expandable member 1446 (e.g., comprising a balloon). When the catheter 1440 is it an appropriate position, for example as illustrated in FIG. 38B, an expandable member 1444 may be expanded, and the capture element 1444 may be expanded by the expandable member 1446. Compared to FIG. 38Ei, FIG. 38Eii shows the expandable member 1446 slightly distally advanced and then in expanded in order to push the capture element 1444 radially outward. The expandable member 1446 may be positioned and/or shaped to expand the capture element 1444 without being distally advanced. As described above, other methods of expanding a capture element 1444 are also possible.

FIG. 38F illustrates an example of a portion of a catheter 1420. The catheter 1420 comprises an ultrasound transducer 1422. The catheter 1420 comprises a capture element 1424 that extends out a side of the catheter 1420. The capture element 1424 may comprise a funnel leading to a lumen 1428, which may optionally comprise an expanded portion 1429. The capture element 1424 is configured to capture a guidewire 1406 and guide the guidewire 1406 into the lumen 1428. The capture element 1424 may be located proximate to the transducer 1422. In accordance with certain targeting systems described herein, the needle 1016 may extend towards the transducer 1422 such that the guidewire 1406 extending out of the needle 1016 would be proximate to the transducer 1422, and thus proximate to the capture element 1424. The capture element 1424 may be proximal to the transducer 1422.

FIG. 38G illustrates another example of a portion of a catheter 1430. The catheter 1430 comprises a transducer 1422. The catheter 1430 comprises a capture element 1434 that extends out a side of the catheter 1430. The capture element 1434 may comprise a partial funnel leading to a lumen 1438, which may optionally comprise an expanded portion 1439. The capture element 1434 may extend partially or fully around a circumference of the catheter 1430. The capture element 1434 is configured to guide a guidewire 1406 into a lumen 1438, which may include an expanded portion 1439. The capture element 1434 may comprise, for example, a portion of the catheter 1430 that is deformed upon reaching body temperature to open an aperture to lumen 1438 as the capture element 1434 expands. The capture element 1434 may be configured to appose a sidewall of a vessel in which the catheter 1430 resides. The features of the catheters 1400, 1420, 1430, 1440 may be combined with the features of the catheter 1020 or other catheters described herein.

Figure 39A:
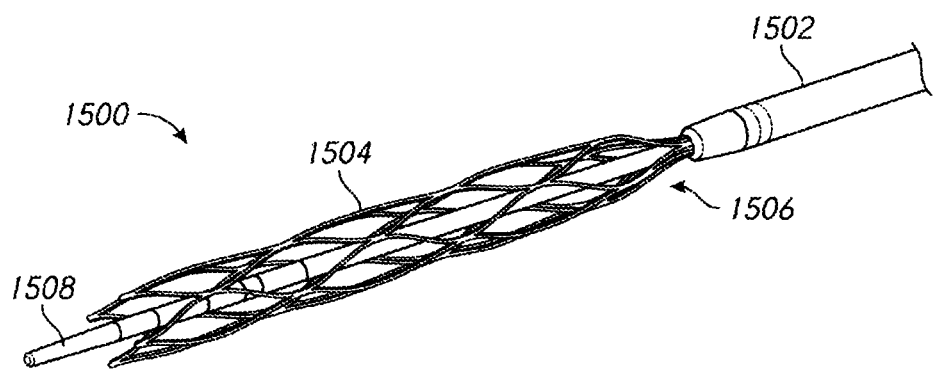
FIG. 39A is a perspective view of an example of a portion of a target catheter.

FIG. 39A is a perspective view of an example of a portion of a target catheter 1500. The target catheter 1500 comprises a sheath 1502 and an expandable structure 1504. The expandable structure 1504 comprises a collapsed state and an expanded state. FIG. 39A shows the expandable structure 1504 in the expanded state. The expandable structure 1504 comprises a plurality of struts that taper towards the proximal end 1506 in the expanded state. The struts form a plurality of cells. In some examples, a guidewire sheath 1508 extends through the sheath 1502 and the expandable structure 1504. The target catheter 1500 may be tracked over a first guidewire extending through the guidewire sheath 1508.

Figure 39B:
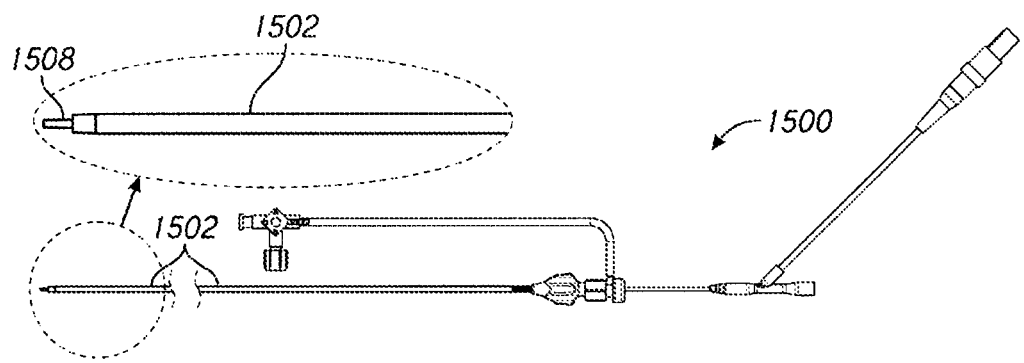
FIG. 39B is a side view of the target catheter of FIG. 39A in a first state.

FIG. 39B is a side view of the target catheter 1500 of FIG. 39A in a first state. The first state may be considered a closed state or a delivery state. In the first state, the expandable structure 1504 is in the collapsed state in the sheath 1502. In some examples, the guidewire sheath 1508 protrudes out of the distal end of the sheath 1502. A proximal end of the target catheter may include flush ports, guidewire ports, and/or the like. A distal end of the catheter may include a targeting sensor (e.g., an ultrasound receiver), a diagnostic sensor (e.g., a pressure sensor), combinations thereof, and/or the like. In some examples, a targeting sensor is proximal to the expandable structure 1504 in the collapsed state and/or in the expanded state. In some examples, a targeting sensor is distal to the expandable structure 1504 in the collapsed state and/or in the expanded state. In some examples, a targeting sensor is longitudinally between a proximal end of the expandable structure 1504 and a distal end of the expandable structure 1504 in the collapsed state and/or in the expanded state.

Figure 39C:
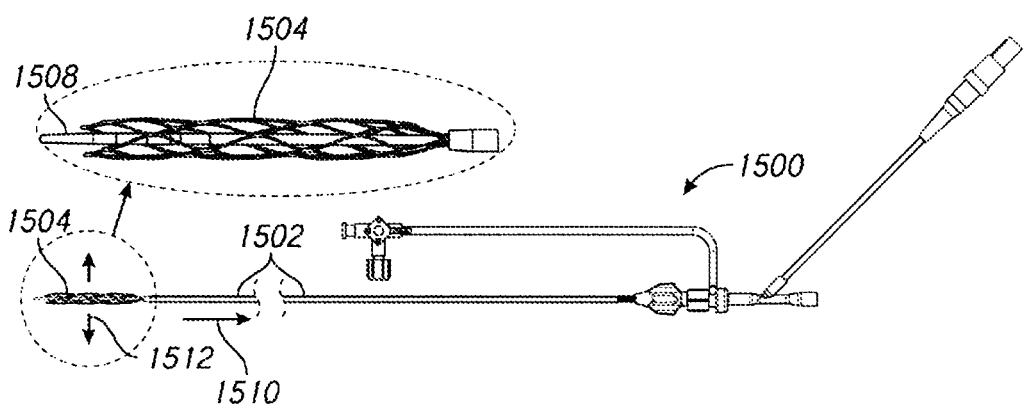
FIG. 39C is a side view of the target catheter of FIG. 39A in a second state.

FIG. 39C is a side view of the target catheter 1500 of FIG. 39A in a second state. The second state may be considered an open state or a deployed state. The expandable structure 1504 can be deployed from the sheath 1502 by distally advancing the expandable structure 1504 and/or proximally retracting the sheath 1502. FIG. 39C shows the relative movement between the sheath 1502 and the expandable structure 1504 by the arrow 1510 and the corresponding radial expansion of the expandable structure 1504 by the arrows 1512. In some examples, the expandable structure 1504 is self-expanding (e.g., comprising a shape-memory material such as nitinol) and is able to assume the expanded state when not confined by the sheath 1502. The expandable structure 1504 can be retrieved in the sheath 1502 by distally advancing the sheath 1502 and/or proximally retracting the expandable structure 1504.

Figure 39D:
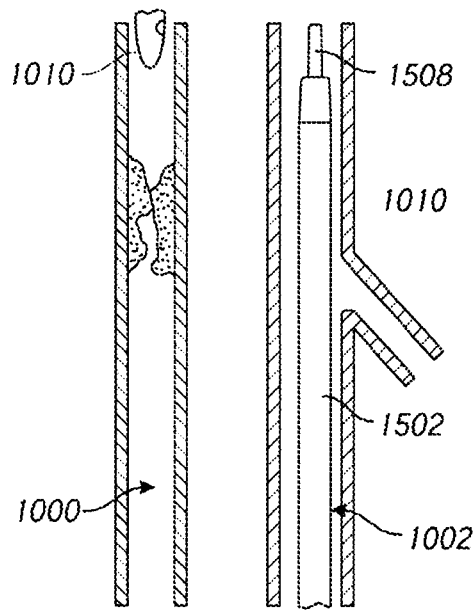
FIGS. 39D-39I schematically illustrate an example method of using the target catheter of FIG. 39A.
Figure 39E:
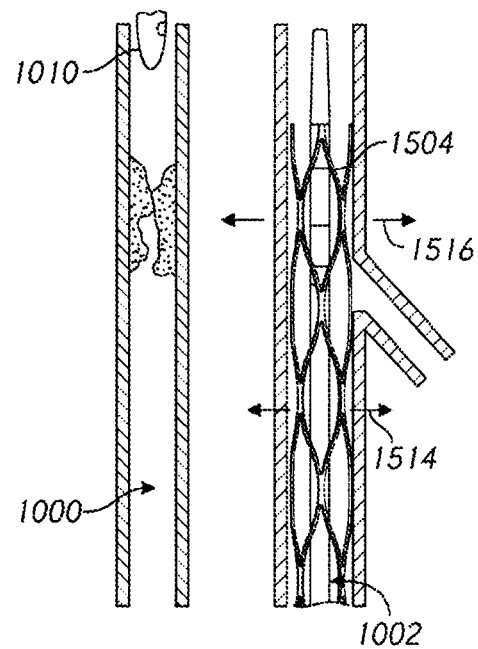

FIGS. 39D-39I schematically illustrate an example method of using the target catheter 1500 of FIG. 39A. In FIG. 39D, a first catheter 1010 is advanced in a first vessel 1000 comprising an occlusion, for example as described herein. The target catheter 1500 is advanced in a second vessel 1002. For example, the target catheter may be tracked over a first guidewire that has been advanced through the second vessel 1002. The distal end of the sheath 1502 may be longitudinally proximate to the occlusion. In FIG. 39E, the expandable structure 1504 is radially expanded, as shown by the arrows 1514. In some examples, expansion of the expandable structure 1504 radially expands the vessel 1002, as shown by the arrows 1516. Expanding the vessel 1002 can increase the target for a needle extending from the first catheter 1010. In some examples in which the second vessel 1002 is a vein, expanding the vessel 1002 can keep the vein open, which can avoid influence of potential or eventual spasm.

Figure 39F:
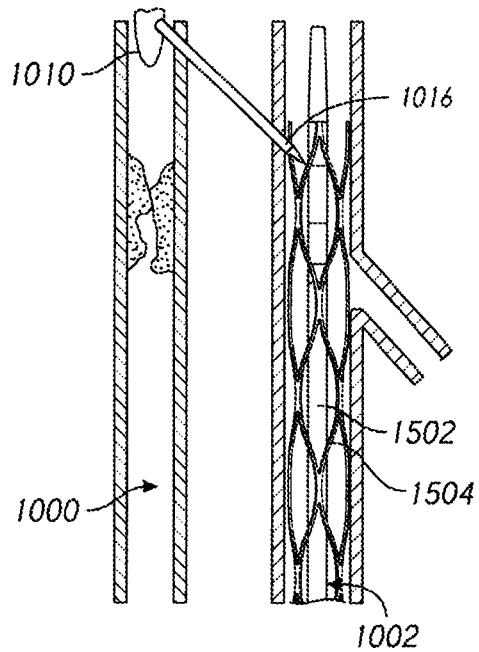

In FIG. 39F, a needle 1016 extends from the first catheter 1010 out of the first vessel 1000, through interstitial tissue, and into the second vessel 1002. In the second vessel 1002, the needle 1016 extends between the proximal end of the expandable structure 1504 and the distal end of the expandable structure 1504. The needle 1016 may extend through a cell of the expandable structure 1504. If the needle 1016 initially contacts a strut of the expandable structure 1504, the strut may be deflected such that the needle 1016 extends through a cell. The tip of the needle 1016 does not necessarily need to pierce the center of the second vessel 1010 because, even if the second vessel 1002 is pierced at an angle, the needle 1016 can extend into the expandable structure 1504 at an angle, and a subsequently deployed second guidewire 1406 can be snared by the expandable structure 1504. The extension of the needle 1016 may be guided using a targeting system (e.g., a directional ultrasound targeting system, for example as described herein). In some examples, the needle may be extended towards the expandable structure 1504, for example using fluoroscopy with or without a targeting system. In certain such examples, the expandable structure 1504 may comprise radiopaque markers and/or the material of the expandable structure 1504 may be radiopaque (e.g., the expandable structure may comprise radiopaque fluid in an expanded (e.g., inflated) stated).

Figure 39G:
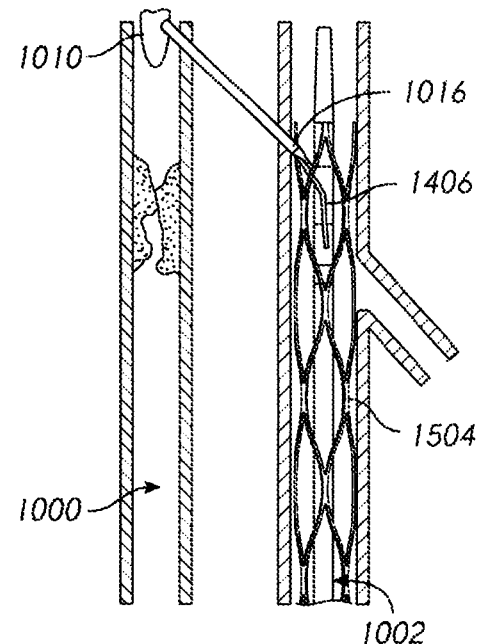
Figure 39H:
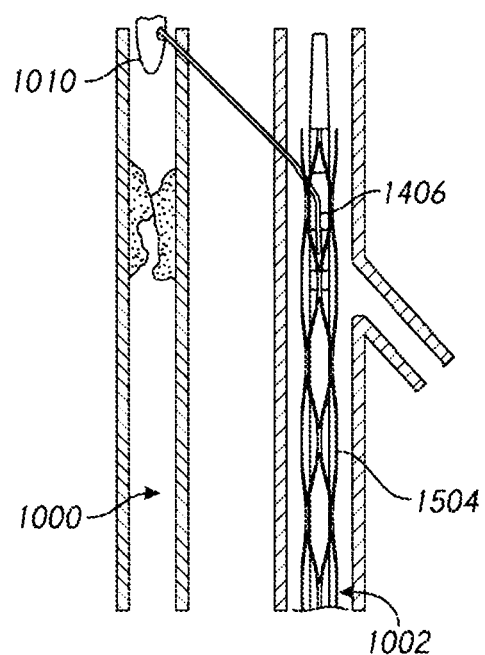
Figure 39I:
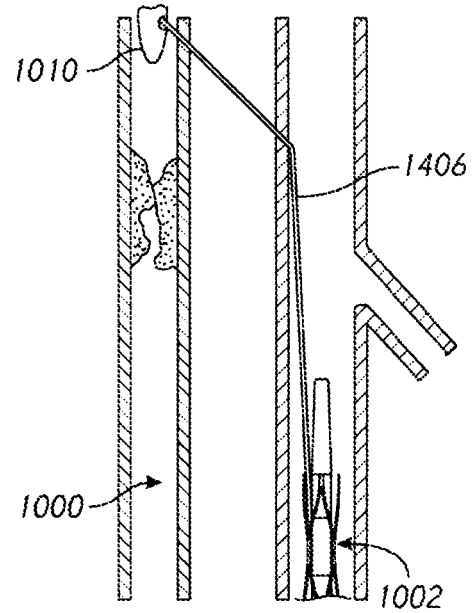

In FIG. 39G, a second guidewire 1406 is advanced through the first catheter 1010 and the needle 1016 into the second vessel 1002. Because the needle 1016 extends into the expandable structure 1504, the second guidewire 1406 extends into the expandable structure 1504. In FIG. 39H, the expandable structure 1504 is collapsed, for example by at least partially retracting the expandable structure 1504 into the sheath 1502. Collapsing the expandable structure 1504 grabs or snares the second guidewire 1406. In some examples, the expandable structure 1504 may optionally be twisted or torqued to help snare the second guidewire 1406. In FIG. 39I, the target catheter 1500 is proximally retracted. Because the second guidewire 1406 is snared by the expandable structure 1504, the second guidewire 1406 is advanced through the second vessel 1002, for example during removing the target catheter 1500 from the second vessel 1002. Catheters comprising a valvulotome, a stent-graft, and the like may be tracked over the second guidewire 1406 and through the second vessel 1002, for example as described herein.

Figure 40A:
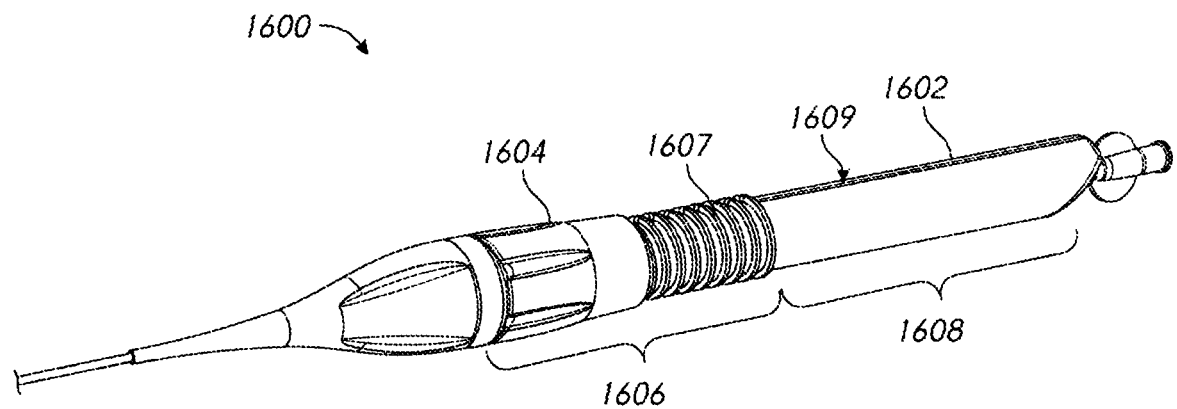
FIG. 40A is a perspective view of an example handle for deploying a tubular structure.

FIG. 40A is a perspective view of an example handle 1600 for deploying a tubular structure. The tubular structure may comprise a stent such as the stent 1122 or a stent-graft such as the stent-graft 1132. In some examples, the handle 1600 may be used to deploy a valvulotome such as the valvulotome 1142, 1300, an expandable structure such as the expandable structure 1504, and the like. The handle 1600 comprises a body 1602 and a knob 1604. The body 1602 comprises a first segment 1606 comprising threads 1607. The body 1602 comprises a second segment 1608 free of threads. A slot 1609 extends from a proximal part of the body 1602 to a distal part of the body 1602.

Figure 40B:
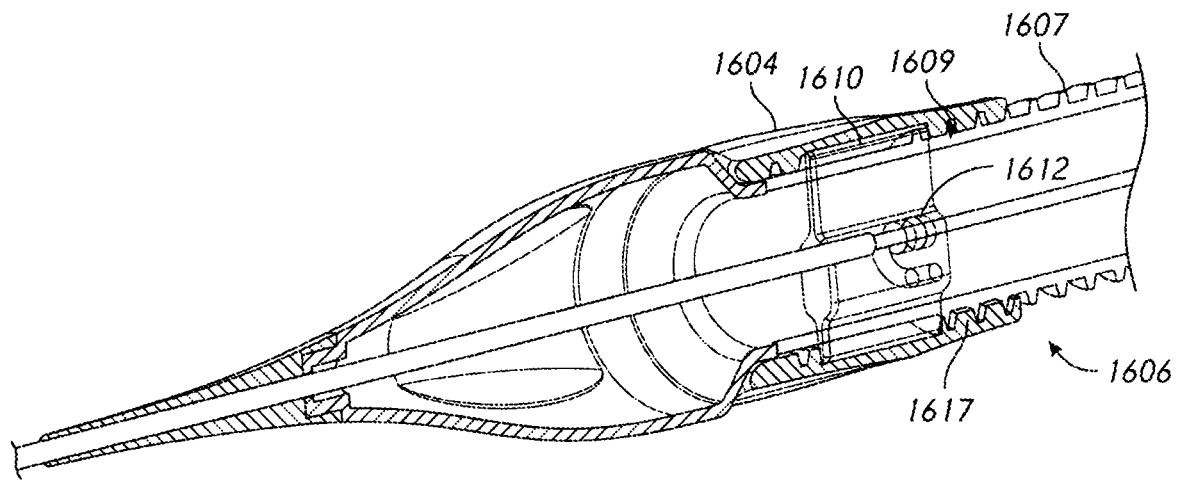
FIG. 40B is an expanded perspective cross-sectional view of a portion of the handle of FIG. 40A.

FIG. 40B is an expanded perspective cross-sectional view of a portion of the handle 1600 of FIG. 40A. The knob 1604 comprises threads 1617 configured to interact with the threads 1607. A slider 1610 extends through the slot 1609. The slider 1610 comprises a connector 1612 coupled to an external sheath such that proximal movement of the slider 1610 proximally retracts the external sheath. As the knob 1604 is rotated, the slider 1610 is proximally retracted, which proximally retracts the external sheath. The initial deployment of a tubular structure may need a higher quantity of force than later deployment because friction between the tubular structure and the external sheath decreases as the tubular structure is deployed from the external sheath. The threads 1607, 1617 can help to transmit higher force by converting rotational force into longitudinal force. Once the knob 1604 is retracted proximal to the threads 1607, the knob 1604 may be proximally pulled, pulling the slider 1610 and thus the external sheath. In some examples, the initial amount of force would be very difficult to effect by proximal pulling but can be accomplished by rotation of the knob 1604. In some examples, rotating the knob 1604 deploys a first amount of the tubular structure and sliding the knob 1604 deploys a second amount of the tubular structure. The first and second amounts total the entire tubular structure. In some examples, the first amount is less than the second amount. For example, the first amount may be between about 10% and about 60% of the second amount (e.g., about 10%, about 20%, about 30%, about 40%, about 50%, about 60%, ranges between such values, and the like).

In some examples, the transition between the first amount and the second amount corresponds to approximately a peak deployment force. The peak deployment force can vary based on, for example, tubular structure design (e.g., length, diameter, radial force, material(s)), outer sheath design (e.g., diameter, material(s), coating(s)), combinations thereof, and the like. In some examples, the transition is at least about one third of the length of the tubular structure. In some examples, the transition is at least about one half of the length of the tubular structure. In some examples, a ratio between the first amount and the second amount can be adjusted by adjusting the threads (e.g., length and/or pitch).

Figure 40C:
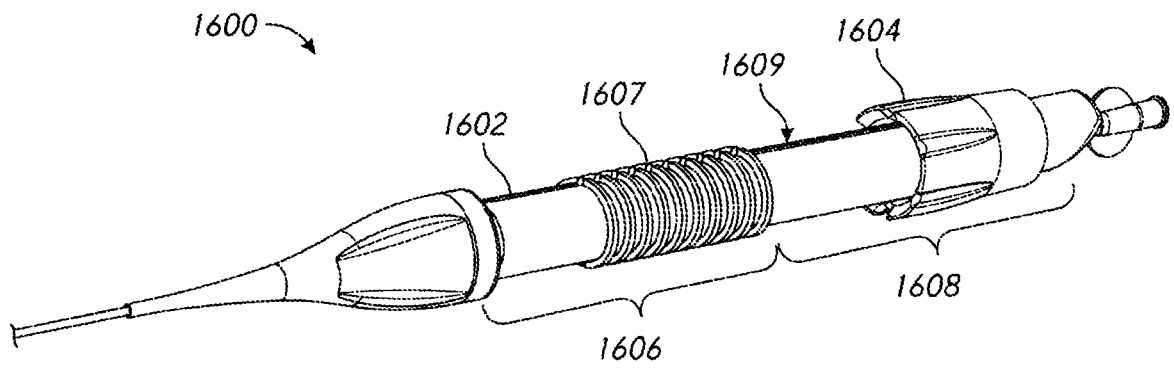
FIG. 40C is a perspective view of the handle of FIG. 40A in a deployed state.
Figure 40D:
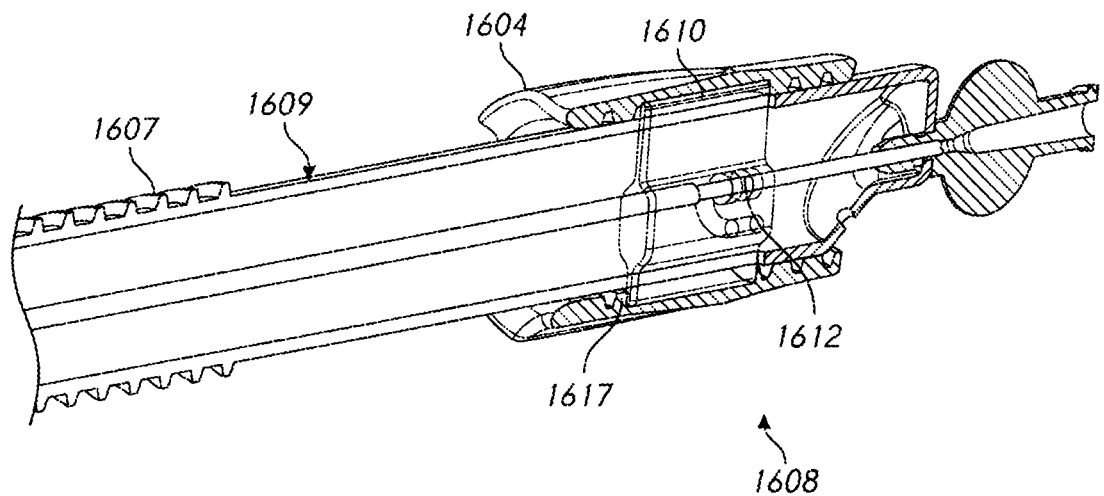
FIG. 40D is an expanded perspective cross-sectional view of a portion of the handle of FIG. 40A in a deployed state.

FIG. 40C is a perspective view of the handle 1600 of FIG. 40A in a deployed state. FIG. 40D is an expanded perspective cross-sectional view of a portion of the handle 1600 of FIG. 40A in a deployed state. The knob 1604 has been rotated and then proximally retracted. Distal to the handle 1600, a tubular structure is deployed. For example, a stent may be deployed from a first vessel, through interstitial tissue, and into a second vessel.

FIG. 41A is a perspective view of an example handle 1700 for deploying a tubular structure. The tubular structure may comprise a stent such as the stent 1122 or a stent-graft such as the stent-graft 1132. In some examples, the handle 1700 may be used to deploy a valvulotome such as the valvulotome 1142, 1300, an expandable structure such as the expandable structure 1504, and the like. The handle 1700 comprises a body 1702 and a knob 1704. The body 1702 optionally includes a shell 1716. A slot 1709 extends from a proximal part of the body 1702 to a distal part of the body 1702.

FIG. 41B is an expanded perspective partially transparent view of a portion of the handle 1700 of FIG. 41A. FIG. 41B shows the handle 1700 from an opposite side compared to FIG. 41A. The knob 1704 is coupled to a gear or worm gear or worm wheel 1706 having teeth 1717 configured to interact with teeth 1707 of a slider member or worm or worm screw 1710. The body 1702 is fixably coupled to an inner shaft assembly. The slider member 1710 if fixably coupled to an outer sheath. In some examples, the inner shaft assembly has a distal end comprising a plurality of radiopaque marker bands which can make a tubular structure pocket visible. A proximal radiopaque marker fixed to the inner shaft assembly can act as a pusher to maintain the longitudinal position of the tubular structure while an outer sheath is proximally retracted. Movement of the slider member 1710 relative to the body 1702 causes movement of the outer sheath relative to the inner shaft assembly. The slider 1710 comprises a first portion 1712, a second portion 1713, and a third portion 1714. The first portion 1712 is fixably coupled to an outer sheath. The first portion 1712 is inside the body 1702. The second portion 1713 protrudes through the slot 1709. The third portion 1714 is wider than the second portion 1713. The third portion 1714 is outside the body 1702, except in examples including a shell 1716. The user interacts with the third portion 1714 once the slider member 1710 is in position to be proximally pulled. The body 1702 may include two slots 1709, for example circumferentially opposite each other. In certain such examples, the slider member 1710 may include two second portions 1713 and two third portions 1714 (e.g., as illustrated in FIG. 41B). Two third portions 1714 may allow a user to grip both sides of the slider member 1710, providing grip that is better than one side. In some examples, the third portion(s) 1714 may comprise features to enhance grip (e.g., textured surfaces, recesses, flanges, etc.).

FIGS. 41C to 41Eiii show an example method of operating the handle 1700 of FIG. 41A. In FIG. 41C, rotation of the knob 1704 causes the gear 1706, including the teeth 1717, to rotate. The teeth 1717 interact with the teeth 1707 of the slider 1710 to convert the rotational force into longitudinal force, proximally retracting the slider member 1710, which proximally retracts an external sheath. The initial deployment of a tubular structure may need a higher quantity of force than later deployment because friction between the tubular structure and the external sheath decreases as the tubular structure is deployed from the external sheath. The shell 1716 may inhibit a user from attempting to proximally retract the slider member 1710 until an amount of the tubular structure is deployed that deploying the remaining amount of the tubular structure does not require a high amount of force. The shell 1716 includes a proximal aperture 1718 that the slider can exit upon proximal retraction.

In FIG. 41Di, the knob 1704 has been rotated until the slider member 1710 is in a proximal position out of the shell 1716. The exposed slider member 1710 may be proximally pulled, thereby pulling the outer sheath. In some examples, the initial amount of force would be very difficult to effect by proximal pulling but can be accomplished by rotation of the knob 1704. FIG. 41Dii shows an example tubular structure 1720 being deployed from an example outer sheath 1722. FIG. 41Dii shows the positions of the tubular structure 1720 and the outer sheath 1722 after the knob 1704 has been rotated until the slider member 1710 is in a position to be proximally retracted (e.g., out of the shell 1716). A first portion 1724 of the tubular structure 1720 has been deployed from the outer sheath 1722.

FIG. 41Ei is a perspective view the handle 1700 of FIG. 41A in a retracted position. FIG. 41Eii is a perspective cross-sectional view the handle 1700 of FIG. 41A in a retracted position. The slider member 1710 has been proximally retracted to a distal part of the body 1702, proximally retracting the outer sheath by a quantity sufficient to deploy an entire tubular structure. FIG. 41Eiii shows the positions of the tubular structure 1720 and the outer sheath 1722 after the slider member 1710 has been proximally retracted to the distal part of the body 1702. A second portion 1726 of the tubular structure 1720 has been deployed from the outer sheath 1722. The first portion 1724 and the second portion 1726 may be an entire length of the tubular structure 1720.

In some examples, rotating the knob 1704 deploys a first amount of the tubular structure and sliding the slider member 1710 deploys a second amount of the tubular structure. The first and second amounts may total the entire tubular structure. In some embodiments, first and second amounts plus a third amount, a fourth amount, etc. may total the entire tubular structure. The third amount, fourth amount, etc. optionally may be deployed using other features. In some examples, the first amount is less than the second amount. For example, the first amount may be between about 10% and about 70% of the second amount (e.g., about 10%, about 20%, about 30%, about 40%, about 50%, about 60%, about 70%, ranges between such values, and the like). In some examples, a ratio of the first amount to the second amount is between about 1:5 and about 5:3 (e.g., about 1:5, about 2:5, about 3:5, about 4:5, about 5:5, about 5:4, about 5:3, ranges between such values, and the like).

With the tubular structure deployed, a catheter coupled to the handle 1700 may be removed from the subject. In some examples in which the tubular structure is coupled to a distal end of the inner shaft assembly, the slider member 1710 may be distally advanced to capture a first portion of the tubular structure. In some examples, capturing the first portion of the tubular structure is an amount that is sufficient to safely remove a catheter coupled to the handle 1700 from the subject. In some examples, the knob 1704 may then be rotated to capture a second portion of the tubular structure.

Figure 42A:
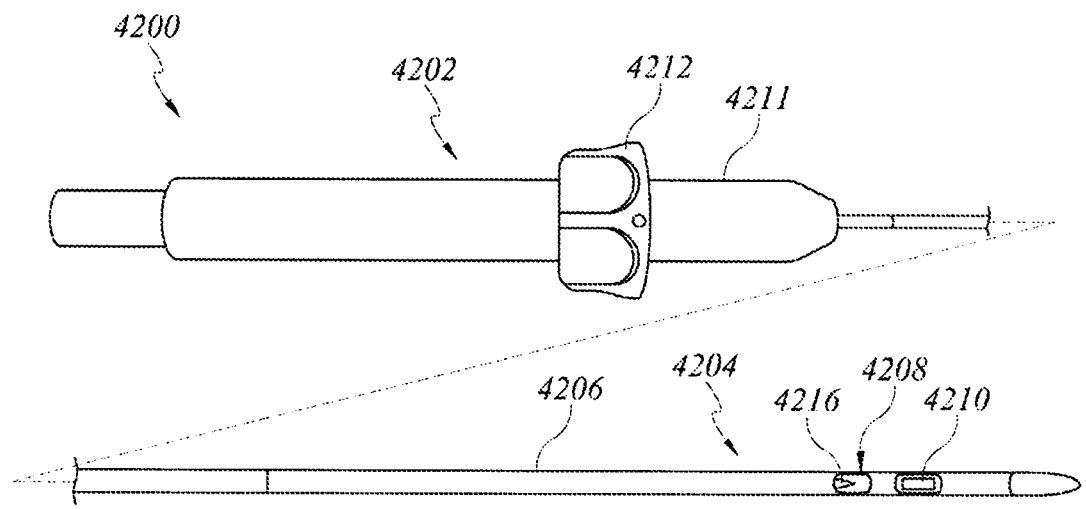
FIG. 42A is a top view of an example embodiment of a launching device.

FIG. 42A is a top view of an example embodiment of a launching device 4200. The launching device 4200 includes a proximal portion 4202 and a distal portion 4204. The distal portion 4204 comprises a catheter 4206. The catheter may have an outer diameter, for example, between about 3 Fr and about 10 Fr (e.g., about 3 Fr, about 4 Fr, about 5 Fr, about 6 Fr, about 7 Fr, about 8 Fr, about 9 Fr, about 10 Fr, ranges between such values, and the like). The catheter 4206 includes a needle lumen 4208. A needle 4216 is configured to extend out of the needle lumen 4208. The proximal portion 4202 includes a handle 4211 and an actuator 4212. When the actuator 4212 is distally advanced and/or the handle 4211 is proximally retracted, the needle 4216 extends out of the needle aperture 4208, for example as described herein with respect to the needle 4216. When the actuator 4212 is proximally retracted and/or the handle 4211 is distally advanced, the needle 4216 retracts back into the needle aperture 4208. Other types of handles or proximal components are also possible. For example, the proximal portion 4202 could comprise an activator switch, lever, knob, etc. such that when the activator is actuated. For another example, the proximal portion 4202 could comprise telescoping elements (e.g., proximal portions of catheters or members coupled thereto) graspable by a user such that the needle 4216 extends out of the needle aperture 4208 upon relative longitudinal movement between the telescoping elements.

The distal portion 4204 comprises a radiopaque marker 4210. The radiopaque marker 4210 comprises a radiopaque material (e.g., tantalum, titanium, nickel, tungsten, platinum, gold, silver, iridium, palladium, tin, zirconium, rhenium, bismuth, molybdenum, barium sulfate, tungsten powder, bismuth subcarbonate, bismuth oxychloride, iodine containing agents such as iohexol (e.g., Omnipaque®, available from Amersham Health, a division of GE Healthcare), combinations thereof, and the like).

Figure 42B:
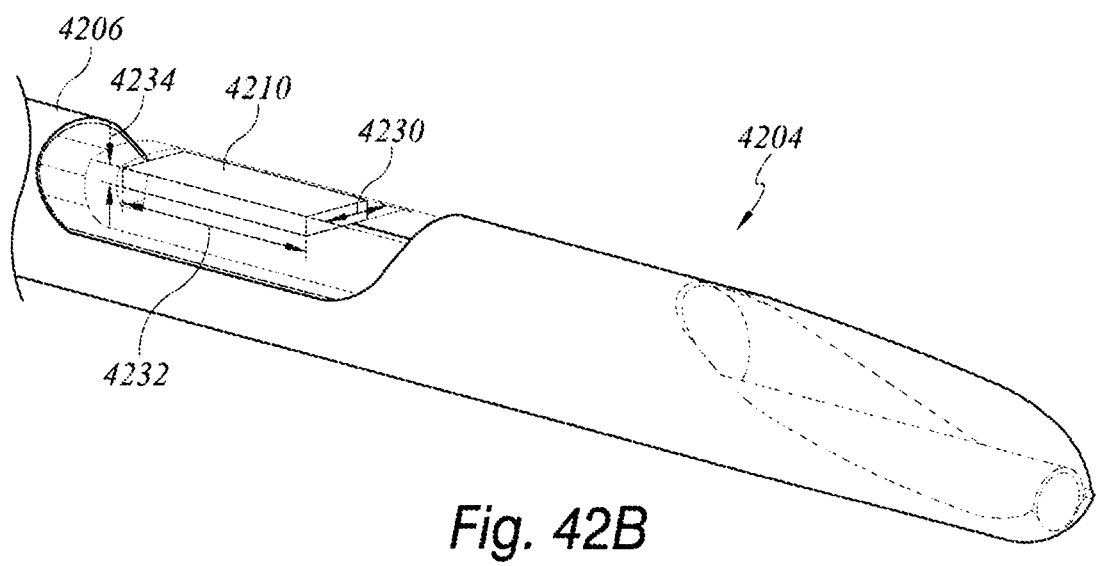
FIG. 42B is a schematic top, side, and distal end perspective view of a distal portion of the launching device of FIG. 42A.
Figure 42B:
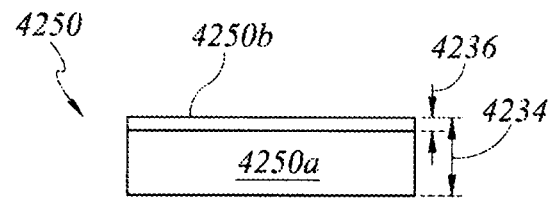

FIG. 42B is a schematic top, side, and distal end perspective view of a distal portion 4204 of the launching device 4200 of FIG. 42A. The radiopaque marker 4210 comprises a flat rectangular (e.g., square) marker. The radiopaque marker 4210 does not conform to the arcuate outer surface of the catheter 4206. The radiopaque marker 4210 may be rectangular, which can include rectangle, square, having adjacent sides that are about 90° to each other, having at least two opposing sides that are substantially parallel to each other (e.g., parallelogram, trapezoid), and/or the like, whether having sharp or rounded corners. Shapes other than rectangular are also possible, but the radiopaque marker 4210 is preferably thin and flat. The radiopaque marker 4210 may be flat, which can include having a thickness less than a certain amount, for example as described herein. The thickness can be between a highest point and a lowest point when the radiopaque marker 4210 is positioned on a flat surface (e.g., a rounded (e.g., following a contour of an outer surface of a catheter) radiopaque marker would have a higher center point than edge points and should not be considered flat). A flat radiopaque marker 4210 may have a ratio of a thickness to a shortest lateral length between about ⅓,₀₀₀ and about ⅓ (e.g., about ⅓,₀₀₀, about ½,₀₀₀, about ⅟₁,₀₀₀, about ⅟₅₀₀, about ⅟₂₅₀, about ⅟₂₀₀, about ⅟₁₀₀, about ⅟₅₀, about ⅟₂₅, about ⅟₁₂, about ⅟₁₀, about ⅕, about ¼, about ⅓, ranges between such values, and the like). A flat radiopaque marker 4210 may have a ratio of a thickness to a longest lateral length between about ⅓,₀₀₀ and about ⅓ (e.g., about ⅓,₀₀₀, about ½,₀₀₀, about ⅟₁,₀₀₀, about ⅟₅₀₀, about ⅟₂₅₀, about ⅟₂₀₀, about ⅟₁₅₀, about ⅟₁₀₀, about ⅟₅₀, about ⅟₂₅, about ⅟₁₂, about ⅟₁₀, about ⅕, about ¼, about ⅓, ranges between such values, and the like). A flat radiopaque marker 4210 may have a thickness such that the radiopaque marker 4210 substantially disappears on fluoroscopy when the radiopaque marker 4210 is perpendicular to the imaging plane.

FIG. 42B also shows a length 4230, width 4232, and thickness 4234 of the marker 4210. In some examples, the radiopaque marker 4210 has a length 4230 between about 1 mm and about 3 mm (e.g., about 1 mm, about 2 mm, about 2.5 mm, about 3 mm, about 3.5 mm, about 4 mm, about 5 mm, ranges between such values, and the like). In some examples, the radiopaque marker 4210 has a width 4232 between about 0.25 mm and about 3 mm (e.g., about 0.25 mm, about 0.5 mm, about 1 mm, about 1.5 mm, about 2 mm, about 3 mm, ranges between such values, and the like). In some embodiments, a ratio of the length 4230 to the width 4232 is between about 1/1 and about 5/1 (e.g., about 1/1, about 2/1, about 2.5/1, about 3/1, about 3.5/1, about 4/1, about 5/1, ranges between such values, and the like). In some examples, the radiopaque marker 4210 has a thickness 4234 between about 0.001 mm and about 1 mm (e.g., about 0.001 mm, about 0.002 mm, about 0.003 mm, about 0.005 mm, about 0.01 mm, about 0.015 mm, about 0.02 mm, about 0.025 mm, about 0.03 mm, about 0.05 mm, about 0.075 mm, about 0.1 mm, about 0.15 mm, about 0.2 mm, about 0.25 mm, about 0.3 mm, about 0.5 mm, about 1 mm, ranges between such values, and the like).

FIG. 42Bi is a schematic side view of another example radiopaque marker 4250. The radiopaque marker 4250 may be include the same or similar features as the radiopaque maker 4210, and may be used in the same or similar systems and methods. The radiopaque marker 4250 comprises a first material 4250a making up a bulk of the radiopaque marker 4250 and a second material 4250b coupled to the first material 4250a. In some examples, a radially outward surface of the radiopaque marker 4250 consists of the second material 4250b. The second material 4250b may be more radiopaque than the first material 4250a (e.g., having a difference enough to discern the second material 4250b under fluoroscopy). In some examples, the second material 4250b is radiopaque and the first material 4250a is radiolucent. The second material 4250b can be coupled to the first material 4250a via cladding, plating, chemical vapor deposition, atomic layer deposition, screen printing, coating (e.g., dip coating, spray coating), adhesion, sputtering, etc. In certain such examples, the second material 4250b can be thinner than the bulk of the entire radiopaque marker 4250. The first material 4250a may be polished or otherwise flattened prior to coupling the second material 4250b, for example to increase the flatness of the second material 4250b coupled thereto. Because the second material 4250b is the material used for alignment of the catheter, the second material 4250b (e.g., not the entire radiopaque marker 4250, not the first material 4250a) by itself may be considered the radiopaque marker.

In some examples, the second material 4250b of the radiopaque marker 4250 has a thickness 4236 that is less than about 2 μm. In some examples, the second material 4250b of the radiopaque marker 4250 has a thickness 4236 between about 1 nm and about 10 μm (e.g., about 1 nm, about 2 nm, about 3 nm, about 5 nm, about 10 nm, about 50 nm, about 100 nm, about 500 nm, about 1 μm, about 2 μm, about 3 μm, about 5 μm, about 10 μm, ranges between such values, and the like). The thickness 4236 of the second material 4250b may depend on the composition of the second material 4250b and/or the coupling technique. For example, a metalized nickel layer may be between about 1 μm and about 2 μm. For another example, a layer of gold may be between about 1 nm and about 5 nm or between about 1 μm and about 3 μm. Other layers of material are also possible. For example, a radiolucent material (e.g., polymer) can be coated over the second material 4250b to inhibit corrosion of the second material 4250b, to allow use of a second material 4250b usually considered non-biocompatible, to follow the contours of the catheter, and/or other reasons. Because the material is radiolucent, the methods described herein are not affected.

The example dimensions, particularly the thickness, can limit a shadowing effect on angioscopes or x-ray or fluoroscopy machines. As appreciated from the discussion herein, accurate identification of a thin radiopaque marker 4210, 4250 is used for alignment of the catheter 4200. A shadow effect may inhibit a user's ability to detect thinness.

The radiopaque marker 4210 is on a side of the catheter 4200, for example as opposed to being along a diameter or a radius. In some embodiments, the radiopaque marker 4210 is on the same side as the needle aperture 4208. In some embodiments, the radiopaque marker 4210 is on an opposite side from the needle aperture 4208. Depending on the position of the radiopaque marker 4210, a goal of the user may be to have the radiopaque marker proximate to or distant from a target catheter.

Figure 42C:
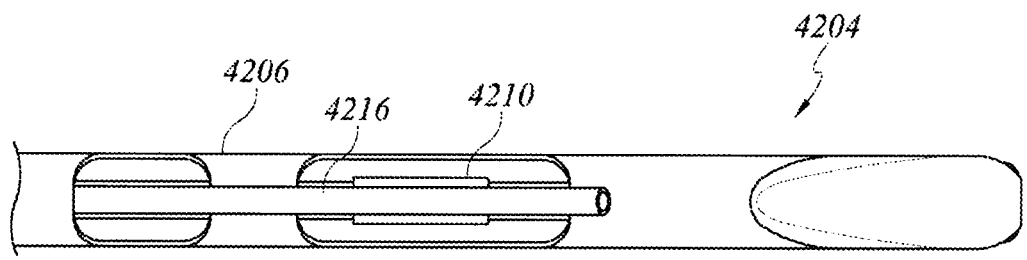
FIG. 42C is a schematic expanded top view of the distal portion of the launching device of FIG. 42A.
Figure 42C:
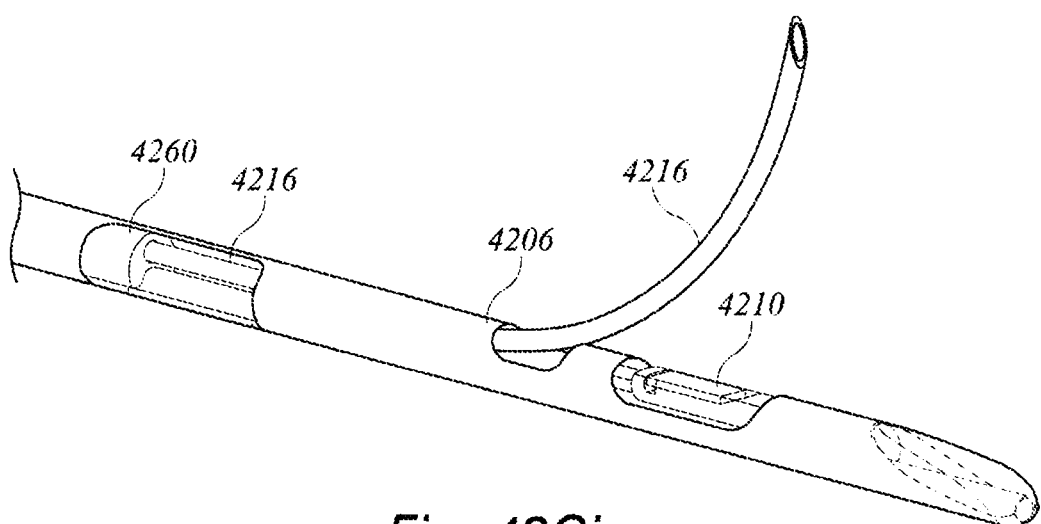

FIG. 42C is a schematic expanded top view of the distal portion 4204 of the launching device 4200 of FIG. 42A. FIG. 42D is a schematic side view of the distal portion 4204 of the launching device 4200 of FIG. 42A. In FIGS. 42C and 42D, the needle 4216 has been extended out of the needle aperture 4208, for example after alignment of the launching device 4200. In some embodiments, the needle 4216 can be extended by operation of the actuator 4212 relative to the handle 4211. Other mechanisms are also possible (e.g., a switch, a slider, a wheel, etc.). A proximal portion 4202 having no mechanism or handle 4211 is possible (e.g., a proximal end of the needle 4216 and a proximal end of the catheter 4206 movable relative to one another by a user holding each proximal end). The needle aperture 4208 is shown proximal to the radiopaque marker 4210, but other options are also possible. For example, the needle aperture 4208 may be distal to the radiopaque marker 4210. For another example, the needle aperture 4208 may be longitudinally aligned with (e.g., radially outward of) the radiopaque marker 4210.

In some examples, the needle 4216 may be longitudinally aligned with the radiopaque marker 4210, extending in a plane perpendicular to the thin axis of the radiopaque marker 4210. Limitation of lateral movement of the needle 4216 can reduce positioning error that might otherwise result even if the alignment of the radiopaque marker 4210 is correct. For example, even if the radiopaque marker 4210 is perfectly aligned, a needle 4216 that does not extend predictably relative to the radiopaque marker 4210 can render the alignment meaningless.

FIGS. 42Ci-42Ciii illustrate an example catheter including a profile 4260 attached to the needle 4216. The profile 4260 slides in a shaped lumen, which can act as a slot and key system to reduce or minimize lateral and/or rotational movement of the needle 4216. The profile 4260 and corresponding lumen can have an asymmetric shape in at least one radial axis. For example, the C-shape of the profile 4260 interacts with a C-shaped surface of the lumen to inhibit or prevent the needle 4216 attached to the profile 4260 from moving laterally. In some examples, the C-shaped surface of the lumen can comprise the outer surface of a guidewire lumen (e.g., for the guidewire 4217 over which the catheter 4200 is tracked). Although illustrated in the context of the catheter 4200 including the radiopaque marker 4210, a profile 4260 can be used to laterally stabilize the needle of other catheters described herein (e.g., catheters comprising an ultrasound transducer). Symmetric shapes are also possible. Some implementations can include a sliding lap joint. Some implementations can include an interlocking tube.

When the catheter 4200 is positioned at a viewing angle parallel to a major axis of the radiopaque marker 4210, for example as shown in FIG. 42D, the smallest area of the marker 4210 is visible, which can indicate alignment with a target catheter, for example. Every shift in angle results in increased visible area, and a goal of the user is to reduce or minimize visible area. Radiopaque markers that are not flat (e.g., that follow the curvature of the catheter or stent) cannot achieve a thin state because the thickness is limited by the curvature and the circumferential extension of that marker. If the radiopaque marker is not flat, it may still be used consistent with some of the methods described herein (e.g., by reducing or minimizing or conversely increasing or maximizing an amount of visible marker). Upon detection of alignment, the needle 4216 can extend out of the needle aperture 4208, out of a first vessel (e.g., an artery) in which the catheter 4200 resides, through interstitial tissue, and into a second vessel (e.g., a vein), for example in which a target catheter resides. Processes as described herein may then be performed (e.g., tracking a guidewire through the needle 4216 and using the guidewire for dilation, stent delivery, a valvulotome, etc. Use of a radiopaque marker 4210, 4250 can reduce or eliminate use of more complicated and/or expensive alignment systems such as ultrasound, electric field, and magnets, but still provide assurance to the user that the needle 4216 will extend into the neighboring vessel.

In comparison to systems in which two radiopaque components need to be aligned (e.g., radiopaque components on opposite sides of a catheter, one radiopaque component on a side of a catheter and a radiopaque component in a middle of a catheter, one radiopaque component on an extendable member and a radiopaque component elsewhere on a catheter), the radiopaque marker 4210, 4250 can provide less doubt about the alignment. For example, a user may wonder whether one of the radiopaque components is not visible in an imaging plane as opposed to being aligned or not, whereas the radiopaque marker 4210, 4250 will be visible when not aligned and substantially invisible or at a minimum thickness when aligned, confirmable by small rotations. The use of shapes (e.g., two radiopaque components forming one shape), bars (e.g., multiple radiopaque components overlapping or separating), etc. can be subjective, whereas the radiopaque marker 4210, 4250 provides a substantially objective measure of whether any additional rotation makes the radiopaque marker 4210, 4250 more or less visible. Certain such shape-based radiopaque component systems may also fail to provide information about the direction of the alignment because the shape can be formed at two or more positions that are, e.g., 180° apart, whereas the radiopaque marker 4210, 4250 is clearly oriented to a desired side. Even if the shapes separate or become misaligned after rotation, the separation of the shapes is non-intuitive as to direction. Certain such shape-based systems simply confirm that rotation has occurred without regard to alignment. A radiopaque dot on a side of a catheter, lacking length and width dimensions, may provide similar limited visibility in all rotational orientations, whereas the radiopaque marker 4210, 4250 shows prominently when not aligned. Subjective alignment of shapes or assessment of widths (as opposed to objective assessment of minimal thickness) can cause a few degrees of misalignment which can cause the needle to miss the second vessel when crossing from a first vessel to a second vessel. A radiopaque hoop, for example around a circumference of a catheter, can provide information about the position of the imaging system to the catheter (e.g., whether parallel or perpendicular to the catheter), but does not provide rotational information about the catheter, such that the change from a circular pattern to a linear pattern is not useful for rotationally aligning the catheter. The elegant nature of the radiopaque marker 4210, 4250 can reduce manufacturing costs, for example because a complex shape and position may be avoided.

Figure 43A:
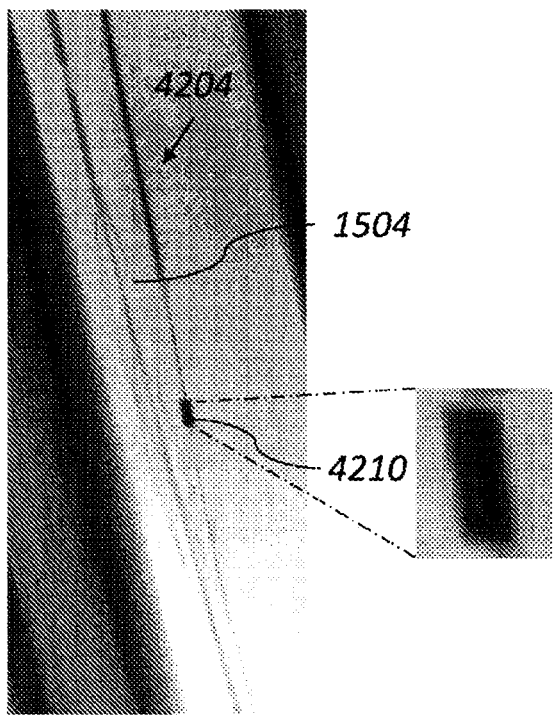
FIGS. 43A-43N schematically illustrate an example method of using a launching device including the distal portion of the launching device of FIG. 42A.
Figure 43B:
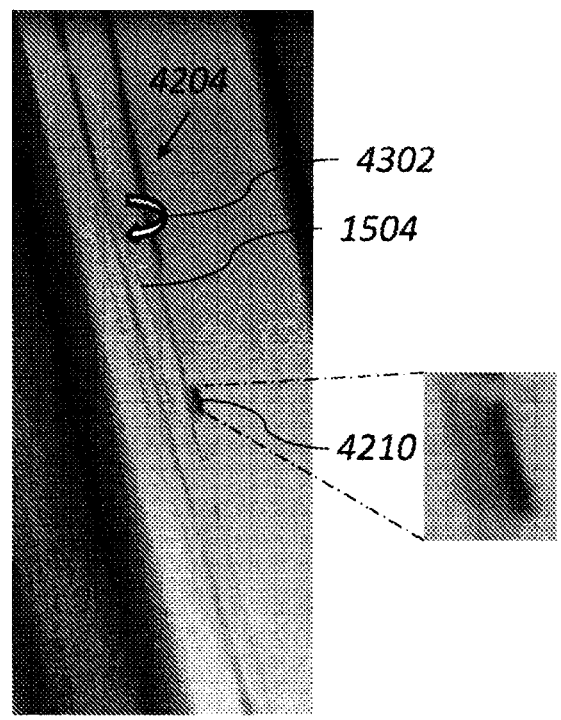
FIGS. 43Oi-43Ovi illustrate an example implementation of alignment using software.
Figure 43C:
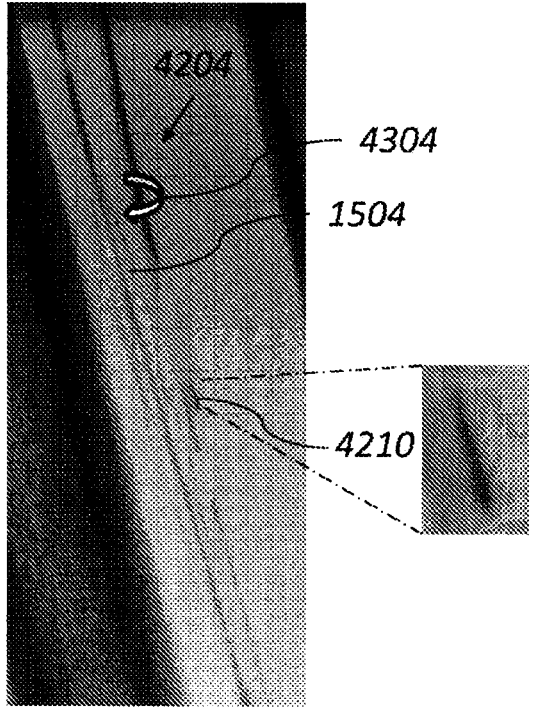
Figure 43D:
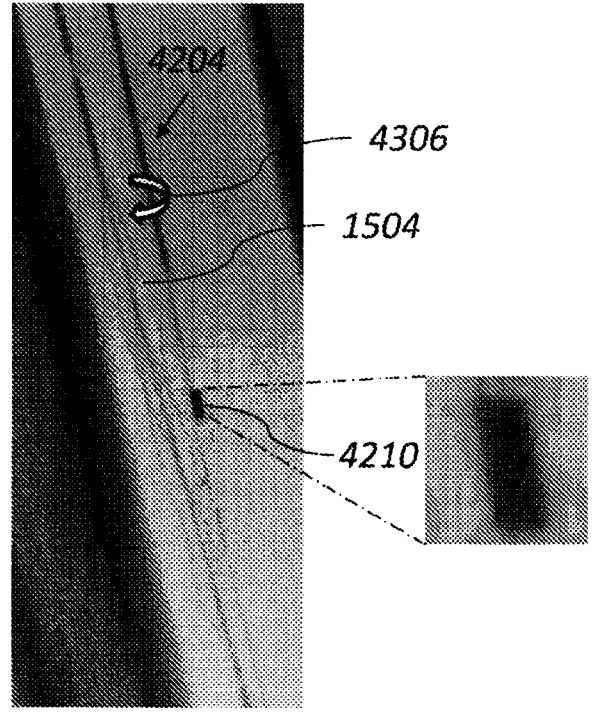
Figure 43E:
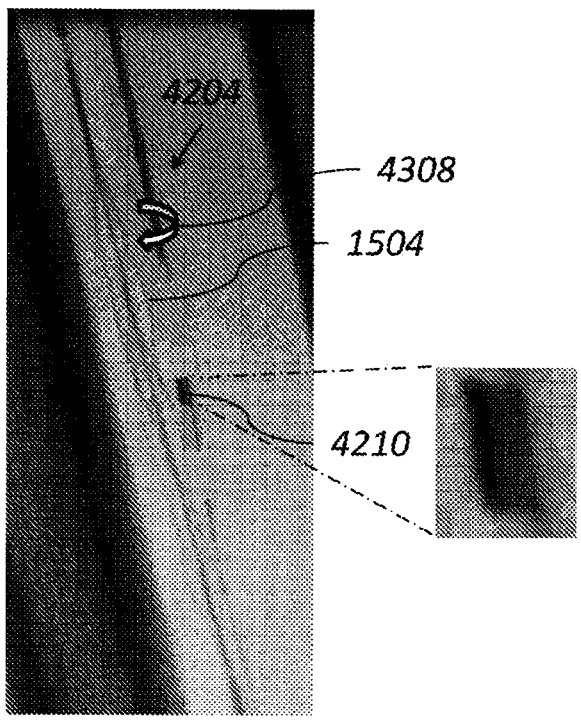
Figure 43F:
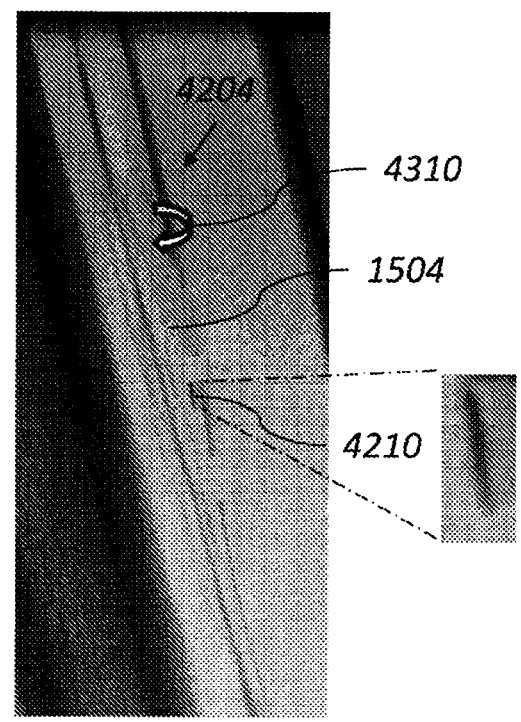
Figure 43G:
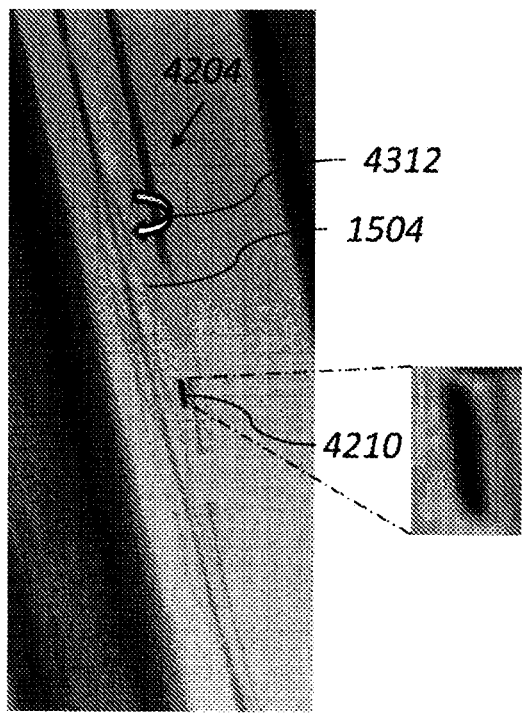
Figure 43H:
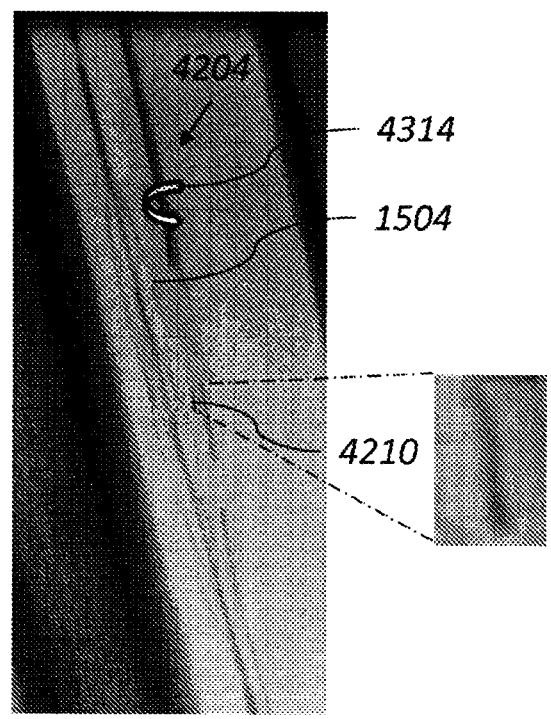
Figure 43H:
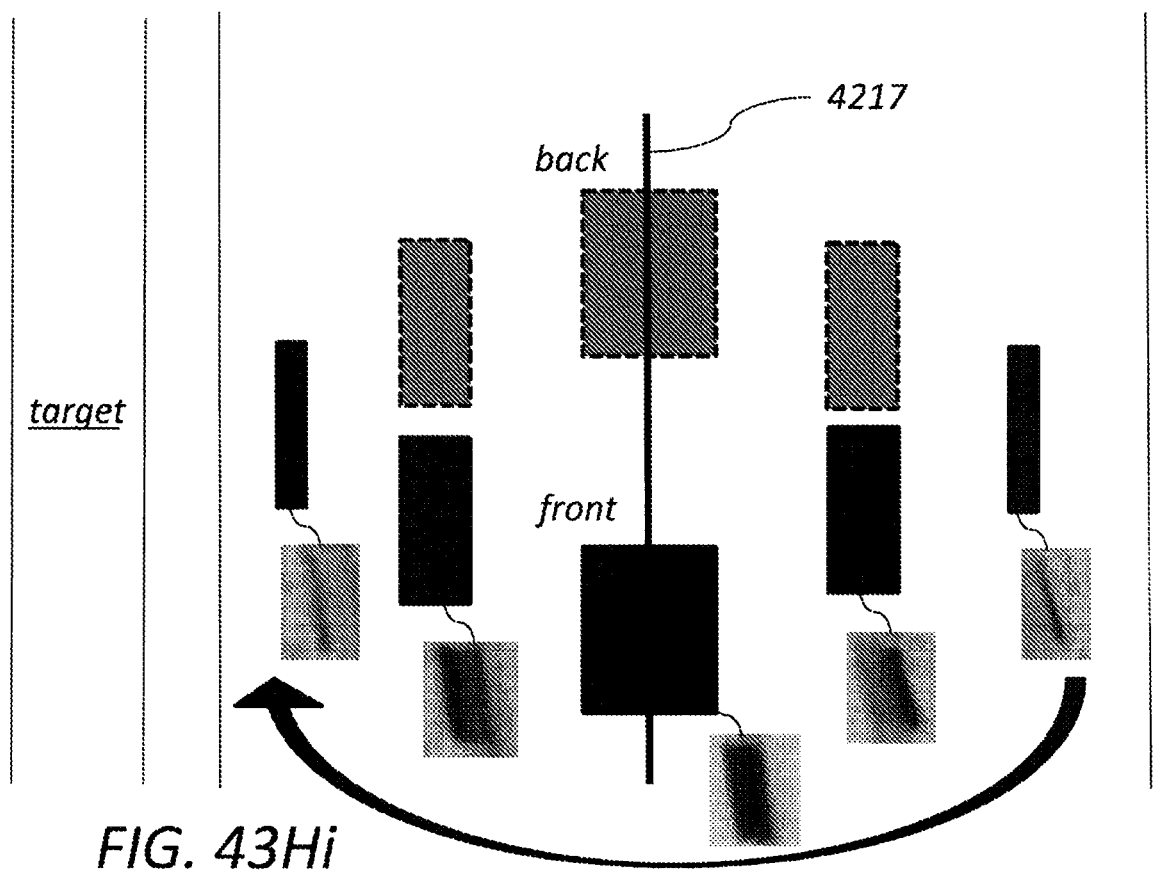
Figure 43I:
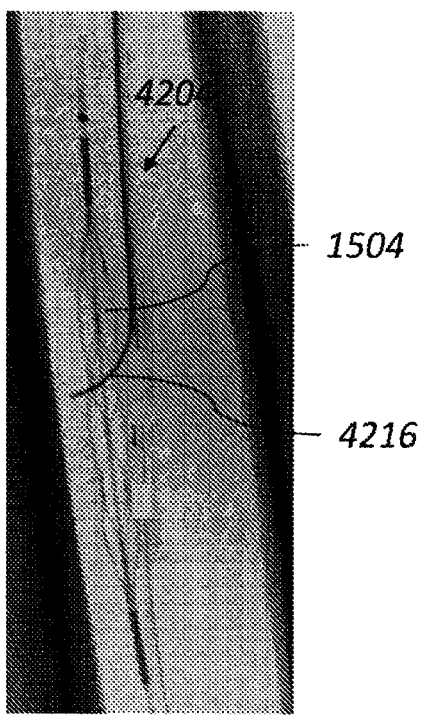
Figure 43J:
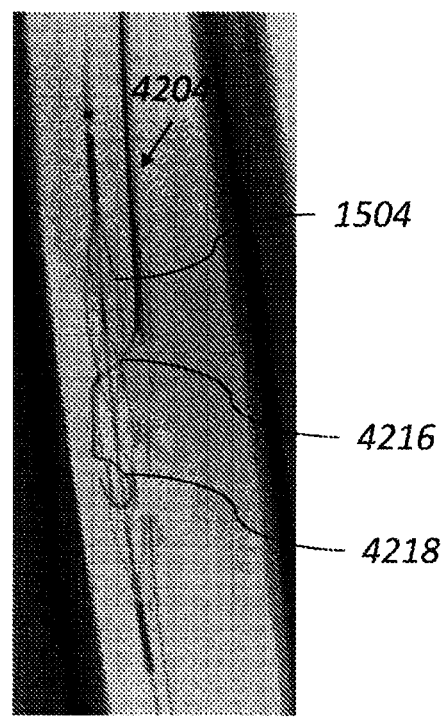
Figure 43K:
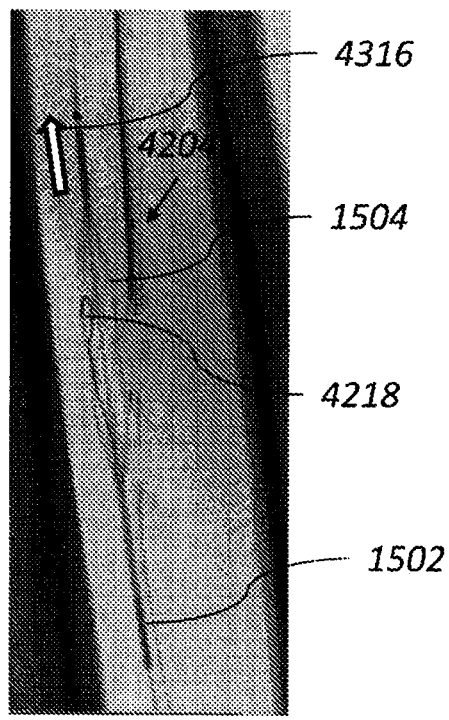
Figure 43L:
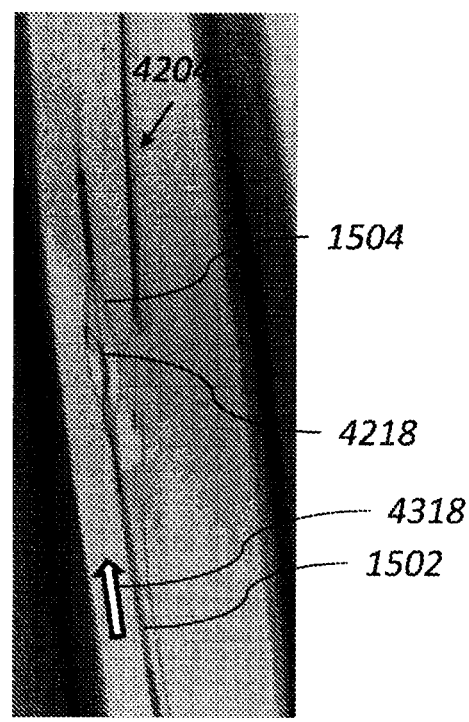
Figure 43M:
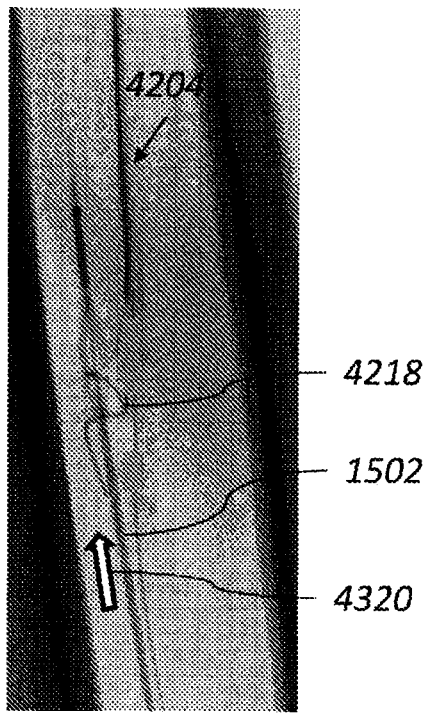
Figure 43N:
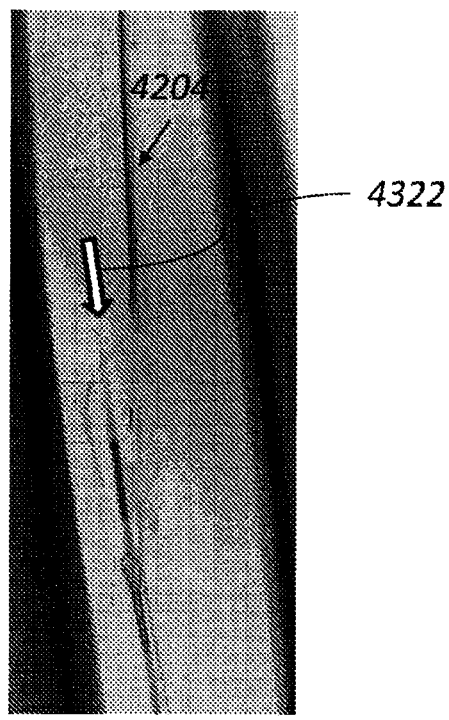

FIGS. 43A-43N schematically illustrate an example method of using a launching device including the distal portion 4204 of the launching device 4200 of FIG. 42A. In FIGS. 43A-43G, the radiopaque marker 4210 is shown in an enlarged view. In some embodiments, the method may begin after performing the method of FIGS. 39A-39E (e.g., expanding an expandable structure or snare 1504 of a target catheter), and certain features may be shared between the methods.

In FIG. 43A, the distal portion 4204 has been longitudinally advanced in a first vessel to a position longitudinally proximate to a snare 1504. The snare 1504 in this example is radiopaque and can be used as a target catheter. Other target catheters are also possible, for example having radiopaque markers on a catheter (e.g., a first radiopaque marker longitudinally spaced from a second radiopaque marker, the markers comprising marker bands in some embodiments, including a balloon filled with radiopaque material, etc. A user can see the radiopaque marker 4210 and a radiopaque feature of a target catheter under fluoroscopy.

In FIG. 43B, the distal portion 4204 is rotated, as indicated by the arrow 4302. During rotation, the radiopaque marker 4210 becomes thinner. In FIG. 43C, the distal portion 4204 is further rotated, as indicated by the arrow 4304. During rotation, the radiopaque marker 4210 becomes thinner. At this point, a user may think that the thin radiopaque marker 4210 indicates alignment, but the radiopaque marker 4210 is on a side of the launching catheter that is opposite the snare 1504. For this arrangement in which the radiopaque marker 4210 is on the same side as the needle aperture 4208, the radiopaque marker 4210 should be proximate to the snare 1504. The radiopaque marker 4210 being relatively proximate or distant to the snare 1504 is viewable during rotation. In some embodiments, a guidewire having radiopaque properties can help determine the side of the radiopaque marker 4210. Because the radiopaque marker 4210 is thin but on the wrong side in FIG. 43C, the user continues alignment.

In FIG. 43D, the distal portion 4204 is further rotated, as indicated by the arrow 4306. During rotation, the radiopaque marker 4210 becomes thicker. In FIG. 43E, the distal portion 4204 is further rotated, as indicated by the arrow 4308. During rotation, the radiopaque marker 4210 becomes thinner. In FIG. 43F, the distal portion 4204 is further rotated, as indicated by the arrow 4310. During rotation, the radiopaque marker 4210 becomes thinner. The radiopaque marker 4210 is now proximate to the snare 1504 and thin, indicating alignment. In some embodiments, the alignment may stop at this point.

In FIG. 43G, the distal portion 4204 continues to be rotated or is over-rotated in the direction indicated by the arrow 4312. During rotation, the radiopaque marker 4210 becomes thicker, indicating that the further rotation is making alignment worse. In FIG. 43H, the distal portion 4204 is rotated in the opposite direction, as indicated by the arrow 4314. During rotation, the radiopaque marker 4210 becomes thinner. The radiopaque marker 4210 is now again proximate to the snare 1504 and thin, indicating alignment. The further rotations of FIGS. 43G and 43H can help to ensure a user that the alignment is correct (e.g., optimized). Rotation of the distal portion 4204 and viewing of the radiopaque marker 4210 can be similar to focusing a camera, where a user can do a coarse adjustment and a fine adjustment. For example, the coarse adjustment can be to determine whether or not the radiopaque marker 4210 is on the side proximate to the snare 1504, and the fine adjustment can be to reduce the area of the radiopaque marker 4210. The alignment may also be described as a pendulum where the user rotates the distal portion 4204 back and forth to find a low or minimum thickness of the radiopaque marker 4210. Thus may include over-rotation, over-swing, over-shoot, etc. to confirm alignment.

FIG. 43Hi schematically shows alignment of a radiopaque marker through a rotational alignment process. A catheter comprising the radiopaque marker is in a first vessel proximate or adjacent to a target vessel. The catheter is tracked over a guidewire 4217 comprising radiopaque material. When the radiopaque marker overlaps the guidewire 4217, either the front or back (or first side and opposite second side) of the radiopaque marker is visible. In this example, the radiopaque marker is on a same side of the catheter as the needle aperture. When the guidewire 4217 is between the radiopaque marker and the target, the catheter is rotationally misaligned by about 90° to about 270°. For example, even if the radiopaque marker is thin, as shown by the right-most illustration in FIG. 43Hi, the catheter would be 180° misaligned. When the radiopaque marker is between the guidewire 4217 and the target, the catheter is rotationally on the correct side of the catheter. When on the correct side of the catheter and thin, as shown by the left-most illustration in FIG. 43Hi, the catheter is aligned. If the radiopaque marker is thin enough, the radiopaque marker may be a thin line or even disappear from the fluoroscopy. If the radiopaque marker is on an opposite side of the catheter as the needle aperture, the process would be the opposite with respect to the guidewire 4217. The process is also possible without a guidewire 4217 or if the guidewire 4217 is not radiopaque, as the user can visualize the radiopaque marker being near or far from the target during rotation. Visualization through a range of rotational positions including the radiopaque marker being thin on both sides can inhibit, minimize, or prevent 180° misalignment.

Once the launching catheter is aligned, the needle 4216 can be extended, as shown in FIG. 43I. Extending the needle may include exiting a first vessel in which the distal portion 4204 resides, traversing interstitial tissue, and entering a second vessel in which the snare 1504 resides. In embodiments, the needle 4216 crosses into the snare 1504. In FIG. 43J, a guidewire 4218 is extended through the needle 4216. The guidewire 4218 thereby extends through the first vessel, through the interstitial tissue, and into the second vessel.

In FIG. 43K, the snare 1504 is moved distally, as indicated by the arrow 4316. The guidewire 4218 also moves distally, indicating that the guidewire 4218 is captured or entangled by the snare 1504. If the snare 1504 is moved distally before retraction of the needle 4216, distal movement of the needle 4216 can confirm engagement with the snare 1504 and/or being in the interior of the target vessel. Verification using the needle 4216 can be before or after advancing the guidewire 4218. In some examples, the needle 4216 can be verified, then the guidewire 4218 can be advanced, and the guidewire 4218 can be verified. In FIG. 43L, the sheath 1502 is distally advanced, as indicated by the arrow 4318, capturing the snare 1504 and the guidewire 4218 entangled with the snare 1504. In FIG. 43M, the sheath 1502 is further distally advanced, as indicated by the arrow 4320, further capturing the snare 1504. In some embodiments, the snare 1504 may not be fully retrievable into the sheath 1502, for example due to the entanglement with the guidewire 4218. The snare 1504 may nevertheless be radially compressed enough to move through the second vessel.

In FIG. 43N, the snare 1504 is proximally retracted, as indicated by the arrow 4322. Because the guidewire 4218 is entangled with the snare 1504, the guidewire 4218 is also proximally retracted in the second vessel, or, relative to the first vessel, distally advanced. As described herein, for example, a snare technique can help to navigate the guidewire 4218 through the second vessel, for example past valves and other difficult vasculature. Catheters comprising a valvulotome, a stent-graft, and the like may be tracked over the guidewire 4218 and through the second vessel, for example as described herein.

Software may be implemented to aid in detection of the radiopaque marker 4210. The software may, for example, establish a "crossing plane" between first and second catheters and/or vessels (e.g., between a first catheter and a second catheter, between a first vessel and a second vessel, between a first catheter in a first vessel and a second vessel). To be "in the crossing plane" generally means, without limitation, that when the user advances a needle from the first vessel to the second vessel, the needle will enter the second vessel. This crossing preferably allows procedures to be performed such that fluid flows between the vessels. The crossing plane may be obtained via fluoroscopy or other imaging systems, for example by rotating the imaging head (e.g., "C-arm") until the two vessels of interest (or a catheter in one or both of the vessels) are substantially at a maximum distance from each other. When the first vessel and second vessel are parallel, and at their maximum distance, one can say that they are in the "crossing plane" now displayed. This can be a challenging task, as measurement between vessels/catheters is typically rudimentary or done "by eye." A software solution can make the process more exact and with fewer user-driven errors (e.g., providing better precision, more reliability), and possibly more quickly.

The software may run in parallel with other software (e.g., imaging software). FIGS. 43Oi-43Ovi illustrate an example implementation of alignment using software. In FIG. **43O*i*, a first catheter 4200 is advanced in a first vessel 4330 and a second catheter 1500 is advanced in a second vessel 4332 proximate to an intended crossing point (e.g., proximate to and/or upstream of an occlusion in the first vessel 4330). The first vessel 4330 may be an artery. The second vessel 4332 may be a vein. The "C-arm" or other holder of an imaging system may be positioned such that it does not immediately provide an appropriate view of the vessels 4330, 4332 and/or catheters 4200, 1500. In FIG. 43Oii, the software measures a distance 4338 between a centerline 4334 of the first catheter 4200 and a centerline 4336 of the second catheter 1500. As the C-arm is rotated, the distance 4338 changes because the imaging plane changes. The system may control the C-arm and/or may be responsive to a user moving the C-arm. When the distance 4338 is at a maximum and/or is greater than a certain amount, the software identifies a crossing plane. The detection may be magnification dependent. When the crossing plane has been identified, the system can send a signal to a user (e.g., audible such as a beep, visual such as changing the color, dashing, thickness, etc. of the centerlines 4334, 4336, tactile such as vibration of a handle, sending a signal to a remote computing device, combinations thereof, and the like). The system may be fully or partially automated (e.g., moving on to the next step without user interaction or only upon user interaction). Combinations of line drawing and/or measurement methods/software may be used. In FIG. 43Oiii, the image of the crossing plane optionally may be oriented as desired (e.g., such that the vessels 4330, 4332 are parallel to the lateral edges of the viewing area). In some implementations, the vessels 4330, 4332 may be filled with contrast in the viewing area, and a distance between their centerlines or an area between the contrast-filled vessels 4330, 4332 could be maximized and/or greater than a certain value to identify the crossing plane. Such techniques may be particularly suitable for non-parallel vessels 4330, 4332. Depending on the imaging system, contrast may be omitted, for example if the vessels 4330, 4332** can be identified without contrast. Combinations of catheter identification and/or vessel identification may be used.

The first catheter 4200 may be rotated as indicated by the arrow 4340 until the radiopaque marker 4210 has a minimum thickness or a thickness lower than a certain value. The software may use edge detection or other methods to identify the thickness of the radiopaque marker 4210 during rotation. FIG. 43Ov shows edge lines 4342, 4344 used to measure a thickness of the radiopaque marker 4210 as a distance between the edge lines. The software may use the same or similar routines to identify edges of the radiopaque marker 4210 as to identify the centerlines 4334, 4336 in FIG. 43Oii. The software may use the same or similar routines to measure the distance between the edge lines 4342, 4344 as the distance 4338 between the centerlines 4334, 4336 in FIG. 43Oii. In some implementations, a pixel count may be used. As described above, the software also accounts for the position of the second vessel and thus can establish whether the thin radiopaque marker is facing the second vessel (or vice versa). Once the software has established that the thickness of the radiopaque marker 4210 indicates that the first catheter 4200 is properly aligned, and that the first catheter 4200 is facing the second vessel 4332, a needle 4216 can extend from the first catheter 4200, out of the first vessel 4330, and into the second vessel 4332. When rotational alignment has been identified (e.g., that the catheter is facing the correct direction and that the crossing needle will be "in the crossing plane"), the system can send a signal to a user (e.g., audible such as a beep, visual such as changing the color, dashing, thickness, etc. of the edge lines 4342, 4344, tactile such as vibration of a handle, sending a signal to a remote computing device, combinations thereof, and the like). The needle extension can be initiated by a user after receiving the signal. The needle extension can be automatic upon indicating alignment. The system may be fully or partially automated (e.g., moving on to the next step without user interaction or only upon user interaction). The second catheter 1500 may be moved longitudinally to move the needle 4216 to confirm that the needle has punctured the expandable member of the second catheter 1500, for example as described herein.

Navigation of a guidewire for retrograde venous access (e.g., against the direction of normal blood flow) can be difficult or even impossible, for example due to venous valves intended to prevent venous reflux and the many tributaries and parallel venous structures. Retrograde guidewire navigation of veins can result in diversion into branches, obstruction as a result of valves, either or both of which can cause spasm and/or perforation. Advancing a guidewire distally past a tibial venous sheath insertion point, for example, can be time-consuming, sometimes taking several hours without a pedal/tibial venogram to provide a road map and/or because the peripheral vasculature, particularly distal to the heart, varies between people. Keeping the access sheath and guidewire in the tibial vein can help tension or tent the vein to allow the exchange catheter and retrograde guidewire to pass distal to the tibial access sheath. Failure to stay in the vein, which can lead to perforations, can cause vein spasms such that a procedure may need to be aborted because the user is unable to access the foot.

Advancing a guidewire around a pedal arch without a venogram or road map can lead to perforate veins and/or induce venous spasm. Perforating a vein can cause a compartment around the vein which essentially flattens the vein, hindering navigation or making navigation impossible. After a perforation, it is possible to wait 15-20 minutes to see if the perforation has resolved, try selecting an alternative venous pathway, or aborting the procedure. The user may elect to try again in a few days, for example when the perforation should be resolved. When advancing a guidewire into the foot, a user can flex the foot, use a reverse Trendelenburg posture (head elevated above feet), and/or apply a tourniquet above the ankle to increase venous pressure, thereby expanding the diameter of the vein and making navigation through valves in the vein easier, but these may not fully address perforation risk.

Antegrade pedal access offers both the opportunity for pedal venous imaging and the passage of a guidewire in a chosen vessel without the complications of valvular obstruction and diversion into branch vessels. A technique to perform consistent antegrade pedal venous access can include, for example, the use of ultrasound, techniques for venous dilatation, and/or fluoroscopic imaging.

When retrograde access to the pedal venous vasculature is desired, an initial antegrade access from the target pedal venous structure can allow the passage of a guidewire without venous valve obstruction, for example, because the guidewire is following the natural course of venous flow. An appropriately-shaped guidewire designed to align to the centerline that is introduced in this fashion has less chance of diversion into the multiple side branches, perforators, and parallel venous structures. Once a guidewire is introduced from the pedal target vein in this antegrade fashion, other catheters and devices can be introduced in a retrograde fashion with limited or without obstruction from valves that are effaced by the guidewire and/or risk of diversion into branch vessels.

Accessing a posterior tibial vein above the ankle and up to a crossing point, then with a crossing guidewire working in a retrograde fashion navigating past the tibial sheath and trying to get to the venous arch in the foot can be difficult, or given certain anatomy, may not even be possible. Understanding the foot anatomy can help a user access desired veins in the foot, for example because a user pass a guidewire into the connecting tibial vein and up to the crossing point, eliminating any confusion on the potential pathway.

Figure 44A:
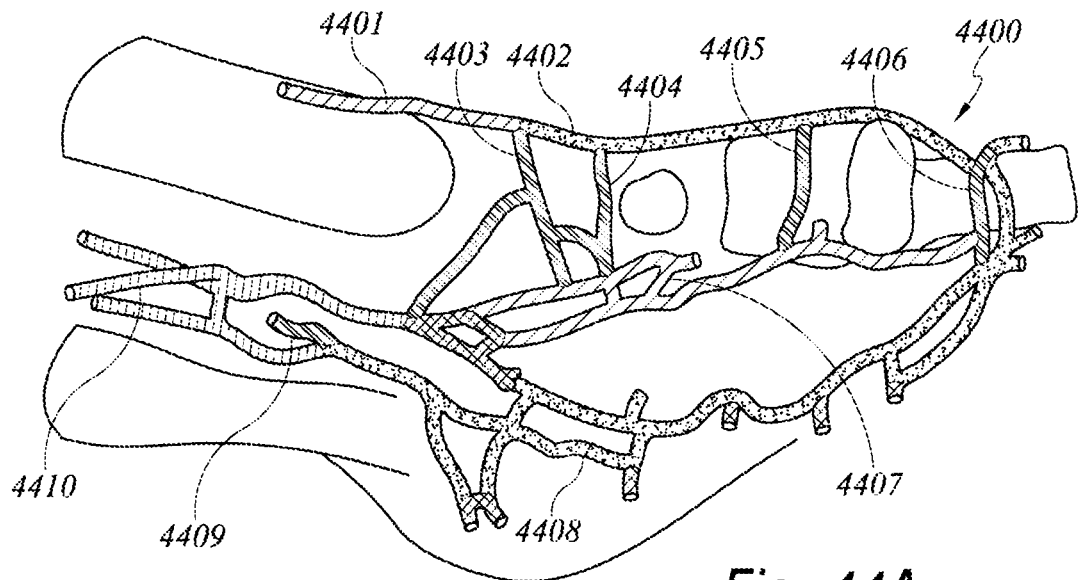
FIGS. 44A-44J schematically illustrate anatomy of an example foot.

FIG. 44A illustrates vascular anatomy of an example foot 4400. The foot 4400 includes a medial marginal vein 4402. The medial marginal vein 4402 continues towards the heart as the great saphenous vein 4401. FIGS. 44E and 44F also show the great saphenous vein 4401. The foot 4400 includes perforating or branch veins feeding the medial marginal vein 4402, including a submalleolar vein 4403, a scaphoid vein 4404, a cuneal vein 4405, and perforating or branch veins feeding these veins. The foot 4400 includes a first intermetatarsal space perforator vein 4406. The submalleolar vein 4403, scaphoid vein 4404, cuneal vein 4405, and first intermetatarsal space perforator vein 4406 are connected to the medial plantar veins 4407. The first intermetatarsal space perforator vein 4406 provides a consistent venous connection from the top or dorsal side of the foot 4400 to the bottom or plantar side of the foot 4400. The lateral functional unit of the foot 4400 includes lateral plantar veins 4408 and a calcaneal perforator vein 4409. In the rear of the foot 4400, the lateral plantar veins 4408 and the calcaneal perforator vein 4409 form two confluences that originate plexiform posterior tibial veins 4010.

Figure 44B:
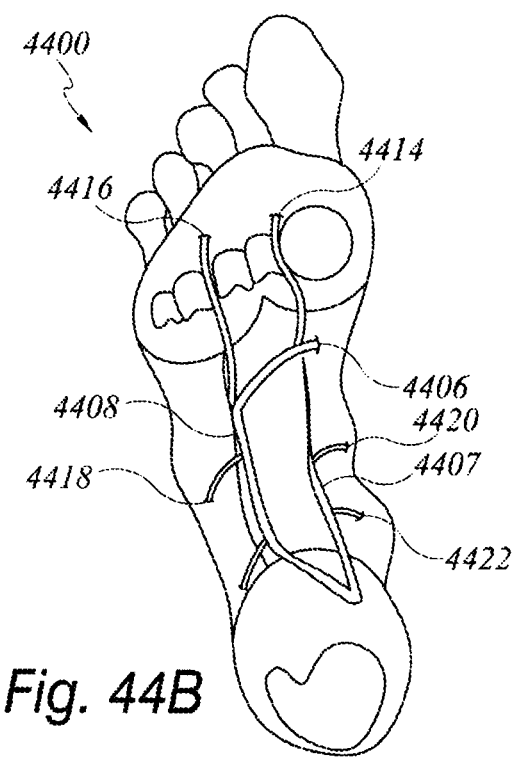

FIG. 44B further illustrates vascular anatomy of the example foot 4400. As also shown in FIG. 44A, the foot 4400 includes a medial plantar vein 4407 and a lateral plantar vein 4408. The bottom of the foot 4400 includes a perforator of the first metatarsal interspace 4406. The foot 4400 includes toe veins including the first digital vein 4414 and the fourth digital vein 4416. The foot 4400 includes a cuboidal perforator 4418. The foot 4400 includes a malleolar perforator 4420. The foot 4400 includes a navicular perforator 4422.

Figure 44C:
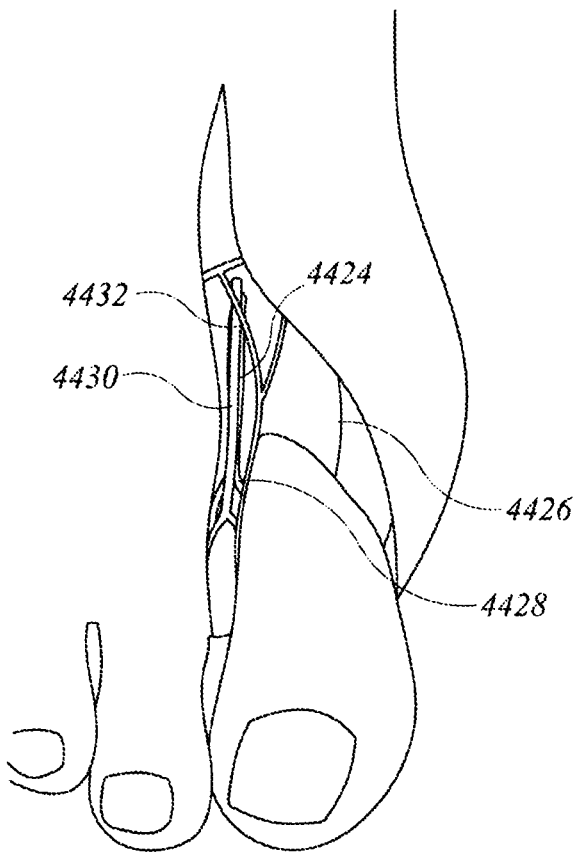
Figure 44D:
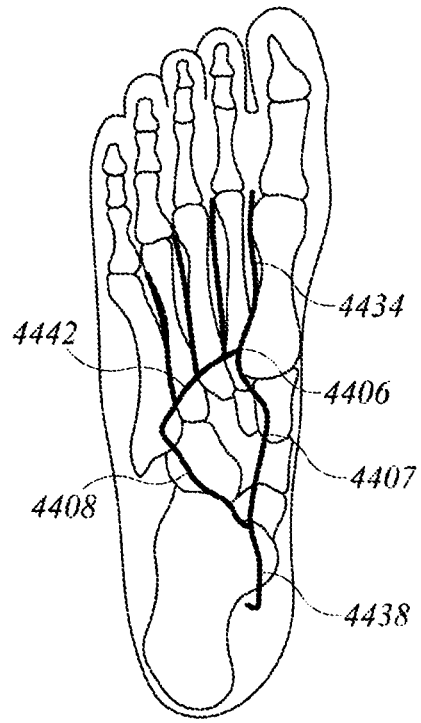
Figure 44E:
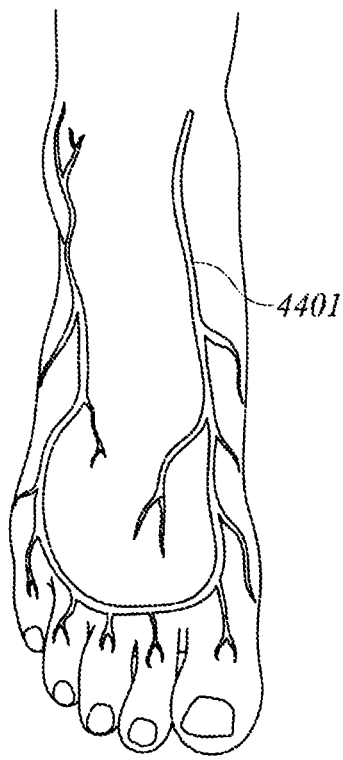
Figure 44F:
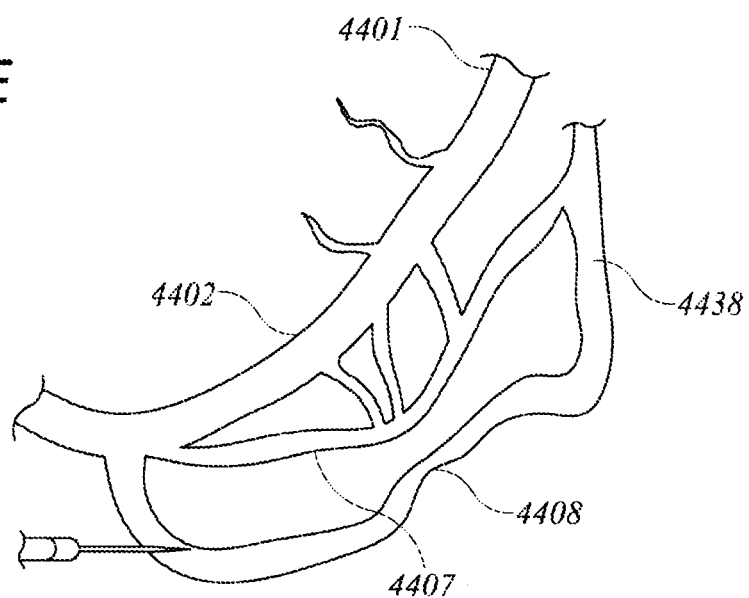

FIG. 44C shows a first dorsal metatarsal artery 4424, and extender 4426, a digital artery to great and second toes 4428, a deep peroneal nerve 4430, and a dorsal vein 4432. FIG. 44D shows plantar metatarsal veins 4434, medial plantar vein 4407, posterior tibial vein 4438, lateral plantar vein 4408, and deep plantar venous arch 4442. FIG. 44D also shows the first metatarsal perforator 4406, which connects plantar to dorsal veins. FIG. 44E shows the posterior tibial vein 4438, the lateral plantar vein 4408, the medial plantar vein 4407, and the medial marginal vein 4402.

Figure 44G:
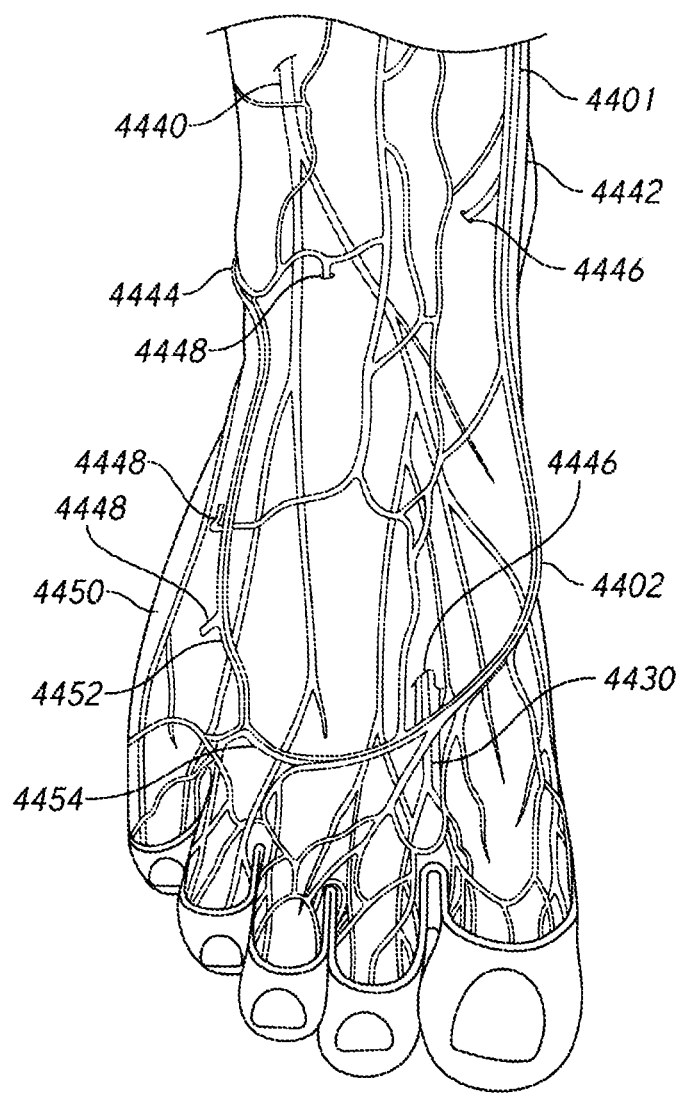

FIG. 44G shows the great saphenous vein 4401, the medial marginal vein 4402, and the deep peroneal nerve 4430. In addition, FIG. 44G shows the superficial peroneal nerve 4440, the saphenous nerve 4442, the small saphenous vein 4444, medial perforating veins 4446, lateral perforating veins 4448, the sural nerve 4450, the lateral marginal vein 4452, and the dorsal venous arch 4454.

Figure 44H:
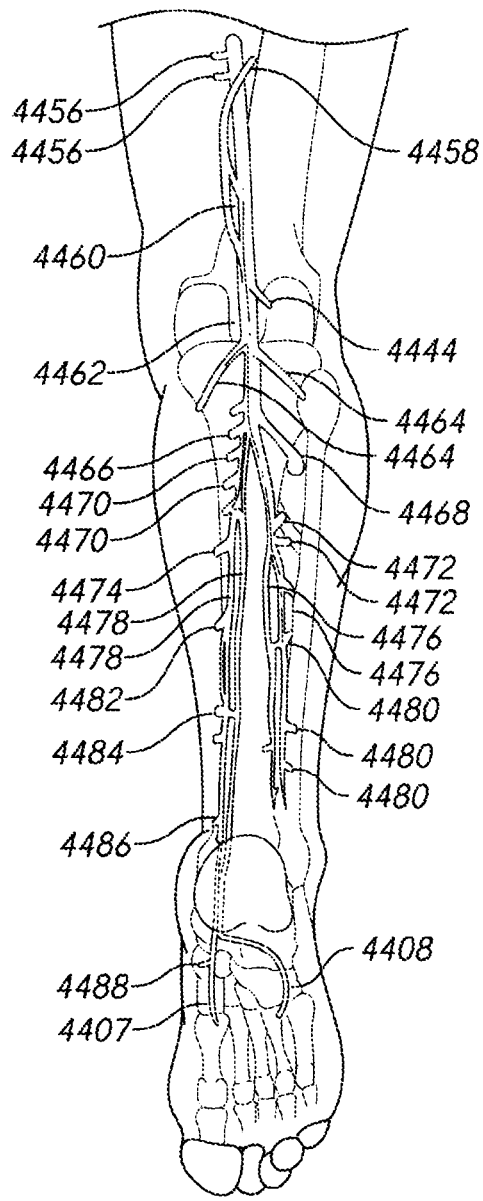

FIG. 44H shows the medial plantar vein 4407, the lateral plantar vein 4408, and the small saphenous vein 4444. In addition, FIG. 44H shows perforators of the femoral canal 4456, an anastomosis to the deep femoral vein 4458, the femoral vein 4460, the popliteal vein 4462, the medial and lateral gastrocnemius veins 4464, a soleal vein 4466, the anterior tibial vein 4468, paratibial perforators 4470, soleal veins 4472, a soleal vein 4474, peroneal veins 4476, posterior tibial veins 4478, lateral leg perforators 4480, the upper posterior tibial perforator 4482, the middle posterior tibial perforator 4484, the lower posterior tibial perforator 4486, and the medial ankle perforator 4488.

Figure 44I:
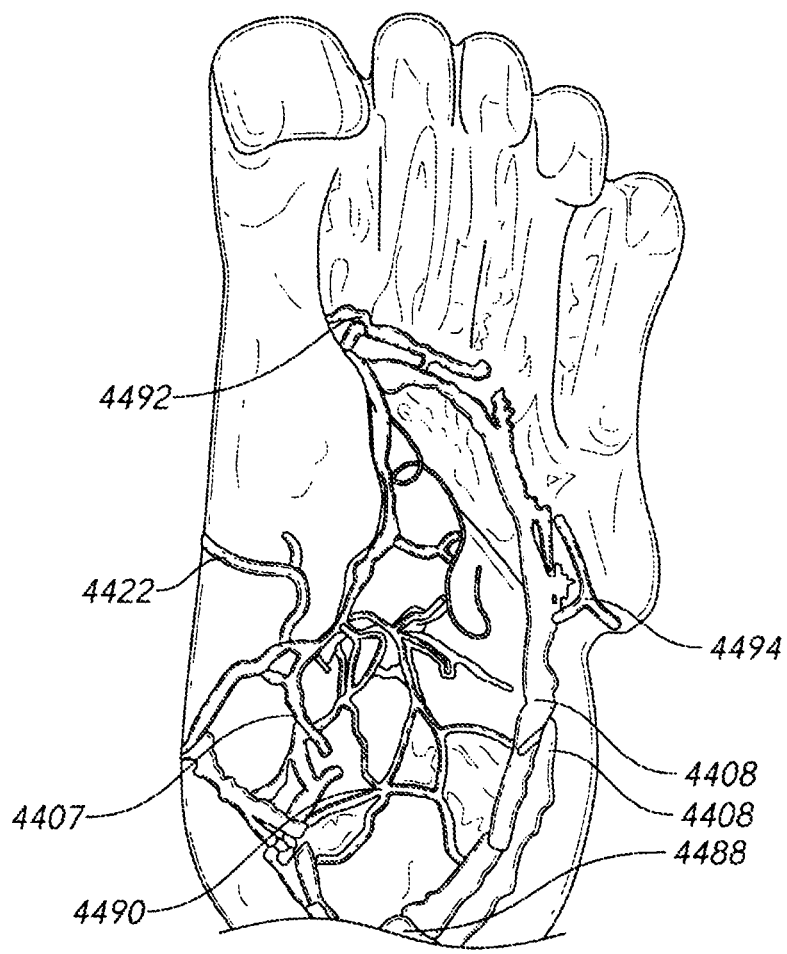

FIG. 44I is an inferior view of an anatomical dissection of lower foot veins. FIG. 44I shows medial plantar veins 4407, lateral plantar veins 4408 (double), and the navicular perforator 4422. In addition, FIG. 44I shows the calcaneal crossroad 4488 of the plantar veins, a plexus-shaped network 4490 of the sole, the perforator 4492 of the intermetatarsal space, and a perforator 4494 of the fifth metatarsal bone.

Figure 44J:
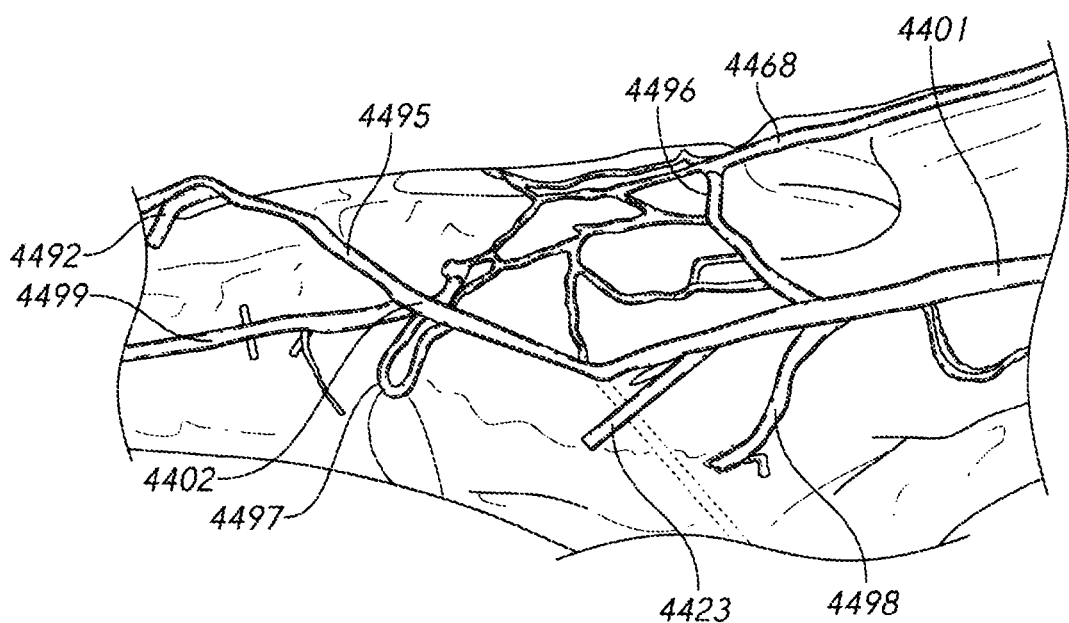

FIG. 44J is a medial view of an anatomical dissection of lower foot veins. FIG. 44J shows medial marginal vein 4402, the great saphenous vein 4401, the anterior tibial vein 4468, and the perforator vein 4492 of the first intermetatarsal space. In addition, FIG. 44J shows a dorsal perforator vein 4496 that is communicating with the anterior tibial vein 4468, the submalleolar foot perforator vein 4498, the navicular perforator vein 4423, the dorsal arcade 4495 of the foot, a dorsal perforator vein 4497, and the dorsal vein 4499 of the Hallux.

Certain techniques of deep vein arterialization of the foot can target arterial inflow at the level of the pedal veins and retrograde flow into the venous pedal arch, which is the continuation of the lateral or medial plantar vein(s) through the first intermetatarsal space perforator and into the anterior tibial venous vein(s).

Figure 45:
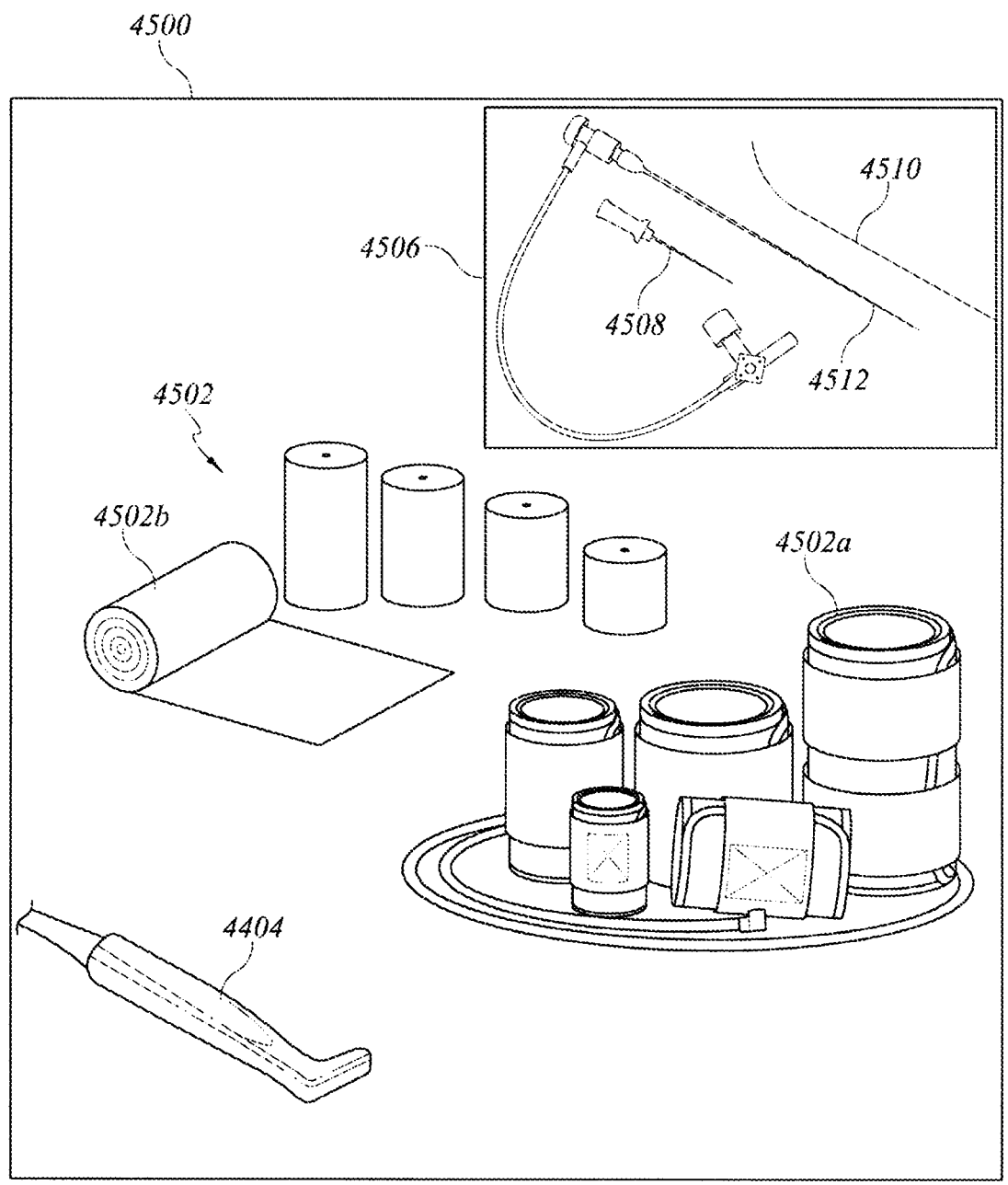
FIG. 45 shows example components of a kit that may be used for pedal access.

FIG. 45 shows example components of a kit 4500 that may be used for pedal access. The kit 4500 includes a tourniquet 4502, an ultrasound probe 4504, and a puncture set 4506. The tourniquet 4502 may comprise a pneumatic tourniquet 4502a. The tourniquet 4502 may comprise an Esmarch tourniquet 4502b. The kit 4500 may comprise a series of tourniquets 4502 having various sizes (e.g., as shown in FIG. 45) and/or various types of tourniquets 4502 (e.g., as shown in FIG. 45). The ultrasound probe 4504 may comprise ultrasound appropriate for high definition venous imaging of target pedal vessels. The kit 4500 may comprise a liquid or gel configured for use with the ultrasound probe 4504. The puncture set 4506 may comprise an echogenic needle 4508 and a guidewire 4510. The needle 4508 would be compatible with the diameter of the guidewire 4510, and may be selected based the depth and anatomic limitations of pedal venous structures. The needle 4508 may be fitted with a Tuohy-Borst adaptor to prevent backflow of blood. The guidewire 4510 may be, for example, 0.018 inches. The puncture set 4506 may comprise a dilator (e.g., a 2.9 Fr inner dilator fitted within a side arm for injection). The kit 4500 may comprise multiples of the described components, additional components, and/or may lack one or more of the described components. Some or all of the components of the kit may be sterile. For example, the ultrasound probe 4504 can be covered with a sterile bag, whereas the puncture set 4506 used must be sterile.

An example procedure, for example using the kit 4500, comprises using an ultrasound probe 4504 on the surface of the foot to guide a puncturer with a needle 4508. A guidewire 4510 is then inserted through the needle 4508. In some embodiments, a dilator 4512, optionally including a side arm for injections, may be optionally tracked over the guidewire 4510. The guidewire 4510 is then removed. Contrast is injected into the dilator 4512 (e.g., through the optional side arm). The volume of contrast may be, for example, about 5 mL to about 50 mL (e.g., about 5 mL, about 10 mL, about 15 mL, about 20 mL, about 25 mL, about 30 mL, about 35 mL, about 40 mL, about 45 mL, about 50 mL, ranges between such values, etc.). The contrast may be a solution, for example about 50% contrast and about 50% saline. The contrast extends to the veins in the top of the foot, the bottom of the foot, and up towards the ankle, providing a roadmap of the venous vasculature in the foot. The same or a different guidewire 4510 may then be inserted into the dilator 4512 and navigated into the venous anatomy of the user's choice based on all of the known veins.

In some examples, the subject can be set in a reverse Trendelenburg position, with the head being elevated above the feet, for example between about 30 degrees and to about 45 degrees. Fluoroscopy (e.g., Digital Subtraction Imaging (DSI) selecting a large (e.g., maximum) frame size that includes all images/pathways of the veins in the foot, for example, can be used to visualize aspects of the procedure.

A first tourniquet can be positioned above the knee and a second tourniquet can be positioned above the ankle on the leg of interest. The first tourniquet can at least partially contribute to expanding the veins below the knee. The second tourniquet may at least partially contribute to expanding the veins below the ankle. The first tourniquet can be the same type and/or size as the second tourniquet (e.g., both being pneumatic tourniquets; both being Esmarch tourniquets; etc.). The first tourniquet can be different than the second tourniquet in size and/or type (e.g., one being a pneumatic tourniquet and the other being an Esmarch tourniquet; both being pneumatic tourniquets having different sizes; etc.). The second tourniquet can block contrast from entering superficial veins, forcing the contrast into the deep veins.

In some embodiments, a metatarsal vein 4434, dorsal or plantar, can be used for injection of contrast. Palpating or tapping the vein of interest with fingers can improve success rate of the vein dilating. When the metatarsal vein 4434 is successfully cannulated, the second tourniquet around that ankle should be tight and/or should remain tight. The subject may be flattened on the table (e.g., if originally in a reverse Trendelenburg position). Contrast may be injected into the venous vasculature from the metatarsal vein 4610 (e.g., for an ascending venogram procedure). Contrast may be injected into the venous vasculature from the great saphenous vein towards the foot (e.g., for a descending venogram procedure). One or both of the tourniquets can block contrast from entering the superficial veins, forcing the contrast into the deep veins. Anteroposterior (AP) and lateral views can be taken under fluoroscopy.

Non-ionic contrast can be used. The contrast may be warmed for ease of use, but is preferably not warmed greater than body temperature. The contrast may comprise a 50/50 mixture or dilution. For example, the contrast may comprise, about 15 mL of contrast diluted with 15 mL of saline. The contrast may comprise a total volume injection between about 5 mL and about 50 mL (e.g., about 5 mL, about 10 mL, about 15 mL, about 20 mL, about 25 mL, about 30 mL, about 35 mL, about 40 mL, about 45 mL, about 50 mL, ranges between such values, etc.). All or substantially all of the veins of the foot that may be potentially used for pedal access may be mapped by this quantity of contrast. More or less contrast can be used based on the subject (e.g., more for larger subjects, less for smaller subjects and/or subjects with partial feet). The second tourniquet around the ankle may be removed after mapping the veins of the foot, keeping the first tourniquet above the knee on and in place.

The injection site may be continuously monitored for possible extravasation of the contrast into soft tissue of the subject's foot. If contrast extravasation is detected, the user may apply slight pressure to the access site to slow down/stop the extravasation, and continue to monitor.

If an occlusion is in an anterior tibial artery, pedal access may target the anterior tibial vein. A tourniquet is first placed above the ankle (e.g., to expand the veins). Guided by ultrasound, ascending venous access (towards the leg) may be obtained with a needle in the dorsal first metatarsal vein 4610 (aligned with the medial vein). A 21 gauge needle, for example, can accommodate a 0.018" guidewire. An atraumatic guidewire (e.g., having a J-shaped tip) can be advanced into the first metatarsal vein 4610. Once the guidewire is in the first metatarsal vein 4610, the needle can be removed, leaving the cannula or inserting an inner dilator. The first metatarsal vein 4610 may then be flushed through a side arm with heparinized saline. If the cannula is not properly positioned in the first metatarsal vein, the skin will blister with saline. Another method for checking positioning is to inject a small amount of a contrast medium (e.g., if the contrast flows through the vein, if the contrast pools around the vein). Another method for checking positioning is to aspirate to see if blood comes out. Preferably, at least one check is performed to make sure the cannula is properly positioned in the vein prior to injection of a large amount of contrast medium. A dorsal and plantar venogram can be performed with an injection of contrast medium (e.g., about 5 mL to about 50 mL). A target tibial vein is selected using the venogram, and the guidewire is advanced to the target tibial vein. The tourniquet can be removed once the guidewire is in the target tibial vein. The guidewire can then be used to track devices (e.g., a target catheter for forming a fistula) through the target tibial vein.

If an occlusion is in a posterior tibial artery, which is more common than an anterior tibial artery, pedal access may target a lateral plantar vein. A tourniquet is first placed above the ankle (e.g., to expand the veins). Guided by ultrasound, ascending venous access (towards the leg) may be obtained with a needle in the dorsal medial marginal vein 4402 (towards the toes). A 21 gauge needle, for example, can accommodate a 0.018" guidewire. An atraumatic first guidewire (e.g., having a J-shaped tip) can be advanced into the first metatarsal vein. Once the first guidewire is in the first metatarsal vein, the needle can be removed, leaving the cannula or inserting an inner dilator. The dorsal medial marginal vein 4402 may then be flushed through a side arm with heparinized saline. If the cannula is not properly positioned in the dorsal medial marginal vein 4402, the skin will blister with saline. Another method for checking positioning is to inject a small amount of a contrast medium and see what happens (e.g., if the contrast flows through the vein, if the contrast pools around the vein). Another method for checking positioning is to aspirate fluid to see if blood comes out. Preferably, at least one check is performed to make sure the cannula is properly positioned in the vein prior to injection of a large amount of contrast medium. A dorsal and plantar venogram can be performed with an injection of contrast medium (e.g., about 5 mL to about 50 mL).

Since the occlusion is in a posterior tibular artery, methods described herein can divert oxygenated blood from the posterior tibial artery into the posterior tibial vein. The larger of the two lateral plantar veins is selected using the venogram, and the first guidewire is advanced to a crossing point or at least above the ankle. Again using ultrasound guidance on the skin, the plantar veins may be surveyed from the bottom of the foot to view the position of the first guidewire.

The second access should be made as distal as possible in the plantar arch with a needle in the lateral plantar vein with the first guidewire therein. A 21 gauge needle, for example, can accommodate a 0.018" guidewire. An atraumatic second guidewire (e.g., having a J-shaped tip) can be advanced into the lateral plantar vein and then into the posterior tibial vein and up to the crossing point. Once the second access has been made, the first guidewire could be removed. In some examples, once the second access point has been selected, the first guidewire could be removed. The ankle tourniquet can be removed once the second guidewire is in the target posterior tibial vein. The second guidewire can then be used to track devices (e.g., a target catheter for forming a fistula) through the target posterior tibial vein. If a user tried to advance the first guidewire to the posterior tibial vein from the top of the foot, the first guidewire would be at a weak position and could tear tissue. The second guidewire is on the bottom of the foot where the veins are larger, and provides more robust access.

Example procedures for performing an ascending venogram, dorsal or plantar, procedure, are described in FIGS. 46A-46H with reference to the anatomy described in FIGS. 44A-44F and the kit 4500 of FIG. 45.

Figure 46A:
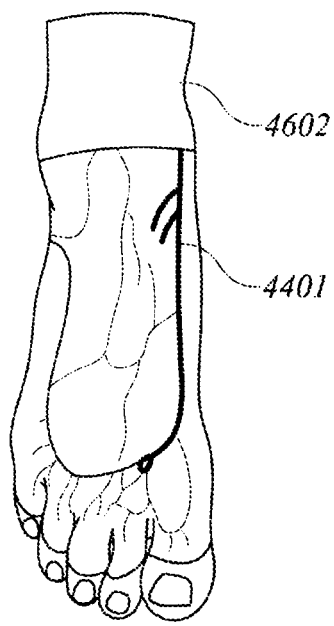
Figure 46B:
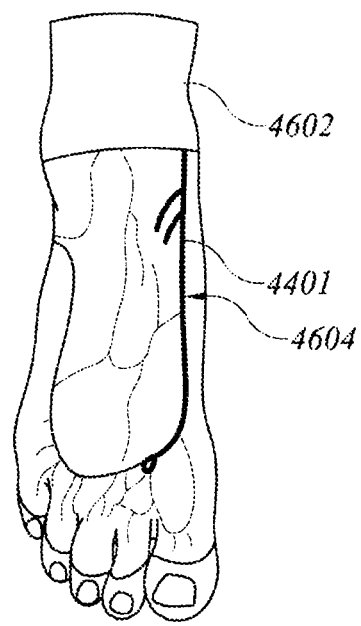
Figure 46C:
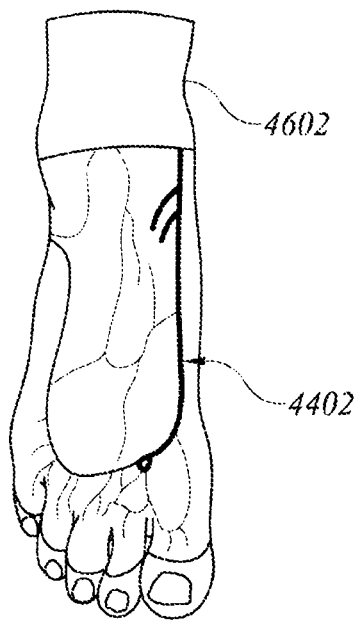
Figure 46D:
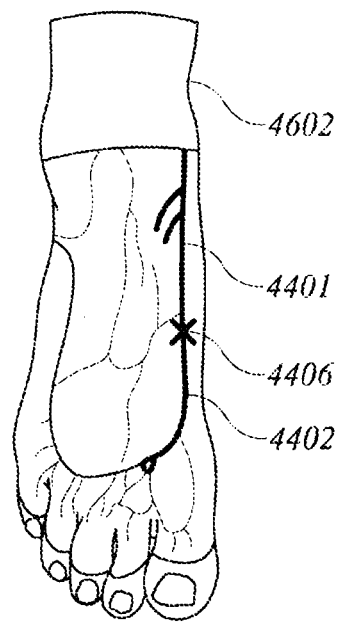

In FIG. 46A, a tourniquet 4602 is placed above the ankle to increase venous pressure in the foot. In FIG. 46B, the great saphenous vein 4401 is located. In some examples, the medial malleolus 4604, which is a prominence on the inner side of the ankle formed by the lower end of the tibia, can be used to help locate the great saphenous vein 4401. In FIG. 46C, the great saphenous vein 4401 is traced toward the toes. The great saphenous vein 4401 leads to the medial marginal vein 4402. The intersection between the great saphenous vein 4401 and the medial marginal vein 4402 is the location of the first access site 4606, marked by a red X in FIG. 46D. Tapping the medial marginal vein 4402, for example with a user's fingers, can increase vasodilation, as schematically illustrated in FIG. 46E. FIG. 46E still shows the first access site 4606.

In FIG. 46F, a first needle 4608 is used at the access site 4606 to access the medial marginal vein 4402 towards the toes. In some examples, the first needle 4608 may comprise a 21 gauge needle. A quantity of contrast fluid is injected through the first needle 4608. In some examples, the contrast comprises contrast fluid diluted with saline. In some examples, the quantity comprises between about 5 mL and about 50 mL (e.g., about 5 mL, about 10 mL, about 15 mL, about 20 mL, about 25 mL, about 30 mL, about 35 mL, about 40 mL, about 45 mL, about 50 mL, ranges between such values, etc.). The contrast provides a roadmap venogram for identifying a second assess site.

Figure 46H:
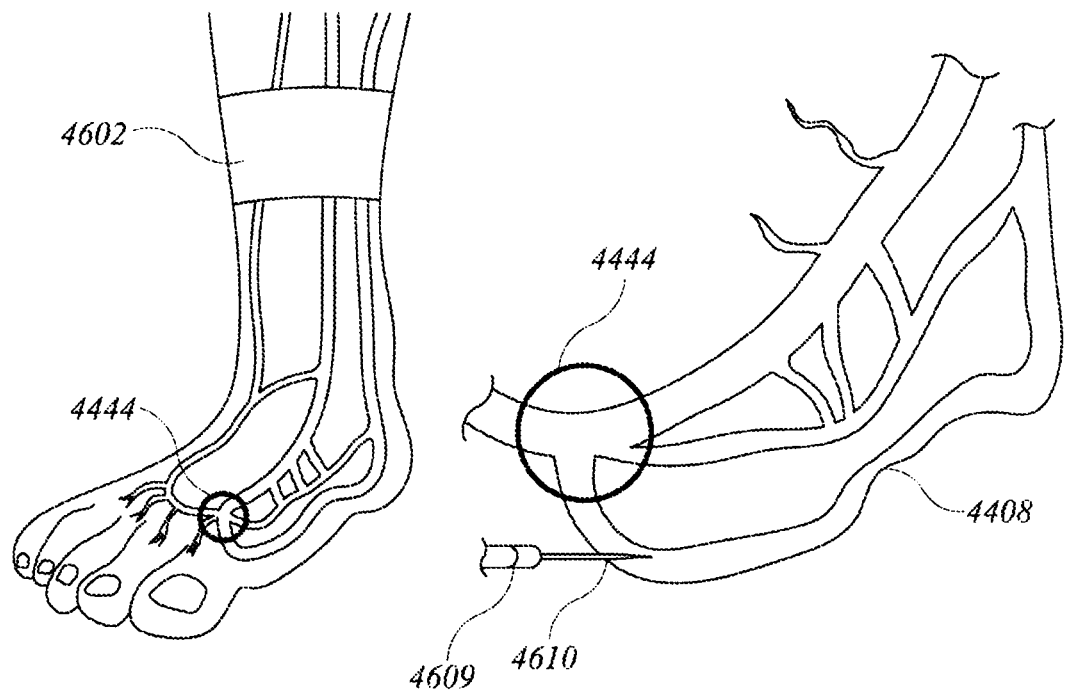
Figure 46I:
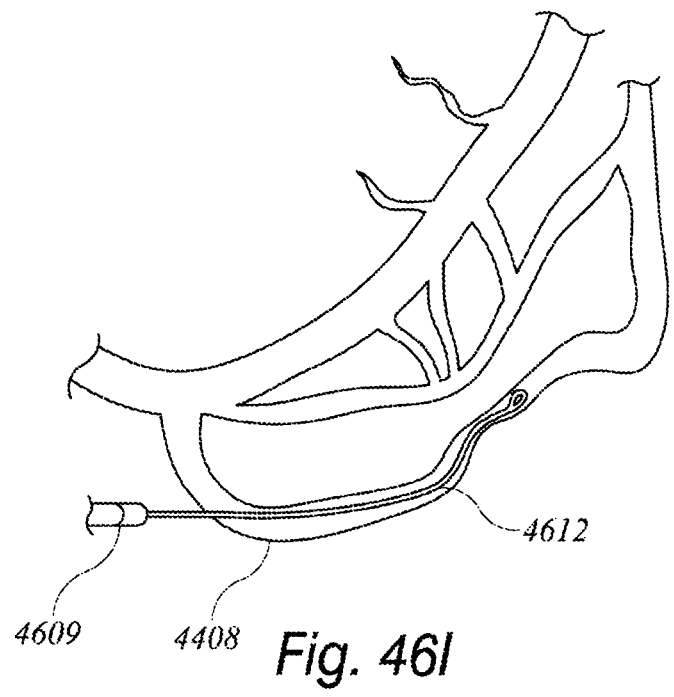
Figure 46J:
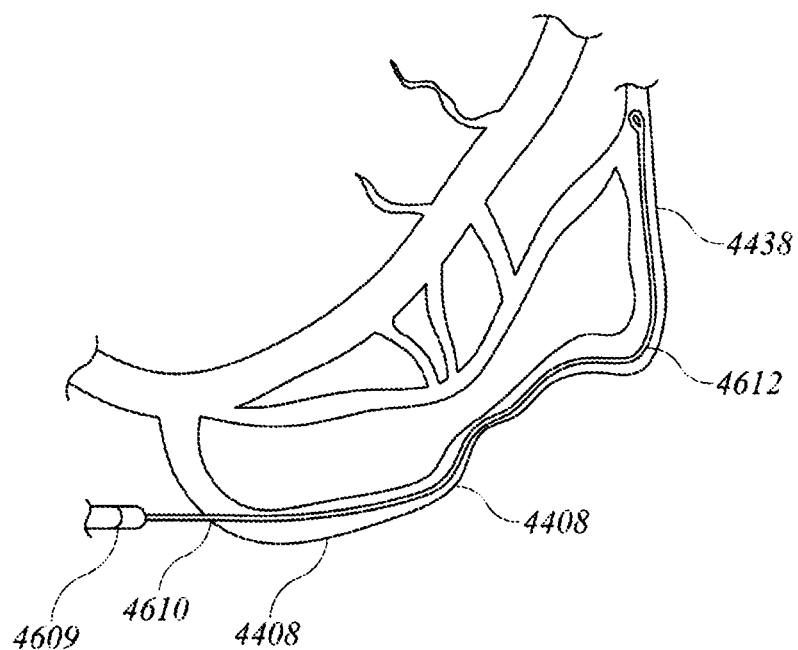

In FIG. 46G, the first metatarsal perforator 4406 connects plantar veins on the bottom of the foot to dorsal veins on the top of the foot. In FIG. 46H, a second needle 4609 is used at a second access site 4610 proximate to the first metatarsal perforator 4406 to access a lateral plantar vein 4408 towards the fifth toe. In some examples, the second needle 4609 may comprise a 21 gauge needle. In FIG. 46I, a guidewire 4612 is used to access the lateral plantar vein 4408, for example with the tip of the guidewire 4612 prolapsed. In some examples, the guidewire 4612 may comprise an 18 gauge guidewire. An 18 gauge guidewire 4612 can fit through the lumen of a 21 gauge needle. In FIG. 46J, the guidewire 4612 is advanced through the lateral plantar vein 4408 into the posterior tibial vein 4438.

Figure 46K:
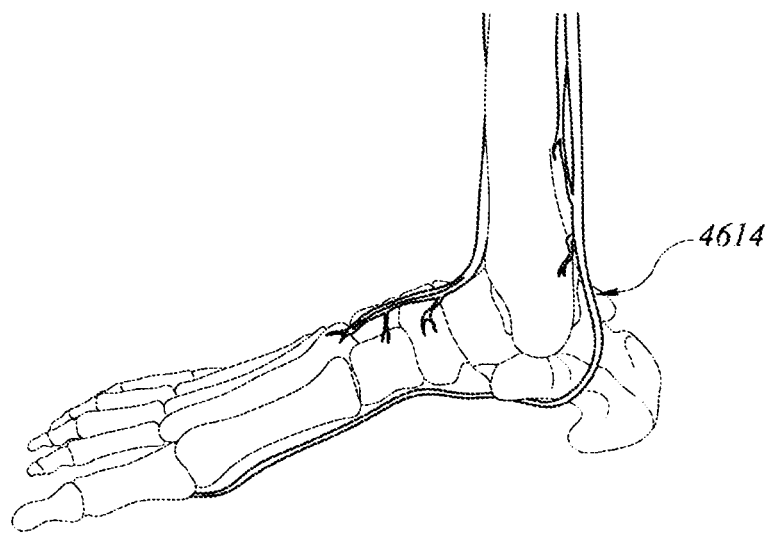

The tourniquet 4602 can be removed. In some examples, the tourniquet 4602 or a different tourniquet can be placed above the knee. Under ultrasound guidance, the tibial vein 4614 with the guidewire 4612 therein can be selected for placement of a tibial access sheath, as shown in FIG. 46K. In some examples, the tibial access sheath comprises a 5 Fr sheath. The guidewire 4612 can be used for a vein targeting procedure, for example as described herein. The guidewire 4612 can be used for over-the-wire procedures such as fistula formation (e.g., a target catheter, a launching catheter), prosthesis placement, valve disabling, vessel lining, etc., as described herein, and the like. The pedal access procedures described herein can advantageously provide unique access point that can provide a greater amount of access to foot vessels, which can provide more flexibility in procedures and/or more access to affect vessels.

In some examples, a method comprises inserting a reentry catheter (e.g., Outback, available from Cordis) into a pedal vein to access a tibial vein, inserting a snaring device in an arterial vasculature, tracking the snaring device to a tibial artery adjacent to the tibial vein, advancing a needle of the reentry catheter from the tibial vein towards the snare in the tibial artery, advancing a wire through the needle, snaring the wire, and retracting the snare out of the arterial vasculature. The wire can be used, for example, to create a fistula, position a prosthesis or multiple prostheses, disable valves, etc., for example as described herein.

The present application discusses several examples in which a guidewire advanced through a fistula from a first vessel into a second vessel is captured by a snare. In some examples, a valvulotome (e.g., reverse valvulotome or two-way valvulotome) is advanced over the guidewire after the guidewire has been pulled through the vessel by the snare. In some examples, a valvulotome or cutting device may be integrated or otherwise incorporate with the snare in a cutting snare system. A cutting snare system can provide advantages such as reducing an overall number of steps in a procedure, reducing a number of device exchanges, reducing procedure time, improving effectiveness of a valvulotome, reducing procedure components, improving procedure cost of goods, and/or other advantages.

FIG. 47A is a perspective view of a portion of an example cutting snare system 4700. The cutting snare system 4700 comprises a snaring mesh 4702 and cutting blades 4706. The snaring mesh 4702 may be cut from a hypotube to form cells capable of or configured to receive a guidewire (e.g., having an area greater than a diameter of a guidewire to be snared) and struts capable of or configured to capture a guidewire. The cutting snare system 4700 may be tracked over a guidewire (e.g., with an outer sheath) or tracked through a lumen of a catheter (e.g., the catheter acting as the outer sheath).

The illustrated cutting snare system 4700 includes four cutting blades 4706 circumferentially spaced by about 90°. Other quantities of blades 4706 are also possible. For example, the cutting snare system 4700 may comprise one to eight cutting blades 4706 (e.g., 1 blade, 2 blades, 3 blades, 4 blades, 5 blades, 6 blades, 7 blades, 8 blades, and ranges between such values). More than 8 cutting blades 4706 are also possible. In some examples (e.g., as shown in FIG. 47A), the cutting blades 4706 may be longitudinally aligned. In some examples, the cutting blades 4706 may be longitudinally offset. In some examples (e.g., as shown in FIG. 47A), the cutting blades 4706 may be evenly circumferentially spaced (e.g., two blades may be circumferentially spaced by about 180°, three blades may be circumferentially spaced by about 120°, four blades may be circumferentially spaced by about 90°, five blades may be circumferentially spaced by about 72°, six blades may be circumferentially spaced by about 60°, seven blades may be circumferentially spaced by about 51°, eight blades may be circumferentially spaced by about 45°, etc.). In some examples, the cutting blades 4706 may be circumferentially unevenly distributed.

The snaring mesh 4702 has a first outer diameter and the cutting blades 4706 have a second outer diameter. In some examples, the second outer diameter is less than the first outer diameter, which can allow the snaring mesh 4702 to appose sidewalls of the second vessel without the cutting blades 4706 cutting the sidewalls of the second vessel. Where cutting of valves in the second vessel is desired, the valves extend into the second vessel and are able to be cut by the cutting blades 4706.

The cutting snare system 4700 has an expanded state and a compressed state. The cutting snare system 4700 may comprise shape memory (e.g., superelastic) material (e.g., nitinol, chromium cobalt, etc.). The cutting snare system 4700 may comprise stainless steel. The cutting snare system 4700 may comprise polymer. The cutting snare system 4700 may be configured to expand from the compressed state towards the expanded state in the absence of radially inward forces (e.g., from a sheath). In some implementations, the cutting snare system 4700 may be expanded upon application of a longitudinal force to one part of the cutting snare system 4700 (e.g., a proximal end or a distal end) relative to another part of the cutting snare system 4700 (e.g., a distal end or a proximal end).

The snaring mesh 4702 can capture a guidewire, for example as described with respect to other procedures herein. Capturing the guidewire may include radially compressing the snaring mesh 4702 towards the compressed state (e.g., by capturing a proximal portion of the cutting snare system 4700 in a sheath, reversing a longitudinal expansion force, etc.). The cutting snare system 4700 is then pulled proximally, as indicated by the arrow 4707. As the cutting snare system 4700 is pulled through the second vessel, the cutting blades 4706 can cut valves of the second vessel using the same movement or physical act. In some examples, the cutting snare system 4700 can be maneuvered across a valve multiple times to increase cutting.

FIGS. 47Bi and 47Bii are side views of another example cutting snare system 4710. The cutting snare system 4710 comprises a snare structure 4712 and a valvulotome structure 4714 in series. The snare structure 4712 may be proximal to the valvulotome structure 4714 (e.g., as illustrated in FIG. 47Bi). The snare structure 4712 may be distal to the valvulotome structure 4714 (e.g., as illustrated in FIG. 47Bi). The snare structure 4712 may be monolithic or integrally formed with the valvulotome structure 4714 (e.g., as illustrated in FIG. 47Bi). For example, the snare structure 4712 and the valvulotome structure 4714 may be cut from a same hypotube. A monolithic snare structure 4712 and valvulotome structure 4714 can, for example, reduce manufacturing complexity, provide strength to a joint between the snare structure 4712 and valvulotome structure 4714, etc. In some implementations, the snare structure 4712 and the valvulotome structure 4714 may be separately formed an coupled together. Separately formed snare structure 4712 and valvulotome structure 4714 can, for example, provide flexibility in materials, provide flexibility in manufacturing methods (e.g., different cutting or shape-setting methods, independent creation to increase throughput), etc. The cutting snare system 4710 may be tracked over a guidewire (e.g., with an outer sheath 4718) or tracked through a lumen of a catheter (e.g., the catheter acting as the outer sheath 4718). The snare structure 4712 and/or the valvulotome structure 4714 can have the same or similar features to the other snare structures and valvulotome structures described herein, for example cells 4713 configured to capture a guidewire, cutting blades 4716, etc.

In some implementations, the snare structure 4712 can be captured in an outer sheath 4718, leaving the valvulotome structure 4714 expanded, when the valvulotome structure 4714 is proximally retracted to cut valves. In some implementations, the snare structure 4712 can be at least partially out of the outer sheath 4718 when the valvulotome structure 4714 is proximally retracted to cut valves. In some implementations, the cutting snare system 4710 can be used solely as a valvulotome, for example by only expanding the valvulotome structure 4714 (e.g., as shown in FIG. 47Bii).

The snaring structure 4712 has a first outer diameter and the valvulotome structure 4714 and/or the blades 4716 have a second outer diameter. In some examples, the second outer diameter is less than the first outer diameter, which can allow the snaring structure 4712 to appose sidewalls of the second vessel without the cutting blades 4716 cutting the sidewalls of the second vessel. Where cutting of valves in the second vessel is desired, the valves extend into the second vessel and are able to be cut by the cutting blades 4716.

FIGS. 47Ci-47Ciii are side views of another example cutting snare system 4720. FIG. 47Civ is a side view of yet another example cutting snare system 4721. The cutting snare system 4720, 4721 comprises a snare structure 4722 and a valvulotome structure 4724 configured to be in series. The valvulotome structure 4724 may telescope inward of the snare structure 4722 (e.g., as illustrated in FIG. 47Ci). The snare structure 4722 may telescope inward of the valvulotome structure 4724 (e.g., as illustrated in FIG. 47Civ). The cutting snare system 4720, 4721 may be tracked over a guidewire (e.g., with an outer sheath 4728) or tracked through a lumen of a catheter (e.g., the catheter acting as the outer sheath 4728). FIG. 47Cii shows the snare structure 4722 and the valvulotome structure 4724 sheathed in the outer sheath 4728 for tracking over a guidewire and/or through a catheter. The snare structure 4722 and/or the valvulotome structure 4724 can have the same or similar features to the other snare structures and valvulotome structures described herein, for example cells 4723 configured to capture a guidewire, cutting blades 4726, etc.

In some implementations, the snare structure 4722 can be at least partially out of the outer sheath 4728 when the valvulotome structure 4724 is proximally retracted to cut valves. In some implementations, the cutting snare system 4720, 4721 can be used solely as a valvulotome, for example by only expanding the valvulotome structure 4724 through the for the cutting snare system 4720 (e.g., as shown in FIG. 47Ciii) and/or by not expanding the snare structure 4722 for the cutting snare system 4721.

In the cutting snare system 4720, the snaring structure 4722 has a first outer diameter and the valvulotome structure 4724 and/or the blades 4726 have a second outer diameter. In some examples, the second outer diameter is less than the first outer diameter, which can allow the snaring structure 4722 to appose sidewalls of the second vessel without the cutting blades 4726 cutting the sidewalls of the second vessel. Where cutting of valves in the second vessel is desired, the valves extend into the second vessel and are able to be cut by the cutting blades 4726.

In the cutting snare system 4721, the snaring structure 4722 has a first outer diameter and the valvulotome structure 4724 and/or the blades 4726 have a second outer diameter. In some examples, the second outer diameter is greater than the first outer diameter, which can allow the snaring structure 4722 to appose sidewalls of the second vessel, for example when the valvulotome structure 4728 is in the outer sheath 4728 and cannot cut the sidewalls of the second vessel. Where cutting of valves in the second vessel is desired, the valves extend into the second vessel and are able to be cut by the cutting blades 4726. The second diameter being greater than the first diameter can allow the cutting blades 4726 to cut more of the valve.

FIGS. 47Di-47Dv are side views of still another example cutting snare system 4730. The cutting snare system 4730 comprises a snare structure 4732 shown in FIG. 47Di and a valvulotome structure 4734 shown in FIG. 47Dii. The snare structure 4732 and/or the valvulotome structure 4734 can have the same or similar features to the other snare structures and valvulotome structures described herein, for example cells 4733 configured to capture a guidewire, cutting blades 4736, etc. The snare structure 4732 and/or the valvulotome structure 4734 may include an atraumatic distal tip, for example a tapered nose.

The outer sheath 4738 can be left in place, for example after another procedure described herein. The cutting snare system 4730 may be tracked through a lumen or multiple lumens of a catheter 4738, which acts as an outer sheath for the cutting snare system 4730. FIG. 47Div shows the snare structure 4732 extending out of the distal end of the outer sheath 4738. The snare structure 4732 can snare a guidewire, for example as described herein. In some implementations, the snare structure 4732 is sized so that the snare structure 4732 and a captured guidewire can be proximally retracted out of the proximal end of the outer sheath 4738. FIG. 47Dv shows the valvulotome structure 4734 extending out of the distal end of the outer sheath 4738. The valvulotome structure 4732 can be proximally retracted in the direction 4737 to cut valves, for example as described herein.

FIGS. 47Ei-47Eiii are side views of still yet another example cutting snare system 4740. FIG. 47Eiv is a side view of another example cutting snare system 4741. The cutting snare system 4740 comprises a snare structure 4742 and an expandable member 4744 radially inward of the snare structure 4742. The cutting snare system 4740 may be tracked over a guidewire (e.g., with an outer sheath 4748) or tracked through a lumen of a catheter (e.g., the catheter acting as the outer sheath 4748).

The snare structure 4742 can have the same or similar features to the other snare structures described herein, for example cells 4743 configured to capture a guidewire, etc. The snare structure 4742 may include an atraumatic distal tip, for example a tapered nose. The expandable structure 4744 comprises, for example, a balloon and/or a plurality of expandable wires. In some implementations, the expandable structure 4744 is coupled to the snare structure 4742 (e.g., as shown in FIGS. 47Ei-47Eiii). This can, for example, help to ensure alignment of the snare structure 4742 and the expandable structure 4744 when applying a cutting force, as described below. In some implementations, the expandable structure 4744 is separate from the snare structure 4742 (e.g., as shown in FIG. 47Eiv). This can, for example, allow more space for a guidewire during snaring, allow the use of various types of expandable members (e.g., selected for a particular vessel), etc.

The outer sheath 4748 can be left in place, for example after another procedure described herein. The cutting snare system 4740 may be tracked through a lumen or multiple lumens of a catheter 4748, which acts as an outer sheath for the cutting snare system 4740. FIG. 47Eii shows the snare structure 4742 extending out of the distal end of the outer sheath 4748. The snare structure 4742 can snare a guidewire, for example as described herein. In some implementations, the snare structure 4742 is sized so that the snare structure 4742 and a captured guidewire can be proximally retracted out of the proximal end of the outer sheath 4748. After the cutting snare system 4740 has been proximally retracted out of the proximal end of the outer sheath 4748, the cutting snare system 4740 may be reinserted into the outer sheath 4748 (e.g., as illustrated in FIG. 47Eiii) and/or over a guidewire. In some implementations, a separate cutting snare system 4740 may be inserted into the outer sheath 4748 and/or over a guidewire.

FIGS. 47Eii and 47Eiii show the cutting snare system 4740 extending out of the distal end of the outer sheath 4748. In some implementations, the cutting snare system 4740 is across a valve (e.g., in a vein). In FIG. 47Eii, the expandable structure 4744 is partially expanded (e.g., inflated) within the snare structure 4742. In FIG. 47Eiii, the expandable structure 4744 is further expanded (e.g., inflated) within the snare structure 4742 until the expandable structure 4744 applies a radially outward force, as indicated by the arrows 4747, to the snare structure. The force can press the struts or mesh of the snare structure 4742 into valve leaflets, which can cut the valve leaflets and/or disable the valve.

The amount of expansion pressure may be related to the sharpness or aggressiveness of the cutting mechanism (e.g., blade, wire, etc.). The expansion pressure may be between about 4 atm (approx. 405 kPa) and about 20 atm (approx. 2,026 kPa) (e.g., about 4 atm (approx. 405 kPa), 7 atm (approx. 709 kPa), 10 atm (approx. 1,013 kPa), 15 atm (approx. 1,520 kPa), 20 atm (approx. 2,026 kPa), ranges between such values, etc.). Pressures higher and lower than those listed may be possible depending on the cutting mechanism.

Lower pressure may be useful for sharp, aggressive cutting blades. In some examples, a lower pressure balloon with a more aggressive blade potentially has the advantage of cutting the valve while causing less trauma to the surrounding vessel tissue. In the initial contact of the blades with the valve, force is localized at the blade. The sharper the blade, the less force required. As the balloon engages the wall, the lower force is maintained, causing less distention to the vein.

Higher pressure may be useful for a mild cutting wire or no wire at all. In some examples, the mechanical properties of the valve tissue make the valve very resistant to traditional balloons. A higher-pressure balloon (e.g., cutting or not) can exert more force that might be needed to defeat the valve. Blades on a cutting balloon may initiate a cut, but the balloon can further propagate these cuts. Higher force may enable greater propagation of the cut, more effectively disabling the valve.

The expandable member 4744 can be deflated or reduced, and the cutting snare system 4740 can be moved, for example to extend across a second valve. The expandable structure 4744 can be again expanded (e.g., inflated) to disable the second valve. The process may be repeated for as many valves as are desired to be disabled.

FIGS. 47Fi and 47Fii are side views of yet another example cutting snare system 4750. The cutting snare system 4750 comprises a structure 4752 that can snare a guidewire in a first state and/or a second state and cut valves in the second state. FIG. 47Fi shows the structure 4752 in the first state, in which the structure 4752 has a generally oval form. The structure 4752 can snare a guidewire, for example as described herein, in the first state.

FIG. 47Fii show the structure 4752 in the second state, in which the structure 4752 includes proximal cutting elements 4754. The structure 4752 in the second state can cut valves, for example as described herein. The structure 4752 in the second state can snare a guidewire, for example as described herein. In certain implementations, the structure 4752 can cut valves while the structure 4752 is proximally retracted with a snared guidewire. In some implementations, the guidewire may be snared with the structure 4752 in the first state, and the structure 4752 may be reinserted to cut the valves in the second state.

In some implementations, the structure 4752 can change from the first state to the second state by applying a longitudinal force 4755 to the structure 4752, for example proximally retracting a distal end of the structure 4752 relative to a proximal end of the structure. Other forces are also possible. For example, twisting or torqueing forces, use of temperature induced martensite, etc.

FIGS. 47Gi-47Giii are side views of still another example cutting snare system 4760. The snare cutting system 4760 may comprise a snare structure 4762 and a valvulotome structure 4764 in series, for example as shown in the cutting snare system 4721 of FIG. 47Civ. The snare structure 4762 and/or the valvulotome structure 4764 can have the same or similar features to the other snare structures and valvulotome structures described herein, for example cells configured to capture a guidewire, cutting blades, etc.

In FIG. 47Gi, the snare structure 4762 and valvulotome structure 4764 are collapsed inside the outer sheath 4768. In FIG. 47Gi, the snare structure 4762 has been distally advanced relative to the outer sheath 4768. The snare structure 4762 can snare a guidewire, for example as described herein.

The snare cutting system 4760 comprises an outer sheath 4768 comprising a plurality of elongate apertures 4765. In FIGS. 47Gii, the valvulotome structure 4764 is visible through the apertures 4765. In FIG. 47Giii, the valvulotome structure 4764 has been rotated relative to the outer sheath 4768 such that the struts of the valvulotome structure 4764 can laterally extend from an intermediate portion of the outer sheath 4768 proximal to the distal end of the outer sheath 4768, as shown in FIG. 47Giii. The valvulotome structure 4764 can be proximally retracted in the direction 4767 to disable valves, for example as described herein.

The procedures described herein generally divert blood from a first cavity (e.g., an occluded artery) to a second cavity (e.g., the lateral plantar vein). In some circumstances, a user may desire to divert blood into a different second cavity than the lateral plantar vein. For example, the lateral plantar vein may be perforated (e.g., due to use for a previous surgical bypass procedure), may be occluded (e.g., due to thrombosis and/or stenosis), may be too far from the first cavity, etc. Blood generally flows from high pressure to low pressure along any available return path, so blood may bypass certain restricted areas, whereas the blood would preferably pass through and/or dwell in extremities. Procedures described herein can include providing retrograde blood flow through a plurality of vessels.

Figure 48A:
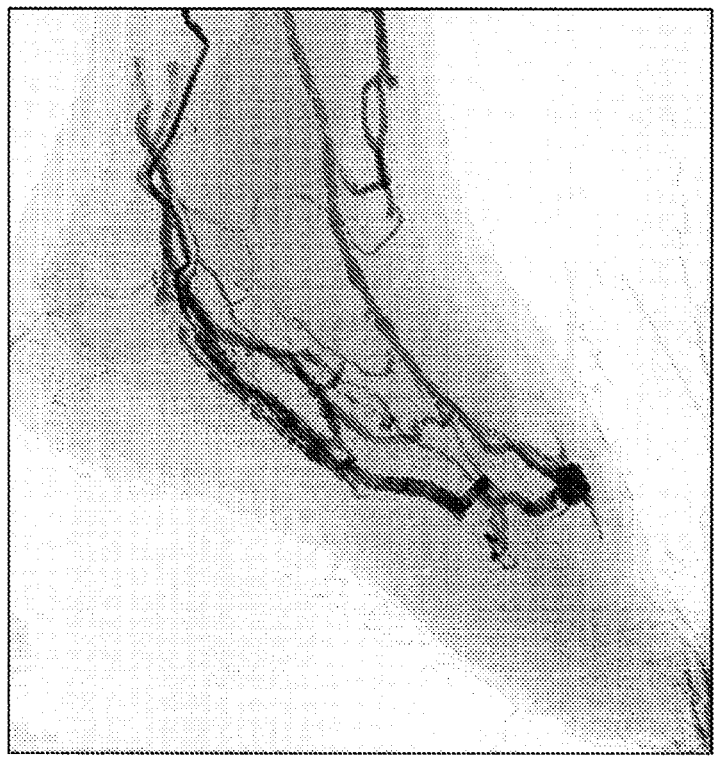
FIG. 48A illustrates an example image of a foot after a venous arterialization procedure.

Occlusions and stenoses in the peripheral arterial system can inhibit or prevent oxygenated blood from reaching the distal limbs/extremities such as the hands and feet. Reduction in peripheral arterial blood flow can impede the body's ability to heal wounds in these areas, and may ultimately result in partial or full amputation of the limb. Arterialization of the venous system, for example as described herein, can allow for oxygenated (normally arterial) blood to reach the distal limb to heal wounds and reduce the risk of amputation. FIG. 48A illustrates an example image of a foot after a venous arterialization procedure. Blood can be seen flowing around major vessels of the foot. Merely establishing a venous circuit with retrograde arterial blood flow may not be enough to drive wound healing.

The quality/performance of the retrograde circuit can be an important consideration, for example including its ability to achieve perfusion of oxygenated arterial blood into the most distal regions of the limb (e.g., forefoot, toes, heel), where wounds are typically present. Achieving distality of blood flow is typically needed for wound healing. If a circuit has been established that has robust flow, the flow may fail to reach the most distal vessels, for example because the blood will tend to return via the "path of least resistance." Methods and devices that allow the establishment of "high quality" retrograde venous circuits in a controlled and planned manner can enable adequate perfusion of the distal limb to heal wounds more effectively and further reduce the risk of amputation. A limb can include an arm and a distal limb could include a hand and/or fingers.

Perfusion in retrograde venous arterialization is a complex function of, for example, blood flow rate, flow volume, pressure, anatomy, physical properties of tissue/blood (e.g., viscosity, etc.), and/or the physical geometry of the circuit (e.g., number of inflow and outflow pathways, size/caliber of the vessels, etc.). Modification of a single or multiple variables may influence one or more other variables, which in turn may increase or decrease the circuit's ability to adequately perfuse blood to the target wound.

An example method of causing perfusion in the retrograde venous circuit is to increase pressure in the circuit by reducing the blood's ability to simply "shunt" back to the venous return to the heart. For example, the embolization of specific "blood-stealing" outflow veins (e.g., side branches) can close off these return veins. Because retrograde blood cannot quickly find a low pressure (low resistance) return pathway, it is forced to move distally, into the small vessels responsible for feeding tissue near the limb surface, where wounds occur. For a given flow rate, reducing the number of outflow vessels will generally increase the pressure in the circuit, increasing the likelihood of distal perfusion. A similar effect can be accomplished via a covered graft, flow-diverting stent, etc. Improving distal perfusion could enhance collateralization and/or neoangiogenesis, which can further improve distal perfusion, for example in the long term.

Figure 48B:
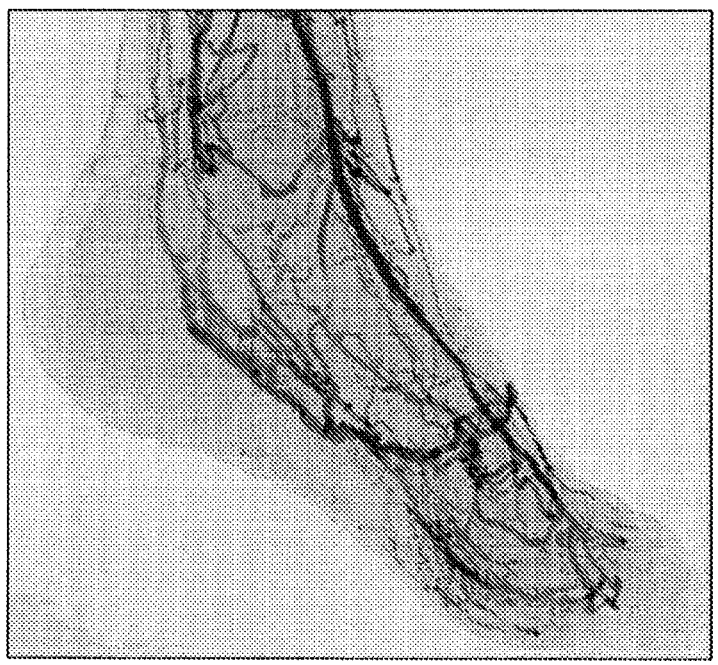
FIG. 48B illustrates another example image of a foot after a venous arterialization procedure.

FIG. 48B illustrates another example image of a foot after a venous arterialization procedure. Compared to FIG. 48A, blood can be seen flowing to many more vessels. Blood flow to more vessels, particularly in an extremity like the foot, can help with wound healing and reduce the risk of amputation. Certain methods described herein can achieve blood flow in all circuits in all veins, including deep and superficial veins. The retrograde flow can start at any peripheral artery, for example as high as the femoral system, continue throughout the tibial system, and continue distal in the foot. For example, the veins that can be claimed by retrograde flow can include greater veins including their redundant veins (e.g., posterior tibial vein, anterior tibial vein, great saphenous vein, small saphenous vein), veins distal to the greater veins and their redundant veins (e.g., lateral plantar vein, lateral marginal vein, medial plantar vein, medial marginal vein, fibular veins, dorsal arcade of the foot, dorsal vein of the Hallux), and perforator veins and their redundant veins that connect the upper and lower vein networks of the foot (e.g., medial foot perforators (inframalleolar, navicular/scaphoid, cuneal), lateral foot perforators (intertendinous, subtendinous), and calcaneal foot perforator). In some implementations, blood can flow to some, a majority, or all of these veins.

Figure 49:
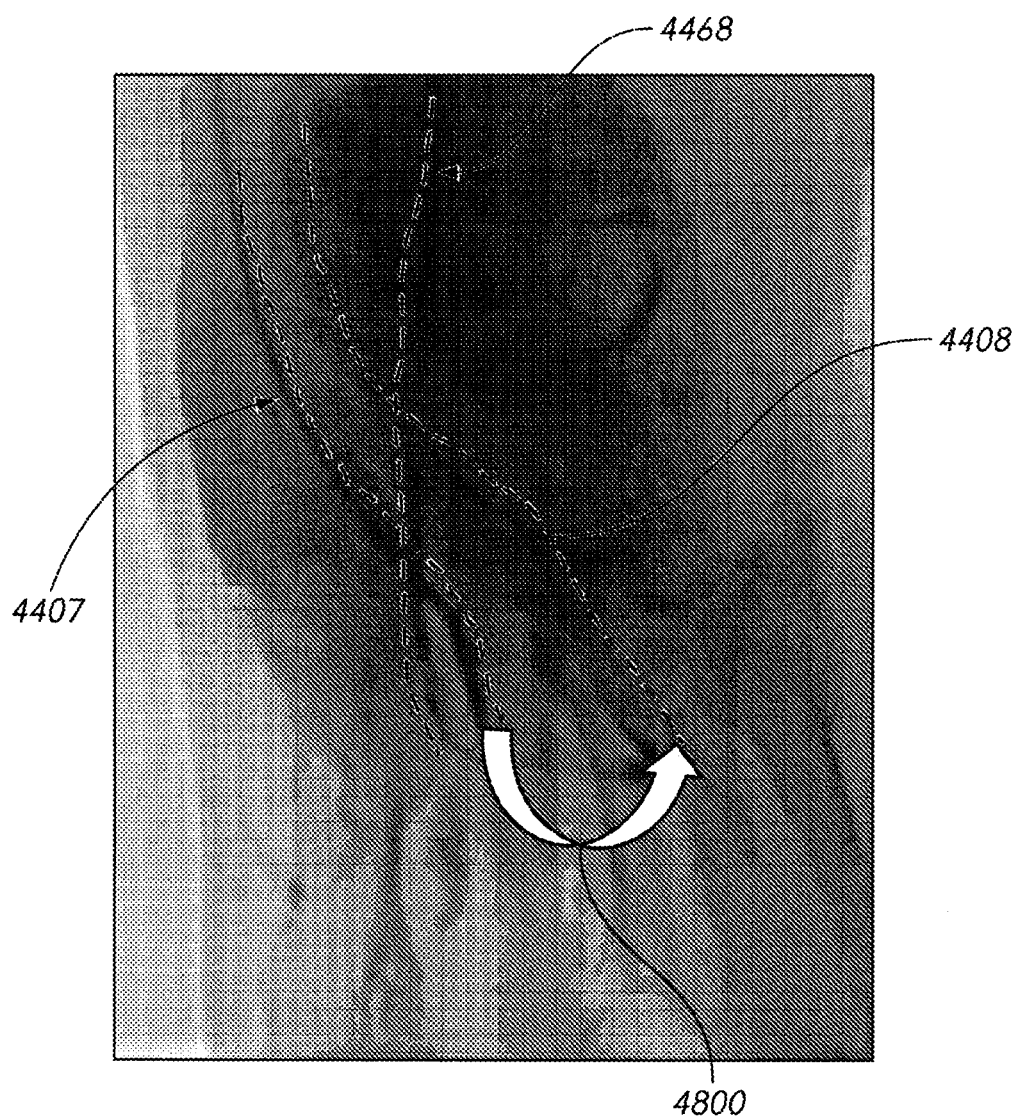
FIG. 49 illustrates an example method of providing blood flow to a plurality of veins.

FIG. 49 illustrates an example method of providing blood flow to a plurality of veins. In an original procedure, blood from an occluded posterior tibial artery was diverted into a medial plantar vein 4407 through a fistula prosthesis (e.g., as described herein). Blood was able to flow from the medial plantar vein 4407 to the anterior tibial vein 4468. In a second procedure several weeks after the first procedure, a loop 4800 was established from the medial plantar vein 4407 to the lateral plantar vein 4408 (e.g., by disabling valves that would otherwise inhibit or prevent flow therebetween). The lateral plantar vein 4408 was accessed downstream of an occlusion therein. A stent was positioned downstream of the fistula in the lateral plantar vein, although the stent could be positioned in any vessel in the retrograde flow circuit for this purpose.

The stent kept the vessel open and patent. The stent kept the valves in the vessel open to permit retrograde flow prosthesis to help maintain a flow deep in the foot, for example by propping open valves. The stent was a paclitaxel-eluting stent (ELUVIA™, available from Boston Scientific), although other drug eluting stents, bare metal stents (e.g., SUPERA®, available from Abbott Vascular), stent-grafts, polymer stents, etc. could also be used. Preferably, the stent can handle the dynamic ankle bend. The stent optionally inhibits or prevents perfusion through sidewalls to or from branch vessels (e.g., by including a graft, having a low porosity such as a flow diverter, etc.). The stent may be small (e.g., 5 Fr, 4 Fr, 3 Fr, or even smaller (e.g., a 3 Fr or 4 Fr woven stent or a 4 Fr or 5 Fr laser cut stent)). The diameter of the stent could be, for example, between about 2 mm and about 6 mm (e.g., about 2 mm, about 3 mm, about 4 mm, about 5 mm, about 6 mm, ranges between such diameters, etc.).

Retrograde flow in the combination of the medial plantar vein 4407 and the lateral plantar vein 4408, which included a vessel on each side of the loop 4800, led to greater perfusion of the arch and the distal foot than either a circuit with only the medial plantar vein or the lateral plantar vein could achieve alone, as blood was forced to flow distally through a collateral network. Without being bound by any particular theory, it is believed that blood was forced to return to the heart via the collateral network rather than larger veins. In some implementations, the lateral plantar vein 4408 could be accessed in the original procedure or after a shorter or longer duration than six weeks. In some implementations, a plurality of fistulas may be formed (e.g., using the procedures described herein) to cause retrograde flow in a plurality of veins. Preferably, the plurality of veins includes one vein on each side of the dorsal venous arch 4454.

In some implementations, retrograde oxygenated blood flow has been established in one or more venous circuits via venous arterialization (e.g., as described herein). Additional methods may be used to further direct flow to specific regions of the foot to increase perfusion.

Some methods can include creating a fistula between a first vessel (e.g., an artery) and a second vessel (e.g., a vein) in the foot (e.g., as opposed to above the ankle), for example using techniques described herein. In the venous system, a plurality of vessels transmit blood back to the heart. The system includes copious redundancy, many interconnections, bifurcations, and confluences. The venous system is a "low pressure" system, as opposed to the higher pressure arterial system. When pressurizing the venous system with arterial blood flow, the blood will take the path of least resistance (e.g., to outflow vessels connected to the low-pressure return, where there are no valves to block flow). Many of these return vessels are proximal to a desired blood path in the distal limb or extremity, and therefore "steal" blood away from the intended target. By terminating one, some, or all of these vessels, flow can be directed and/or pressure can be increased to help increase distal perfusion in a controlled manner.

Figure 50:
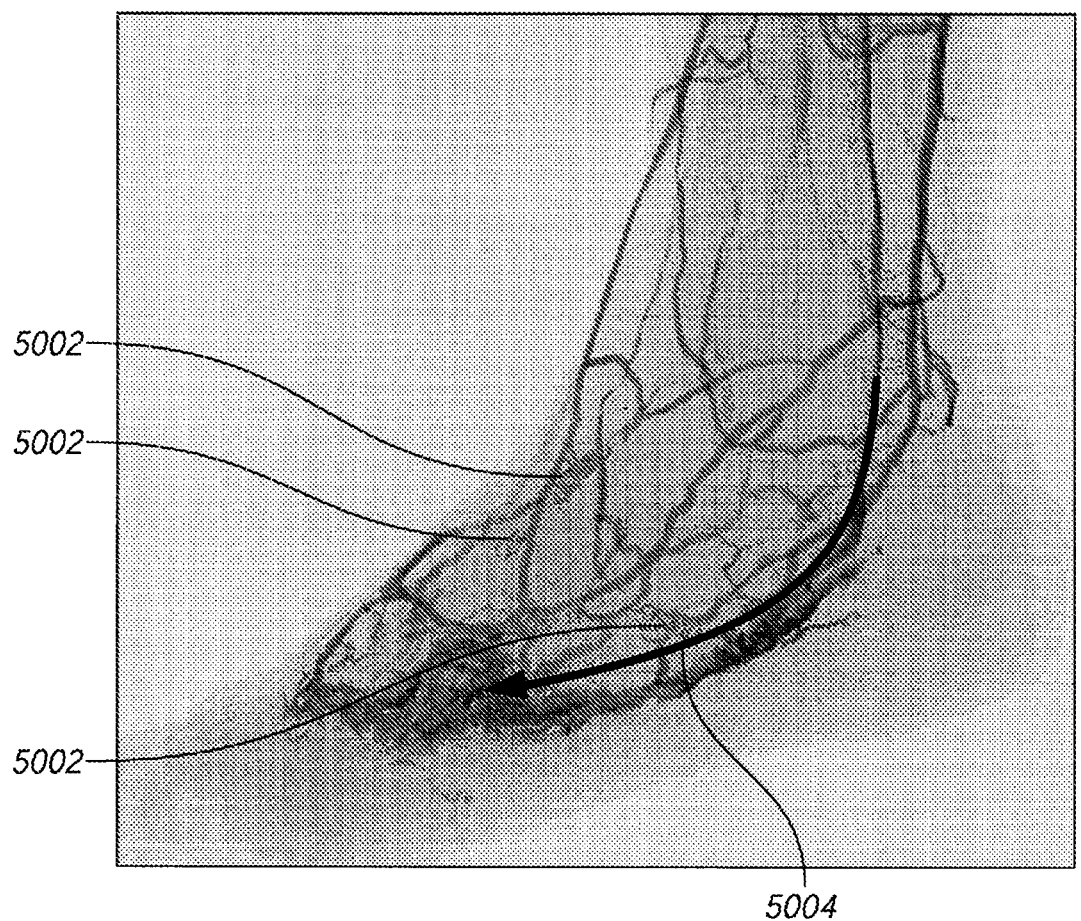
FIG. 50 illustrates a method of using embolization coils to prevent vessel steal and redirect blood distally.

Some methods can include limiting and/or adjusting an outflow in the venous system (e.g., limiting vessel steal or shunting of blood). For example, a stent or stent graft can channel blood past stealing vessels. For another example, bifurcating veins or side branches can be embolized (e.g., via coils, microspheres, liquid embolics, laser, etc.). FIG. 50 illustrates a method of using embolization coils 5002 to prevent vessel steal and redirect blood distally, as annotated by the arrow 5004, which indicates a direction of oxygenated blood flow.

Some methods can include physically directing the retrograde, oxygenated blood into multiple target veins instead of a single target vein (e.g., as described above with respect to FIG. 49). For example, valves can be disabled (e.g., using a valvulotome, balloon, stent, etc.) in more than one vein. Distal pedal access as described herein may help with such disabling by providing access to all of the desired veins including valves to be disabled. Valvulotomes as described herein may help with such disabling by allowing ablation during distal advancement and/or during advancement or retraction. For another example, multiple venous arterializations can be performed to direct the flow of oxygenated blood from two or more arteries into two or more veins, for example one or each using methods described herein. For another example, an increase in pressure in the venous system is able to overcome resistance of the valves, which can aid in perfusion when the pressure increase occurs in veins extending to the distal extremity (e.g., foot, hand, toes, fingers).

Some methods can include applying external pressure (e.g., cuff, tourniquet, wrap) to increase blood pressure in the foot by limiting venous outflow, for example because blood has nowhere to go but distal. The pressure application can be continuous or intermittent. Combinations of these methods are possible, and other methods are possible.

Certain fistula prostheses described herein are configured to direct 100% or all of the fluid from a first vessel into a second vessel. Such a configuration may be most suitable, for example, for treatment of an artery having chronic total occlusion in which the prosthesis is positioned proximate to the occlusion, as anything downstream of the occlusion was likely already occluded. In some circumstances, the artery is not totally occluded, can be at least partially opened, treatment includes placement of the prosthesis well upstream of the occlusion such that healthy branch arteries still providing some benefit might be starved of blood or "jailed," and/or "vessel steal" reduces flow to other vessels. Placement up stream can be the result of a diseased or calcified artery being difficult to cross (e.g., due to calcification, due to compromised and/or poor inflow, etc.) and/or stent. Fluid moves from high pressure to low pressure, so when a high pressure artery is connected to a low pressure vein, blood may have a tendency to flow to the vein, which can compromise or "steal" the amount of blood that flows to other arteries (e.g., peroneal artery). Reduced blood flow in other arteries may cause ischemia and/or pain in anatomy supplied by the vessels having blood stolen therefrom.

Allowing at least some blood to continue to flow in the first vessel, or distal arterial flow preservation, may provide one or more advantages. For example, intentionally placing the prosthesis upstream of an occlusion can allow the crossing and stenting in the first vessel to be in a healthier portion of the first vessel (e.g., little to no calcification, good inflow, etc.) and/or a portion of the first vessel that may be easier to cross into the second vessel. Freedom of placement position can provide significant flexibility to a user. For another example, blood can continue to flow to downstream branch vessels can maintain the existing arterial network, such as maintaining the benefit of those branch vessels. For yet another example, vessel steal can be inhibited or prevented because the blood can continue to flow in the arterial system. Ischemia and/or pain caused from stolen blood might be avoided. For another example, interventional procedures (e.g., plain, drug eluting, and/or scoring angioplasty, atherectomy, PTA, etc.) may be performed downstream of the prosthesis and/or in conjunction with the procedure, allowing percutaneous crossing to be further used as adjunctive therapy with more traditional treatments. Venous arterialization may be performed on a larger class of subjects. For example, while Rutherford Class 5 or 6 patients typically have a critical limb ischemia or chronic total occlusion, Rutherford Class 3 or 4 (or lower) patients may have peripheral artery disease or claudication that only partially occludes an artery. In contrast to other so-called fenestrated stent grafts, such as descending aortic stent grafts with specific cutouts for connecting additional stent grafts to form artificial branch arteries to, for example, the kidneys, or such as aortic stent grafts with specific cutouts to permit perfusion to vessels carrying blood to the head or arms, the windows of the fenestrated stent grafts described herein permit perfusion to continue to the distal parent, and the blood flowing through the main lumen of the fenestrated stent graft is diverted into a second vessel different than the parent.

Figure 51A:
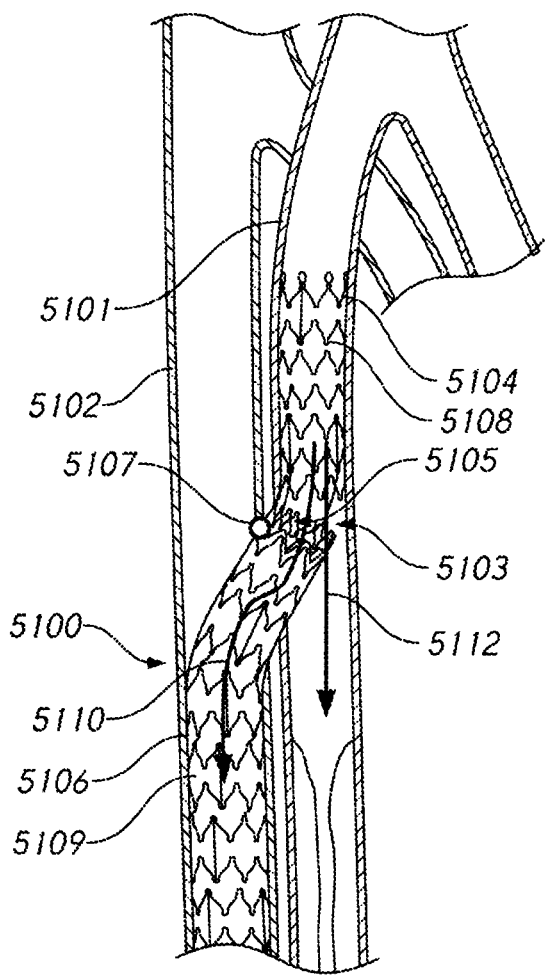
FIG. 51A is a partial cross-section of an example device providing fluid flow from a first vessel to a second vessel and through the first vessel.

FIG. 51A is a partial cross-section of an example device 5100 providing fluid flow from a first vessel 5101 to a second vessel 5102 and through the first vessel 5101. The first vessel 5101 is at least partially occluded. The first vessel 5101 may comprise an artery (e.g., a peripheral artery such as a tibial artery) and the second vessel 5102 may comprise a vein (e.g., a peripheral vein such as a tibial vein). The device 5100 allows at least some blood to continue to flow in the first vessel 5101, and may provide one or more of the distal arterial flow preservation advantages described herein.

The device 5100 comprises a first section 5104 and a second section 5106. The first section 5104 generally abuts or partially overlaps the second section 5106. The device 5100 may comprise a radiopaque marker 5107 showing a transition 5105 between the first section 5104 and the second section 5106. The marker 5107 may be, for example, swaged, electroplated, a threaded wire, a band, change in strut pattern, change in cell structure, etc.

The first section 5104 comprises a stent structure 5108. The stent structure 5108 may comprise woven and/or knitted wires, cut struts, combinations thereof, etc. The first section 5104 comprises pores or apertures 5103 that allow blood to flow into the proximal end of the stent structure 5108 into the stent structure 5108, and then from inside the stent structure 5108 to outside the stent structure 5108, and downstream in the first vessel 5101, as indicated by the arrow 5112. The stent structure 5108 is configured to anchor the first section 5104 in the first vessel 5101. The first section 5104 may comprise a radiopaque marker, for example at the proximal end of the first section 5104. The device 5100 may comprise an additional section proximal to the first section 5104.

The second section 5106 comprises the stent structure 5108 and a covering or graft 5109. The stent structure 5108 may be the same or different (e.g., having at least one parameter that is different (e.g., cell structure, density, porosity, material, dimensions such as diameter, thickness, and/or length), etc.) between the first section 5104 and the second section 5106, and/or within the first section 5104 and/or the second section 5106. The second section 5106 may be integral or monolithic with the first section 5104. The graft 5109 of the second section 5106 is configured to provide a fluid flow passage from the first vessel 5101 to the second vessel 5102, as indicated by the arrow 5110. Blood can flow through the second vessel 5102 as described herein. The graft 5109 preferably does not comprise pores configured to allow blood flow from inside to outside. The stent structure 5108 is configured to anchor the first section 5106 in the second vessel 5102. The second section 5106 may comprise a radiopaque marker, for example at the distal end of the second section 5106. The device 5100 may comprise an additional section distal to the second section 5106. The proximal end of the graft 5109 may be generally perpendicular to a longitudinal axis of the device 5100, which could provide ease of manufacturing and/or deployment (e.g., because rotational orientation does not matter). The proximal edge of the graft 5109 may include a pattern, for example straight, angled, scalloped, eccentric, etc.

Figure 51B:
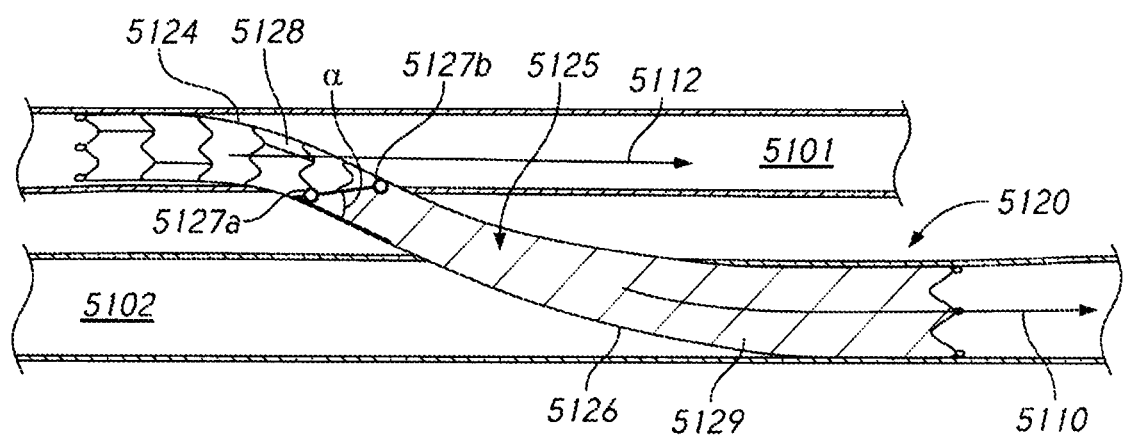
FIG. 51B is a side view of another example device providing fluid flow from a first vessel to a second vessel and through the first vessel.

FIG. 51B is a side view of another example device 5120 providing fluid flow from a first vessel 5101 to a second vessel 5102 and through the first vessel 5101. The device 5120 allows at least some blood to continue to flow in the first vessel 5101, and may provide one or more of the distal arterial flow preservation advantages described herein. The device 5120 may share several of the features of the device 5100 (e.g., first section 5124, second section 5126, stent structure 5128, graft 5129, etc.). The transition 5125 of the device 5120 is not generally perpendicular, but is at an angle α, to the longitudinal axis of the device 5120. The angle α may be measured against a sidewall (e.g., as shown in FIG. 51B), which may be an easy measurement because there is solid material forming both sides of the angle α. The angle α may be measured against an artificial longitudinal axis extending through the device 5120, which may be an easy measurement when sidewalls of the device 5120 are tapered in the transition 5125. The angle α may be, for example, between about 10° and about 70° (e.g., about 10°, about 20°, about 30°, about 40°, about 50°, about 60°, about 70°, ranges between such values, etc.). Higher and lower angles α are also possible, for example for indications in which the second vessel 5102 is close to the first vessel 5101 or far from the first vessel 5101, respectively. The angled transition 5125 may provide better continued flow through the first vessel 5101, as indicated by the arrow 5112, because less of the first vessel 5101 is occluded. Deploying the device 5120 may comprise rotationally orienting the device 5120, for example in the orientation shown in FIG. 51B. The device 5120 may comprise a first radiopaque marker 5127a at the proximal-most point of the transition 5125 and a second radiopaque marker 5127b at the distal-most point of the transition 5125, for example because material for the graft 5129 may be generally radiolucent.

Figure 51C:
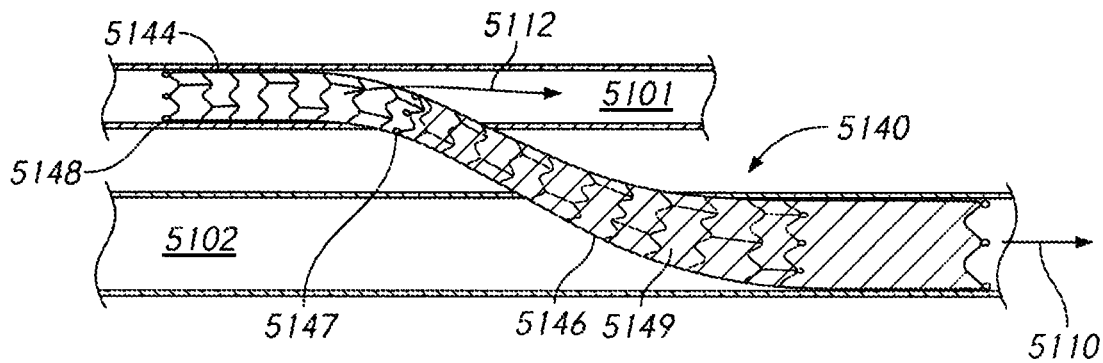
FIG. 51C is a side view of yet another example device providing fluid flow from a first vessel to a second vessel and through the first vessel.

FIG. 51C is a side view of yet another example device 5140 providing fluid flow from a first vessel 5101 to a second vessel 5102 and through the first vessel 5101. The device 5140 allows at least some blood to continue to flow in the first vessel 5101, and may provide one or more of the distal arterial flow preservation advantages described herein. The device 5140 may share several of the features of the device 5100 (e.g., first section 5144, second section 5146, stent structure 5148, graft 5149, etc.). The stent structure 5148 may be the same or different (e.g., having at least one parameter that is different (e.g., cell structure, density, porosity, material, dimensions such as diameter, thickness, and/or length), etc.)) between the first section 5144 and the second section 5146, and/or within the first section 5144 and/or the second section 5146. In some implementations, the second section 5146 may lack a stent structure.

The first section 5144 and the second section 5146 of the device 5140 are separate and deployed sequentially. For example, the first section 5144 may be deployed first and the second section 5146 may be deployed second, with the distal segment of the first section 5144 radially outward of the proximal segment of the second section 5146. The first section 5144 can establish structural support for the fistula. For another example, the second section 5146 may be deployed first and the first section 5144 may be deployed second, with the distal segment of the first section 5144 radially inward of the proximal segment of the second section 5146. The first section 5144 can help prop open the fistula, provide radial outward pressure on the segment of the second section 5166 that overlaps with the first section 5144, and/or reduce turbulence effects that otherwise might be caused by the proximal end of the second section 5146. At least one of the first section 5144 or the second section 5146 may comprise an anchor configured to inhibit or prevent relative movement between the first section 5144 and the second section 5146 after deployment. For example, the anchors may include radially-outward protrusions, hooks, barbs, detents, etc., which may be in the stent structure 5148 or attached to the first section 5144 and/or the second section 5146. In some implementations, the anchors may comprise a ratchet. For example, the first section 5144 and the second section 5146 may be relatively longitudinally and/or rotationally moved relative to each other, for example segment-by-segment, until locked in place. Anchors may facilitate orientation of the device 5140 (e.g., only being anchored when properly oriented). The anchor may interact with the other of the first section 5144 and/or the second section 5146 and/or may interact with the first vessel 5101, the second vessel 5102, and/or interstitial tissue. Limiting relative movement can help to maintain the graft 5149 boundary to ensure that the first vessel 5101 is not jailed. The device 5140 may provide a user with ease of deployment. For example, the first section 5144 can be comfortably deployed to support the first vessel 5101 without much accuracy. Then, the second section 5146 can be deployed using a more accurate deployment system to hit the target (e.g., the proximal end hitting an edge of the first vessel 5101) to ensure that the first vessel 5101 is not jailed.

The first section 5144 anchors in the first vessel 5101, extends through interstitial tissue, and into the second vessel 5102. The second section extends from at least partially in the first vessel 5101, through interstitial tissue, and anchors in the second vessel 5102. At least some segment of the first section 5144 does not overlap with the second section 5146. The non-overlapping segment of the first section 5144 is free from graft material, which allows blood to continue to flow in the first vessel 5101, as shown by the arrow 5112. The second section 5146 allows blood to flow into and through the second vessel 5102, as shown by the arrow 5110. The proximal end of the graft 5149 of the second section 5146 may be substantially perpendicular (e.g., as shown in FIG. 51C), or may be angled (e.g., like the graft 5129 described with respect to the device 5120). The proximal and/or distal ends of the first section 5144 and/or the second section 5146 may comprise a radiopaque marker 5147, for example to help a user determine an anchoring position, an amount of overlap, a rotational orientation, etc.

Figure 51D:
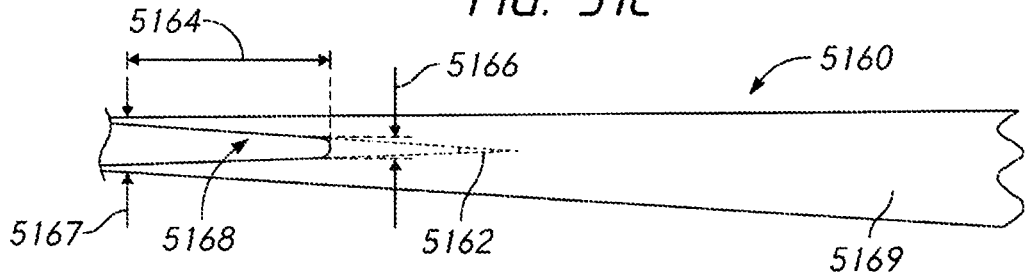
FIG. 51D is a side view of still another example device providing fluid flow from a first vessel to a second vessel and through the first vessel.

FIG. 51D is a side view of still another example device 5160 providing fluid flow from a first vessel to a second vessel and through the first vessel. The device 5160 allows at least some blood to continue to flow in the first vessel, and may provide one or more of the distal arterial flow preservation advantages described herein. The device 5160 may share several of the features of the devices 5100, 5120 (e.g., first section, second section, stent structure, graft 5169, etc.). Only the graft 5169 is shown in FIG. 51D for simplicity. The graft 5169 includes a cutout 5168 where the device 5160 does not include the graft 5169 such that the stent structure is bare. The percentage of bare circumference is variable along the length of the device 5160, for example a V-shaped cutout 5168 (e.g., as shown in FIG. 51D) that reduces from a first percentage (e.g., about 50%) of bare stent structure to a second percentage (e.g., about 10%) of bare stent structure less than the first percentage as the device 5160 extends distally. A lower percentage may be advantageous for orienting the device 5160. The percentage generally relates to the flow resistance through the first vessel. In anatomy where more flow is desired (e.g., proximal or upstream in the first vessel (e.g., closer to the groin)), the percentage may be higher so that more blood can flow to the larger and/or more numerous vessels downstream. In anatomy where less flow is desired (e.g., distal or downstream in the first vessel (e.g., closer to the foot)), the percentage may be lower so that more blood can flow to the second vessel.

In general, the cutout 5169 of the device 5160 can be at least partially defined using a few variables that describe the opening in the covering: the angle 5162 from proximal to distal; the length 5164; the width 5166 at the proximal end of the cutout 5169; and/or the width 5167 at the distal end of the cutout 5169. These variables can be adjusted or tuned to correspond to any overall shape, with other features (such as scallops) possible at a more detailed level. The device 5169 can include as many cutouts as desired, at any length along the device 5160.

Figure 52A:
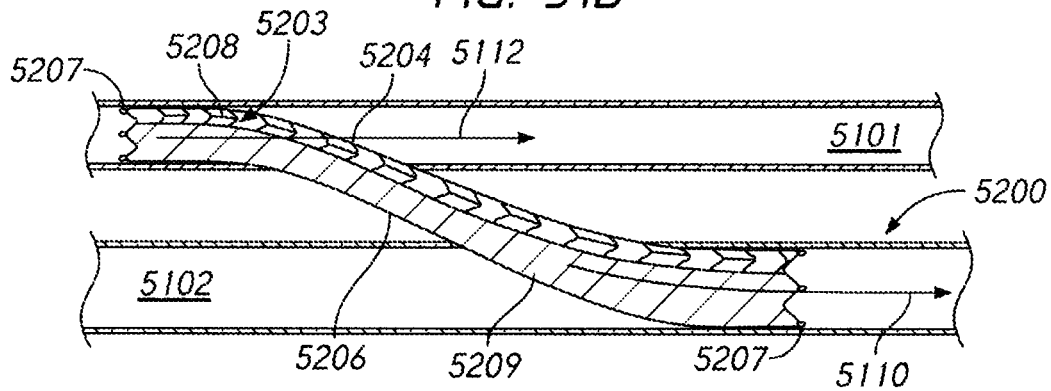
FIG. 52A is a side view of still another example device providing fluid flow from a first vessel to a second vessel and through the first vessel.

FIG. 52A is a side view of still another example device 5200 providing fluid flow from a first vessel 5101 to a second vessel 5102 and through the first vessel 5101. The device 5200 allows at least some blood to continue to flow in the first vessel 5101, and may provide one or more of the distal arterial flow preservation advantages described herein. The device 5200 comprises a first section 5204 and a second section 5206. The first section 5204 at least partially longitudinally overlaps the second section 5206. In some examples, the proximal end and/or distal end of the first section 5204 is substantially longitudinally aligned with the respective proximal and/or distal end of the second section 5206. Each of the first section 5204 and the second section 5206 anchors in each of the first vessel 5101 and the second vessel 5102. The proximal and/or distal ends, and/or other parts (e.g., a longitudinal center), of the first section 5204 and/or the second section 5206 may comprise a radiopaque marker 5207.

The first section 5204 comprises a stent structure 5208, for example like the stent structure 5108. The first section 5204 comprises pores or apertures 5203 that allow blood to flow into the proximal end and/or through the pores 5203 of the stent structure 5208 into the stent structure 5208, and then flow from inside the stent structure 5208 to outside the stent structure 5208, and downstream in the first vessel 5101, as indicated by the arrow 5112. As described herein, only the first section 5204 may comprise the stent structure 5208 or the both the first section 5204 and the second section 5206 may comprise the stent structure 5208.

The second section 5206 comprises a covering or graft 5209 and optionally the stent structure 5208. In embodiments comprising the stent structure 5208, the stent structure 5208 may be the same or different (e.g., having at least one parameter that is different (e.g., cell structure, density, porosity, material, dimensions such as diameter, thickness, and/or length), etc.) between the first section 5204 and the second section 5206, and/or within the first section 5204 and/or the second section 5206. The graft 5209 of the second section 5206 is configured to provide a fluid flow passage from the first vessel 5101 to the second vessel 5102, as indicated by the arrow 5110. Blood can flow through the second vessel 5102 as described herein. The graft 5209 preferably does not comprise pores configured to allow blood flow from inside to outside.

The second section 5206 may be integral or monolithic with the first section 5204. The first section 5204 and the second section 5206 may be deployed at substantially the same time. The first section 5204 may be separate from the second section 5206 such that they may be deployed substantially simultaneously or at least partially separately. In some implementations, the stent structure may have a figure-8 cross section, in which the first section 5204 comprises the top half of the 8 and the second section 5206 comprises the bottom half of the 8. In some implementations, the stent structure 5208 may form a lumen and the graft 5209 may extend across the lumen, forming two flow paths: a first porous flow path through the first section 5204 and a second nonporous flow path through the second section 5206. Because both the first section 5204 and the second section 5206 extend into the second vessel 5102, positioning of the device 5200 may be simplified, for example because rotational orientation generally does not affect function, although a user may prefer that the second section 5206 be adjacent to the second vessel 5102. The inventors have discovered that, surprisingly, some blood flow access to interstitial tissue does not negate the benefits provided by the fistula.

FIG. 52A may provide partially-circumferential fenestration, in which a certain percentage of the circumference of the stent structure 5208 is bare (not covered by the graft 5209). FIG. 52A illustrates the entire length of the device 5200 including the graft 5209. In some examples, only a partial length of the device 5200 includes the graft 5209 (e.g., the proximal segment being bare). In some examples, only a partial length of the device 5200 includes the graft 5209 being partially circumferential (e.g., the proximal segment being partially circumferential) while the remainder of the device 5200 includes a fully circumferential graft 5209. The percentage of bare circumference may be, for example, between about 5% and about 75% (e.g., about 5%, about 10%, about 20%, about 30%, about 40%, about 50%, about 60%, about 75%, ranges between these values, etc.).

Figure 52B:
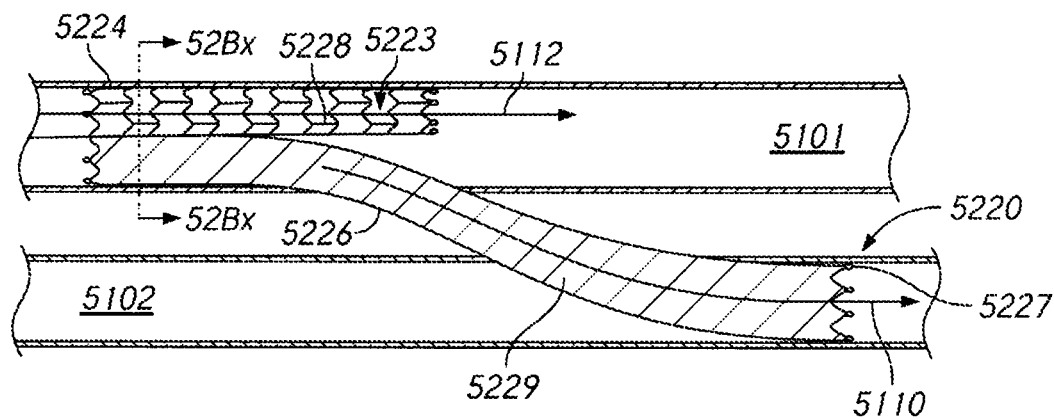
FIG. 52Bi is a side view of still yet another example device providing fluid flow from a first vessel to a second vessel and through the first vessel.

FIG. 52Bi is a side view of still yet another example device 5220 providing fluid flow from a first vessel 5101 to a second vessel 5102 and through the first vessel 5101. The device 5220 allows at least some blood to continue to flow in the first vessel 5101, and may provide one or more of the distal arterial flow preservation advantages described herein. The device 5220 may share several of the features of the device 5200 (e.g., first section 5224, second section 5226, stent structure 5228, graft 5229, etc.). The first section 5224 does not extend into the second vessel 5102. Rather, the first section 5224 terminates in the first vessel 5101. In some examples, the proximal end the first section 5224 is substantially longitudinally aligned with the proximal end of the second section 5226 (e.g., as shown in FIG. 52Bi). In some examples, the proximal end the first section 5224 is not longitudinally aligned with the proximal end of the second section 5226, for example originating proximal to the proximal end of the second section 5226 or distal to the proximal end of the second section 5226. The second section 5226 extends through interstitial tissue and into the second vessel 5102. The diameter of the second section 5226 may change from the proximal end to the distal end, for example like the tapered or angled stents described herein (e.g., having one or more cylindrical portions and one or more tapered portions).

The first section 5224 optionally comprises pores 5223, for example as described with respect to FIG. 52A. In some implementations, the first section 5224 may be devoid of pores, because blood can flow through a lumen of the first section 5224 and downstream in the first vessel 5101, as indicated by the arrow 5112. In some implementations, the first section 5224 may comprise a simple structure such as one or more rings or extensions configured to push the second section 5226 against the wall of the first vessel 5101. Blood can flow past the simple structure and downstream in the first vessel 5101.

Because the second section 5226 extends into the second vessel 5102 regardless of the position of the first section, positioning of the device 5220 may be simplified, for example because rotational orientation generally does not affect function, although a user may prefer that the second section 5226 be adjacent to the second vessel 5102. The first section 5224 may be integral or monolithic with the second section 5226, and they may be deployed at substantially the same time. The first section 5224 may be separate from the second section 5226 such that they may be deployed substantially simultaneously or at least partially separately.

FIG. 52Bii is an example cross-sectional view of the device 5220 of FIG. 52Bi across the line 52Bx-52Bx. As described as a possible implementation with respect to FIG. 52A, the first section 5224 and the second section 5226 form a figure-8. FIG. 52Bii shows the graft 5229 of the second section 5226 inward of the stent structure 5228, although the graft 5229 may be otherwise coupled to the stent structure 5228, have a different stent structure, or be devoid of a stent structure. Although shown as generally circular, the cross-sections of the first section 5224 and the second section 5226 could be oval or have other shapes configured to occupy more of the first vessel 5101 and/or the second vessel 5102 including, for example, semicircular, polygonal, etc.

FIG. 52Biii is another example cross-sectional view of the device 5220 of FIG. 52Bi across the line 52Bx-52Bx. As described as a possible implementation with respect to FIG. 52A, the graft 5229 extends across a lumen of the stent structure 5228 to form two flow paths.

FIG. 52Ci is a side view of another example device 5230 providing fluid flow from a first vessel 5101 to a second vessel 5102 and through the first vessel 5101. The device 5230 allows at least some blood to continue to flow in the first vessel 5101, and may provide one or more of the distal arterial flow preservation advantages described herein. The device 5230 may share several of the features of the devices 5200, 5220 (e.g., first section 5234, second section 5236, stent structure 5238, graft 5239, radiopaque marker 5237, etc.). Like the device 5220, the first section 5234 does not extend into the second vessel 5102. Rather, the first section 5234 terminates in the first vessel 5101. Distal to the branching of the second section 5234, the first section 5234 expands to anchor the first section 5234 in the first vessel 5101. Certain such configurations can provide good anchoring in the first vessel 5101, for example resisting rotation or other forces.

FIG. 52Cii is a cross-sectional view of the device 5230 of FIG. 52Ci across the line 52Cii-52Cii. The first section 5234 is crescent or bean shaped around a round shape of the second section 5236. The first section 5234 can revert to a round shape distal to the branching of the second section 5236. Such a cross section is also a possible implementation with respect to the devices 5200, 5210.

FIG. 52D is a side view of yet another example device 5240 providing fluid flow from a first vessel 5101 to a second vessel 5102 and through the first vessel 5101. The device 5240 allows at least some blood to continue to flow in the first vessel 5101, and may provide one or more of the distal arterial flow preservation advantages described herein. The device 5240 may share several of the features of the devices 5100, 5230 (e.g., the first section 5244 comprising an uncovered stent, the second section 5246 comprising a graft, etc.). The first section 5244 comprises a tapered portion 5245 configured to narrow from a first diameter to a second diameter smaller than the first diameter. The tapered portion 5245 comprises pores 5243 configured to allow blood to flow around the second section 5406 and continue to flow in the first vessel 5101, as shown by the arrows 5112. Blood that flows into the second section 5246 is diverted into the second vessel 5102, as shown by the arrow 5110. The device 5240 may provide particular advantages in larger vessels (e.g., proximal to occlusions before an artery begins to naturally taper and narrow). The self-centering nature of the device 5240 can provide an all-in-one solution for centering the second section 5246 in a large vessel to permit flow around the second section 5246, while also gathering some of the flow for the second vessel 5102. The tapered section 5425 could substantially center the proximal end of the second section 5246 in the first vessel (e.g., as shown in FIG. 52D). The tapered section 5425 could push the proximal end of the second section 5246 to a side of the first vessel (e.g., a side towards the second vessel 5102 (e.g., to reduce occlusion of the first vessel 5101), a side away from the second vessel 5102 (e.g., to reduce a bend angle of the second section 5426).

The first section 5424 may be integral with the second section 5426. For example, the first section and the second section may share a stent structure that is covered with graft material distal to the tapered portion 5425. The first section 5424 may be separate from the second section 5426 and deployed sequentially. For example, the first section 5424 may be deployed in the first vessel 5101 and then the second section 5426 may be deployed through the first section 5424 with the proximal end of the second section 5426 overlapping the distal end of the first section 5424.

FIG. 53A is a side view of still another example device 5300 providing fluid flow from a first vessel 5101 to a second vessel 5102 and through the first vessel 5101. The device 5300 allows at least some blood to continue to flow in the first vessel 5101, and may provide one or more of the distal arterial flow preservation advantages described herein. The device 5300 may share several of the features of the device 5100 or more particularly the second section 5106 (e.g., stent structure 5308, graft 5309, radiopaque markers 5307, etc.). The graft 5309 extends substantially the entire length of the device 5300, although sections proximal and distal to the illustrated device 5300 are also possible. The device 5300 comprises windows or fenestrations 5303 lacking the graft 5309. The graft 5309 may be removed to form the windows 5303, or not formed in the first place. Manufacturing the device 5300 with the windows 5303 may simplify a placement procedure (e.g., deploy the device 5300 and confirm rotational alignment) and/or reduce risk of creating thrombus. In some implementations, the device 5300 may comprise circumferential or spiral slits along at least a segment of the graft 5309 such that when the device 5300 bends the slits separate. The device 5760 of FIG. 57F is one such example. The graft 5309 may overlap to guard against undesired leakage. A segment comprising the bend in the second vessel 5102 is desirably devoid of such slits. Such a configuration may further simplify a placement procedure by automatically opening the windows 5303. The windows 5303 allow blood to flow into the proximal end of the device 5300 into the device 5300, and then from inside the device 5300 to outside the device 5300, and downstream in the first vessel 5101, as indicated by the arrow 5112. Blood that does not exit the windows 5303 may flow into and through the second vessel 5102, as shown by the arrow 5110. The radiopaque marker 5307 may be indicative of a side of the device 5300 comprising the window 5303. An edge or outline or sides or ends of the window 5303 may be marked by a radiopaque marker. The stent structure exposed by the window 5303 may be clad with radiopaque material.

FIGS. 53Bi-53Biii illustrate an example method of in situ formation of an example device 5320 providing fluid flow from a first vessel 5101 to a second vessel 5102 and through the first vessel 5101. The device 5320 allows at least some blood to continue to flow in the first vessel 5101, and may provide one or more of the distal arterial flow preservation advantages described herein. The device 5320 may share several of the features of the device 5300, but is not manufactured with windows or structure such as slits configured to form windows.

In FIG. 53Bi, a preliminary device 5310 is anchored in the first vessel 5101, extends through interstitial tissue, and is anchored in the second vessel 5102. In this way, the preliminary device 5310 shares many features with many fistula prostheses described herein, and any such prostheses may be used as the preliminary device 5310. A guidewire 5312 extends through a side of the preliminary device 5310. The guidewire 5312 may be navigated from a vasculature access point and puncture through the side of the preliminary device 5310. The guidewire may be integrated with the preliminary device 5310 such that the guidewire 5312 already extends through the side of the preliminary device 5310 after placement of the preliminary device 5310.

In FIG. 53Bii, an expansion device 5314 (e.g., plain balloon, drug eluting balloon, scoring balloon, expandable filaments, dilator, combinations thereof, etc.) is tracked over the guidewire 5312 and extends through the side of the preliminary device 5310. In some implementations, a fenestration device such as a laser atherectomy tool (e.g., Turbo Elite®, available from Spectranetics) may be used. The expansion device 5314 is radially expanded, as shown by the arrows 5316, to form a large window 5323 (FIG. 53Biii) and making the device 5320 in situ. The window 5323 allows blood to flow into the proximal end of the device 5320 into the device 5320, and then from inside the device 5320 to outside the device 5320, and downstream in the first vessel 5101, as indicated by the arrow 5112. Blood that does not exit the window 5323 may flow into and through the second vessel 5102, as shown by the arrow 5110. In some implementations, the expansion device 5314 may comprise a dilator tracked over the guidewire 5312. In some implementations, the guidewire 5312 may puncture the side of the preliminary device 5310 to form several small windows, one or more of which may optionally be expanded.

FIG. 53Ci shows an example cell pattern for a stent structure 5348 of a fenestrated device. FIG. 53Cii shows an example of the stent structure 5348 of FIG. 53Ci partially covered in graft 5349 and including a window 5343. The cell pattern includes a first longitudinal segment 5342, a second longitudinal segment 5344, and a third longitudinal segment 5346. The first longitudinal segment 5342 comprises a first cell pattern configured to anchor in a first vessel (e.g., an artery). The second longitudinal segment 5344 comprises a second cell pattern configured to anchor in a second vessel (e.g., a vein). The third longitudinal segment 5346 is longitudinally between the first longitudinal segment 5346 and the second longitudinal segment 5344. The third longitudinal segment 5346 comprises a third cell pattern configured to be more easily punctured during a fenestration process. For example, the third cell pattern may be more porous than the first cell pattern and/or the second cell pattern. In some implementations, the pores of the third cell pattern are sized for a typical angioplasty balloon (e.g., about 1.5 mm to about 5 mm (e.g., about 1.5 mm, about 2 mm, about 2.5 mm, about 3 mm, about 3.5 mm, about 4 mm, about 4.5 mm, about 5 mm, ranges between such values, etc.) or about 1.8 $mm^2$ to about 19.6 $mm^2$ (e.g., about 1.8 $mm^2$, about 3.1 $mm^2$, about 4.9 $mm^2$, about 7.1 $mm^2$, about 9.6 $mm^2$, about 12.6 $mm^2$, about 15.9 $mm^2$, about 19.6 $mm^2$, ranges between such values, etc.)) for positioning below the knee, about 4 mm to about 10 mm (e.g., about 4 mm, about 5 mm, about 6 mm, about 7 mm, about 8 mm, about 9 mm, about 10 mm, ranges between such values, etc.) or about 12.6 $mm^2$ to about 78.5 $mm^2$ (e.g., about 12.6 $mm^2$, about 19.6 $mm^2$, about 28.3 $mm^2$, about 38.5 $mm^2$, about 50.3 $mm^2$, about 63.6 $mm^2$, about 78.5 $mm^2$, ranges between such values, etc.)) for positioning above the knee, etc.). For another example, the third cell pattern may be less dense than the first cell pattern and/or the second cell pattern. For yet another example, the third cell pattern may comprise fewer struts than the first cell pattern and/or the second cell pattern. The reduced amount of metal in the third cell pattern makes the third segment easier to puncture to form the window 5343 in the graft 5349. The third cell pattern may improve hemodynamics (e.g., because less metal is in the flow path shown by the arrow 5112. The first cell pattern may be the same as or different from the second cell pattern. For example, the first cell pattern may have a radial force and/or flexibility configured for placement in an artery and/or the second cell pattern may have a radial force and/or flexibility configured for placement in a vein. The third segment 5344 may be flexible, for example suitable for taking a bend and/or placement in a challenging biomechanical region, (e.g., popliteal, SFA, etc.). In some implementations, the third cell pattern comprises deformable regions with improved elongation and/or elastic properties to facilitate fenestration with reduced or no risk of damage when displaced by expandable member.

The stent structure 5348 and/or the graft 5349 may comprise one or more radiopaque markers 5347 to demarcate the transition between the first segment 5342 and the third segment 5346 and/or the transition between the second segment 5344 and the third segment 5346. The radiopaque marker 5347 may be coupled to struts of the stent structure 5348, electroplated to the stent structure 5348, woven through the struts of the stent structure 5348, etc. The radiopaque marker 5347 may be radiopaque material incorporated into the graft 5349. The catheter used to deliver the device may comprise one or more corresponding radiopaque markers to facilitate placement.

FIG. 53Di illustrates an example method of in situ formation of an example device providing fluid flow from a first vessel to a second vessel and through the first vessel. The device allows at least some blood to continue to flow in the first vessel, and may provide one or more of the distal arterial flow preservation advantages described herein. The device may share several of the features of the device 5300, but is not manufactured with windows or structure such as slits configured to form windows. In FIG. 53Di, a preliminary device 5360 is anchored in the first vessel, extends through interstitial tissue, and (not shown) is anchored in a second vessel. In this way, the preliminary device 5360 shares many features with many fistula prostheses described herein, and any such prostheses may be used as the preliminary device 5360.

FIG. 53Di shows an example fenestration device including an expandable member 5362 (e.g., balloon, temporary stent, etc.), a tapered segment 5364, and a puncturer 5366. The expandable member 5362 is configured to center the device in the vessel and/or to stabilize the device during the application of a fenestration formation force. The expandable member 5362 may comprise, for example, a balloon, a stent mesh, supportive arms, etc.

The tapered segment 5364 is configured to stabilize the puncturer 5366 during the application of a fenestration formation force and/or to be tracked over the puncturer 5366 to expand the window formed by the puncturer 5366. The tapered segment 5364 may include features similar to the CXI® support catheter, available from Cook. The tapered segment 5364 is optionally longitudinally movable relative to the expandable member 5362.

FIG. 53Dii shows an example tapered segment 5374 usable with the device of FIG. 53Di. The tapered segment 5374 comprises an angle 5375. When the puncturer 5366 exits the distal end of the tapered segment 5374, the puncturer 5366 follows the angle 5375 and continues straight.

FIG. 53Diii shows another example tapered segment 5384 usable with the device of FIG. 53Di. The tapered segment 5384 comprises a lumen 5382. The distal end of the lumen 5382 comprises a ramped surface 5383. When the guidewire exits the distal end of the lumen 5382, the guidewire is deflected by the ramped surface 5383 and extends out of the tapered segment 5384 at an angle 5385 and continues straight. The tapered segment 5384 optionally comprises a straight lumen that exits the distal end of the tapered segment 5384, for example selectable by the user for advancing the guidewire without an angle. The lumen 5382 may comprise different sizes for the angled exit and the straight exit, for example and without limitation, 0.018" (approx. 0.45 mm) for the angled exit and 0.014" (approx. 0.36 mm) for the straight exit).

The tapered segment 5364, 5374, 5384 enters the small opening created by the puncturer 5366 and expands the hole. The expansion of the hole may complete the fenestration, or may make the hole appropriate for receiving an expandable member. In some implementations, the expandable member 5362 may be collapsed after serving its anchoring function and then used to expand the hole. In some implementations, a different expandable member may be used to expand the hole.

The puncturer 5366 is configured to puncture the graft of the preliminary device 5360, for example being relatively stiff, having a sharp distal tip, etc. The puncturer 5366 is longitudinally movable relative to the expandable member 5362 and the tapered segment 5364. The puncturer 5366 may comprise a needle or cannula. The puncturer 5366 may comprise a reentry device. The puncturer 5366 may comprise an atherectomy device, a laser, a guidewire (e.g., distal tip original or modified (e.g., stiffened and/or sharpened)), etc.

FIGS. 53Ei and 53Eii illustrate an example method of aligning a puncturer 5366 for in situ formation of an example device providing fluid flow from a first vessel 5101 to a second vessel 5102 and through the first vessel 5101. The device comprises a radiopaque marker 5390, for example as described herein with respect to the radiopaque marker 4210. For example, the marker 5390 may be on one side of a lumen through which a guidewire extends and oriented with respect to the angle of the tapered segment 5374. The marker 5390 may be on the same side as the taper (e.g., as shown in FIGS. 53Ei and 53Eii). The marker 5390 may be on the opposite side as the taper. The marker 5390 may be parallel to the taper. As described with respect to the marker 4210, the user may utilize the crossing plane to know where the puncturer 5366 will pierce the graft. In some implementations, a target 5392 may be positioned in the first vessel 5101 distal to the device 5360. The target 5392 may comprise, for example, a guidewire, a marking stent, a biodegradable marker, contrast (e.g., pooled proximate an occlusion), etc.

FIG. 54A is a side view of yet still another example device 5400 providing fluid flow from a first vessel 5101 to a second vessel 5102 and through the first vessel 5101. The device 5400 allows at least some blood to continue to flow in the first vessel 5101, and may provide one or more of the distal arterial flow preservation advantages described herein.

The device 5400 may share several of the features of the device 5140 (e.g., the first section 5404 comprising an uncovered stent, the second section 5406 comprising a graft, etc.) and/or the device 5320 (e.g., the second section 5406 being similar to the device 5320).

The first section 5404 and the second section 5406 of the device 5400 are separate and deployed sequentially. For example, the second section 5406 may be deployed first. The user may form a window in the second section 5406 (e.g., as described with respect to FIGS. 53Bi-53Biii) or the second section 5406 may be manufactured with a window. The second section 5406 ay anchor in the first vessel 5101, extend through interstitial tissue, and anchor in the second vessel 5102. The second section 5406 allows blood to flow into and through the second vessel 5102, as shown by the arrow 5110. The first section 5404 may be deployed second, with the distal segment of the first section 5404 extending through the window of the second section 5406. The first section 5404 anchors in the first vessel 5101. Blood can flow into the first section 5404 and continue to flow in the first vessel 5101, as shown by the arrow 5112. The first section 5404 can provide a predictable and/or durable fenestration diameter, which may better preserve the fenestration. The stent structure of the first section 5404 is porous, which allows blood to flow into the second section 5406. The proximal and/or distal ends of the first section 5404 and/or the second section 5406 may comprise a radiopaque marker 5407, for example to help a user determine an anchoring position, an amount of overlap, a rotational orientation (e.g., if manufactured with the window), etc. Although FIG. 54A shows the proximal end of the first section 5404 as being proximal to the proximal end of the second section 5406, the proximal end of the first section 5404 may be distal to or aligned with the proximal end of the second section 5406. The device 5400 may be considered a bifurcated stent that is formed in situ. The first section 5404 may be a first leg and the second section 5406 may be a second leg.

FIG. 54Bi is a side view of another example device 5410 providing fluid flow from a first vessel 5101 to a second vessel 5102 and through the first vessel 5101. The device 5410 allows at least some blood to continue to flow in the first vessel 5101, and may provide one or more of the distal arterial flow preservation advantages described herein. The device 5410 may share several of the features of the device 5400 (e.g., the first section 5404 comprising an uncovered stent, the second section 5406 comprising a graft, etc.). The device 5410 is manufactured with the first section 5414 and the second section 5416 being configured to bifurcate upon deployment of the device 5410. For example, the distal end of the first section 5414 may be configured (e.g., shape set) to remain straight such that the first section 5414 extends out of a window in the second section 5416, which curves into the second vessel 5102. For another example, the first section 5414 may comprise a flap coupled to the second section 5416.

FIG. 54Bii is a side view of another example device 5415 providing fluid flow from a first vessel 5101 to a second vessel 5102 and through the first vessel 5101. The device 5415 allows at least some blood to continue to flow in the first vessel 5101, and may provide one or more of the distal arterial flow preservation advantages described herein. The device 5415 may share several of the features of the device 5410. The device 5415 comprises a plurality of flaps 5417. The flaps 5417 can replicate the action of a valve, for example opening (protruding radially outward) under pulsatile flow. The flaps 5417 can comprise graft material (e.g., ePTFE). The flaps 5417 can comprise a structure that acts as a hinge for the radial outward protrusion. The device 5415 can maintain a proper amount of blood flow in each vessel 5101, 5102, and others, for example by regulating the flow into the second vessel 5102 with excess flow and/or pressure being bled off distal in the first vessel 5101. The flaps 5417 can be distributed across a proximal segment of the device 5415 configured to be in the first vessel 5101 (e.g., as shown in FIG. 54Bii). The flaps 5417 that appose a vessel wall would not open, but the flaps 5417 that are in a bend of the device 5415 could open. Flaps 5417 that are proximate a branch vessel of the first vessel 5101 could also open to preserve flow into that branch vessel.

FIG. 54C is a side view of yet another example device 5420 providing fluid flow from a first vessel 5101 to a second vessel 5102 and through the first vessel 5101. The device 5420 allows at least some blood to continue to flow in the first vessel 5101, and may provide one or more of the distal arterial flow preservation advantages described herein. The device 5420 comprises a first section 5424 and a second section 5426. The second section 5426 may share several features of the second section 5406 of the device 5400 (e.g., a graft and a window 5423). The second section 5426 may comprise two windows 5423, one having a similar function to the window 5323 of the device 5320 (e.g., allowing blood to continue to flow in the first vessel 5101) and one having a similar function to the window of the second section 5406 of the device 5400 (e.g., configured to have the first section 5424 extend therethrough). The second section 5426 may have a single elongate window 5423 that serves both functions. The first section 5424 and the second section 5426 may be separate. For example, the first section 5424 may extend through a side of the second section 5426 (e.g., as described with respect to the device 5400), then anchor in a branch vessel 5425, allowing blood to flow into the device 5420 and through the branch vessel 5425, as shown by the arrow 5114. The first section 5424 may comprise a stent structure to anchor the first section 5424 in the branch vessel 5425. Anchoring the first section 5424 in the branch vessel 5425 can help to anchor and position the entire device 5420. The first section 5424 may comprise a graft to help guide blood into the branch vessel 5425. The device 5420 may lack the first section 5424, in which case blood could flow through the window 5423 into the branch vessel 5425. The first section 5424 and the second section 5426 may be monolithic with the first section 5424 configured to extend from the second section 5426, for example as described with respect to the device 5410. The second section 5426 may lack the window 5423 and the first section 5424 may comprise the window 5423. No matter the precise configuration, the device 5420 maintains fluid flow from the first vessel 5101 into the branch vessel 5425, as shown by the arrow 5114, and through the first vessel 5101, as shown by the arrow 5112, and also diverts fluid flow into the second vessel 5102, as shown by the arrow 5110.

The devices described herein can be self-expanding, for example comprising shape memory (e.g., superelastic) material that expands upon release from a catheter. The devices described herein can be balloon expandable. For example, if placement accuracy of the device is important, such as at a crossing point of the fistula or near a bifurcation, a balloon expandable device can be expanded only when rotationally and/or longitudinally positioned as desired.

FIG. 55A is a side view of still another example device 5500 providing fluid flow from a first vessel to a second vessel and through the first vessel. FIG. 55B shows the device 5500 of FIG. 55A positioned in a first vessel 5101, extending through interstitial tissue, and into a second vessel 5102. The device 5500 does not or only slightly protrudes into the first vessel 5101. Blood flowing through the first vessel 5101 can continue to flow in the first vessel 5101, as shown by the arrow 5112. Blood flowing through the first vessel 5101 may also be diverted into the second vessel 5102, as shown by the arrow 5110. The device 5500 allows at least some blood to continue to flow in the first vessel 5101, and may provide one or more of the distal arterial flow preservation advantages described herein. The device 5500 may share several of the features of the other devices disclosed herein (e.g., a stent structure, a graft, etc.). The device 5500 comprises a stent with flares or anchoring features 5502 configured to anchor the device 5500 in the first vessel 5101 and an elongate section 5504 configured to extend through interstitial tissue and into the second vessel 5102. The device 5500 may comprise one flare 5502 or a plurality of flares 5502 (e.g., two flares 5502 as shown in FIG. 55A). The flares 5502 could be covered or uncovered. The elongate section 5504 is preferably covered. The device 5500 may include a laser cut stent, a woven stent, or a combination thereof, for example as described herein. The flares 5502 and the elongate section 5504 are substantially symmetrical such that rotational alignment of the device 5504 is not needed. In some implementations, a length of the flares 5502 is approximately half of the diameter of the flares 5502, which can help to secure the device 5500 against the first vessel 5101. The flares 5502 of the device 5500 are generally annular.

FIG. 55C shows yet still another example device 5520 providing fluid flow from a first vessel 5101 to a second vessel 5102 and through the first vessel 5101. Blood flowing through the first vessel 5101 can continue to flow in the first vessel 5101, as shown by the arrow 5112. Blood flowing through the first vessel 5101 may also be diverted into the second vessel 5102, as shown by the arrow 5110. The device 5520 allows at least some blood to continue to flow in the first vessel 5101, and may provide one or more of the distal arterial flow preservation advantages described herein. The device 5520 may share several of the features of the device 5500 (e.g., flares or anchoring features 5522, an elongate section 5524, etc.). FIG. 55D is a distal end view of the device 5520 of FIG. 55C implanted in the first vessel 5101 and the second vessel 5102. The flares 5520 appose a sidewall of the first vessel 5101. The elongate section 5524 apposes sidewalls of the second vessel 5102.

FIG. 55Ei is a top view of a device 5520a sharing features of the device 5520 of FIGS. 55C and 55D. The device 5520a comprises four flares 5522a projecting radially outward. The flares 5522a are symmetrical about the device 5520a. The flares 5520a each project radially outward by about a radius of the device 5520a. The flares 5520a are wires or struts formed into an arc shape. Such a shape may provide atraumatic anchoring, although tips of the arcs may penetrate or deform the vessel wall.

FIG. 55Eii is a top view of another device 5520b sharing features of the device 5520 of FIGS. 55C and 55D. The device 5520b comprises four flares 5522b projecting radially outward. The flares 5522b are symmetrical about the device 5520b. The flares 5520b each project radially outward by about half a radius of the device 5520a. The flares 5520b are solid material (e.g., struts cut into the illustrated shape). More material may provide a same amount of anchoring with less length.

FIG. 55F shows yet still another example device 5530 providing fluid flow from a first vessel 5101 to a second vessel 5102 and through the first vessel 5101. The device 5530 allows at least some blood to continue to flow in the first vessel 5101, and may provide one or more of the distal arterial flow preservation advantages described herein. The device 5530 may share several of the features of the device 5520 (e.g., flares or anchoring features 5532, an elongate section 5534, etc.).

FIG. 55G is a top view of the device 5530 of FIG. 55F. The device 5530 comprises six flares 5532 projecting radially outward. The flares 5532 are asymmetrical or eccentric about the device 5530. Some of the flares 5532 are longer than other flares. Referring again to FIG. 55F, the longer flare(s) 5532 may be oriented distally in the first vessel 5101, which can provide an opposition force to a direction of blood flow.

FIG. 56A is a side view of still another example device 5600 providing fluid flow from a first vessel 5101 to a second vessel 5102 and through the first vessel 5101. The device 5600 allows at least some blood to continue to flow in the first vessel 5101, and may provide one or more of the distal arterial flow preservation advantages described herein. The device 5600 may share several features with the prosthesis 540 of FIG. 25C (e.g., a plurality of filaments woven into a woven structure, different porosity longitudinal sections, etc.).

The prosthesis 540 comprises an embodiment comprising a low porosity first longitudinal section 544 and a high porosity second longitudinal section 546, with other longitudinal sections also possible. The device 5600 may be considered a variation on the prosthesis 540. The device 5600 comprises a first section 5604, a second section 5606, and a third section 5608 between the first section 5604 and the second section 5606. The first section 5604 has a low porosity, for example low enough to divert flow such as in a flow diverting stent, as described herein. The second section 5606 has a low porosity, for example low enough to divert flow such as in a flow diverting stent as described herein. The first section 5604 and/or the second section 5606 direct blood to flow from the first vessel 5101 into the second vessel 5102, as shown by the arrow 5110. The first section may have higher porosity. The third section 5608 has a porosity that allows blood to continue to flow in the first vessel 5101, as shown by the arrow 5112. The device 5600 may be woven (e.g., as shown in FIG. 56). Changes in weave parameters (e.g., braid angle, wire count, etc.) may cause different porosities. The device 5600 may comprise cut struts (e.g., having different cell patterns or other parameters to change porosity). Compared to known flow diverting stents that are placed in neurovasculature, the device 5600 has a larger diameter (e.g., as described for the fistula prostheses described herein) and/or have a conical or tapered shape (e.g., as described for the fistula prostheses described herein). In embodiments in which the device 5600 is woven, the filaments may be larger than neurovascular flow diverting stents (e.g., between about 50 μm and about 100 μm), which can provide durability sufficient to withstand higher flow and pressures associated with peripheral arterial blood flow. Flow diverting structures may be suitable for any of the sections described herein as comprising a graft. The porosity of the device 5600 may permit stent-in-stent deployment, for example for long pathways in interstitial tissue.

FIG. 56B is a graph showing flow through a parent vessel and a side branch with and without a device 5600 of FIG. 56A for different values of porosity of the device 5600. The flow rate for the pre-operation side branch is shown by the left-pointing outlined triangle 5610, which is about 0.18 mL/s. The flow rate for the pre-operation distal parent is shown by the right-pointing outlined triangle 5612, which is about 0.2 mL/s. Since the pre-operation points 5610, 5612 do not include a device 5600, the porosity of the absent device 5600 may be considered 100%. The flow rate for the post-operation side branch is shown by the left-pointing filled triangles 5614. The flow rate for the post-operation distal parent is shown by the right-pointing filled triangles 5616. The highest porosity tested was about 89%, which increased the flow in the distal parent to about 0.22 mL/s and reduced the flow in the side branch to about 0.16 mL/s. The lowest porosity tested was about 35%, which increased the flow in the distal parent to about 0.32 mL/s and reduced the flow in the side branch to about 0.07 mL/s. The lower the porosity, the more flow is diverted away from the side branch and to the distal parent, with an inflection point at about 60%. Thus, the porosity of some or all of the device 5600 and/or the devices described below for directing flow below an ankle, can be selected based on a desired amount of flow diversion.

FIG. 57A illustrates an example device 5700 for directing flow below an ankle. The device 5700 may be a flow focalizing stent configured to preferentially direct flow through a lumen of the device 5700. The device 5700 may reduce, inhibit, or prevent steal in veins distal to a direction of reversed blood flow (reversed relative to normal blood flow in veins), for example in a percutaneous deep venous arterialization circuit. Certain features of woven devices described herein, for example the devices 500, 520, 540, may be incorporated into the device 5700.

As discussed herein, one potential advantage to venous arterialization is improving perfusion of oxygenated to the extremities such as the distal foot. Lining veins with devices such as stent grafts (e.g., the stent grafts 1132 described herein) can help to direct flow towards an extremity, but due to current mechanical limitations, stent grafts are generally not indicated for use in smaller vessels or in vessels that experience large mechanical forces. The device 5700 has a design that is robust and flexible enough to withstand biomechanical forces and flex at the ankle. Branch vessels distal to the stent grafts can steal oxygenated blood that is intended to be driven to the distal foot. Near the calcaneus or heel bone, for example, there are a large number of connecting veins that lead to larger return veins of the leg (e.g., saphenous vein). A small amount of steal may provide some benefit, for example maintaining a higher flow rate, which can be better for patency. The device 5700 has a design that is generally drives flow to the distal foot, but may still provide some perfusion to branch vessels, thereby fine tuning the steal.

The device 5700 comprises a plurality of wires or filaments woven together in a dense pattern. At least some or all of the filaments comprise a shape memory material (e.g., a superelastic material such as nitinol, chromium cobalt, etc.). In a deployed state, such material is generally better suited to withstand biomechanical forces and maintain a low profile. The filaments may have a diameter or cross-section between about 50 μm and about 100 μm (e.g., about 50 μm, about 60 μm, about 75 μm, about 90 μm, about 100 μm, ranges between such values, etc.). The device 5700 may comprise between 16 filaments and 96 filaments (e.g., about 16 filaments, about 32 filaments, about 48 filaments, about 64 filaments, about 96 filaments, ranges between such values, etc.). The number of filaments is preferably even, and more preferably divisible by 6 and/or 8.

The device 5700 could have an expanded diameter appropriate for placement in a vein in an ankle, for example between about 4 mm and about 8 mm (e.g., about 4 mm, about 5 mm, about 6 mm, about 7 mm, about 8 mm, ranges between such values, etc.). In some implementations, the one or both ends of the device 5700 may be flared to have an increased diameter, which could help to anchor the device 5700 in the vessel. The device 5700 may be substantially cylindrical in an expanded state (e.g., as shown in FIG. 57A). The device 5700 may be conical, for example configured to taper from a first diameter at a distal end to a second smaller diameter at a proximal end. As opposed to conical stents that may be placed in an artery that reduce in size from proximal to distal, the device 5700 may increase in size from proximal to distal, for example to correspond to the anatomy of the vein, which increases in size towards the heart. The change in diameter may be, for example, between about 2 mm and about 9 mm (e.g., about 2 mm, about 3 mm, about 4 mm, about 5 mm, about 6 mm, about 7 mm, about 8 mm, about 9 mm, ranges between such values, etc.). For a device 5700 placed below the knee, the change in diameter may be, for example, between about 3 mm and about 6 mm (e.g., about 3 mm, about 4 mm, about 5 mm, about 6 mm, ranges between such values, etc.). The device 5700 may have a length between about 50 mm and about 150 mm (e.g., about 50 mm, about 75 mm, about 100 mm, about 125 mm, about 150 mm, ranges between such values, etc.).

Porosity between about 60% and about 78% is known to be useful for flow diverting neurovascular stents to divert blood from aneurysms but permit perfusion to branch vessels. The porosity of the device 5700 may be less than 78%, or more preferably less than 60%, to inhibit perfusion to branch vessels. For flow preservation, porosity in the range of about 60% and about 75% is a "sweet spot" allowing for adequate preservation of flow across a bifurcation. Porosity less than about 50% can dramatically reduce flow in a bifurcating vessel.

Pore size may also influence hemodynamics. For example, higher picks per inch (PPI) can result in smaller pore size, which can decrease flow into an aneurysm or a branch vessel, and lower PPI can result in a larger pore size, which can allow perfusion into branch vessels. PPI reflects an amount of filament material exists in a square inch (approx. 6.5 $cm^2$) of the device 5700. The PPI may range from about 50 PPI to about 500 PPI, (e.g., about 50 PPI, about 100 PPI, about 150 PPI, about 200 PPI, about 300 PPI, about 400 PPI, about 500 PPI, ranges between such values, etc.).

In some implementations, the device 5700 may comprise a higher porosity and graft material. For example, the device 5700 may comprise a high flexibility laser cut pattern with a polymer covering. Certain such designs may include a perforated or perforatable covering. The device 5700 is different from neurovascular flow diverting stents in a number of meaningful ways. For example, the device 5700 has a larger diameter, has a larger delivery profile (e.g., greater than 3 Fr), has a longer length, is tapered to be larger towards the heart, has less porosity, has a higher radial force, and/or has a higher compression resistance, any one of which would be contraindicated for neurovasculature.

The filaments of the device 5700 are woven together to have a high braid angle, which can provide a high radial force. For example, the braid angle may be between about 120° and about 179°, (e.g., about 120°, about 130°, about 140°, about 150°, about 160°, about 170°, about 179°, ranges between such values, etc.). Compression resistance may be, for example, between about 0.4 N/mm and about 1.1 N/mm (e.g., about 0.4 N/mm, about 0.5 N/mm, about 0.6 N/mm, about 0.7 N/mm, about 0.8 N/mm, about 0.9 N/mm, about 1 N/mm, about 1.1 N/mm, ranges between such values, etc.). As a basis of comparison, a resistive force of about 1 N/mm may be strong enough to prop open a valve. Chronic outward force may be, for example, between about 0.25 N/mm and about 0.6 N/mm (e.g., about 0.25 N/mm, about 0.3 N/mm, about 0.35 N/mm, about 0.4 N/mm, about 0.45 N/mm, about 0.5 N/mm, about 0.55 N/mm, about 0.6 N/mm, ranges between such values, etc.). These force values can vary, for example, based on wire diameter and braid angle. A larger wire diameter has a higher radial force than a smaller wire diameter (e.g., 76 μm can be about 2 N/mm while 50 μm can be about 1 N/mm). In some implementations, the radial force is sufficient to prop open venous valves, which may or may not have been disabled (e.g., by a cutting device, balloon, etc.). In some implementations, the radial force is sufficient to expand the vein, which is generally flexible, which can provide a dimensionally known fluid flow channel.

The ends of the filaments of the device 5700 may be truncated as the device 5700 is cut to length. The filaments are small enough that there is low risk of puncturing the vein or causing issues with fluid flow. A limited amount of puncturing by free filament ends may help to anchor the device 5700 in place. In some implementations, the ends of the filaments may be treated, such as by bending, coiling, welding, coupling to end treatment devices, back-braided, etc.

FIG. 57Bi illustrates a first example of blood flow through a vein 5701 proximate to an ankle. A vein 5701 (e.g., posterior tibial vein) is lined with a stent graft 1132, for example as described herein. The stent graft 1132 only extends to approximately the position of the ankle, as shown by the dashed line. Blood flowing through the vein 5701 can continue towards the foot and the lateral plantar network, as shown by the arrow 5712. However, blood flowing through the vein may be stolen by the branch vessel 5703 (e.g., calcaneal perforator), as shown by the arrow 5714, such that the foot may not be properly perfused.

FIG. 57Bii illustrates a second example of blood flow through a vein proximate to an ankle. Like FIG. 57Bi, the vein 5701 is lined with a stent graft 1132 that only extends to approximately the position of the ankle. In FIG. 57Bii, the device 5700 is positioned below the stent graft 1132 in the ankle. Blood flowing through the vein 5701 can continue towards the foot and the lateral plantar network, as shown by the arrow 5712. Blood flowing through the vein may not be stolen by the branch vessel 5703 because the device 5700 diverts flow away from the vessel 5703. As such, the foot may be better perfused than without the device 5700. The device 5700 may be deployed from the foot (e.g., using a guidewire extending from the foot as described herein) and/or from femoral access. The device 5700 may longitudinally overlap with the stent graft 1132. For example, the device 5700 may be radially outward of the stent graft 1132. In certain such implementations, the device 5700 may be deployed before the stent graft 1132.

FIGS. 57Ci-57Ciii illustrate example variations on woven flow diverting devices 5720, 5730, 5740 sharing features with the device 5700 of FIG. 57A. The devices 5720, 5730, 5740 each have a wire diameter of 75 μm and a nominal braid angle of 140°, but have different porosities when expanded to different diameters. The device 5720 of FIG. 57Ci has a diameter of 5.5 mm and a porosity of 44%. The device 5730 of FIG. 57Cii has a diameter of 5 mm and a porosity of 72%. The device 5740 of FIG. 57Ciii has a diameter of 4.5 mm and a porosity of 83%. Depending on the amount of oversizing of the device, different porosity can be achieved. Varying the amount of porosity can allow a user to tune the amount of permitted steal. Generally, more oversized devices can permit more steal. Referring again to FIG. 56B, the device 5720 can increase the flow in the distal parent to about 0.31 mL/s and to decrease the flow in the branch vessel to about 0.08 mL/s; the device 5730 can increase the flow in the distal parent to about 0.26 mL/s and to decrease the flow in the branch vessel to about 0.13 mL/s; and the device 5740 can increase the flow in the distal parent to about 0.23 mL/s and to decrease the flow in the branch vessel to about 0.16 mL/s.

FIG. 57Di illustrates a device 5750 in which a portion 5752 of the graft covering 5759 is perforated with a plurality of openings, controlled in size, to achieve a certain level of porosity to manage flow through the graft covering. In some implementations, the entire graft covering 5759 may be perforated. The openings may be created with laser processing, mechanical perforation, as part of a covering process (e.g., ePTFE sintering), composite assembly of ePTFE with porous membrane, etc. The shape, size, and/or pattern of the openings may be selected as desired. The pore size should be large enough to allow desired blood flow.

FIG. 57Dii is a schematic side view of the device 5750 of FIG. 57Di showing the effect of the porous region on fluid flow. A selected amount of fluid can flow through the porous region 5752, for example to a branch vessel, as shown by the arrow 5714. A remainder of fluid can flow to the distal parent, as shown by the arrow 5712. The device 5750 can also or alternatively be used in a fistula to direct flow from a first vessel to a second vessel and to maintain a selected amount of flow in the first vessel.

FIG. 57E is a schematic spectrum of porosity showing the effect of porosity on steal. The spectrum ranges from 0% porosity (a covered stent without any pores) to 100% porosity (no stent). From a porosity of about 0% to about 50%, the device effectively prevents steal. Between a porosity of about 60% and about 75%, flow preservation is achieved. Greater than about 86% porosity, little or no flow diversion is achieved.

FIG. 57Fi is a side view of another example device 5760 configured to provide fluid flow from a first vessel to a second vessel and through the first vessel. FIG. 57Fii is an expanded view of the device 5760 of 57Fi in the area 57Fii. The device 5760 may share several of the features of the other devices disclosed herein (e.g., a stent structure, a graft, etc.). The device 5760 comprises a plurality of slits 5762, which are easier to see in FIG. 57Fii. The device 5760 is shown in FIG. 57Fi is in a straight configuration such that the slits 5762 are in a closed configuration.

FIG. 57Fiii shows the device 5760 positioned in a first vessel 5101, extending through interstitial tissue, and into a second vessel 5102. FIG. 57Fii is an expanded view of the device 5760 of 57Fiii in the area 57Fiv. Blood flowing through the first vessel 5101 can continue to flow in the first vessel 5101, as shown by the arrow 5112. Blood flowing through the first vessel 5101 may also be diverted into the second vessel 5102, as shown by the arrow 5110. The device 5760 allows at least some blood to continue to flow in the first vessel 5101, and may provide one or more of the distal arterial flow preservation advantages described herein. When the device 5760 is flexed due to the bend towards the second vessel, the slits 5762o on the outside of the bend are spread open, while the slits 5762c on the inside of the bend are compressed together and the slits 5762c proximal and distal to the bend remain closed. The open slits 5762c allow blood to flow through the device 5760, as indicated by the arrows 5112, as best seen in FIG. 57Fiv.

FIG. 58A is a side view of an example occlusive implant 5800. FIGS. 58Bi-58Biii illustrate an example method of in situ coupling of the occlusive implant 5800 and an example device providing fluid flow from a first vessel 5101 to a second vessel 5102 and through the first vessel 5101. FIG. 58Biii shows the implant 5800 and a device 5810 as part of an occlusive system that allows at least some blood to continue to flow in the first vessel 5101, as shown by the arrow 5112, and may provide one or more of the distal arterial flow preservation advantages described herein. The implant 5800 can inhibit or prevent the stealing of arterial blood in the venous return to the heart.

Because blood may have originally been flowing in the second vessel 5102 from right to left (e.g., if the second vessel 5012 is a vein) prior to arterialization after which the blood flows from left to right, as indicated by the arrow 5110, and/or because access to the second vessel 5102 (e.g., via a targeting system, a snare system, a system to deploy the device 5800, etc.) may have been from the right side, discussions of proximal, distal, upstream, downstream, etc. can be confusing such that reference may be made to the left and right with respect to FIGS. 58A-58Biii.

The implant 5800 comprises a first part 5802. The first part 5802 comprises an occlusive implant. The first part 5802 is configured to occlude the second vessel 5102 to the left of a fistula prosthesis (e.g., the device 5810). The occlusive implant may include, for example, but not limited to, an expandable mesh, a sponge, a plug (e.g., Amplatzer®, available from Abbott, MVP™, available from Medtronic), a coil or plurality of coils (e.g., Concerto™, available from Medtronic, Interlock™ and VortX®, available from Boston Scientific, AZUR®, available from Terumo, MReye®, available from Cook), an embolic liquid (e.g., Onyx®, available from Medtronic), hydrogel (e.g., Bead Block™ available from Boston Scientific), microspheres (e.g., HydroPearl®, available from Terumo), an implantable balloon, combinations thereof, etc. Any system or method that occludes the second vessel 5102 to the left of a fistula prosthesis may be suitable for the first part 5802.

The implant 5800 optionally comprises a second part 5804 coupled to the first part 5802. The second part 5804 comprises a coil or other anchor configured to attach the first part 5802 to a fistula prosthesis (e.g., the device 5810). The second part 5804 can inhibit the first part 5802 from drifting to the left. The second part 5804 may be omitted if, for example, there is low likelihood that the first part 5802 will drift to the left or become dislodged. If the second vessel 5102 is a vein, the path to the left goes to the heart, so downstream release of an embolization device should be avoided.

In FIG. 58Bi, the device 5810 is positioned in the first vessel 5101, through interstitial tissue, and into the second vessel 5102, for example as described herein. The device 5810 may comprise an uncovered stent that allows blood to flow through pores to the right of FIG. 58Bi, as shown by the arrow 5112. Other fistula flow devices, for example as described herein, can be used in conjunction with the implant 5800. For example, if the device 5120 is deployed too far to the right in FIG. 51B, there may be a blood flow path to the left of the second vessel 5102. The implant 5800 can help to close such blood flow path.

FIG. 58Bi also shows a guidewire 5812 extended through the device 5810 in the second vessel 5102. The guidewire 5812 may be used to deploy the implant 5800. In FIG. 58Bii, the first part 5802 if the implant 5800 is deployed in the second vessel 5102. The first part 5802 is tethered to the second part 5804, which is then exposed by withdrawal of a catheter 5814, as indicated by the arrow 5816. The second part 5804 may uncoil as it is released from the catheter 5814. The uncoiling of the second part occurs inside the device 5810 such that the second part 5804 anchors against an inner sidewall of the device 5810 and applies a pulling force on the first part 5802.

FIG. 58C is a side view of an example occlusive implant system comprising the implant 5800. The system also comprises the device 5810. Blood can flow through the device 5810 in the first vessel 5101, as shown by the arrow 5112. Blood can also flow into the device 5810 from the first vessel 5101, through interstitial tissue, and to the right in the second vessel 5102, as shown be the arrow 5110. Blood that flows into the device 5810 from the first vessel 5101, through interstitial tissue, and attempts to flow to the left in the second vessel 5102, as shown be the arrow 5118, is stopped by the first part 5802.

The fistula prostheses described herein, for example but not limited to the devices 5100, 5120, 5140, 5200, 5220, 5230, 5240, 5300, 5320, 5400, 5410, 5420, 5600, 5810, can preserve flow through the first vessel. The device may have a variable cell geometry to suit the mechanical requirements of the disease state and/or increase flow where needed. For example, larger cells may be provided in the region of fenestration and/or proximate a bifurcation. For another example, smaller cells at the ends can aid in deployment accuracy and/or wall apposition. Radiopaque markings can aid in rotational and/or longitudinal alignment, for example to provide a user with an indication of where the covering begins. Delivery systems may be configured to rotate the device to position the fenestration such that blood flow through the first vessel is preserved. Additional devices can be provided in a system, for example to aid in creating fenestrations, placing an occlusive implant, etc.

Referring again to FIGS. 52Ci and 52Cii as an example applicable to the fistula prostheses described herein, including but not limited to the devices 5100, 5120, 5140, 5200, 5220, 5230, 5240, 5300, 5320, 5400, 5410, 5420, 5600, 5810, if the diameter of the first vessel 5101 is X mm, the diameter of the second section 5236 (e.g., the proximal end of the second section 5236) may be between about 0.25X and about 0.75X (e.g., about 0.25X, about 0.35X, about 0.4X, about 0.45X, about 0.5X, about 0.6X, about 0.75X, ranges between such values, etc.). The ratio may depend, for example, on the diameter X of the first vessel 5101, the diameter of the second vessel 5102, the amount of occlusion in the first vessel 5101, the position in the first vessel 5101 (e.g., the ratio generally being smaller upstream because more branch vessels downstream of the first vessel 5101 are still supplied), the type of prosthesis, etc. The prostheses may be provided as a suite of prostheses from which a user may select a desired ratio.

FIG. 59Ai illustrates a third example of blood flow through a vein 5901 proximate to an ankle. The vein 5901 (e.g., posterior tibial vein) is lined with a stent graft 1132, for example as described herein. The stent graft 1132 only extends to approximately the position of the ankle. Blood flowing through the vein 5901 can continue towards the foot and the lateral plantar network. The distal outflow transition to the vein at the distal end 1903 of the stent graft 1132 is not controlled, which can result in sudden transitions in the flow path, which could increase the risk of turbulence.

FIG. 59Aii illustrates a fourth example of blood flow through a vein 5901 proximate to an ankle. Like FIG. 59Ai, the vein 5901 is lined with a stent graft 1132 that only extends to approximately the position of the ankle. In FIG. 59Aii, a device 5900 is positioned below the stent graft 1132 in the ankle. Blood flowing through the vein 5901 can continue towards the foot and the lateral plantar network. The use of the device 5900 can control the transition from the distal end 5903 of the device 1132 to inhibit or prevent diameter and angle changes that may be detrimental to flow.

FIG. 59B illustrates the device 5900 of FIG. 59Aii overlapping a stent graft 1132. The device 5900 comprises an overlap portion 5902 and a tapered portion 5904. The overlap portion 5902 may be cylindrical, tapered, and/or a combination thereof. In some implementations, the proximal end of the device 5900 comprises a radiopaque marker 5912 and the distal end of the stent graft 1132 comprises a radiopaque marker 5914. When the marker 5912 is upstream of the marker 5914, the user can be assured that the device 5900 overlaps the stent graft 1132 to achieve the desired flow effects. The device 5900 and/or the stent graft 1132 may comprise another radiopaque marker to ensure an appropriate amount of overlap (e.g., demarcating the start of the tapered portion 5904).

The tapered portion 5904 tapers from a first diameter 5906 to a second diameter 5908 less than the first diameter 5906. The first diameter 5906 may be, for example, between about 2 mm and about 10 mm (e.g., about 2 mm, about 3 mm, about 4 mm, about 5 mm, about 6 mm, about 7 mm, about 8 mm, about 9 mm, about 10 mm, ranges between such values, etc.). The second diameter 5908 may be, for example, between about 1 mm and about 8 mm (e.g., about 1 mm, about 2 mm, about 3 mm, about 4 mm, about 5 mm, about 6 mm, about 7 mm, about 8 mm, ranges between such values, etc.). The tapered portion 5904 has a length 5910. The length 5910 may be, for example, between about 5 mm and about 100 mm (e.g., about 5 mm, about 10 mm, about 25 mm, about 50 mm, about 75 mm, about 100 mm, ranges between such values, etc.). The device 5900 can be tuned in diameter, length, taper angle, etc. based on, for example, inflow conditions, outflow geometry, flow rate, pressure, etc. to produce or optimize the possibility for laminar flow conditions inside and/or distal to the stent graft 1132. For example, specific desired flow rates may be possible based on the second diameter 5908 and/or pressure in the device 5900.

FIG. 60 is a partially transparent view showing certain vasculature of a left lower leg. The vasculature includes a P3 segment 6002 of the popliteal artery. The P3 segment 6002 branches into the anterior tibial artery 6004 and the tibioperoneal trunk 6006. The tibioperoneal trunk or TP trunk or TPT 6006 branches into the posterior tibial artery 6008 and the peroneal artery 6010. The box 6012 shows an example area where the posterior tibial artery 6008 often includes an occlusion. In several of the methods described herein, the crossing from the posterior tibial artery 6008 to the posterior tibial vein 4438 is in the area of the box 6012, which is proximate to the occlusion 6014. In some implementations, the crossing can be further upstream of the occlusion 6014, for example in the P3 segment 6002 or the tibioperoneal trunk 6004 or proximal in the posterior tibial artery 6008 (e.g., spaced from the occlusion 6014). The P3 segment 6002 and the tibioperoneal trunk 6006 are usually larger and less diseased than the posterior tibial artery 6008. Crossing from the P3 segment 6002 or the tibioperoneal trunk 6006 or proximal in the posterior tibial artery 6008 can improve inflow to the venous arterialization. The fistula prosthesis can be placed in the P3 segment 6002 or the tibioperoneal trunk 6006 with reduced fear of jailing other arteries. Placement of a fistula prosthesis (e.g., having the ability to maintain flow in the artery distal to the fistula) upstream of the occlusion can open the procedures described herein to a broader patient population (e.g., high risk patients in addition to no-option patients). Placement of a fistula prosthesis (e.g., having the ability to maintain flow in the artery distal to the fistula) upstream of the occlusion can reduce the risk of steal-induced ischemia with proper management of blood flow volumes in the fistula prosthesis. Other arteries that can be used for procedures described herein include, but are not limited to, the anterior tibial artery (ATA) and the peroneal or fibular peroneal. The posterior tibial vein 4438 can be targeted, in several circumstances, regardless of which vessel is occluded.

The P3 segment 6002 and the tibioperoneal trunk 6006 are major supply vessels to the lower limb. In seeking to move the artery-vein connection proximally to the P3 segment 6002 or the tibioperoneal trunk 6006, there is an increased risk of diverting too much blood from the arterial tree given their larger diameters and blood volumes. Stealing too much blood from these arteries 6002, 6006 by diverting blood into a vein can lead to ischemia in the tissues they supply. The amount of steal can be influenced by several factors such as geometry (diameter, lumen shape), pressure gradients (arterial to venous, other stealing veins distal to the crossing like the greater saphenous vein), number of available flow paths, arterial blood supply, and the like. As described herein, some prostheses can divert blood from an artery to a vein and still provide blood flow through the artery distal to the fistula. Although such arterial flow preserving venous arterialization can maintain blood flow in the artery distal to the artery-vein connection, diverting too much blood can still be a serious risk.

Controlling the flow in the prosthesis can be important to the health of the subject. Specific prosthesis geometry can achieve the desired flow in the arterialized vein. Nominal blood flow in the higher arteries is about 750 mL/min. Flow rates through arterialized veins described herein can be between about 50 mL/min and about 500 mL/min, (e.g., about 50 mL/min, about 100 mL/min, about 150 mL/min, about 200 mL/min, about 250 mL/min, about 300 mL/min, about 350 mL/min, about 400 mL/min, about 450 mL/min, about 500 mL/min, ranges between such values, etc.), which has been found to be sufficient to reduce distal limb ischemia. Flow rates higher than 500 mL/min may also be sufficient (e.g., when the fistula prosthesis is placed far upstream of an occlusion). Flow rates lower than 50 mL/min may also be sufficient (e.g., when the fistula prosthesis is placed far down a leg). A prosthesis diameter between about 2 mm and about 3.5 mm (e.g., about 2 mm, about 2.5 mm, about 3 mm, about 3.5 mm, ranges between such values, etc.) can provide thus sufficient blood flow, depending on flow characteristics and anatomy (e.g., resistance or pulling by downstream vessels). If some blood is allowed to continue to flow through the artery, the diverted blood preferably provides similar flow while also enabling proximal crossing locations.

FIG. 61A illustrates an example of a prosthesis 6100 that can be placed upstream of an occlusion. The prosthesis 6100 comprises a first segment 6101, a second segment 6102, a third segment 6103, a fourth segment 6104, and a fifth segment 6105. The lengths, diameters, and shapes of the segments 6101-6105 in FIG. 61A are schematic only. The first segment 6101 is configured to anchor in a proximal artery (e.g., the P3 segment 6002 or the tibioperoneal trunk 6006). The first segment 6101 is configured to span interstitial tissue between the artery and a vein. The fifth segment 6105 is configured to anchor in a proximal vein. The third segment 6103 is preferably configured to reside in the vein. The third segment 6103 is narrower than the first segment 6101. The second segment 6102 tapers from the first segment 6101 to the third segment 6103. The third segment 6103 is preferably narrower than the fifth segment 6105 (e.g., as shown in FIG. 61A), which can provide better hemodynamics than terminating the prosthesis 6100 at the third segment 6103 or positioning the third segment 6103 too close to one end. The fourth segment 6104 tapers from the third segment 6103 to the fifth segment 6105. The fourth segment 6104 and the fifth segment 6105 may optionally be omitted.

The narrowness of the third segment 6103 can limit the flow of blood (e.g., by increasing the flow resistance) through the prosthesis 6100. The amount of blood that can flow through the third segment 6103 is less than the amount of blood that can flow through the first segment 6101 and the fifth segment 6105. The second segment 6102 and the fourth segment 6104 provide a gentle transition from the arterial diameter to the third segment 6103 and from the third segment 6103 to the venous diameter, respectively. Such gentle transitions can help produce laminar flow and/or reduce turbulence in the prosthesis 6100. Overall, the prosthesis 6100 has an hourglass shape. The third segment 6103 does not include a balloon. The third segment 6103 does not include a pump. The third segment 6103 does not include leaflets or other valve components. The third segment 6103 does not include embolic filtering components. The third segment 6103 is not configured to cause embolization. The third segment 6103 does not make up for oversizing of the first segment 6101 and/or the fifth segment 6105, which are purposefully sized to anchor in first and second vessels. The narrowing of the third segment 6103 is contrary to the teaching of peripheral vascular prostheses configured to prop open the vessel to allow as much blood flow as possible. Certain elements (such as one or more of the balloon, pump, filter, etc.) are optionally excluded in some embodiments and present in others.

FIG. 61B illustrates another example of a prosthesis 6120 that can be placed upstream of an occlusion. The prosthesis 6120 comprises a first segment 6121, a second segment 6122, and a third segment 6123. The lengths, diameters, and shapes of the segments 6121-6125 in FIG. 61B are schematic only. The first segment 6121 is configured to anchor in a proximal artery (e.g., the P3 segment 6002 or the tibioperoneal trunk 6006). The first segment 6121 is configured to span interstitial tissue between the artery and a vein. The third segment 6123 is preferably configured to reside in the vein. The third segment 6123 is narrower than the first segment 6121. The second segment 6122 tapers from the first segment 6121 to the third segment 6123. The prosthesis 6120 may be similar to the prosthesis 6100 with the fourth segment 6104 and the fifth segment 6105 omitted (e.g., then prosthesis 6120 gently tapering down to a diameter (e.g., about 3.5 mm or about 4 mm) in the second segment 6122 and then staying at that diameter in the third segment 6123. The narrowness of the third segment 6123 can, for example, provide the prosthesis 6120 with at least some of the benefits of the third segment 6103 of the prosthesis 6100 (e.g., limiting the flow of blood through the prosthesis 6120).

FIG. 61C illustrates yet another example of a prosthesis 6150 that can be placed upstream of an occlusion. The prosthesis 6150 may share several features of the device 5300, for example a stent structure 6158, graft 6159, radiopaque markers, etc. The prosthesis 6150 may provide the ability to provide fluid flow from a first vessel 5101 to a second vessel 5102, as shown by the arrow 5110, and through the first vessel 5101, as shown by the arrow 5112. In the example illustrated in FIG. 61C, the first vessel 5101 is the P3 segment 6002, although other vessels are also possible. The prosthesis 6150 allows at least some blood to continue to flow in the first vessel 5101, and may provide one or more of the distal arterial flow preservation advantages described herein. The prosthesis 6150 comprises windows or fenestrations 6160 lacking the graft 6159. The graft 6159 may be removed to form the windows 6160, or not formed in the first place, for example as described herein. The prosthesis 6150 may share several features of the prosthesis 6100 such as the shape and order of the segments 6101-6105. For example, the prosthesis 6150 comprises a first segment 6151 anchored in the first vessel 5101 and extending through interstitial tissue. For another example, the prosthesis 6150 comprises a third segment 6153 in the second vessel 5102. The third segment 6153 limits flow through the prosthesis 6150 (e.g., by increasing the flow resistance) and therefore into the second vessel 5102. The third segment 6103 does not cause increased pressure because the third segment 6103 allows excess pressure to dissipate by continuing in the first vessel 5101. This limiting of flow can limit vessel steal. This limiting of flow can also provide hemodynamics such that sufficient blood continues to flow in the first vessel 5101, for example downstream in the vessel 5101 and to a branch vessel 5425. An excess of blood can flow into the first segment, so the angle of the fistula does not affect the amount of blood that is able to flow through the third segment 6103 and therefore into the second vessel 5102. Although the combination of the shape of the prosthesis 6100 and certain features of the device 5100 are shown in FIG. 61C, it will be appreciated that the combination of the shape of the prosthesis 6100 and certain features of other devices described herein, including but not limited to the devices 5100, 5120, 5140, 5160, 5200, 5220, 5230, 5240, 5300, 5310, 5320, 5360, 5400, 5410, 5415, 5420, 5500, 5520, 5530, 5600, 5750, 5760, 5810.

The upstream fistula crossing described herein can be combined with other methods described herein (e.g., radiopaque marker targeting, bifurcation identification, expandable member puncturing, guidewire snaring, vein lining, valve disabling, pedal access, etc.). For example, a method of placing the prosthesis 6150 may comprise using a radiopaque marker on a crossing catheter in a first vessel to target a radiopaque expandable member in a second vessel, and placing the prosthesis 6150 (e.g., using a balloon to expand at least one of the segments 6151-6155). The method may comprise puncturing the expandable member in the second vessel, snaring a guidewire, proximally retracting the snared guidewire out of the second vessel, and tracking devices such as a prosthesis delivery catheter, vein liner catheter, valve disabling device, etc. over the guidewire.

In some implementations, the stent structure 6158 may narrow in the third segment 6153 and the graft 6159 may follow the curvature of the stent structure 6158 to also narrow in the third segment. Such an implementation may be easier to manufacture, for example.

FIG. 61D illustrates still another example of a prosthesis 6180 that can be placed upstream of an occlusion. The prosthesis 6180 may share features of the prosthesis 6150. In FIG. 61D, the stent structure 6188 does not narrow in the third segment 6183. Rather than following the curvature of the stent structure 6188, the graft 6189 narrows within the stent structure 6188 in the third segment 6183.

FIG. 62A illustrates an example of a prosthesis 6200 that can be placed upstream of an occlusion. The prosthesis 6200 comprises a first segment 6201, a second segment 6202, a third segment 6203, a fourth segment 6204, and a fifth segment 6205. The first segment 6201 is configured to anchor in a proximal artery (e.g., the P3 segment 6002 or the tibioperoneal trunk 6006). The first segment 6201 is substantially cylindrical. The first segment 6201 has a diameter 6206. The diameter 6206 can be, for example, between about 5 mm and about 7 mm (e.g., about 5 mm, about 5.5 mm, about 6 mm, about 6.5 mm, about 7 mm, ranges between such values, etc.). The fifth segment 6205 is configured to anchor in a proximal vein. The fifth segment 6205 is substantially cylindrical. The fifth segment 6205 has a diameter 6207. The diameter 6207 can be, for example, between about 5 mm and about 7 mm (e.g., about 5 mm, about 5.5 mm, about 6 mm, about 6.5 mm, about 7 mm, ranges between such values, etc.). The diameter 6206 can be the same as the diameter 6207.

The third segment 6203 is preferably configured to reside in the vein. The third segment 6203 may be configured to reside in interstitial tissue or at least partially in the artery. The third segment 6203 is substantially cylindrical. Other geometries that could increase flow resistance are also possible (e.g., oval, slotted, etc.). The third segment 6203 has a diameter 6208. The diameter 6208 can be, for example, between about 2.5 mm and about 5 mm (e.g., about 2.5 mm, about 3 mm, about 3.5 mm, about 4 mm, about 4.5 mm, about 5 mm, ranges between such values, etc.). The diameter 6208 is less than the diameter 6206. The diameter 6208 may be less than the diameter 6207. The second segment 6202 tapers from the diameter 6206 to the diameter 6208. The fourth segment 6204 tapers from the diameter 6208 to the diameter 6207.

The segments 6121-6125 can be shape set to take the shapes and/or diameters shown in FIG. 62A. In some implementations, an expansion balloon can be used to shape one or more of the segments 6121-6125. For example, slow inflation and longitudinal movement of a balloon or other expandable member can form the tapered segments 6122 and/or 6124.

FIG. 62B illustrates another example of another prosthesis 6220 that can be placed upstream of an occlusion. The prosthesis 6220 is similar to the prosthesis 6200, except that the diameter 6226 is smaller than the diameter 6227. The diameter 6226 can be, for example, between about 4 mm and about 6 mm (e.g., about 4 mm, about 4.5 mm, about 5 mm, about 5.5 mm, about 6 mm, ranges between such values, etc.). The diameter 6227 can be, for example, between about 5 mm and about 7 mm (e.g., about 5 mm, about 5.5 mm, about 6 mm, about 6.5 mm, about 7 mm, ranges between such values, etc.). The diameter 6228 is smaller than the diameters 6226, 6227. The diameter 6228 can be, for example, between about 2.5 mm and about 5 mm (e.g., about 2.5 mm, about 3 mm, about 3.5 mm, about 4 mm, about 4.5 mm, about 5 mm, ranges between such values, etc.).

FIG. 62C illustrates yet another example of a prosthesis 6240 that can be placed upstream of an occlusion. The prosthesis 6240 can share some features of the prosthesis 6200, except that the prosthesis 6240 lacks the first and second segments. The prosthesis 6240 comprises the third segment 6243, the fourth segment 6244, and the fifth segment 6245. The diameter 6247 of the fifth segment 6245 can be, for example, between about 5 mm and about 7 mm (e.g., about 5 mm, about 5.5 mm, about 6 mm, about 6.5 mm, about 7 mm, ranges between such values, etc.). The diameter 6248 of the third segment 6243 is smaller than the diameter 6247. The diameter 6428 can be, for example, between about 2.5 mm and about 5 mm (e.g., about 2.5 mm, about 3 mm, about 3.5 mm, about 4 mm, about 4.5 mm, about 5 mm, ranges between such values, etc.). The prosthesis 6240 may be a modification, for example, of the device 5200, 5220, 5230, 5240, etc. where the prosthesis does not necessarily directly anchor in the first vessel.

FIG. 62D illustrates still another example of a prosthesis 6260 that can be placed upstream of an occlusion. The prosthesis 6260 can share some features of the prosthesis 6200, except that the prosthesis 6260 lacks the second segment. The prosthesis 6260 comprises the first segment 6261, the third segment 6263, the fourth segment 6264, and the fifth segment 6265. The first segment 6261 is configured to anchor in the artery. Rather than the first segment 6261 spanning interstitial tissue and tapering to the third segment 6263, the third segment 6263 extends transversely from the first segment 6261. The third segment 6263 extends at least partially through interstitial tissue and may enter the vein. The diameter 6266 of the first segment 6261 can be, for example, between about 5 mm and about 7 mm (e.g., about 5 mm, about 5.5 mm, about 6 mm, about 6.5 mm, about 7 mm, ranges between such values, etc.). The diameter 6267 of the fifth segment 6265 can be, for example, between about 5 mm and about 7 mm (e.g., about 5 mm, about 5.5 mm, about 6 mm, about 6.5 mm, about 7 mm, ranges between such values, etc.). The diameter 6268 of the third segment 6263 is smaller than the diameter 6267. The diameter 6428 can be, for example, between about 2.5 mm and about 5 mm (e.g., about 2.5 mm, about 3 mm, about 3.5 mm, about 4 mm, about 4.5 mm, about 5 mm, ranges between such values, etc.). The prosthesis 6260 may be a modification, for example, of the device 5400, 5410, etc. where the prosthesis does not necessarily have a segment that anchors in the first vessel and then extends through interstitial tissue.

FIG. 63A illustrates an example of a prosthesis 6300 that can be placed upstream of an occlusion. The prosthesis 6300 can share features of the prosthesis 6100 (e.g., the first segment 6301, the second segment 6302, the third segment 6303, the fourth segment 6304, the fifth segment 6305, the diameter 6306, the diameter 6307, the narrow diameter 6308, etc.). The first segment 6301 of the prosthesis 6300 comprises a flange 6310. The illustrated flange 6310 is configured to help the first segment 6301 anchor in the artery. The flange 6310 could be additionally or alternatively configured to anchor in the vein and/or interstitial tissue. The flange 6310 can comprise, for example, extensions, loops, struts, arms, times, etc. The flange 6310 can be configured to anchor the prosthesis 6300 to properly align a fenestrated portion. The flange 6310 can allow the prosthesis 6300 to be used in a variety of vessels and subjects. For example, the flange 6310 can help the first segment 6301 to anchor in a P3 segment 6002, a tibioperoneal trunk 6006, or a posterior tibial artery 6008 (e.g., spaced from an occlusion 6014 where the posterior tibial artery 6008 is larger, proximate to an occlusion 6014 where anchoring may be difficult due to vessel wall irregularity). The flange 6310 has a diameter 6309 greater than the diameter 6306. The diameter 6309 may be, for example, between about 8 mm and about 12 mm (e.g., about 8 mm, about 9 mm, about 9.5 mm, about 10 mm, about 10.5 mm, about 11 mm, about 12 mm, ranges between such values, etc.). The diameter 6309 may be, for example, between about 50% and about 90% (e.g., about 50%, about 60%, about 70%, about 80%, about 90%, ranges between such values, etc.) greater than the diameter 6306, which may have the dimensions of the diameters 6206, 6226 just as all dimensions described herein may be shared amongst the various devices depending on context. The flange 6310 may be integral with the stent structure. The flange 6310 may be coupled to the first segment 6301. The flange 6310 may be in a central part of the first segment 6301 (e.g., as shown in FIG. 63A). The flange 6310 may be proximate to a proximal end of the first segment 6301. The flange 6310 may be proximate to a distal end of the first segment 6301.

FIG. 63B illustrates another example of a prosthesis 6330 that can be placed upstream of an occlusion. The prosthesis 6330 can share features of the prosthesis 6300 (e.g., the flange 6340). The prosthesis 6330 comprises a stent structure 6338 and a graft 6339. The stent structure 6338 is illustrated as being a woven structure, although cut struts and combinations thereof are also possible, for example as described herein. The flange 6340 is integral with the stent structure 6338. The graft 6339 is coupled to the stent structure 6338 distal to the flange 6340. The graft 6339 comprises a window 6333 to allow blood to continue to flow in the vessel in which the first segment 6331 is placed. In some implementations, the flange 6310 spaces the first segment 6331 from the vessel wall such that blood can continue to flow around the first segment 6331 so as to continue to flow in the vessel in which the first segment 6331 is placed (e.g., as described with respect to the device 5240). In certain such implementations, the window 6333 may be omitted.

FIG. 63C illustrates yet another example of a prosthesis 6350 that can be placed upstream of an occlusion. The prosthesis 6350 can share features of the prosthesis 6300 (e.g., the flange 6360), except that the prosthesis 6350 does not include a first or second segment. The flange 6310 is coupled to the third segment 6353. The flange 6360 may be in a central part of the third segment 6353. The flange 6360 may be proximate to a proximal end of the third segment 6353 (e.g., as shown in FIG. 63C). The flange 6360 may be proximate to a distal end of the third segment 6353. The flange 6360 spaces the third segment 6353 from the vessel wall such that blood can continue to flow around the first segment 6353 so as to continue to flow in the vessel in which the third segment 6353 is placed (e.g., as described with respect to the device 5240). The narrow third segment 6353 limits the amount of blood that can flow through the prosthesis 6350 into the second vessel.

FIG. 64 illustrates an example of a flow limiting implant 6400. The implant 6400 comprises a first segment 6401, a second segment 6402, and a third segment 6403. The first segment 6401 and the third segment 6403 are configured to anchor the implant 6400 in the prosthesis and/or the vessel. The second segment 6402 comprises a narrow cylindrical section that can limit flow through the implant 6400, for example as described with respect to certain third segments herein. The implant 6400 can provide the flow limiting benefits to devices that do not have a flow limiting element, such as described herein or commercially available devices that may be suitable for placement in a fistula.

FIG. 65 illustrates still another example of a prosthesis 6500 that can be placed upstream of an occlusion. The prosthesis 6500 can share features of the prosthesis 6200, for example comprising a first segment 6501, a second segment 6502, a third segment 6503, a fourth segment 6504, and a fifth segment 6505. The third segment 6503 comprises a flexible or elastic material, which may be called a flexible venturi or a self-regulating valve. As velocity increases in a fluid, pressure decreases. Because the third segment 6503 comprises a flexible material, a decrease in pressure draws the walls of the prosthesis inward, effectively reducing the diameter of the third segment. This reduction in diameter can reduce the flow rate, compensating as conditions in distal limb (e.g., foot) change over time (maturation) and/or are modified (e.g., by intentional occlusion of stealing veins). The third segment 6503 could be fully flexible, for example able to narrow (e.g., as shown in FIG. 65) or widen to the diameter of the first segment 6501 and/or the fifth segment 6505. The largest diameter of the third segment 6503 could be limited to ensure limited flow under any conditions. For example, the maximum diameter of the third segment 6503 could be, for example, between about 2.5 mm and about 5 mm (e.g., about 2.5 mm, about 3 mm, about 3.5 mm, about 4 mm, about 4.5 mm, about 5 mm, ranges between such values, etc.). In some implementations, a rigid stents structure could limit expansion of the third segment 6503 and a flexible graft structure could allow narrowing of the third segment 6503.

In some implementations, the devices described herein, including the fenestrated stents (e.g., positioned upstream of or longitudinally-spaced from an arterial occlusion), may be used in a venous arterialization procedure. In certain such procedures, vein lining stents (e.g., as described herein or other liners) can be placed in the vein. The vein liner can help to prop open venous valves. The vein liner can close off branch vessels. The vein liner can be placed in the vein prior to placing a prosthesis in the fistula. The vein liner can overlap with the fistula prosthesis. In some implementations, the devices described herein, including the fenestrated stents (e.g., positioned upstream of or longitudinally-spaced from an arterial occlusion), can be used in a percutaneous or surgical bypass procedure. In certain such procedures, a fenestrated stent can be used to extend from an artery to a vein (or other appropriate second vessel). A second, non-fenestrated stent, can be used to extend from the vein back into the artery or into another vessel. A liner can be deployed in the bypass vessel, for example between the two fistula prostheses. In certain such procedures, a fenestrated stent can be used to extend from an artery to a harvested or artificial vessel. A second, non-fenestrated stent, can be used to extend from the harvested or artificial vessel back into the artery or into another vessel. A liner can be deployed in the harvested or artificial vessel, for example between the two fistula prostheses.

Although some example embodiments have been disclosed herein in detail, this has been done by way of example and for the purposes of illustration only. The aforementioned embodiments are not intended to be limiting with respect to the scope of the appended claims, which follow. It is contemplated by the inventors that various substitutions, alterations, and modifications may be made to the invention without departing from the spirit and scope of the invention as defined by the claims. For example, although described herein with respect to alignment of catheters including a needle, the systems and methods described herein may be used to align other types of catheters, for example guide catheters that navigate vasculature including bifurcations, embolic material (e.g., coil) delivery catheters, directional atherectomy catheters, neurostimulation or ablation catheters that should be have a rotational orientation to target a nerve, etc. For another example, although described herein with respect vascular catheters, the systems and methods described herein may be used to align endoscopes, transcutaneous devices, etc. For yet another example, although certain procedures may be described with respect to a needle crossing from an artery to a vein, crossing from a first artery to a second artery, crossing from a first vein to a second vein, crossing from a vein to an artery, crossing from a first vessel to a second vessel, crossing from a first cavity to a second cavity, crossing from a cavity to a vessel, and crossing from a vessel to a cavity are possible.

While the devices described herein may be used in applications in which the fluid that flows through the device is a liquid such as blood, the devices could also or alternatively be used in applications such as tracheal or bronchial surgery where the fluid is a gas, such as air. In some embodiments, the fluid may contain solid matter, for example emboli or, in gastric surgery where the fluid includes food particles.

While the invention is susceptible to various modifications, and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "making valves in the first vessel incompetent" include "instructing making valves in the first vessel incompetent." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 mm" includes "10 mm." Terms or phrases preceded by a term such as "substantially" include the recited term or phrase. For example, "substantially parallel" includes "parallel."

What is claimed is:

1. A method of increasing blood perfusion in a vein in a foot for a venous arterialization procedure, the method comprising:
   diverting blood flow from an artery to a first vein, diverting blood flow from the artery to the first vein comprising creating a fistula between the artery and the first vein;
   accessing a second vein in a foot at a location distal to the fistula;
   disabling one or more valves in the second vein to facilitate blood flow distally from the fistula to the second vein in the foot, disabling one or more valves comprising:
      positioning a stent in the second vein;
      expanding the stent in the second vein to open one or more valves in the second vein to reduce inhibition of retrograde blood flow by the one or more valves; and
   providing blood flow distally from the artery, through the fistula, and to the foot through the stent in the second vein, providing blood flow distally comprising permitting blood flow through a sidewall of the stent to permit blood flow to branch vessels located adjacent to the stent.

2. The method of claim 1, wherein the second vein is a continuation of the first vein.

3. The method of claim 1, wherein the stent comprises a bare metal stent.

4. The method of claim 1, wherein the stent comprises a drug eluting stent.

5. The method of claim 1, wherein the stent comprises a polymer stent.

6. The method of claim 1, wherein the stent comprises a laser cut stent.

7. The method of claim 1, wherein the stent comprises a diameter between about 2 mm and about 6 mm.

8. The method of claim 1, wherein the second vein comprises a lateral plantar vein, a lateral marginal vein, a medial plantar vein, a medial marginal vein, a fibular vein, a dorsal arcade of the foot, or a dorsal vein of a Hallux.

9. A method of increasing blood perfusion in a vein in a foot for a venous arterialization procedure, the method comprising:
diverting blood flow from an artery to a vein, diverting blood flow from the artery to the vein comprising creating a fistula between the artery and the vein;
disabling one or more venous valves in a foot to facilitate retrograde blood flow from the fistula to the foot, disabling one or more venous valves comprising expanding a stent in the foot to open the one or more venous valves in the foot to reduce inhibition of retrograde blood flow by the one or more venous valves; and
providing retrograde blood flow from the artery, through the fistula, and to the foot through the stent in the foot, wherein providing the retrograde blood flow comprises permitting at least a portion of the retrograde blood flow through a sidewall of the stent to permit blood flow to branch vessels located adjacent to the stent.

10. The method of claim 9, wherein the stent is positioned at a location distal to the fistula.

11. The method of claim 9, wherein the stent comprises a bare metal stent.

12. The method of claim 9, wherein the stent comprises a drug eluting stent.

13. The method of claim 9, wherein the stent comprises a polymer stent.

14. The method of claim 9, wherein the stent comprises a laser cut stent.

15. The method of claim 9, wherein the stent comprises a diameter between about 2 mm and about 6 mm.

16. The method of claim 9, wherein the stent is positioned at a location distal to the fistula, and wherein the stent comprises a diameter between about 2 mm and about 6 mm.

17. A method of increasing blood perfusion in a vein in a foot for a venous arterialization procedure, the method comprising:
diverting blood flow from an artery to a vein, diverting blood flow from the artery to the vein comprising creating a fistula between the artery and the vein;
disabling one or more venous valves in a foot to facilitate retrograde blood flow from the fistula to the foot, disabling one or more venous valves comprising expanding a stent in the foot to open the one or more venous valves in the foot to reduce inhibition of retrograde blood flow by the one or more venous valves,
wherein the one or more venous valves are located within a lateral plantar vein, a lateral marginal vein, a medial plantar vein, a medial marginal vein, a fibular vein, a dorsal arcade of the foot, or a dorsal vein of a Hallux; and
providing retrograde blood flow from the artery, through the fistula, and to the foot through the stent in the foot.

18. A method of increasing blood perfusion in a vein in a foot for a venous arterialization procedure, the method comprising:
disabling one or more venous valves in a foot to facilitate retrograde blood flow in a vein of the foot, disabling the one or more venous valves comprising expanding a stent in the foot to open the one or more venous valves in the foot to reduce inhibition of retrograde blood flow by the one or more venous valves; and
providing retrograde blood flow to the foot through the stent in the foot, wherein providing the retrograde blood flow comprises permitting at least a portion of the retrograde blood flow through a sidewall of the stent to permit blood flow to branch vessels located adjacent to the stent.

19. The method of claim 18, wherein providing the retrograde blood flow comprises providing the retrograde blood flow from a fistula between an artery and a vein and to the foot through the stent in the foot.

20. The method of claim 19, wherein the stent is positioned at a location distal to the fistula.

21. The method of claim 18, wherein the stent comprises a bare metal stent.

22. The method of claim 18, wherein the stent comprises a drug eluting stent.

23. The method of claim 18, wherein the stent comprises a polymer stent.

24. The method of claim 18, wherein the stent comprises a laser cut stent.

25. The method of claim 18, wherein the stent comprises a diameter between about 2 mm and about 6 mm.

26. A method of increasing blood perfusion in a vein in a foot for a venous arterialization procedure, the method comprising:
disabling one or more venous valves in a foot to facilitate retrograde blood flow in a vein of the foot, disabling one or more venous valves comprising expanding a stent in the foot to open the one or more venous valves in the foot to reduce inhibition of retrograde blood flow by the one or more venous valves,
wherein the one or more venous valves are located within a lateral plantar vein, a lateral marginal vein, a medial plantar vein, a medial marginal vein, a fibular vein, a dorsal arcade of the foot, or a dorsal vein of a Hallux; and
providing retrograde blood flow to the foot through the stent in the foot.

27. A method of increasing blood perfusion in a vein in a foot for a venous arterialization procedure, the method comprising:
disabling one or more venous valves in a foot to facilitate retrograde blood flow in a vein of the foot, disabling one or more venous valves comprising expanding a stent in the foot to open the one or more venous valves in the foot to reduce inhibition of retrograde blood flow by the one or more venous valves; and
providing retrograde blood flow to the foot through the stent in the foot, wherein providing the retrograde blood flow comprises:
providing the retrograde blood flow from a fistula between an artery and a vein and to the foot through the stent in the foot,
permitting at least a portion of the retrograde blood flow through a sidewall of the stent to permit blood flow to branch vessels located adjacent to the stent,
wherein the stent is positioned at a location distal to the fistula, and
wherein the stent comprises a diameter between about 2 mm and about 6 mm.

* * * * *